US011066392B2

(12) United States Patent
Balog et al.

(10) Patent No.: US 11,066,392 B2
(45) Date of Patent: Jul. 20, 2021

(54) INHIBITORS OF INDOLEAMINE 2,3-DIOXYGENASE AND METHODS OF THEIR USE

(71) Applicant: BRISTOL-MYERS SQUIBB COMPANY, Princeton, NJ (US)

(72) Inventors: James Aaron Balog, Lambertville, NJ (US); Emily Charlotte Cherney, Newtown, PA (US); Liping Zhang, East Windsor, NJ (US); Audris Huang, New Hope, PA (US); Weifang Shan, Princeton, NJ (US); David K. Williams, Delran, NJ (US); Xiao Zhu, Winchester, MA (US); Weiwei Guo, Chatham Township, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/612,076

(22) PCT Filed: May 10, 2018

(86) PCT No.: PCT/US2018/032013
§ 371 (c)(1),
(2) Date: Nov. 8, 2019

(87) PCT Pub. No.: WO2018/209049
PCT Pub. Date: Nov. 15, 2018

(65) Prior Publication Data
US 2020/0095231 A1    Mar. 26, 2020

Related U.S. Application Data

(60) Provisional application No. 62/505,584, filed on May 12, 2017.

(51) Int. Cl.
| *A61P 35/00* | (2006.01) |
| *A61K 31/444* | (2006.01) |
| *A61K 31/4709* | (2006.01) |
| *A61K 31/4375* | (2006.01) |
| *A61K 31/497* | (2006.01) |
| *A61K 31/506* | (2006.01) |
| *C07D 401/12* | (2006.01) |
| *C07D 403/12* | (2006.01) |
| *C07D 471/04* | (2006.01) |
| *C07D 213/85* | (2006.01) |

(52) U.S. Cl.
CPC ......... *C07D 403/12* (2013.01); *C07D 213/85* (2013.01); *C07D 401/12* (2013.01); *C07D 471/04* (2013.01); *A61P 35/00* (2018.01)

(58) Field of Classification Search
CPC ... A61P 35/00; A61K 31/444; A61K 31/4709; A61K 31/4375; A61K 31/497; A61K 31/506; C07D 401/12; C07D 403/12; C07D 471/04
See application file for complete search history.

(56) References Cited

U.S. PATENT DOCUMENTS

| 9,598,422 | B2 | 3/2017 | Beck et al. |
| 2007/0167426 | A1 | 7/2007 | Siddiqui et al. |
| 2009/0155311 | A1 | 6/2009 | Chen et al. |

FOREIGN PATENT DOCUMENTS

| WO | 2004/094409 A1 | 11/2004 |
| WO | 2006/029879 | 3/2006 |
| WO | 2006/105021 A2 | 10/2006 |
| WO | 2006/122150 A1 | 11/2006 |
| WO | 2007/005874 A2 | 1/2007 |
| WO | 2007/075598 A2 | 7/2007 |
| WO | 2008/036642 A2 | 3/2008 |
| WO | 2008/036653 A2 | 3/2008 |
| WO | 2009/009116 | 1/2009 |
| WO | 2009/044273 | 4/2009 |
| WO | 2009/073620 A2 | 6/2009 |
| WO | 2010/019570 | 2/2010 |
| WO | 2010/077634 A1 | 7/2010 |
| WO | 2011/028683 | 3/2011 |
| WO | 2011/056652 | 5/2011 |
| WO | 2011/070024 | 6/2011 |
| WO | 2011/107553 A1 | 9/2011 |
| WO | 2011/131407 A1 | 10/2011 |
| WO | 2011/140249 A2 | 11/2011 |
| WO | 2012/032433 | 3/2012 |
| WO | 2012/142237 A1 | 10/2012 |
| WO | 2012/145493 A1 | 10/2012 |
| WO | 2013/079174 | 6/2013 |
| WO | 2013/087699 | 6/2013 |
| WO | 2013/119716 A1 | 8/2013 |
| WO | 2013/132044 A1 | 9/2013 |
| WO | 2013/169264 A1 | 11/2013 |
| WO | 2014/008218 | 1/2014 |

(Continued)

OTHER PUBLICATIONS

Ball et al, Characterization of an indoleamine 2, 3-dioxygenase-like protein found in humans and mice, Gene, Jul. 1, 2007;396(1)203-213.
Brandacher et al, Prognostic value of indoleamine 2, 3-dioxygenase expression in colorectal cancer: effect on tumor-infiltrating T cells, Clinical cancer research, Feb. 15, 2006;12(4):1144-1151.
Bundgaard H. (C) Means to enhance penetration:(1) Prodrugs as a means to improve the delivery of peptide drugs, Advanced Drug Delivery Reviews, Jan. 1, 1992;8(1):1-38.
Bundgaard, H., Chapter 5: "Design and Application of Prodrugs", A Textbook of Drug Design and Development, pp. 113-191, Krogsgaard-Larsen, P., et al., eds., Harwood Academic Publishers, 1991.
Evans et al., Asymmetric alkylation reactions of chiral imide enolates. A practical approach to the enantioselective synthesis of. alpha.-substituted carboxylic acid derivatives, Journal of the American Chemical Society, Mar. 1982;104(6):1737-1739.

(Continued)

*Primary Examiner* — Brenda L Coleman
(74) *Attorney, Agent, or Firm* — BakerHostetler

(57) ABSTRACT

There are disclosed compounds that modulate or inhibit the enzymatic activity of indoleamine 2,3-dioxygenase (IDO), pharmaceutical compositions containing said compounds and methods of treating proliferative disorders, such as cancer, viral infections and/or inflammatory disorders utilizing the compounds of the invention.

24 Claims, No Drawings

(56) References Cited

FOREIGN PATENT DOCUMENTS

| WO | 2014/036357 A1 | 3/2014 |
|---|---|---|
| WO | 2016/073738 A2 | 5/2016 |
| WO | 2016/073770 A1 | 5/2016 |
| WO | 2016/073774 A2 | 5/2016 |

OTHER PUBLICATIONS

Gaspari ot al. "Structure-Activity Study of Brassinin Derivatives as Indoleamlne 2,3- Dioxygenase Inhibitors", J Med Chem. 2006. vol. 49(2), pp. 684-692, entire document, especially: abstract; p. 21, Scheme 1, e.g. products 2, 3, 4 and 7.

Goldstein et al., Biological efficacy of a chimeric antibody to the epidermal growth factor receptor in a human tumor xenograft model. Clinical Cancer Research, Nov. 1, 1995;1(11):1311-1318.

Ishiyama et al., Palladium (0)-catalyzed cross-coupling reaction of alkoxydiboron with haloarenes: a direct procedure for arylboronic esters, The Journal of Organic Chemistry, Nov. 1995;60(23):7508-7510.

Kakeya et al., Studies on Prodrugs of Cephalosporins. I. Synthesis and Biological Properties of Glycyloxybenzoyloxymethyl and Glycylaminobenzoyloxymethyl Esters of 7ß-[2-(2-Aminothiazol-4-yl)-(Z)-2-methoxyiminoacetamido]-3-methyl-3-cephem-4-carboxylic Acid, Chemical and pharmaceutical bulletin, Feb. 25, 1984;32(2):692-698.

Kohl et al., Inhibition of famesyltransferase induces regression of mammary and salivary carcinomas in ras transgenic mice, Nature medicine. Aug. 1995;1(8):792-797.

Littlejohn et al., Expression and purification of recombinant human indoleamine 2, 3-dioxygenase, Protein expression and purification, Jun. 1, 2000;19(1):22-29.

Nielsen et al., Glycolamide esters as biolabile prodrugs of carboxylic acid agents: synthesis, stability, bioconversion, and physicochemical properties, Journal of Pharmaceutical Sciences, Apr. 1988;77(4)285-298.

Pubchem, Substance Record for SID 111585117. Create Date: Mar. 7, 2011. Retrieved on Jun. 22, 2017. Retrieved from the Internet: https://pubchem.ncbi.nlm.nih.gov/substance/111585117, entire document.

Pubchem, Substance Record for SID 121181436. Create Date: May 5, 2011. Retrieved on Jun. 22, 2017. Retrieved from the Internet: https://pubchem.ncbi.nlm.nih.gov/substance/121181436. entire document.

Sarkar et al., Induction of indoleamine 2, 3-dioxygenase by interferon-? in human islets, Diabetes, Jan. 1, 2007;56(1):72-79.

Sausville et al., Cyclin-dependent kinase modulators studied at the NCI: pre-clinical and clinical studies, Current Medicinal Chemistry—Anti-Cancer Agents, Jan. 1, 2003;3(1):47-56.

Scheller et al., Paclitaxel balloon coating, a novel method for prevention and therapy of restenosis, Circulation, Aug. 17, 2004;110(7):810-814.

Sekulic et al., A direct linkage between the phosphoinositide 3-kinase-AKT signaling pathway and the mammalian target of rapamycin in mitogen-stimulated and transformed cells, Cancer research, Jul. 1, 2000;60(13):3504-3513.

Serafini et al., Myeloid suppressor cells in cancer: recruitment, phenotype, properties, and mechanisms of immune suppression, in Seminars in cancer biology Feb. 1, 2006 (vol. 16, No. 1, pp. 53-65). Academic Press.

Surry et al., "Dialkylbiaryl Phosphines in Pd-Catalyzed Amination: A User's Guide", Chem. Sci., 2011, 2, 27-50.

Vlahos et al., A specific inhibitor of phosphatidylinositol 3-kinase, 2-(4-morpholinyl)-8-phenyl-4H-1-benzopyran-4-one (LY294002), Journal of Biological Chemistry, J. Biol. Chem, 1994, 269, 5241-5248.

Widder, K., et al., eds., Methods of Enzymology, Academic Press, 1985, 112, 309-396.

Zou et al., "Heck-type coupling vs. conjugate addition in phosphine-rhodium catalyzed reactions of aryl boronic acids with a,ß-unsaturated carbonyl compounds: a systematic investigation", Dalton Trans., 2007, 28, 3055-3064.

INHIBITORS OF INDOLEAMINE 2,3-DIOXYGENASE AND METHODS OF THEIR USE

CROSS-REFERENCE TO RELATED APPLICATIONS

This application is the National Stage of International Patent Application No. PCT/US2018/032013, filed May 10, 2018 which claims the benefit of U.S. application No. 62/505,584, filed May 12, 2017, the disclosures of which are incorporated herein by reference in their entireties.

FIELD OF THE INVENTION

The invention relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Indoleamine 2,3-dioxygenase (IDO; also known as IDO1) is an IFN-γ target gene that plays a role in immunomodulation. IDO is an oxidoreductase and one of two enzymes that catalyze the first and rate-limiting step in the conversion of tryptophan to N-formyl-kynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron-bound dioxygenase are necessary for activity. A homolog to IDO (IDO2) has been identified that shares 44% amino acid sequence homology with IDO, but its function is largely distinct from that of IDO. (See, e.g., Serafini, P. et al., *Semin. Cancer Biol.*, 16(1):53-65 (February 2006) and Ball, H. J. et al., Gene, 396(1):203-213 (Jul. 1, 2007)).

IDO plays a major role in immune regulation, and its immunosuppressive function manifests in several manners. Importantly, IDO regulates immunity at the T cell level, and a *nexus* exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4):1144-1151 (Feb. 15, 2006)).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in PCT Publication No. WO 2004/094409.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

SUMMARY OF THE INVENTION

The invention is directed to compounds of formula I, formula II, and formula III:

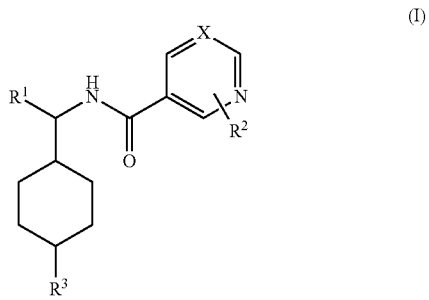

(I)

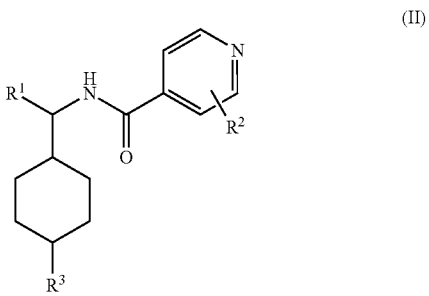

(II)

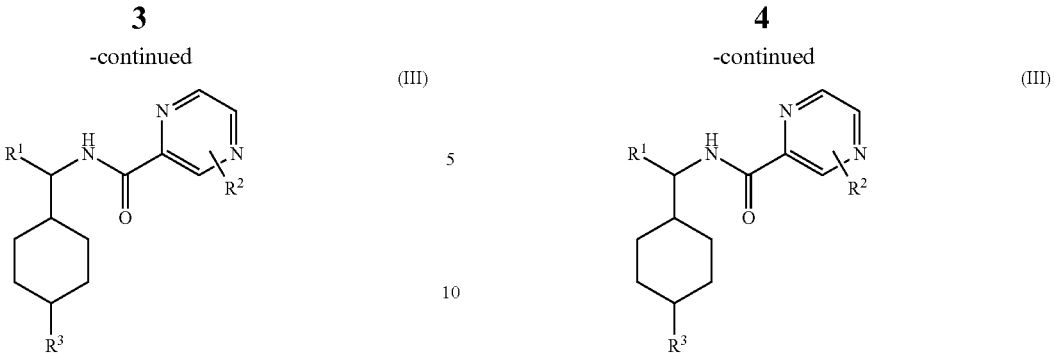

wherein X is CH, CR⁴, or N; $R^1$ is $C_{1-6}$alkyl, $C_{0-6}$alk-O—$C_{1-6}$alkyl, $C_{0-6}$alk-O—$C_{1-6}$alk-O—$C_{1-6}$alkyl, $C_{0-6}$alk-CN, or $C_{0-6}$alk-heterocycloalkyl; $R^2$ is H, —NH₂; —NH($C_{1-6}$alkyl); —N($C_{1-6}$alkyl)($C_{1-6}$alkyl), $C_{1-6}$alkyl, $d_1$-$d_{13}$-$C_{1-6}$alkyl, $C_{1-6}$alkoxy, $d_1$-$d_{13}$-$C_{1-6}$alkoxy, OH, halo, heterocycloalkyl, or heteroaryl; $R^3$ pyridyl; pyrimidinyl; quinolinyl; or naphthyridinyl, wherein the pyridyl, pyrimidinyl, quinolinyl, or naphthyridinyl is optionally substituted on any atom with 1, 2 or 3 R substituents that are independently $C_{1-6}$alkyl, $d_1$-$d_{13}$-$C_{1-6}$alkyl, halo$C_{1-6}$alkyl, halo$C_{1-6}$alkoxy, $C_{1-6}$alkoxy, $d_1$-$d_{13}$-$C_{1-6}$alkoxy, OH, or halo; and $R^4$ is NH₂; —NH($C_{1-6}$alkyl); —N($C_{1-6}$alkyl)($C_{1-6}$alkyl), $C_{1-6}$alkyl; $C_{1-6}$alkoxy, OH, halo, heterocycloalkyl, or heteroaryl.

Also within the scope of the invention are pharmaceutically acceptable salts, stereoisomers, tautomers, and solvates of the compounds of formula I, formula II, and formula III.

The invention is also directed to pharmaceutical compositions comprising one or more compounds of formula I, formula II, and/or formula III. The invention is also directed to methods of treating, e.g., cancer using one or more compounds of formula I, formula II, and/or formula III.

DETAILED DESCRIPTION OF THE INVENTION

Compounds of the Invention

The invention is directed to compounds of formula I, formula II, and formula III:

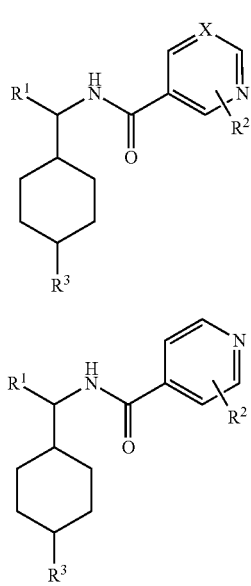

According to the disclosure, X is CH, CR⁴, or N. In some aspects, X is CH. In other aspects, X is N.

In other aspects, X is CR⁴, wherein R⁴ is NH₂; —NH($C_{1-6}$alkyl); —N($C_{1-6}$alkyl)($C_{1-6}$alkyl), $C_{1-6}$alkyl; $C_{1-6}$alkoxy, OH, halo, heterocycloalkyl, or heteroaryl. For example, in some aspects, X is C—NH₂. In other aspects, X is C—NH($C_{1-6}$alkyl), for example C—NH(Me), C—NH(Et), C—NH(n-Pr), C—NH(i-Pr), C—NH(n-Bu), C—NH(t-Bu), and the like. In other aspects, X is C—N($C_{1-6}$alkyl)($C_{1-6}$alkyl), wherein each $C_1$-$C_6$alkyl is independently selected from, for example, methyl, ethyl, n-propyl, i-propyl, n-butyl, t-butyl, and the like. In other aspects, X is C—$C_{1-6}$alkyl, for example, C-Me, C-Et, C-n-Pr, C-i-Pr, C-n-Bu, C-t-Bu, and the like. In other aspects, X is C—$C_{1-6}$alkoxy, for example, C—OMe, C-OEt, C—O—Pr$^n$, C—O—Pr$^i$, C—O—Bu$^n$, C—O—Bu$^t$, and the like. In other aspects, X is C—OH. In other aspects, X is C-halo, for example, C—F, C—Cl, C—Br, or C—I. In other aspects, X is C-heterocycloalkyl. In other aspects, X is C-heteroaryl.

According to the disclosure, $R^1$ is $C_{1-6}$alkyl, $C_{0-6}$alk-O—$C_{1-6}$alkyl, $C_{0-6}$alk-O—$C_{1-6}$alk-O—$C_{1-6}$alkyl, $C_{0-6}$alk-CN, or $C_{0-6}$alk-heterocycloalkyl. In some aspects, $R^1$ is $C_{1-6}$alkyl, for example, methyl, ethyl, propyl, isopropyl, butyl, or t-butyl.

In other aspects, $R^1$ is $C_{0-6}$alk-O—$C_{1-6}$alkyl, for example $C_0$alk-O—$C_{1-6}$alkyl, $C_1$alk-O—$C_{1-6}$alkyl, $C_2$alk-O—$C_{1-6}$alkyl, $C_3$alk-O—$C_{1-6}$alkyl, $C_4$alk-O—$C_{1-6}$alkyl, $C_5$alk-O—$C_{1-6}$alkyl, $C_6$alk-O—$C_{1-6}$alkyl, $C_{0-6}$alk-O—$C_1$alkyl, $C_{0-6}$alk-O—$C_2$alkyl, $C_{0-6}$alk-O—$C_3$alkyl, $C_{0-6}$alk-O—$C_4$alkyl, $C_{0-6}$alk-O—$C_5$alkyl, and $C_{0-6}$alk-O—$C_6$alkyl.

In other aspects, $R^1$ is $C_{0-6}$alk-O—$C_{1-6}$alk-O—$C_{1-6}$alkyl, for example, $C_0$alk-O—$C_{1-6}$alk-O—$C_{1-6}$alkyl, $C_1$alk-O—$C_{1-6}$alk-O—$C_{1-6}$alkyl, $C_2$alk-O—$C_{1-6}$alk-O—$C_{1-6}$alkyl, $C_3$alk-O—$C_{1-6}$alk-O—$C_{1-6}$alkyl, $C_4$alk-O—$C_{1-6}$alk-O—$C_{1-6}$alkyl, $C_5$alk-O—$C_{1-6}$alk-O—$C_{1-6}$alkyl, $C_6$alk-O—$C_{1-6}$alk-O—$C_{1-6}$alkyl, $C_{0-6}$alk-O—$C_{1-6}$alk-O—$C_1$alkyl, $C_{0-6}$alk-O—$C_{1-6}$alk-O—$C_2$alkyl, $C_{0-6}$alk-O—$C_{1-6}$alk-O—$C_3$alkyl, $C_{0-6}$alk-O—$C_{1-6}$alk-O—$C_4$alkyl, $C_{0-6}$alk-O—$C_{1-6}$alk-O—$C_5$alkyl, and $C_{0-6}$alk-O—$C_{1-6}$alk-O—$C_6$alkyl.

In alternative embodiments, $R^1$ is a polyalkylene glycol moiety, for example, a polyethylene glycol moiety, e.g., —(CH₂CH₂—O)n-CH₂CH₂OH, wherein n is an integer of at least 1, preferably more than 1.

In other aspects, $R^1$ is $C_{0-6}$alk-CN, for example, $C_0$alk-CN, $C_1$alk-CN, $C_2$alk-CN, $C_3$alk-CN, $C_4$alk-CN, $C_5$alk-CN, and $C_6$alk-CN.

In other aspects, $R^1$ is $C_{0-6}$alk-heterocycloalkyl, for example, $C_0$alk-heterocycloalkyl, $C_1$alk-heterocycloalkyl, $C_2$alk-heterocycloalkyl, $C_3$alk-heterocycloalkyl, $C_4$alk-heterocycloalkyl, $C_5$alk-heterocycloalkyl, and $C_6$alk-heterocycloalkyl. In some embodiments wherein $R^1$ is $C_{0-6}$alk-heterocycloalkyl, the heterocycloalkyl is unsubstituted. In other embodiments wherein $R^1$ is $C_{0-6}$alk-heterocycloalkyl, the heterocycloalkyl is substituted with one, two or three substituents independently selected from $C_{1-6}$alkyl, for example, methyl, ethyl, propyl, isopropyl, butyl, and t-butyl. Preferred heterocycloalkyl moieties include, for example, oxiranyl, oxetanyl, tetrahydrofuranyl, tetrahydropyranyl, aziridinyl, azetidinyl, pyrrolidinyl, piperidinyl, morpholinyl, and piperazinyl.

According to the disclosure, compounds of the invention may include one or more $R^2$ groups. According to the disclosure, each $R^2$ is independently H, —$NH_2$; —$NH(C_{1-6}$alkyl); —$N(C_{1-6}$alkyl$)(C_{1-6}$alkyl$)$, $C_{1-6}$alkyl, $d_1$-$d_{13}$-$C_{1-6}$alkyl, $C_{1-6}$alkoxy, $d_1$-$d_{13}$-$C_{1-6}$alkoxy, OH, halo, heterocycloalkyl, or heteroaryl. In some aspects, $R^2$ is H. According to the disclosure, each $R^2$ is independently —$NH_2$; —$NH(C_{1-6}$alkyl); —$N(C_{1-6}$alkyl$)(C_{1-6}$alkyl$)$, $C_{1-6}$alkyl; $C_{1-6}$alkoxy, OH, halo, aryl, heterocycloalkyl, or heteroaryl. Also according to the disclosure, each $R^2$ is independently —$NH_2$; —$NH(C_{1-6}$alkyl); —$N(C_{1-6}$alkyl$)(C_{1-6}$alkyl$)$, $C_{1-6}$alkyl, $d_1$-$d_{13}$-$C_{1-6}$alkyl, $C_{1-6}$alkoxy, $d_1$-$d_{13}$-$C_{1-6}$alkoxy, OH, halo, heterocycloalkyl, or heteroaryl. Also according to the disclosure, each $R^2$ is independently —$NH_2$; —$NH(C_{1-6}$alkyl); —$N(C_{1-6}$alkyl$)(C_{1-6}$alkyl$)$, $C_{1-6}$alkyl, $C_{1-6}$alkoxy, $d_1$-$d_{13}$-$C_{1-6}$alkoxy, OH, halo, heterocycloalkyl, or heteroaryl.

In some aspects, $R^2$ is —$NH_2$; —$NH(C_{1-6}$alkyl); or —$N(C_{1-6}$alkyl$)(C_{1-6}$alkyl$)$. In some aspects, $R^2$ is —$NH_2$. In other aspects, $R^2$ is —$NH(C_{1-6}$alkyl$)$, for example, —NH(Me), —NH(Et), —NH(n-Pr), —NH(i-Pr), —NH(n-Bu), —NH(t-Bu), and the like. In other aspects, $R^2$ is —$N(C_{1-6}$alkyl$)(C_{1-6}$alkyl$)$, wherein each $C_1$-$C_6$alkyl is independently selected from, for example, methyl, ethyl, n-propyl, i-propyl, n-butyl, t-butyl, and the like.

In some aspects, $R^2$ is $C_{1-6}$alkyl, for example, methyl, ethyl, n-propyl, isopropyl, butyl, and t-butyl.

In some aspects, $R^2$ is $d_1$-$d_{13}$-$C_{1-6}$alkyl, for example, $d_1$-$d_3$-methyl, $d_1$-$d_5$-ethyl, $d_1$-$d_7$-n-propyl, $d_1$-$d_7$-isopropyl, $d_1$-$d_9$-butyl, and $d_1$-$d_9$-t-butyl.

In some aspects, $R^2$ is $C_{1-6}$alkoxy, for example, —OMe, —OEt, —O—$Pr^n$, —O—$Pr^i$, —O-$Bu^n$, —O-$Bu^t$, and the like.

In some aspects, $R^2$ is $d_1$-$d_{13}$-$C_{1-6}$alkoxy, for example, —O $d_1$-$d_3$-Me, —O $d_1$-$d_5$-Et, —O-$d_1$-$d_7$-$Pr^n$, —O-$d_1$-$d_7$-$Pr^i$, —O-$d_1$-$d_9$-$Bu^n$, —O-$d_1$-$d_9$-$Bu^t$, and the like.

In some aspects, $R^2$ is —OH.

In some aspects, $R^2$ is halo, for example, F, Cl, Br, or I, with F and Cl being particularly preferred.

In some aspects, $R^2$ is aryl, preferably phenyl. In some aspects, the aryl is unsubstituted. In other aspects, the aryl is substituted with one or more substituents, preferably one substituent, independently selected from $C_{1-6}$alkyl, $C_{0-6}$alk-O—$C_{1-6}$alkyl, $C_{0-6}$alk-O—$C_{1-6}$alk-O—$C_{1-6}$alkyl, $C_{0-6}$alk-CN, or $C_{0-6}$alk-heterocycloalkyl.

In some aspects, $R^2$ is heterocycloalkyl. Preferred heterocycloalkyl moieties include, for example, oxiranyl, oxetanyl, tetrahydrofuranyl, tetrahydropyranyl, aziridinyl, azetidinyl, pyrrolidinyl, piperidinyl, morpholinyl, and piperazinyl. In some aspects, the heterocycloalkyl moiety is unsubstituted. In other aspects, the heterocycloalkyl moiety is substituted with one or more substituents independently selected from $C_{1-6}$alkyl, $C_{0-6}$alk-O—$C_{1-6}$alkyl, $C_{0-6}$alk-O—$C_{1-6}$alk-O—$C_{1-6}$alkyl, $C_{0-6}$alk-CN, or $C_{0-6}$alk-heterocycloalkyl.

In some aspects, $R^2$ is heteroaryl. Preferred heteroaryl moieties include, for example, imidazolyl, pyrrolyl, thiazolyl, pyridyl, pyrimidinyl, and pyridazinyl In some aspects, the heteroaryl is unsubstituted. In other aspects, the heteroaryl is substituted with one or more substituents independently selected from $C_{1-6}$alkyl, $C_{0-6}$alk-O—$C_{1-6}$alkyl, $C_{0-6}$alk-O—$C_{1-6}$alk-O—$C_{1-6}$alkyl, $C_{0-6}$alk-CN, or $C_{0-6}$alk-heterocycloalkyl.

According to the disclosure, $R^3$ is pyridyl; pyrimidinyl; quinolinyl; or naphthyridinyl, wherein the pyridyl, pyrimidinyl, quinolinyl, or naphthyridinyl is optionally substituted on any atom with 1, 2 or 3 R substituents that are independently $C_{1-6}$alkyl, $d_1$-$d_{13}$-$C_{1-6}$alkyl, halo$C_{1-6}$alkyl, halo$C_{1-6}$alkoxy, $C_{1-6}$alkoxy, $d_1$-$d_{13}$-$C_{1-6}$alkoxy, OH, or halo. In some aspects, the pyridyl, pyrimidinyl, quinolinyl, or naphthyridinyl is optionally substituted on any atom with 1, 2 or 3 R substituents that are independently $C_{1-6}$alkyl, halo$C_{1-6}$alkyl, halo$C_{1-6}$alkoxy, $C_{1-6}$alkoxy, $d_1$-$d_{13}$-$C_{1-6}$alkoxy, OH, or halo. In some aspects, $R^3$ is unsubstituted pyridyl. In some aspects, $R^3$ is unsubstituted pyrimidinyl. In some aspects, $R^3$ is unsubstituted quinolinyl. In some aspects, $R^3$ is unsubstituted naphthyridinyl.

In some aspects, $R^3$ is pyridyl; pyrimidinyl; quinolinyl, or naphthyridinyl, wherein the pyridyl, pyrimidinyl, quinolinyl, or naphthyridinyl is substituted on any atom with 1, 2 or 3 R substituents, preferably 1 or 2 R substituents, that are independently $C_{1-6}$alkyl, $d_1$-$d_{13}$-$C_{1-6}$alkyl, halo$C_{1-6}$alkyl, halo$C_{1-6}$alkoxy, $C_{1-6}$alkoxy, $d_1$-$d_{13}$-$C_{1-6}$alkoxy, OH, or halo. In some aspects, $R^3$ is pyridyl; pyrimidinyl; quinolinyl, or naphthyridinyl, wherein the pyridyl, pyrimidinyl, quinolinyl, or naphthyridinyl is substituted on any atom with 1, 2 or 3 R substituents, preferably 1 or 2 R substituents, that are independently $C_{1-6}$alkyl, halo$C_{1-6}$alkyl, halo$C_{1-6}$alkoxy, $C_{1-6}$alkoxy, $d_1$-$d_{13}$-$C_{1-6}$alkoxy, OH, or halo.

In some aspects, $R^3$ is pyridyl substituted with 1, 2 or 3 R substituents, preferably 1 or 2 R substituents, that are independently $C_{1-6}$alkyl, $d_1$-$d_{13}$-$C_{1-6}$alkyl, halo$C_{1-6}$alkyl, halo$C_{1-6}$alkoxy, $C_{1-6}$alkoxy, $d_1$-$d_{13}$-$C_{1-6}$alkoxy, OH, or halo. In some aspects, $R^3$ is pyridyl substituted with 1, 2 or 3 R substituents, preferably 1 or 2 R substituents, that are independently $C_{1-6}$alkyl, halo$C_{1-6}$alkyl, halo$C_{1-6}$alkoxy, $C_{1-6}$alkoxy, $d_1$-$d_{13}$-$C_{1-6}$alkoxy, OH, or halo. For example, in some aspects, $R^3$ is pyridyl substituted with at least one $C_{1-6}$alkyl, for example, methyl, ethyl, propyl, isopropyl, butyl, s-butyl, t-butyl, pentyl, or hexyl. In some aspects, $R^3$ is pyridyl substituted with at least one $d_1$-$d_{13}C_{1-6}$alkyl, for example, $d_1$-$d_3$methyl, $d_1$-$d_5$ethyl, $d_1$-$d_7$propyl, $d_1$-$d_7$isopropyl, $d_1$-$d_9$butyl, $d_1$-$d_9$s-butyl, $d_1$-$d_9$t-butyl, $d_1$-$d_{11}$pentyl, or $d_1$-$d_{13}$hexyl. In some aspects, $R^3$ is pyridyl substituted with at least one halo$C_{1-6}$alkyl, for example, $CHF_2$ or $CF_3$. In some aspects, $R^3$ is pyridyl substituted with at least one halo$C_{1-6}$alkoxy, for example, —$OCHF_2$ or —$OCF_3$. In some aspects, $R^3$ is pyridyl substituted with at least one $C_{1-6}$alkoxy, for example, methoxy, ethoxy, propoxy, isoproxy, butoxy, or t-butoxy. In some aspects, $R^3$ is pyridyl substituted with at least one $d_1$-$d_{13}C_{1-6}$alkoxy, for example, $d_1$-$d_3$methoxy, $d_1$-$d_5$ethoxy, $d_1$-$d_7$propoxy, $d_1$-$d_7$isoproxy, $d_1$-$d_9$butoxy, or $d_1$-$d_9$t-butoxy. In some aspects, $R^3$ is pyridyl substituted with at least one OH. In some aspects, $R^3$ is pyridyl substituted with at least one halo, for example with at least one halo independently selected from F, Cl, Br, and I, with F and Cl being preferred. In some aspects, $R^3$ is pyridyl substituted with two halo, each independently selected from F, Cl, Br, and I, with F and Cl being preferred. In some aspects, $R^3$ is pyridyl substituted with one halo and one other substituent that is $C_{1-6}$alkyl, $d_1$-$d_{13}C_{1-6}$alkyl, halo$C_{1-6}$alkyl, halo$C_{1-6}$alkoxy, $C_{1-6}$alkoxy, $d_1$-$d_{13}C_{1-6}$alkoxy, or OH. In some aspects, $R^3$ is pyridyl substituted with one halo$C_{1-6}$alkyl and one other substituent that is $C_{1-6}$alkyl, $d_1$-$d_{13}C_{1-6}$alkyl, halo$C_{1-6}$alkoxy, $C_{1-6}$alkoxy, $d_1$-$d_{13}C_{1-6}$alkoxy, OH, or halo. In some aspects, $R^3$ is pyridyl substituted with one $C_{1-6}$alkyl and one other substituent that is haloC$_{1-6}$alkoxy, C$_{1-6}$alkoxy, OH, or halo. In some aspects, R$^3$ is pyridyl substituted with one —OH and one other substituent that is C$_{1-6}$alkyl, haloC$_{1-6}$alkoxy, C$_{1-6}$alkoxy, or halo.

In some aspects, R$^3$ is pyrimidinyl substituted with 1, 2 or 3 R substituents, preferably 1 or 2 R substituents, that are independently C$_{1-6}$alkyl, d$_1$-d$_{13}$-C$_{1-6}$alkyl, haloC$_{1-6}$alkyl, haloC$_{1-6}$alkoxy, C$_{1-6}$alkoxy, d$_1$-d$_{13}$-C$_{1-6}$alkoxy, OH, or halo. In some aspects, R$^3$ is pyrimidinyl substituted with 1, 2 or 3 R substituents, preferably 1 or 2 R substituents, that are independently C$_{1-6}$alkyl, haloC$_{1-6}$alkyl, haloC$_{1-6}$alkoxy, C$_{1-6}$alkoxy, d$_1$-d$_{13}$-C$_{1-6}$alkoxy, OH, or halo. For example, in some aspects, R$^3$ is pyrimidinyl substituted with at least one C$_{1-6}$alkyl, for example, methyl, ethyl, propyl, isopropyl, butyl, s-butyl, t-butyl, pentyl, or hexyl. In some aspects, R$^3$ is pyrimidinyl substituted with at least one d$_1$-d$_{13}$C$_{1-6}$alkyl, for example, d$_1$-d$_3$methyl, d$_1$-d$_5$ethyl, d$_1$-d$_7$propyl, d$_1$-d$_7$isopropyl, d$_1$-d$_9$butyl, d$_1$-d$_9$s-butyl, d$_1$-d$_9$t-butyl, d$_1$-d$_{11}$pentyl, or d$_1$-d$_{13}$hexyl. In some aspects, R$^3$ is pyrimidinyl substituted with at least one haloC$_{1-6}$alkyl, for example, CHF$_2$ or CF$_3$. In some aspects, R$^3$ is pyrimidinyl substituted with at least one haloC$_{1-6}$alkoxy, for example, —OCHF$_2$ or —OCF$_3$. In some aspects, R$^3$ is pyrimidinyl substituted with at least one C$_{1-6}$alkoxy, for example, methoxy, ethoxy, propoxy, isoproxy, butoxy, or t-butoxy. In some aspects, R$^3$ is pyrimidinyl substituted with at least one d$_1$-d$_{13}$C$_{1-6}$alkoxy, for example, d$_1$-d$_3$methoxy, d$_1$-d$_5$ethoxy, d$_1$-d$_7$propoxy, d$_1$-d$_7$isoproxy, d$_1$-d$_9$butoxy, or d$_1$-d$_9$t-butoxy. In some aspects, R$^3$ is pyrimidinyl substituted with at least one OH. In some aspects, R$^3$ is pyrimidinyl substituted with at least one halo, for example with at least one halo independently selected from F, Cl, Br, and I, with F and Cl being preferred. In some aspects, R$^3$ is pyrimidinyl substituted with two halo, each independently selected from F, Cl, Br, and I, with F and Cl being preferred. In some aspects, R$^3$ is pyrimidinyl substituted with one halo and one other substituent that is C$_{1-6}$alkyl, d$_1$-d$_{13}$C$_{1-6}$alkyl, haloC$_{1-6}$alkyl, haloC$_{1-6}$alkoxy, C$_{1-6}$alkoxy, d$_1$-d$_{13}$C$_{1-6}$alkoxy, or OH. In some aspects, R$^3$ is pyrimidinyl substituted with one haloC$_{1-6}$ alkyl and one other substituent that is C$_{1-6}$alkyl, d$_1$-d$_{13}$C$_{1-6}$alkyl, haloC$_{1-6}$alkoxy, C$_{1-6}$alkoxy, d$_1$-d$_{13}$C$_{1-6}$alkoxy, OH, or halo. In some aspects, R$^3$ is pyrimidinyl substituted with one C$_{1-6}$alkyl and one other substituent that is haloC$_{1-6}$alkoxy, C$_{1-6}$alkoxy, OH, or halo. In some aspects, R$^3$ is pyrimidinyl substituted with one —OH and one other substituent that is C$_{1-6}$alkyl, haloC$_{1-6}$alkoxy, C$_{1-6}$alkoxy, or halo.

In some aspects, R$^3$ is quinolinyl substituted with 1, 2 or 3 R substituents, preferably 1 or 2 R substituents, that are independently C$_{1-6}$alkyl, d$_1$-d$_{13}$-C$_{1-6}$alkyl, haloC$_{1-6}$alkyl, haloC$_{1-6}$alkoxy, C$_{1-6}$alkoxy, d$_1$-d$_{13}$-C$_{1-6}$alkoxy, OH, or halo. In some aspects, R$^3$ is quinolinyl substituted with 1, 2 or 3 R substituents, preferably 1 or 2 R substituents, that are independently C$_{1-6}$alkyl, haloC$_{1-6}$alkyl, haloC$_{1-6}$alkoxy, C$_{1-6}$alkoxy, d$_1$-d$_{13}$-C$_{1-6}$alkoxy, OH, or halo. For example, in some aspects, R$^3$ is quinolinyl substituted with at least one C$_{1-6}$alkyl, for example, methyl, ethyl, propyl, isopropyl, butyl, s-butyl, t-butyl, pentyl, or hexyl. In some aspects, R$^3$ is quinolinyl substituted with at least one d$_1$-d$_{13}$C$_{1-6}$alkyl, for example, d$_1$-d$_3$methyl, d$_1$-d$_5$ethyl, d$_1$-d$_7$propyl, d$_1$-d$_7$isopropyl, d$_1$-d$_9$butyl, d$_1$-d$_9$s-butyl, d$_1$-d$_9$t-butyl, d$_1$-d$_{11}$pentyl, or d$_1$-d$_{13}$hexyl. In some aspects, R$^3$ is quinolinyl substituted with at least one haloC$_{1-6}$alkyl, for example, CHF$_2$ or CF$_3$. In some aspects, R$^3$ is quinolinyl substituted with at least one haloC$_{1-6}$alkoxy, for example, —OCHF$_2$ or —OCF$_3$. In some aspects, R$^3$ is quinolinyl substituted with at least one C$_{1-6}$alkoxy, for example, methoxy, ethoxy, propoxy, isoproxy, butoxy, or t-butoxy. In some aspects, R$^3$ is quinolinyl substituted with at least one d$_1$-d$_{13}$C$_{1-6}$alkoxy, for example, d$_1$-d$_3$methoxy, d$_1$-d$_5$ethoxy, d$_1$-d$_7$propoxy, d$_1$-d$_7$isoproxy, d$_1$-d$_9$butoxy, or d$_1$-d$_9$t-butoxy. In some aspects, R$^3$ is quinolinyl substituted with at least one OH. In some aspects, R$^3$ is quinolinyl substituted with at least one halo, for example with at least one halo independently selected from F, Cl, Br, and I, with F and Cl being preferred. In some aspects, R$^3$ is quinolinyl substituted with two halo, each independently selected from F, Cl, Br, and I, with F and Cl being preferred. In some aspects, R$^3$ is quinolinyl substituted with one halo and one other substituent that is C$_{1-6}$alkyl, d$_1$-d$_{13}$C$_{1-6}$alkyl, haloC$_{1-6}$alkyl, haloC$_{1-6}$ alkoxy, C$_{1-6}$alkoxy, d$_1$-d$_{13}$C$_{1-6}$alkoxy, or OH. In some aspects, R$^3$ is quinolinyl substituted with one haloC$_{1-6}$ alkyl and one other substituent that is C$_{1-6}$alkyl, d$_1$-d$_{13}$C$_{1-6}$ alkyl, haloC$_{1-6}$alkoxy, C$_{1-6}$alkoxy, d$_1$-d$_{13}$C$_{1-6}$alkoxy, OH, or halo. In some aspects, R$^3$ is quinolinyl substituted with one C$_{1-6}$alkyl and one other substituent that is haloC$_{1-6}$alkoxy, C$_{1-6}$alkoxy, OH, or halo. In some aspects, R$^3$ is quinolinyl substituted with one —OH and one other substituent that is C$_{1-6}$alkyl, haloC$_{1-6}$alkoxy, C$_{1-6}$alkoxy, or halo.

In some aspects, R$^3$ is naphthyridinyl substituted with 1, 2 or 3 R substituents, preferably 1 or 2 R substituents, that are independently C$_{1-6}$alkyl, d$_1$-d$_{13}$-C$_{1-6}$alkyl, haloC$_{1-6}$alkyl, haloC$_{1-6}$alkoxy, C$_{1-6}$alkoxy, d$_1$-d$_{13}$-C$_{1-6}$alkoxy, OH, or halo. In some aspects, R$^3$ is naphthyridinyl substituted with 1, 2 or 3 R substituents, preferably 1 or 2 R substituents, that are independently C$_{1-6}$alkyl, haloC$_{1-6}$alkyl, haloC$_{1-6}$alkoxy, C$_{1-6}$alkoxy, d$_1$-d$_{13}$-C$_{1-6}$alkoxy, OH, or halo. For example, in some aspects, R$^3$ is naphthyridinyl substituted with at least one C$_{1-6}$alkyl, for example, methyl, ethyl, propyl, isopropyl, butyl, s-butyl, t-butyl, pentyl, or hexyl. In some aspects, R$^3$ is naphthyridinyl substituted with at least one d$_1$-d$_{13}$C$_{1-6}$ alkyl, for example, d$_1$-d$_3$methyl, d$_1$-d$_5$ethyl, d$_1$-d$_7$propyl, d$_1$-d$_7$isopropyl, d$_1$-d$_9$butyl, d$_1$-d$_9$s-butyl, d$_1$-d$_9$t-butyl, d$_1$-d$_{11}$pentyl, or d$_1$-d$_{13}$hexyl. In some aspects, R$^3$ is naphthyridinyl substituted with at least one haloC$_{1-6}$alkyl, for example, CHF$_2$ or CF$_3$. In some aspects, R$^3$ is naphthyridinyl substituted with at least one haloC$_{1-6}$alkoxy, for example, —OCHF$_2$ or —OCF$_3$. In some aspects, R$^3$ is naphthyridinyl substituted with at least one C$_{1-6}$alkoxy, for example, methoxy, ethoxy, propoxy, isoproxy, butoxy, or t-butoxy. In some aspects, R$^3$ is naphthyridinyl substituted with at least one d$_1$-d$_{13}$C$_{1-6}$alkoxy, for example, d$_1$-d$_3$methoxy, d$_1$-d$_5$ethoxy, d$_1$-d$_7$propoxy, d$_1$-d$_7$isoproxy, d$_1$-d$_9$butoxy, or d$_1$-d$_9$t-butoxy. In some aspects, R$^3$ is naphthyridinyl substituted with at least one OH. In some aspects, R$^3$ is naphthyridinyl substituted with at least one halo, for example with at least one halo independently selected from F, Cl, Br, and I, with F and Cl being preferred. In some aspects, R$^3$ is naphthyridinyl substituted with two halo, each independently selected from F, Cl, Br, and I, with F and Cl being preferred. In some aspects, R$^3$ is naphthyridinyl substituted with one halo and one other substituent that is C$_{1-6}$alkyl, d$_1$-d$_{13}$C$_{1-6}$alkyl, haloC$_{1-6}$alkyl, haloC$_{1-6}$alkoxy, C$_{1-6}$alkoxy, d$_1$-d$_{13}$C$_{1-6}$alkoxy, or OH. In some aspects, R$^3$ is naphthyridinyl substituted with one haloC$_{1-6}$alkyl and one other substituent that is C$_{1-6}$alkyl, d$_1$-d$_{13}$C$_{1-6}$alkyl, haloC$_{1-6}$ alkoxy, C$_{1-6}$alkoxy, d$_1$-d$_{13}$C$_{1-6}$alkoxy, OH, or halo. In some aspects, R$^3$ is naphthyridinyl substituted with one C$_{1-6}$alkyl and one other substituent that is haloC$_{1-6}$alkoxy, C$_{1-6}$alkoxy, OH, or halo. In some aspects, R$^3$ is naphthyridinyl substituted with one —OH and one other substituent that is C$_{1-6}$alkyl, haloC$_{1-6}$alkoxy, C$_{1-6}$alkoxy, or halo.

Pharmaceutically acceptable salts, stereoisomers, tautomers, and solvates of all embodiments of formulas I, II, and/or III are also within the scope of the invention.
Preferred sub-formulas of formula I, formula II, and formula III are those wherein R³ is pyridyl, for example:
(I-A)
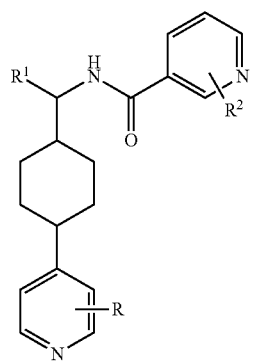
(I-AA)
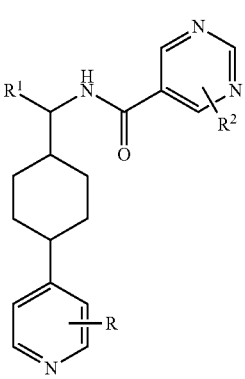
(I-B)
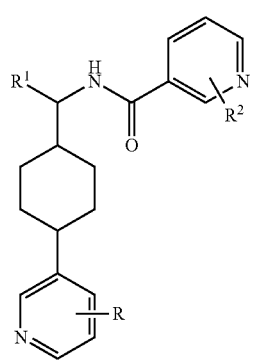
(I-BB)
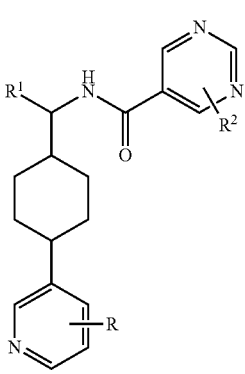
-continued
(I-C)
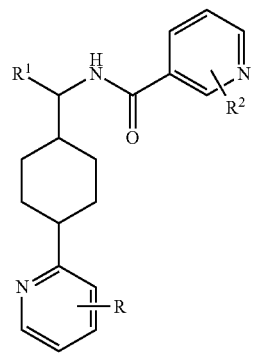
(I-CC)
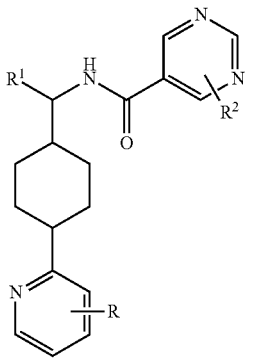
(II-A)
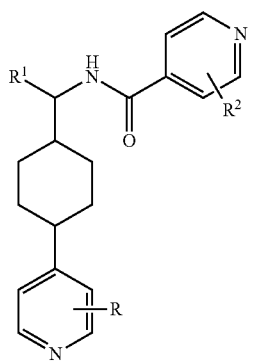
(II-B)
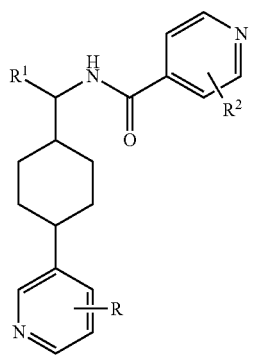

(II-C) 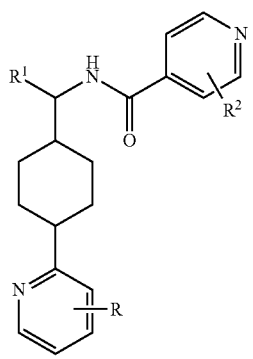
(III-A) 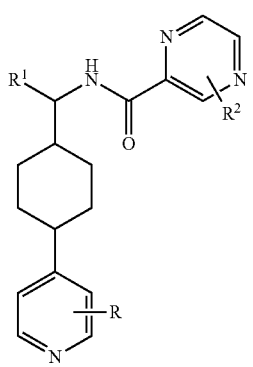
(III-B) 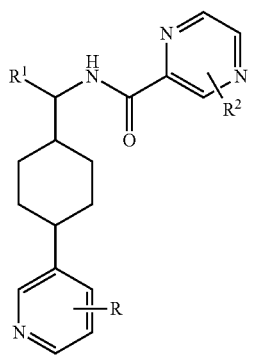
(III-C) 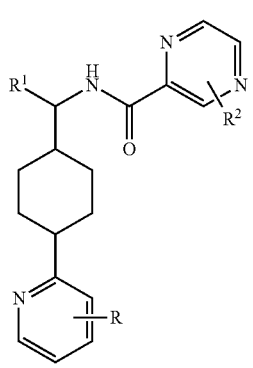
(I-D) 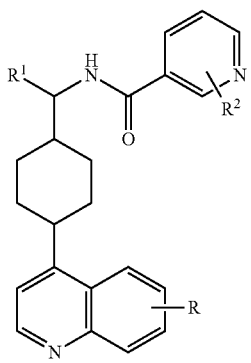
(I-DD) 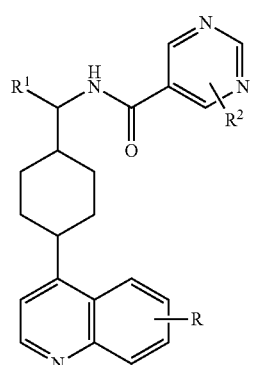
(I-E) 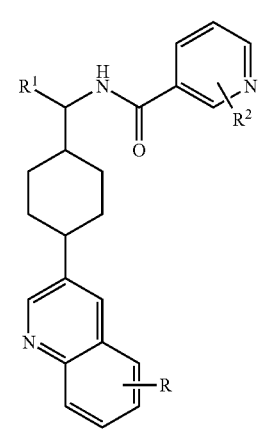
(I-EE) 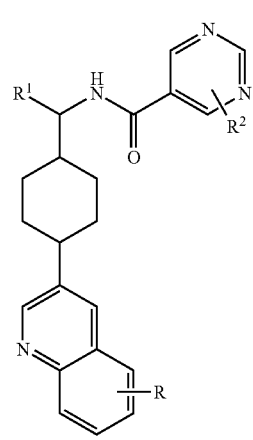
Preferred sub-formulas of formula I, formula II, and formula III are those wherein R³ is quinolinyl, for example:

(II-D)
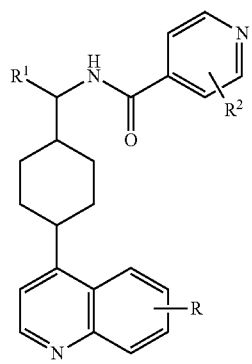
(II-E)
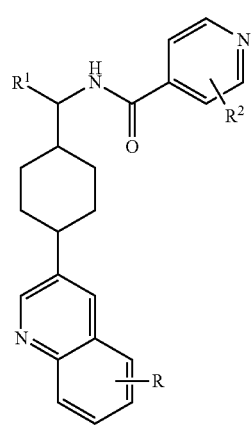
(III-D)
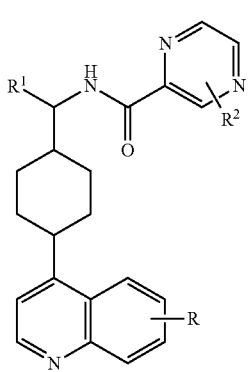
(III-E)
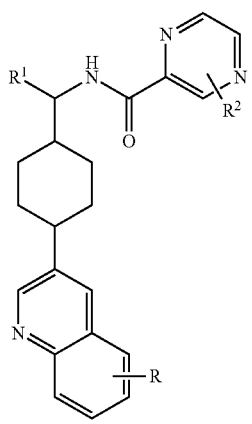
Preferred sub-formulas of formula I, formula II, and formula III are those wherein R³ is naphthyridinyl, for example:
(I-F)
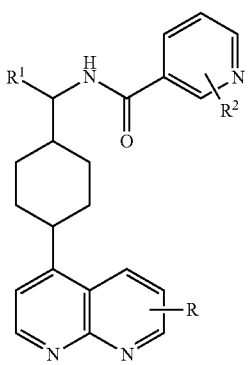
(I-FF)
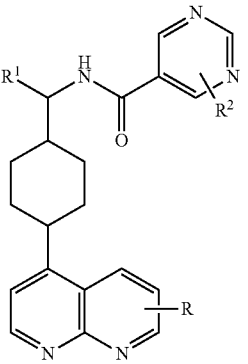
(II-F)
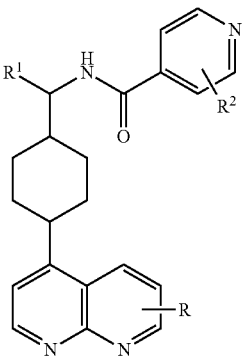
(III-F)
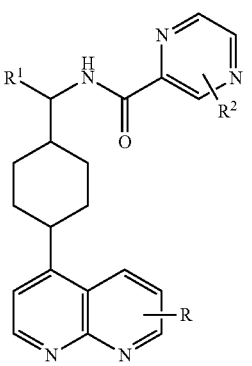
Preferred sub-formulas of formula I, formula II, and formula III are those wherein R³ is pyrimidinyl, for example:

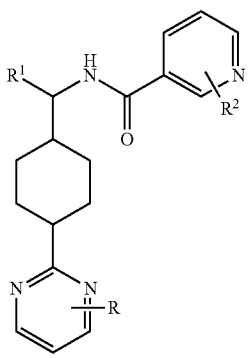

(I-G)

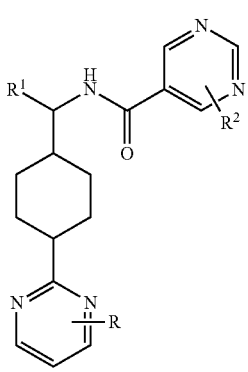

(I-GG)

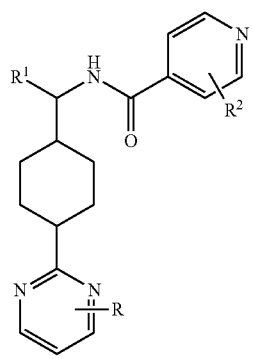

(II-G)

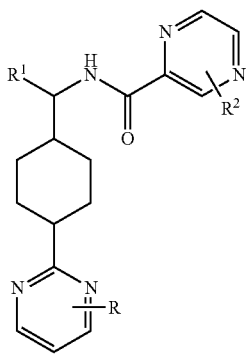

(III-G)

In another embodiment, the compounds of the invention have human IDO IC$_{50}$ values>50 nM. In another embodiment, the compounds of the invention have human IDO IC$_{50}$ values≤50 nM. In another embodiment, the compounds of the invention have human IDO IC$_{50}$ values<5 nM.

Other Embodiments of the Invention

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmacytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus, Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membranoproliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barré syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anticancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anticancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY®. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anticancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anticancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anticancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anticancer agents also include those that block immune cell migration such as antagonists to chemokine receptors, including CCR2 and CCR4.

Other anticancer agents also include those that augment the immune system such as adjuvants or adoptive T cell transfer.

Anticancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as famesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (2000)); (v) cell cycle kinase inhibitors such as, for example, flavopiridol and UCN-O1 (see, for example, Sausville, *Curr. Med. Chem. Anti-Canc. Agents*, 3:47-56 (2003)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas I and II.

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, Coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see, e.g., Scheller et al., *Circulation*, 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-I0652; emtricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfinavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Combination with an Immuno-Oncology Agent

Further provided herein are methods of treatment wherein a compound of formula I or formula II or formula III is administered with one or more immuno-oncology agents. The immuno-oncology agents used herein, also known as cancer immunotherapies, are effective to enhance, stimulate, and/or upregulate immune responses in a subject.

In one aspect, the Compound of formula I or formula II or formula III is sequentially administered prior to administration of the immuno-oncology agent. In another aspect, the Compound of formula I or formula II or formula III is administered concurrently with the immunology-oncology agent. In yet another aspect, the Compound of formula I or formula II or formula III is sequentially administered after administration of the immuno-oncology agent.

In another aspect, the Compound of formula I or formula II or formula III may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-ß, VEGF, and other immunosuppressive cytokines) or a cytokine that stimulates T cell activation, for stimulating an immune response.

In one aspect, T cell responses can be stimulated by a combination of the Compound of Formula I or formula II or formula III and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with the Compound of formula I or formula II or formula III for the treatment of cancer include antagonists of inhibitory receptors on NK cells or agonists of activating receptors on NK cells. For example, the Compound of formula I or formula II or formula III can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249, WO 13/169264, WO 14/036357).

In another aspect, the Compound of formula I or formula II or formula III can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY® (ipilimumab) or tremelimumab.

In another aspect, the immuno-oncology agent is a PD-1 antagonist, such as an antagonistic PD-1 antibody. Suitable PD-1 antibodies include, for example, OPDIVO® (nivolumab), KEYTRUDA® (pembrolizumab), or MEDI-0680 (AMP-514; WO 2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224.

In another aspect, the immuno-oncology agent is a PD-L1 antagonist, such as an antagonistic PD-L1 antibody. Suitable PD-L1 antibodies include, for example, MPDL3280A (RG7446; WO 2010/077634), durvalumab (MED14736), BMS-936559 (WO 2007/005874), and MSB0010718C (WO 2013/79174).

In another aspect, the immuno-oncology agent is a LAG-3 antagonist, such as an antagonistic LAG-3 antibody. Suitable LAG3 antibodies include, for example, BMS-986016 (WO 10/19570, WO 14/08218), or IMP-731 or IMP-321 (WO 08/132601, WO 09/44273).

In another aspect, the immuno-oncology agent is a CD137 (4-1BB) agonist, such as an agonistic CD137 antibody. Suitable CD137 antibodies include, for example, urelumab and PF-05082566 (WO 12/32433).

In another aspect, the immuno-oncology agent is a GITR agonist, such as an agonistic GITR antibody. Suitable GITR antibodies include, for example, BMS-986153, BMS-986156, TRX-518 (WO 06/105021, WO 09/009116) and MK-4166 (WO 11/028683).

In another aspect, the immuno-oncology agent is an IDO antagonist. Suitable IDO antagonists include, for example, INCB-024360 (WO 2006/122150, WO 07/75598, WO 08/36653, WO 08/36642), indoximod, or NLG-919 (WO 09/73620, WO 09/1156652, WO 11/56652, WO 12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO 06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO 11/109400).

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of formula I and/or formula II and/or formula III, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, Jr., L. V. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans-(or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purpose of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the terms "alkyl" and "alkylene" (also referred to as "alk") are intended to include both branched and straight-chain saturated aliphatic hydrocarbon groups having the specified number of carbon atoms. For example, "$C_1$-$C_6$ alkyl" or "$C_{1-6}$ alkyl" denotes alkyl having 1 to 6 carbon atoms. Example alkyl groups include, but are not limited to, methyl (Me), ethyl (Et), propyl (Pr) (e.g., n-propyl (Pr$^n$ or n-Pr) and isopropyl (Pr$^i$ or i-Pr)), butyl (Bu) (e.g., n-butyl (Bu$^n$ or n-Bu), isobutyl (Bu$^i$ or i-Bu), t-butyl (Bu$^t$ or t-Bu)), and pentyl (Pn) (e.g., n-pentyl, isopentyl, neopentyl). "$C_1$-$C_6$alkylene" denotes alkylene having 1 to 6 carbon atoms. Example alkylene groups include, but are not limited to, methylene (—$CH_2$—), ethylene (—$CH_2CH_2$—), —$CH_2CH(CH_3)$—$CH_2$—, and the like. $C_0$alk refers to a bond.

As used herein, d-alkyl or alkyl-d refers to the replacement of one or more hydrogen atoms of the alkyl group with one or more deuterium atoms. For example $d_1$-alkyl or alkyl-$d_1$ refers to the replacement of one hydrogen atom of the alkyl group being replaced with one deuterium atom. In other aspects, "$d_1$-$d_{13}$-$C_{1-6}$alkyl" refers to the replacement of one to 13 hydrogen atoms in a $C_{1-6}$alkyl group with one to 13 deuterium atoms. Exemplary $d_1$-$d_{13}$-$C_{1-6}$alkyl groups include —$CH_2$-$CD_3$ (wherein "D" is deuterium) and —$CD_3$.

As used herein, "alkoxy" refers to —O-alkyl moieties wherein the alkyl moiety includes both branched and straight-chain saturated aliphatic hydrocarbon groups having the specified number of carbon atoms. For example, "$C_1$-$C_6$ alkoxy" or "$C_{1-6}$ alkoxy" denotes alkoxy having 1 to 6 carbon atoms. Example alkoxy groups include, but are not limited to, methoxy (OMe), ethoxy (OEt), propoxy (OPr) (e.g., On-propyl (OPr$^n$ or On-Pr) and isopropoxy (OPr$^i$ or Oi-Pr)), butoxy (OBu) (e.g., On-butyl (OBu$^n$ or On-Bu), isobutoxy (OBu$^i$ or Oi-Bu), t-butoxy (Ot-butyl) (OBu$^t$ or Ot-Bu)), and pentoxy (OPn) (e.g., On-pentyl, Oisopentyl, Oneopentyl).

As used herein, d-alkoxy or alkoxy-d refers to the replacement of one or more hydrogen atoms of the alkyl group with one or more deuterium atoms. For example di-alkoxy or alkoxy-di refers to the replacement of one hydrogen atom of the alkoxy group being replaced with one deuterium atom. In other aspects, "$d_1$-$d_{13}$-$C_{1-6}$alkoxy" refers to the replacement of one to 13 hydrogen atoms in a $C_{1-6}$alkoxy group with one to 13 deuterium atoms. Exemplary $d_1$-$d_{13}$-$C_{1-6}$ alkoxy groups include —O—$CH_2$—$CD_3$ (wherein "D" is deuterium) and —$OCD_3$.

As used herein, "aryl" refers to an aromatic ring system which includes, but not limited to phenyl, biphenyl, indanyl, 1-naphthyl, 2-naphthyl and terahydronaphthyl.

"Halo" or "halogen" includes fluoro, chloro, bromo, and iodo.

"Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

The term "heterocycloalkyl" refers to hydrocarbon rings having the indicated number of ring atoms, e.g., $C_3$-$C_6$cycloalkyl or $C_3$-$C_{12}$cycloalkyl, and being fully saturated and including one or more heteroatoms selected from O, N, and S. "Heterocycloalkyl" is also meant to refer to bicyclic and polycyclic hydrocarbon rings. Exemplary heterocycloalkyl moieties include oxiranyl, oxetanyl, aziridinyl, azetidinyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl, tetrahydropyranyl, and morpholinyl.

The term "heteroaryl" refers to refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like.

As referred to herein, the term "substituted" means that at least one hydrogen atom is replaced with a non-hydrogen group, provided that normal valencies are maintained and that the substitution results in a stable compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, Jr., L. V., ed., *Remington: The Science and Practice of Pharmacy,* 22nd Edition, Pharmaceutical Press, London, UK (2012). The disclosure of which is hereby incorporated by reference.

In addition, compounds of formula I and formula II and formula III may have prodrug forms. Any compound that will be converted in vivo to provide the bioactive agent (i.e., a compound of formula I or II) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5: "Design and Application of Prodrugs", *A Textbook of Drug Design and Development*, pp. 113-191, Krogsgaard-Larsen, P. et al., eds., Harwood Academic Publishers (1991);
c) Bundgaard, H., *Adv. Drug Deliv. Rev.*, 8:1-38 (1992);
d) Nielsen, N. M. et al., *J. Pharm. Sci.*, 77:285 (1988);
e) Kakeya, N. et al., *Chem. Pharm. Bull.*, 32:692 (1984); and
g) Rautio, J., ed., *Prodrugs and Targeted Delivery (Methods and Principles in Medicinal Chemistry)*, Vol. 47, Wiley-VCH (2011).

Compounds containing a carboxy group can form physiologically hydrolyzable esters that serve as prodrugs by being hydrolyzed in the body to yield formula I or formula II or formula III compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I or formula II or formula III include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well-known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (Second Edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Third Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example, when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared from starting materials which are known in the chemical literature or are commercially available by methods such as those illustrated in the following Schemes utilizing chemical transformations known to those skilled in the art of organic chemistry. Solvents, temperatures, pressures, and other reaction conditions may readily be selected by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

Reference can also be made to International Application Nos. PCT/US2015/059271, PCT/US2015/059311, and PCT/US2015/059316.

References to many of these chemical transformations employed herein can be found in Smith, M. B. et al., March's Advanced Organic Chemistry Reactions, Mechanisms, and Structure, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., Protective Groups in Organic Synthesis, Third Edition, Wiley-Interscience, New York (1999).

EXAMPLES

The following Examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbecco's Modification of Eagle's Medium; EDTA=ethylenediaminetetraacetic acid.

The compounds of the present invention may be prepared from starting materials which are known in the chemical literature or are commercially available by methods such as those illustrated in the following Schemes utilizing chemical transformations known to those skilled in the art of organic chemistry. Solvents, temperatures, pressures, and other reaction conditions may readily be selected by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

References to many of these chemical transformations employed herein can be found in Smith, M. B. et al., March's Advanced Organic Chemistry Reactions, Mechanisms, and Structure, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., Protective Groups in Organic Synthesis, Third Edition, Wiley-Interscience, New York (1999).

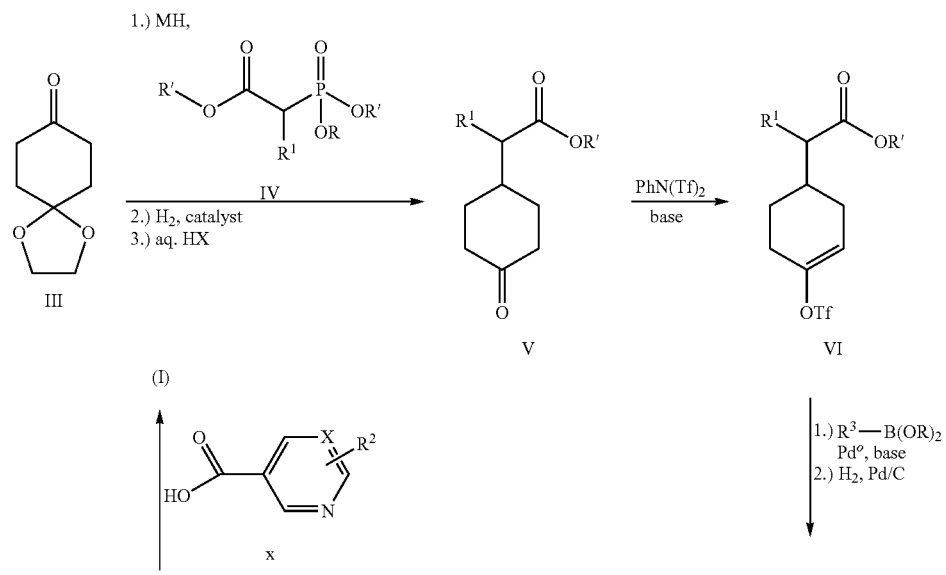

Scheme 1

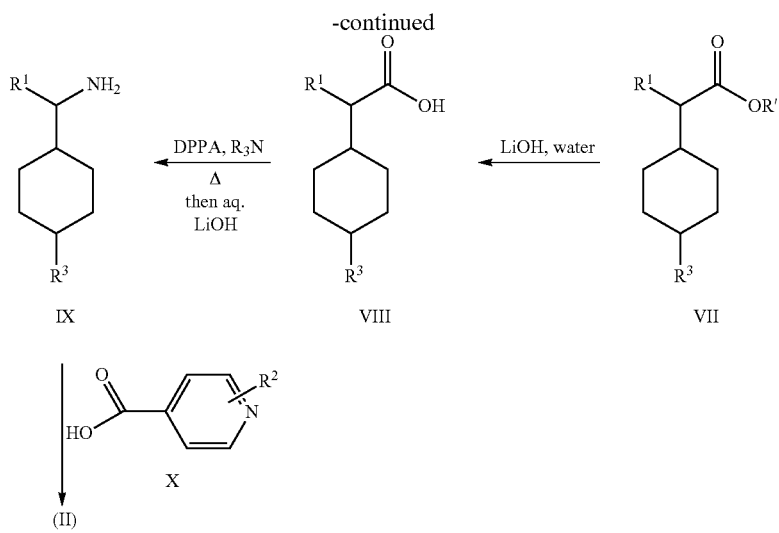

Treatment of a phosphonoacetate ester (IV), with a base such as sodium hydride in a solvent such as THF (Scheme 1) followed by a ketone of the general structure III affords a trisubstituted olefin. Substituted analogs of III ($R^1$ is not H) afford tetrasubstituted olefins. This method and additional methods described below are transformations familiar to those skilled in the art of organic/medicinal chemistry. Alternative methods for olefination and the transformations described below are known and will be selected by one skilled in the art based on their applicability to the specific substrate under consideration. Reduction is accomplished by stirring or shaking a solution of the olefin in a suitable solvent under an atmosphere or more of H2 in the presence of a catalyst, normally palladium on carbon. Hydrolysis of the ketal group affords a ketone of the general structure V. Typically, this is accomplished by heating with an aqueous acid such as HCl in the presence of a co-solvent such as THF. In addition to the cyclic ethylene glycol-based ketal shown, other cyclic and acyclic ketal protecting groups could be used. Ketones are deprotonated with bases such as LiHMDS and react with N-phenyltrifluoromethanesulfonimide or similar reagents to afford triflates of the general structure VI. These triflates participate in Suzuki couplings (T. Ishiyama, M. Murata, N. Miyaura, *J. Org. Chem.*, 1995, 60, 7508-7510) with boronic acids or esters $R^3$—$B(OR)_2$ to afford coupled products. Many variations on this reaction are known, but generally it involves heating the two substrates and a catalyst such as $(Ph_3P)_4Pd$ in a solvent such as DMF with a base such as aq. potassium carbonate. Reduction of the olefin provides intermediate VII (where V=a bond and E=CH). Intermediates VII (and later intermediates) may be obtained as mixtures of cis and trans isomers. Methods for control of the stereochemical outcome of the above reactions are known to those familiar in the art of organic/medicinal chemistry. Additionally, methods for the separation of these isomers are known and described in detail in the synthetic examples. Saponification of the ester by heating with aq. LiOH or a similar base, generally in the presence of an organic co-solvent such as THF affords carboxylic acids VIII. Acids VIII can be rearranged, usually by heating with DPPA and triethylamine (Curtius and related rearrangements), and the intermediate isocyanates react with aq. base to afford primary amines IX. These can react with the carboxylic acids X and XI and peptide coupling reagents to afford a compounds of the invention (I) and (II). For a recent review of peptide coupling methods see: Ayman El-Faham and Fernando Albericio. Chem. Rev. 2011, 111, 6557-6602.

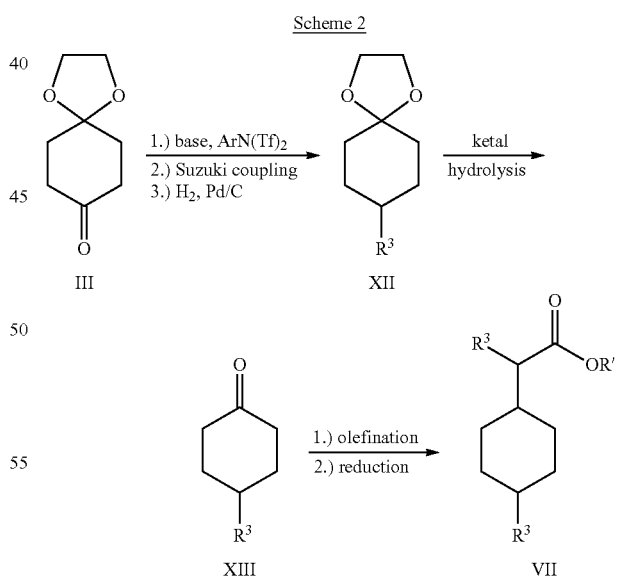

Scheme 2 illustrates a method of making intermediate VII by performing the steps of Scheme 1 in a different order. Intermediate III can be converted to a triflate as described above and coupled with a boronic acid or ester $R^3$—$B(OR)_2$ to give intermediate XII. Ketal hydrolysis affords ketone XIII. Transformation to intermediate VII is accomplished by olefination and reduction as described above.

Scheme 3

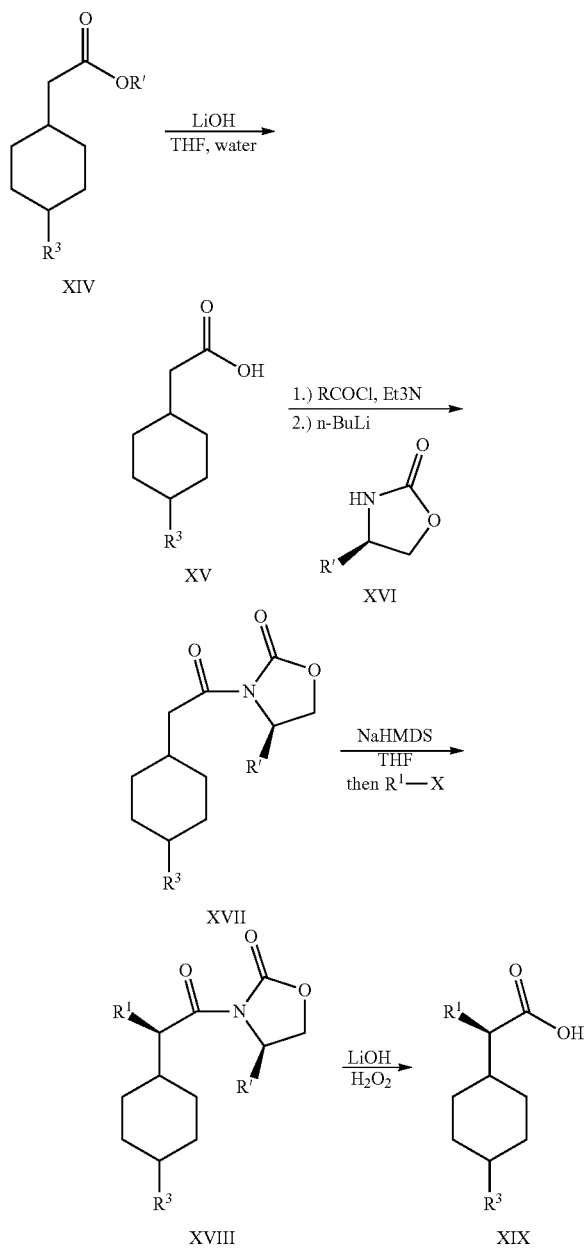

Scheme 3 illustrates a method for controlling the absolute stereochemistry of intermediate VII and materials arising from it. Saponification of esters XIV provides carboxylic acids XV. Treatment of these acids with an acid chloride such as pivaloyl chloride provides a mixed anhydride intermediate. In a separate vessel, an optically pure oxazolidinone of known stereochemistry and general structure XVI is deprotonated by treatment with a strong base such as n-BuLi. These activated species are combined to form the acyloxazolidinone XVII which is deprotonated by bases such as NaHMDS. Alkylation of the resulting enolate proceeds with predictable control of stereochemistry at the newly-formed center to provide materials XVIII. Removal of the chiral auxiliary to give optically-active carboxylic acids XIX is accomplished by treatment with a solution of basic hydrogen peroxide. For a review of the history and scope of this reaction see: D. A. Evans, M. D. Ennis, D. J. Mathre. J. Am. Chem. Soc., 1982, 104 (6), pp 1737-1739.

In addition to the above general schemes, the compounds described herein can be prepared by representative methods as provided in the Examples below.

Analytical HPLC/MS/SFC was performed using the following methods:

Method A: Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA.

Method B: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.00 mL/min; Detection: UV at 220 nm.

Method C: Preparative Chromatographic Conditions: Instrument: Berger Prep SFC MGII; Column: Chiral OD 25×3 cm ID, 5 mm; Flow rate: 85.0 mL/min; Mobile Phase: 85/15 CO$_2$/MeOH; Detector Wavelength: 220 nm.

Method D: Analytical Chromatographic Conditions: Instrument: Berger analytical SFC (LVL-L4021 Lab); Column: Chiral OD 250×4.6 mm ID, 5 mm; Flow rate: 2.0 mL/min; Mobile Phase: 70/30 CO$_2$/MeOH; Detector Wavelength: 220 nm.

Method E: Preparative Chromatographic Conditions: Instrument: Berger Prep SFC MGII; Column: Chiral IC 25×3 cm, 5 mm; Flow rate: 85.0 mL/min; Mobile Phase: 70/30 CO$_2$/MeOH; Detector Wavelength: 220 nm.

Method F: Analytical Chromatographic Conditions: Instrument: Aurora analytical SFC (LVL-L4021 Lab); Column: Chiral IC 250×4.6 mm ID, 5 mm; Flow rate: 2.0 mL/min; Mobile Phase: 70/30 CO$_2$/MeOH; Detector Wavelength: 220 nm.

Method G: Preparative Chromatographic Conditions: Instrument: Berger Prep SFC MGII; Column: Chiral OJ 25×3 cm, 5 mm; Flow rate: 85.0 mL/min; Mobile Phase: 70/30 CO$_2$/MeOH; Detector Wavelength: 220 nm.

Method H: Analytical Chromatographic Conditions: Instrument: Aurora analytical SFC (LVL-L4021 Lab); Column: Chiral OJ 250×4.6 mm ID, 5 mm; Flow rate: 2.0 mL/min; Mobile Phase: 70/30 CO$_2$/MeOH; Detector Wavelength: 220 nm.

Method I: Preparative Chromatographic Conditions: Instrument: Berger Prep SFC MGII; Column: Chiral OJ (repaired) 25×3 cm, 5 μm; Flow rate: 85.0 mL/min; Mobile Phase: 82/18 CO$_2$/MeOH; Detector Wavelength: 220 nm.

Method J: Analytical Chromatographic Conditions: Instrument: Aurora analytical SFC; Column: Chiral OJ (repaired) 250×4.6 mm ID, 5 μm; Flow rate: 2.0 mL/min; Mobile Phase: 80/20 CO$_2$/MeOH; Detector Wavelength: 220 nm.

Method K: Preparative Chromatographic Conditions: Instrument: Berger Prep SFC MGII Column: Chiral AD 25×3 cm, 5 μm; Flow rate: 85.0 mL/min; Mobile Phase: 70/30 CO$_2$/MeOH; Detector Wavelength: 220 nm.

Method L: Analytical Chromatographic Conditions: Instrument: Aurora analytical SFC (LVL-L4021 Lab); Column: Chiral AD 250×4.6 mm ID, 5 m; Flow rate: 2.0 mL/min; Mobile Phase: 70/30 CO$_2$/MeOH; Detector Wavelength: 220 nm.

Method M: Preparative Chromatographic Conditions: Instrument: Berger Prep SFC MGII Column: Chiral OZ 25×3 cm, 5 mm; Flow rate: 85.0 mL/min; Mobile Phase: 80/20 CO$_2$/MeOH/ACN 25:75; Detector Wavelength: 220 nm.

Method N: Analytical Chromatographic Conditions: Instrument: Aurora analytical SFC (LVL-L4021 Lab); Column: Chiral OZ 250×4.6 mm ID, 5 mm; Flow rate: 2.0 mL/min; Mobile Phase: 80/20 CO$_2$/MeOH/ACN 25:75; Detector Wavelength: 220 nm.

Method O: Analytical Chromatographic Conditions: Column: Chiralpak IC, 4.6×100 mm, 5 micron (analytical); Flow Rate: 2 mL/min; Oven Temperature: 40° C.; BPR setting: 1700 psi; UV wavelength: 220 nm; Mobile Phase: 80% CO2/20% MeOH-0.1% DEA (isocratic).

Method P: Preparative Chromatographic Conditions: Instrument: Berger Prep SFC MGII; Column: AD-H 25×5 cm ID, 5 μm; Flow rate: 300 mL/min; Mobile Phase: 88/12 CO$_2$/MeOH;

Method Q: Preparative Chromatographic Conditions: Column: IC 25×5 cm ID, 5 μm; Flow rate: 300 mL/min; Mobile Phase: 75/25 CO$_2$/MeOH; Detector Wavelength: 220 nm.

Method R: Preparative Chromatographic Conditions: Column: IC 25×0.46 cm ID, 5 μm; Flow rate: 3.0 mL/min; Mobile Phase: 80/20 CO$_2$/MeOH; Detector Wavelength: 200-400 nm.

Method S: Preparative Chromatographic Conditions: Column: OJ-H 25×3 cm ID, 5 μm; Flow rate: 150 mL/min; Mobile Phase: 90/10 CO$_2$/MeOH; Detector Wavelength: 220 nm.

Method T: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min.

Method U: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

$^1$H NMR spectra (unless otherwise noted) were obtained with JEOL or Bruker FOURIER® transform spectrometers operating at 400 MHz or 500 MHz.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for CD$_3$SOCD$_2$H, 3.30 ppm for CD$_2$HOD, 1.94 for CHD$_2$CN, 7.26 ppm for CHCl$_3$, 5.32 ppm for CDHCl$_2$). Abbreviations used in the description of NMR peaks: "a"=apparent, "br. s."=broad singlet Example 1

N—((R)-1-((1s,4s)-4-(6-Fluoroquinolin-4-yl)cyclohexyl)ethyl)-6'-methoxy-2,3'-bipyridine-5-carboxamide

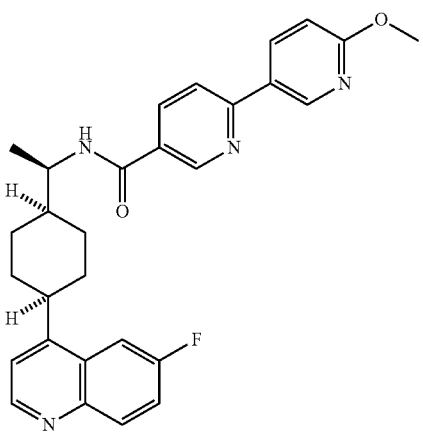 [SMILES: COc1ccc(-c2ccc(C(=O)N[C@H](C)[C@H]3CC[C@@H](c4ccnc5ccc(F)cc54)CC3)cn2)cn1]

1A. Methyl 6'-methoxy-2,3'-bipyridine-5-carboxylate

The reaction mixture of 2-methoxy-5-pyridineboronic acid (0.184 g, 1.204 mmol), methyl 6-bromonicotinate (0.2 g, 0.926 mmol), PdCl$_2$(dppf) (0.068 g, 0.093 mmol) and 2 M Na$_2$CO$_3$ aqueous solution (0.93 mL, 1.85 mmol) in dioxane (5 mL) was purged with nitrogen stream for 3 min, then heated at 90° C. for 3 h. The reaction mixture was diluted with ethyl acetate and saturated NaHCO$_3$ solution. The organic layer was concentrated in vacuo and the residue was dissolved in DCM and purified by silica gel column flash chromatography, eluting with 0-40% ethyl acetate in hexane to give Intermediate 1A (white solid, 0.15 g, 0.614 mmol, 66.3% yield). LC-MS Anal. Calc'd for C$_{13}$H$_{12}$N$_2$O$_3$ 244.09, found [M+H] 245.0, T$_r$=0.84 min (Method A). $^1$H NMR (400 MHz, chloroform-d) δ 9.26 (dd, J=2.2, 0.9 Hz, 1H), 8.84 (dd, J=2.5, 0.7 Hz, 1H), 8.47-8.22 (m, 2H), 7.76 (dd, J=8.3, 0.9 Hz, 1H), 6.88 (dd, J=8.7, 0.7 Hz, 1H), 4.02 (s, 3H), 3.98 (s, 3H).

1B. 6'-Methoxy-2,3'-bipyridine-5-carboxylic Acid

To a solution of methyl 6'-methoxy-[2,3'-bipyridine]-5-carboxylate (0.15 g, 0.614 mmol) in THF (2 mL) and MeOH (2 mL) was added 2 M lithium hydroxide solution (1.84 mL, 3.68 mmol). The reaction mixture was stirred at rt for 2 h. To the reaction mixture was added 1 N HCl solution dropwise to adjust pH to about 6. The solid was filtered and washed with distilled water, ether and dried on high vacuum. to give Intermediate 1B (white solid, 0.115 g, 0.50 mmol, 81% yield). LC-MS Anal. Calc'd for C$_{12}$H$_{10}$N$_2$O$_3$ 230.07, found [M+H] 231.0. T$_r$=0.68 min (Method A). $^1$H NMR (400 MHz, DMSO-d$_6$) δ 13.36 (s, 1H), 9.12 (d, J=1.5 Hz, 1H), 8.97 (d, J=2.2 Hz, 1H), 8.45 (dd, J=8.7, 2.5 Hz, 1H), 8.31 (dd, J=8.4, 2.2 Hz, 1H), 8.14-8.01 (m, 1H), 6.97 (d, J=8.8 Hz, 1H), 3.94 (s, 3H).

Example 1 N—((R)-1-((1s,4s)-4-(6-Fluoroquinolin-4-yl)cyclohexyl)ethyl)-6'-methoxy-2,3'-bipyridine-5-carboxamide To a solution of 6'-methoxy-[2,3'-bipyridine]-5-carboxylic acid (18.3 mg, 0.079 mmol) in DMF (1 mL) was added HATU (33 mg, 0.090 mmol). The reaction mixture was stirred at rt for 10 min, followed by addition of (R)-1-((1s,4S)-4-(6-fluoroquinolin-4-yl)cyclohexyl)ethanamine (18 mg, 0.066 mmol) (see, e.g., WO 2016/073774, PCT/US 2015/059316 intermediate 40L) and N-methyl morpholine (0.032 mL, 0.26 mmol). The resulting mixture was stirred at rt for 2 h. The reaction mixture was concentrated in vacuo and the residue was dissolved in MeOH, filtered, and purified via preparative HPLC to give Example 1 (18 mg, 0.037 mmol, 56% yield). LC-MS Anal. Calc'd for $C_{29}H_{29}FN_4O_2$ 484.23, found [M+H] 485.4. $T_r$=1.37 min (Method B). $^1$H NMR (500 MHz, DMSO-$d_6$) δ 9.05 (s, 1H), 8.90 (s, 1H), 8.81 (d, J=4.4 Hz, 1H), 8.52 (d, J=8.8 Hz, 1H), 8.40 (dd, J=8.7, 2.0 Hz, 1H), 8.25 (d, J=6.8 Hz, 1H), 8.08 (dd, J=9.1, 5.9 Hz, 1H), 8.04 (d, J=8.3 Hz, 1H), 7.95 (d, J=8.8 Hz, 1H), 7.65 (t, J=7.5 Hz, 1H), 7.48 (d, J=4.4 Hz, 1H), 6.95 (d, J=8.7 Hz, 1H), 4.45 (d, J=6.4 Hz, 1H), 3.90 (s, 3H), 3.62 (d, J=3.8 Hz, 1H), 1.94-1.76 (m, 5H), 1.75-1.56 (m, 4H), 1.22 (br. s., 3H).

Examples 2-9

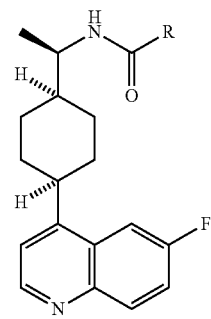

Examples 2-9 were prepared from Intermediate (WO 2016/073774, PCT/US 2015/059316 intermediate 40L) following the procedure for Example 1 using the corresponding acid.

| Ex. No. | Name | R | Tr (min) Method B * | [M + H]+ |
|---|---|---|---|---|
| Example 2 | N-((R)-1-((1s,4S)-4-(6-Fluoroquinolin-4-yl)cyclohexyl)ethyl)-6-methoxynicotinamide | | 1.26 | 408.2 |
| Example 3 | N-((R)-1-((1s,4S)-4-(6-Fluoroquinolin-4-yl)cyclohexyl)ethyl)-6-hydroxynicotinamide | | 0.97 | 394.3 |
| Example 4 | N-((R)-1-((1s,4S)-4-(6-Fluoroquinolin-4-yl)cyclohexyl)ethyl)-6-(1H-pyrazol-1-yl)nicotinamide | | 1.34 | 444.0 |
| Example 5 | 6-Chloro-N-((R)-1-((1s,4S)-4-(6-fluoroquinolin-4-yl)cyclohexyl)ethyl)nicotinamide | | 1.59 | 412.2 |
| Example 6 | (R)-1-((1s,4S)-4-(6-Fluoroquinolin-4-yl)cyclohexyl)-N-methylethanamine | | 1.36 | 528.4 |
| Example 7 | 6-Fluoro-N-((R)-1-((1s,4S)-4-(6-fluoroquinolin-4-yl)cyclohexyl)ethyl)nicotinamide | | 1.38 | 395.9 |

-continued

| Ex. No. | Name | R | Tr (min) Method B * | [M + H]+ |
|---|---|---|---|---|
| Example 8 | N-((R)-1-((1s,4S)-4-(6-Fluoroquinolin-4-yl)cyclohexyl)ethyl)-2-methoxypyrimidine-5-carboxamide | 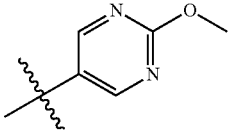 [SMILES: *c1cnc(OC)nc1] | 1.26 | 409.1 |
| Example 9 | N-((R)-1-((1s,4S)-4-(6-Fluoroquinolin-4-yl)cyclohexyl)ethyl)-2-methylpyrimidine-5-carboxamide | 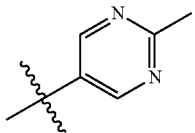 [SMILES: *c1cnc(C)nc1] | 1.25 | 393.0 |

* unless otherwise noted

Four Isomers of Example 10 N-(1-(4-(6-Fluoroquinolin-4-yl)cyclohexyl)propyl)-6-methoxynicotinamide

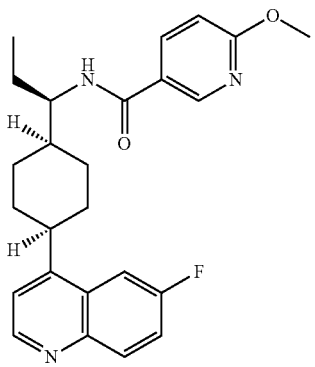

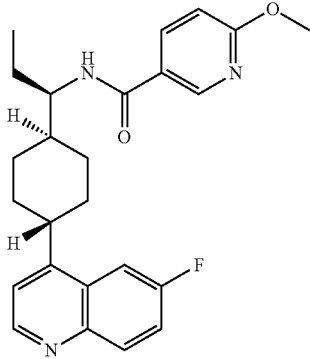

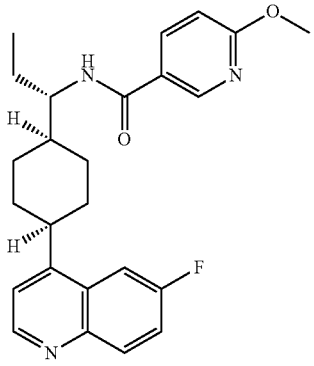

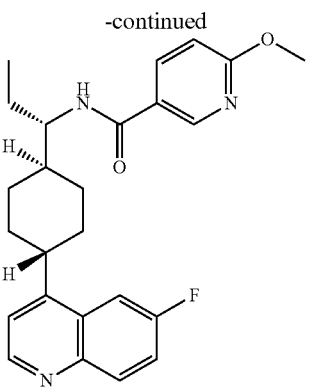

10A. Ethyl 2-(4-(6-fluoroquinolin-4-yl)cyclohex-3-en-1-yl)acetate

Ethyl 2-(4-(4,4,5,5-tetramethyl-1,3,2-dioxaborolan-2-yl)cyclohex-3-en-1-yl)acetate (WO 2016/073774, PCT/US 2015/059316 Intermediate 164E) (5 g, 17.00 mmol) was taken up in dioxane (28.3 ml) and water (7.08 ml). 4-chloro-6-fluoroquinoline (2.57 g, 14.15 mmol) was added followed by $K_2CO_3$ (5.87 g, 42.5 mmol). The reaction mixture was bubble with nitrogen gas for 5 minutes before the addition of Pd(Ph$_3$P)$_4$ (0.327 g, 0.283 mmol). After addition, reaction was vacated and backfilled with $N_2$ three times and then sealed (sealed vial parafilmed) and heated to 100° C. for 16 hours. The reaction was concentrated in vacuo and purified directly via silica gel flash column chromatography to give Intermediate 10A (4.22 g, 13.47 mmol, 95% yield). LC-MS Anal. Calc'd for $C_{19}H_{20}FNO_2$ 313.15, found [M+H] 314.1 $T_r$=0.75 min (Method A).

10B. Ethyl 2-(4-(6-fluoroquinolin-4-yl)cyclohexyl)acetate

Intermediate 10A (4.22 g, 13.47 mmol) was dissolved in MeOH (67.3 ml) and ammonium formate (4.25 g, 67.3 mmol) was added. The vessel was equipt with a reflux condenser and vacated and flushed with nitrogen gas 3 times. Then, palladium on carbon (0.143 g, 1.347 mmol) (wet, degussa type) was added and the reaction was heated to reflux for 1 hour. The reaction was cooled, concentrated in vacuo, and diluted with DCM. Solids were filtered off and the filtrate was concentrated to give crude Intermediate 10B (4.20 g, 13.32 mmol, 99% yield) as a mixture of cis- and trans-diastereomers. LC-MS Anal. Calc'd for $C_{19}H_{22}FNO_2$ 315.16, found [M+H] 316.2 $T_r$=0.76 min (Method A).

10C. Ethyl 2-(4-(6-fluoroquinolin-4-yl)cyclohexyl)butanoate

To the flask containing THF (6 mL) was added lithium diisopropylamide (2.0 M solution in THF) (3.17 mL, 6.34 mmol) at −78° C., followed by addition of 1,3-dimethyltetrahydropyrimidin-2(1H)-one (0.573 mL, 4.76 mmol) and a solution of ethyl 2-(4-(6-fluoroquinolin-4-yl)cyclohexyl)acetate (1.0 g, 3.17 mmol) in THF (10 mL) dropwise at −78° C. The resulting mixture turned into brown solution and stirred at −78° C. for 1 h, then iodoethane (0.51 mL, 6.34 mmol) was added slowly. The reaction mixture was then stirred at ice bath temperature for 1 h, warmed to rt over night. The reaction was quenched by pouring into water and extracting with EtOAc. Combined organic layer was washed with brine, dried with $MgSO_4$, filtered and concentrated in vacuo. The residue was dissolved in DCM and purified by silica gel flash chromatography, eluting with 0-20% ethyl acetate in hexane to give Intermediate 10C (oil, 0.81 g, 2.359 mmol, 74.4% yield). LC-MS Anal. Calc'd for $C_{21}H_{26}FNO_2$, 343.19 found [M+H] 344.3. $T_r$=0.87-0.88 min (Method A). $^1H$ NMR (400 MHz, CHLOROFORM-d) δ 8.88-8.77 (m, 1H), 8.18-8.06 (m, 1H), 7.66 (dd, J=10.6, 2.6 Hz, 1H), 7.47 (ddd, J=9.2, 8.0, 2.9 Hz, 1H), 7.36 (d, J=4.6 Hz, 1H), 4.25-4.15 (m, 2H), 3.34-3.09 (m, 1H), 2.70-2.16 (m, 1H), 2.13-1.49 (m, 13H), 1.36-1.24 (m, 3H), 1.00-0.90 (m, 3H).

10D. 2-((1r,4r)-4-(6-Fluoroquinolin-4-yl)cyclohexyl)butanoic Acid

To a solution of ethyl 2-(4-(6-fluoroquinolin-4-yl)cyclohexyl)butanoate (0.81 g, 2.359 mmol) in THF (4 mL) and MeOH (7 mL) was added 2.0 M LiOH aqueous solution (7.1 mL, 14.2 mmol) slowly. The reaction mixture was stirred at rt over night. Next day, to the reaction mixture was added more LiOH solution (7.1 mL, 14.2 mmol) and the resulting reaction mixture was heated at 70° C. for 28 h. The reaction mixture was cooled down and to the mixture was added ethyl acetate. The aqueous layer was separated and to the aqueous layer was added 1N HCl solution to adjust pH to 5-6. The resulting mixture was diluted with water and $CHCl_3$: 2-propanol (2:1). The organic layer was separated and dried over $MgSO_4$. The filtrate was concentrated in vacuo to give Intermediate 10D as a mixture of cis- and trans-(3:2) isomer (0.64 g, 2.029 mmol, 86% yield). LC-MS Anal. Calc'd for $C_{19}H_{22}FNO_2$ 315.16 found [M+H] 316.3. $T_r$=0.72 min (Method A). $^1H$ NMR (400 MHz, chloroform-d) δ 8.83 (d, J=4.4 Hz, 1H), 8.30-8.03 (m, 1H), 7.67 (dd, J=10.6, 2.4 Hz, 1H), 7.48 (ddd, J=9.2, 7.9, 2.6 Hz, 1H), 7.38 (d, J=4.6 Hz, 1H), 7.32-7.27 (m, 1H), 3.37-3.07 (m, 1H), 2.77-2.21 (m, 1H), 2.11-1.30 (m, 11H), 1.07-1.00 (m, 3H).

10E. 1-(4-(6-Fluoroquinolin-4-yl)cyclohexyl)propan-1-amine

To a suspension of 2-(4-(6-fluoroquinolin-4-yl)cyclohexyl)butanoic acid (0.31 g, 0.983 mmol) in toluene (8 mL) were added diphenylphosphoryl azide (0.245 mL, 1.13 mmol) and triethylamine (0.15 mL, 1.28 mmol). The reaction mixture turned into clear solution after addition of TEA. The vial was sealed and heated to 70° C. for 2.5 h. The reaction mixture was concentrated under reduced pressure. To the residue was added THF (10 mL) and 2.0 M lithium hydroxide solution (4.91 mL, 9.83 mmol) and the resulting mixture was stirred at rt for 1 h. The reaction mixture was acidified with 1N HCl (white precipitate forms) and extracted with EtOAc to remove DPPA related impurities. Then the aqueous layer was basified with 1N NaOH (precipitate forms again) and extracted with EtOAc four times. The basic extracts were combined, dried over $MgSO_4$ and the filtrate was concentrated in vacuo to give colorless oil as a mixture of cis- and trans-, dried on high vacuum over night to give Intermediate 10E (oil, 0.245 g, 0.855 mmol, 87% yield). LC-MS Anal. Calc'd for $C_{18}H_{23}FN_2$ 286.19, found [M+H] 287.3. $T_r$=0.54 min, 0.55 min (Method A). $^1H$ NMR (400 MHz, chloroform-d) δ 8.81 (d, J=4.6 Hz, 1H), 8.12 (dd, J=9.1, 5.8 Hz, 1H), 7.67 (dd, J=10.6, 2.6 Hz, 1H), 7.47 (ddd, J=9.2, 8.0, 2.9 Hz, 1H), 7.37-7.28 (m, 1H), 3.41-3.09 (m, 1H), 2.97-2.50 (m, 1H), 2.19-1.23 (m, 11H), 1.06-0.93 (m, 3H).

Example 10, Four Isomers N-(1-(4-(6-Fluoroquinolin-4-yl)cyclohexyl)propyl)-6-methoxynicotinamide To a solution of 6-methoxynicotinic acid (26.9 mg, 0.176 mmol) in DMF (1.5 mL) was added HATU (72.5 mg, 0.191 mmol). The reaction mixture was stirred at rt for 3 min, followed by addition of a solution of 1-(4-(6-fluoroquinolin-4-yl)cyclohexyl)propan-1-amine (42 mg, 0.147 mmol) in THF (0.7 mL) and DIPEA (0.051 mL, 0.293 mmol). The reaction mixture was stirred at rt over night. The reaction mixture was concentrated in vacuo. and the residue was dissolved in MeOH, filtered, and purified via preparative HPLC to give four isomers mixture. The isomers were further separated by preparative SFC (35% $MeOH/CO_2$ on Lux-4 column) to give four isolates. (absolute stereochemistry was not determined).

First elute (16.2 mg, 0.037 mmol, 24.9% yield). LC-MS Anal. Calc'd for $C_{25}H_{28}FN_3O_2$ 420.21, found [M+H] 421.9. $T_r$=1.55 min (Method B). $T_r$=3.8 min over 10 min run (35% $MeOH/CO_2$ on Lux-4 column). $^1H$ NMR (500 MHz, DMSO-$d_6$) δ 8.81 (d, J=4.6 Hz, 1H), 8.66 (d, J=2.1 Hz, 1H), 8.17-8.03 (m, 3H), 7.94 (dd, J=10.8, 2.6 Hz, 1H), 7.65 (td, J=8.7, 2.7 Hz, 1H), 7.46 (d, J=4.3 Hz, 1H), 6.88 (d, J=8.5 Hz, 1H), 4.37-4.16 (m, 1H), 3.88 (s, 3H), 3.37 (br. s., 1H), 1.93-1.52 (m, 10H), 1.46-1.29 (m, 1H), 0.87 (t, J=7.2 Hz, 3H).

Second elute (17.8 mg, 0.041 mmol, 27.6% yield). LC-MS Anal. Calc'd for $C_{25}H_{28}FN_3O_2$ 420.21, found [M+H] 421.9. $T_r$=1.55 min (Method B). $T_r$=4.8 min over 10 min run (35% $MeOH/CO_2$ on Lux-4 column). $^1H$ NMR (500 MHz, DMSO-$d_6$) δ 8.82 (d, J=4.6 Hz, 1H), 8.67 (d, J=2.1 Hz, 1H), 8.20-8.03 (m, 3H), 7.94 (dd, J=11.0, 2.7 Hz, 1H), 7.73-7.58 (m, 1H), 7.46 (d, J=4.3 Hz, 1H), 6.88 (d, J=8.9 Hz, 1H), 4.29 (d, J=8.5 Hz, 1H), 3.89 (s, 3H), 3.38 (br. s., 1H), 1.94-1.54 (m, 10H), 1.47-1.32 (m, 1H), 0.87 (t, J=7.3 Hz, 3H).

Third elute (9.4 mg, 0.022 mmol, 15.1% yield). LC-MS Anal. Calc'd for $C_{25}H_{28}FN_3O_2$ 420.21, found [M+H] 421.9. $T_r$=1.55 min (Method B). $T_r$=5.8 min over 10 min run (35% $MeOH/CO_2$ on Lux-4 column). $^1H$ NMR (500 MHz, DMSO-$d_6$) δ 8.79 (d, J=4.4 Hz, 1H), 8.70 (s, 1H), 8.16 (dd, J=8.6, 1.9 Hz, 1H), 8.11-8.03 (m, 2H), 7.99 (d, J=8.7 Hz, 1H), 7.70-7.56 (m, 1H), 7.43 (d, J=4.4 Hz, 1H), 6.90 (d, J=8.7 Hz, 1H), 3.90 (s, 3H), 3.82 (d, J=8.5 Hz, 1H), 3.45-3.20 (m, 1H), 1.91 (br. s., 4H), 1.73-1.29 (m, 7H), 0.87 (t, J=7.2 Hz, 3H).

Fourth elute (10.8 mg, 0.025 mmol, 17.1% yield). LC-MS Anal. Calc'd for $C_{25}H_{28}FN_3O_2$ 420.21, found [M+H] 421.9. $T_r$=1.55 min (Method B). $T_r$=7.7 min over 10 min run (35% $MeOH/CO_2$ on Lux-4 column). $^1H$ NMR (500 MHz, DMSO-d$_6$) δ 8.79 (d, J=4.5 Hz, 1H), 8.70 (s, 1H), 8.16 (dd, J=8.6, 1.9 Hz, 1H), 8.11-8.03 (m, 2H), 7.98 (d, J=8.9 Hz, 1H), 7.65 (t, J=7.5 Hz, 1H), 7.43 (d, J=4.4 Hz, 1H), 6.89 (d, J=8.7 Hz, 1H), 3.90 (s, 3H), 3.86-3.74 (m, 1H), 3.46-3.23 (m, 1H), 1.90 (br. s., 4H), 1.73-1.31 (m, 7H), 0.87 (t, J=7.2 Hz, 3H).

Example 11, Two Isomers

6-Methoxy-N-(1-((1s,4s)-4-(6-(trifluoromethyl)quinolin-4-yl)cyclohexyl)propyl)nicotinamide

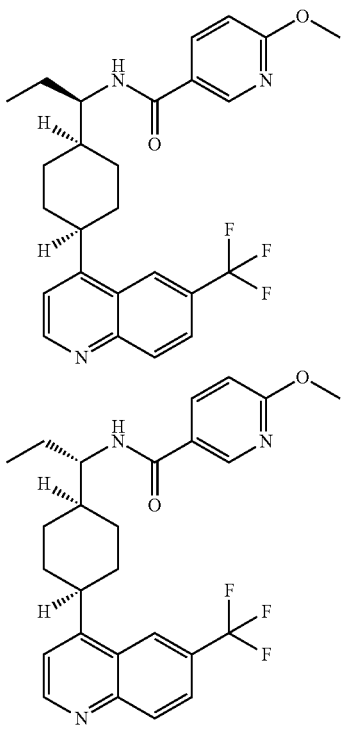

11A. Ethyl 2-(4-(6-(trifluoromethyl)quinolin-4-yl) cyclohex-3-enyl)acetate

To a solution of 4-chloro-6-(trifluoromethyl)quinoline (2.05 g, 8.85 mmol), ethyl 2-(4-(4,4,5,5-tetramethyl-1,3,2-dioxaborolan-2-yl)cyclohex-3-en-1-yl)acetate (3.12 g, 10.62 mmol) in 1,4-dioxane (35 mL) was added potassium carbonate (3.67 g, 26.6 mmol) and water (7 mL). The reaction mixture was purged with nitrogen stream for 3 min, followed by addition of Pd(Ph$_3$P)$_4$ (0.409 g, 0.354 mmol). The resulting mixture was heated at 100° C. under nitrogen stream for over night. The reaction mixture was cooled down and diluted with ethyl acetate and saturated NaHCO$_3$ solution. The organic layer was separated and washed with sat. NaHCO$_3$ solution, and dried over MgSO$_4$. The filtrate was concentrated in vacuo and the residue was purified via silica gel flash column chromatography, eluting with 0-50% ethyl acetate in hexane to give Intermediate 11A (oil, 3.0 g, 8.26 mmol, 93% yield). LC-MS Anal. Calc'd for C$_{20}$H$_{20}$F$_3$NO$_2$, 363.14, found [M+H] 364.5. T$_r$=0.97 min (Method A). $^1$H NMR (400 MHz, chloroform-d) δ: 8.95 (d, J=4.5 Hz, 1H), 8.31 (s, 1H), 8.22 (d, J=8.8 Hz, 1H), 7.87 (dd, J=8.8, 2.0 Hz, 1H), 7.29 (d, J=4.5 Hz, 1H), 5.86 (dd, J=2.8, 1.7 Hz, 1H), 4.20 (q, J=7.2 Hz, 2H), 2.65-2.24 (m, 5H), 2.15-1.96 (m, 2H), 1.73-1.54 (m, 2H), 1.36-1.29 (m, 3H).

11B. Ethyl 2-(4-(6-(trifluoromethyl)quinolin-4-yl) cyclohexyl)acetate

The reaction mixture of ethyl 2-(4-(6-(trifluoromethyl)quinolin-4-yl)cyclohex-3-en-1-yl)acetate (3.0 g, 8.26 mmol), ammonium formate (2.08 g, 33.0 mmol) in MeOH (50 mL) was purged with nitrogen stream for 3 min, followed by addition of Pd—C (0.88 g, 0.41 mmol). The resulting mixture was heated at 85° C. for 2 h. The reaction mixture was cooled down. The reaction mixture was filtered through a celite pad and the filter cake was washed with MeOH. The filtrate was concentrated in vacuo. The residue was extracted with ethyl acetate and washed with saturated NaHCO$_3$ solution, brine successively. The organic layer was dried over MgSO$_4$ and the filtrate was concentrated in vacuo to give Intermediate 11B (oil, 2.6 g, 7.12 mmol, 86% yield) as a mixture of cis- and trans-diastereomers. LC-MS Anal. Calc'd for C$_{20}$H$_{22}$F$_3$NO$_2$ 365.16, found [M+H] 366.2. T$_r$=0.94 min (Method A). $^1$H NMR (400 MHz, chloroform-d) δ 9.05-8.85 (m, 1H), 8.36 (s, 1H), 8.24 (d, J=8.8 Hz, 1H), 7.88 (dd, J=8.9, 1.7 Hz, 1H), 7.51-7.33 (m, 1H), 4.29-4.03 (m, 2H), 3.51-3.23 (m, 1H), 2.61-2.29 (m, 2H), 2.12-1.35 (m, 9H), 1.32-1.21 (m, 3H).

11C. Ethyl 2-((1s,4s)-4-(6-(trifluoromethyl)quinolin-4-yl)cyclohexyl)butanoate

To the flask containing THF (15 mL) was added lithium diisopropylamide (2.0 M solution in THF) (7.65 mL, 15.30 mmol) at −78° C., followed by addition of 1,3-dimethyltetrahydropyrimidin-2(1H)-one (1.29 mL, 10.67 mmol) and a solution of ethyl 2-(4-(6-(trifluoromethyl)quinolin-4-yl)cyclohexyl)acetate (2.6 g, 7.12 mmol) in THF (10 mL) dropwise at −78° C. The resulting mixture turned into dark brown solution and stirred at −78° C. for 1 h, then iodoethane (1.14 mL, 14.23 mmol) was added slowly. The reaction mixture was warmed to rt and stirred for 3 h. The reaction mixture was quenched by pouring into water and extracted with EtOAc. Combined organics was washed with brine, dried with MgSO$_4$, filtered and the filtrate was concentrated in vacuo. The extract was purified via silica gel flash column chromatography, eluting with 0-20% ethyl acetate in hexane to give the major cis isomer Intermediate 11C (oil, 1.1 g, 2.77 mmol, 39% yield).The cis isomer contaminated with small amount of trans isomer. The cis isomer was confirmed by NMR experimentals. LC-MS Anal. Calc'd for C$_{22}$H$_{26}$F$_3$NO$_2$ 393.19, found [M+H] 394.3. T$_r$=0.97 min (Method A). $^1$H NMR (400 MHz, chloroform-d) δ 8.97 (d, J=4.6 Hz, 1H), 8.37 (s, 1H), 8.24 (d, J=8.8 Hz, 1H), 7.88 (dd, J=8.8, 2.0 Hz, 1H), 7.46 (d, J=4.6 Hz, 1H), 4.20 (q, J=7.2 Hz, 2H), 3.57-3.32 (m, 1H), 2.64 (td, J=10.8, 4.0 Hz, 1H), 2.14-1.58 (m, 11H), 1.29 (t, J=7.2 Hz, 3H), 0.95 (t, J=7.4 Hz, 3H).

11D. 2-((1s,4s)-4-(6-(Trifluoromethyl)quinolin-4-yl) cyclohexyl)butanoic acid

To the reaction mixture of major isomer ethyl 2-((1s,4s)-4-(6-(trifluoromethyl)quinolin-4-yl)cyclohexyl)butanoate (1.1 g, 2.80 mmol) in THF (20 mL) and MeOH (8 mL) was added lithium hydroxide solution (2.0 M solution) (13.98 mL, 28.0 mmol). The resulting mixture was heated at 65° C. over weekend. The reaction mixture was cooled down and diluted with water. To the mixture was added 1 N HCl solution to adjust pH to about 5. White solid crashed out at pH 5-6. The resulting mixture was extracted with ethyl acetate twice. The organic layer was separated, washed with brine, and dried over MgSO$_4$. The filtrate was concentrated in vacuo to give Intermediate 11D (yellow solid, 0.93 g, 2.55 mmol, 91% yield). LC-MS Anal. Calc'd for C$_{20}$H$_{22}$F$_3$NO$_2$ 365.16, found [M+H] 366.3. T$_r$=0.81 min (Method A). $^1$H NMR (400 MHz, DMSO-d$_6$) δ 12.10 (br. s., 1H), 8.99 (d, J=4.6 Hz, 1H), 8.57 (s, 1H), 8.23 (d, J=8.8 Hz, 1H), 8.00 (dd, J=8.7, 1.9 Hz, 1H), 7.65 (d, J=4.6 Hz, 1H), 3.61 (d, J=10.3 Hz, 1H), 1.96-1.54 (m, 11H), 1.49-1.29 (m, 1H), 0.90 (t, J=7.4 Hz, 3H).

11E. 1-((1s,4s)-4-(6-(Trifluoromethyl)quinolin-4-yl)cyclohexyl)propan-1-amine

To a suspension of 2-((1s,4s)-4-(6-(trifluoromethyl)quinolin-4-yl)cyclohexyl)butanoic acid (0.58 g, 1.587 mmol) inToluene (15 mL) were added DPPA (0.40 mL, 1.825 mmol) and triethylamine (0.240 mL, 2.064 mmol). The reaction mixture turned into clear solution after addition of TEA. The reaction mixture was heated to 70° C. for 2 h. After about 2 h, the reaction mixture was cooled to rt. The reaction mixture was concentrated under reduced pressure. To the residue was added THF (15 mL) and lithium hydroxide aqueous solution (7.94 mL, 15.87 mmol) and the resulting mixture was stirred at rt for 20 h. The reaction mixture acidified with 1N HCl and extracted with EtOAc to remove DPPA related impurities. Then the aqueous layer was basified with 1N NaOH and extracted with EtOAc four times. The basic extracts were combined, dried over MgSO$_4$ and the filtrate was concentrated in vacuo to give Intermediate 11E (colorless oil, 0.47 g, 1.397 mmol, 88% yield). LC-MS Anal. Calc'd for C$_{19}$H$_{23}$F$_3$N$_2$ 336.18, found [M+H] 337.2. T$_r$=0.62 min (Method A). $^1$H NMR (400 MHz, chloroform-d) δ 8.95 (d, J=4.6 Hz, 1H), 8.38 (s, 1H), 8.24 (d, J=8.8 Hz, 1H), 7.88 (dd, J=8.8, 1.8 Hz, 1H), 7.45 (d, J=4.6 Hz, 1H), 3.57-3.44 (m, 1H), 2.90 (td, J=8.5, 3.0 Hz, 1H), 2.22-1.20 (m, 13H), 1.01 (d, J=15.0 Hz, 3H).

Example 11, Two Isomers 6-Methoxy-N-(1-((1s,4s)-4-(6-(trifluoromethyl)quinolin-4-yl)cyclohexyl)propyl)nicotinamide To a solution of 6-methoxynicotinic acid (11.5 mg, 0.075 mmol) in DMF (1.5 mL) was added HATU (30.9 mg, 0.081 mmol). The reaction mixture was stirred at rt for 10 min, followed by addition of a solution of 1-((1s,4s)-4-(6-(trifluoromethyl)quinolin-4-yl)cyclohexyl)propan-1-amine (21 mg, 0.062 mmol) in THF (0.8 mL) and DIPEA (0.022 mL, 0.125 mmol). The reaction mixture was stirred at rt for 2 h. The reaction mixture was concentrated in vacuo and the residue was dissolved in MeOH, filtered, and purified via preparative HPLC to give a mixture of two isomers. The isomers were further separated by preparative SFC (Method C) to give two isolates. (absolute stereochemistry was not determined).

First elute (7.2 mg, 0.015 mmol, 24.2% yield). LC-MS Anal. Calc'd for C$_{26}$H$_{28}$F3N$_3$O$_2$ 471.21, found [M+H] 472.1. T$_r$=1.72 min (Method B). T$_r$=8.9 min over 15 min run (Method D). $^1$H NMR (500 MHz, DMSO-d$_6$) δ 9.02 (d, J=4.5 Hz, 1H), 8.69 (d, J=2.1 Hz, 1H), 8.56 (s, 1H), 8.24 (d, J=8.8 Hz, 1H), 8.18-8.07 (m, 2H), 8.01 (br d, J=7.8 Hz, 1H), 7.60 (d, J=4.5 Hz, 1H), 6.89 (d, J=8.7 Hz, 1H), 4.31 (br d, J=7.5 Hz, 1H), 3.90 (s, 3H), 3.60 (br s, 1H), 1.96-1.34 (m, 11H), 0.89 (t, J=7.3 Hz, 3H).

Second elute (7.6 mg, 0.016 mmol, 25.6% yield). LC-MS Anal. Calc'd for C$_{26}$H$_{28}$F3N$_3$O$_2$ 471.21, found [M+H] 472.1. T$_r$=1.72 min (Method B). T$_r$=10.0 min over 15 min run (Method D). $^1$H NMR (500 MHz, DMSO-d$_6$) δ 9.02 (d, J=4.5 Hz, 1H), 8.69 (d, J=2.1 Hz, 1H), 8.56 (s, 1H), 8.24 (d, J=8.8 Hz, 1H), 8.18-8.07 (m, 2H), 8.01 (br d, J=7.8 Hz, 1H), 7.60 (d, J=4.5 Hz, 1H), 6.89 (d, J=8.7 Hz, 1H), 4.31 (br d, J=7.5 Hz, 1H), 3.90 (s, 3H), 3.60 (br s, 1H), 1.96-1.34 (m, 11H), 0.89 (t, J=7.3 Hz, 3H).

Example 12, Two Isomers

6-Methoxy-N-(2-methoxy-1-((1s,4s)-4-(6-(trifluoromethyl)quinolin-4-yl)cyclohexyl)ethyl)nicotinamide

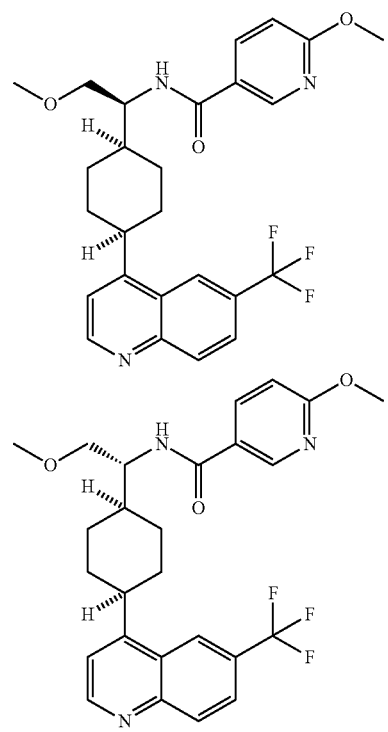

12A. Ethyl 2-((1s,4s)-4-(6-(trifluoromethyl)quinolin-4-yl)cyclohexyl)acetate

The reaction mixture of ethyl 2-(4-(6-(trifluoromethyl)quinolin-4-yl)cyclohex-3-en-1-yl)acetate (Intermediate 11A, 4.8 g, 13.21 mmol), ammonium formate (2.50 g, 39.6 mmol) in MeOH (80 mL) was purged with nitrogen stream, then evacuated, followed by addition of Pd—C (1.125 g, 0.528 mmol, 10% wt. wet). The resulting mixture was heated at 78° C. for 2 h. The reaction mixture was cooled down. To the reaction mixture was added more Pd—C (1.125 g, 0.528 mmol) (0.5 g) and MeOH (20 mL) and the reaction mixture was heated at 78° C. over night. The reaction mixture was filtered and the filter cake was washed with MeOH. The filtrate was concentrated in vacuo. The residue was diluted with ethyl acetate and saturated NaHCO$_3$ solution. The organic layer was separated and concentrated in vacuo to give colorless oil. The isomers was separated by SFC (Method 12% MeOH on OJ-H column) to give major isomer Intermediate 12A (colorless oil, 2.5 g, 6.84 mmol, 51.8% yield). LC-MS Anal. Calc'd for $C_{20}H_{22}F_3NO_2$ 365.16, found [M+H]366.1. $T_r$=092 min (Method A). $^1$H NMR (400 MHz, chloroform-d) δ 8.96 (d, J=4.6 Hz, 1H), 8.36 (s, 1H), 8.24 (d, J=8.8 Hz, 1H), 7.88 (dd, J=8.8, 1.8 Hz, 1H), 7.43 (d, J=4.6 Hz, 1H), 4.18 (q, J=7.0 Hz, 2H), 3.46-3.31 (m, 1H), 2.57-2.43 (m, 3H), 1.99-1.72 (m, 8H), 1.29 (t, J=7.0 Hz, 3H).

12B. Ethyl 3-methoxy-2-((1s,4s)-4-(6-(trifluoromethyl)quinolin-4-yl)cyclohexyl) propanoate To the flask containing THF (10 mL) was added LDA solution (1.5 M solution in cyclohexane) (3.65 mL, 5.47 mmol) at −78° C., followed by addition of 1,3-dimethyltetrahydropyrimidin-2(1H)-one (0.4 mL, 3.3 mmol) and a solution of ethyl 2-((1 s,4s)-4-(6-(trifluoromethyl)quinolin-4-yl)cyclohexyl)acetate (0.8 g, 2.189 mmol) in THF (5 mL) dropwise at −78° C. The resulting mixture turned into brown color and was stirred at −78° C. for 1 h, then MOMCl (0.25 mL, 3.28 mmol) was added slowly. The reaction mixture was stirred at −78° C. for 2 h, then stirred at rt for 20 h. The reaction mixture was quenched with water and the resulting mixture was extracted with ethyl acetate. The organic layer was separated and washed with brine, dried over $MgSO_4$. The filtrate was concentrated in vacuo. The residue was dissolved in DCM and purified via a gel flash column chromatography, eluting with 0-50% ethyl acetate in hexane to give Intermediate 12B (light yellow oil, 0.39 g, 0.953 mmol, 43.5% yield). LC-MS Anal. Calc'd for $C_{22}H_{26}F_3NO_3$ 409.18, found [M+H] 410.2. $T_r$=0.96 min (Method A). $^1$H NMR (400 MHz, chloroform-d) δ 8.97 (d, J=4.6 Hz, 1H), 8.36 (s, 1H), 8.24 (d, J=8.8 Hz, 1H), 7.88 (dd, J=8.8, 1.8 Hz, 1H), 7.45 (d, J=4.6 Hz, 1H), 4.22 (dddd, J=18.2, 11.1, 7.1, 3.6 Hz, 2H), 3.76-3.54 (m, 2H), 3.49-3.40 (m, 1H), 3.38-3.35 (m, 3H), 3.06 (ddd, J=11.0, 9.1, 5.0 Hz, 1H), 2.29-1.67 (m, 9H), 1.29 (t, J=7.2 Hz, 3H).

12C. 3-Methoxy-2-((1s,4s)-4-(6-(trifluoromethyl)quinolin-4-yl)cyclohexyl)propanoic Acid To a solution of ethyl 3-methoxy-2-((1s,4s)-4-(6-(trifluoromethyl)quinolin-4-yl)cyclohexyl) propanoate (0.49 g, 1.197 mmol) in THF (6 mL) and MeOH (6 mL) was added LiOH solution (2.0 M solution) (7.2 mL, 14.4 mmol). The reaction mixture was heated at 70° C. for 5 h. The reaction mixture was cooled down and to the mixture was added water and 1 N HCl to adjust pH to 6 and 2 mL of acetic acid was added to adjust pH to 4. White solid precipitated out and the resulting mixture was extracted with ethyl acetate. The organic layer was separated and dried over $MgSO_4$. The filtrate was concentrated in vacuo to give Intermediate 12C (white solid, 0.38 g, 0.996 mmol, 83% yield). Analytical sample was purified by preparative HPLC. LC-MS Anal. Calc'd for $C_{20}H_{22}F_3NO_3$ 381.15, found [M+H] 382.2. $T_r$=0.75 min (Method A). $^1$H NMR (400 MHz, METHANOL-$d_4$) δ 9.07 (d, J=5.3 Hz, 1H), 8.68 (s, 1H), 8.30 (d, J=8.8 Hz, 1H), 8.15 (dd, J=8.9, 1.7 Hz, 1H), 7.91 (d, J=5.3 Hz, 1H), 3.90-3.52 (m, 3H), 3.40-3.34 (m, 3H), 3.07 (ddd, J=11.1, 9.0, 4.8 Hz, 1H), 2.19-1.67 (m, 9H).

12D. 2-Methoxy-1-((1s,4s)-4-(6-(trifluoromethyl)quinolin-4-yl)cyclohexyl)ethan-1-amine To a suspension of 3-methoxy-2-((1s,4s)-4-(6-(trifluoromethyl)quinolin-4-yl)cyclohexyl) propanoic acid (0.26 g, 0.682 mmol) in Toluene (8 mL) were added DPPA (0.18 mL, 0.818 mmol) and TEA (0.15 mL, 1.03 mmol). The reaction mixture in a sealed vial turned into clear solution after addition of TEA. The reaction mixture was heated to 70° C. for 2 h. The reaction mixture was concentrated under reduced pressure. To the residue was added THF (8 mL) and LiOH aqueous solution (2.0 M solution) (1.70 mL, 3.41 mmol) and the resulting mixture was stirred at rt for 18 h. The reaction mixture acidified with 1N HCl and extracted with EtOAc to remove DPPA related impurities. Then the aqueous layer was basified with 1N NaOH and the resulting mixture was extracted with EtOAc 3 times. The basic extracts were combined, dried over $MgSO_4$ and the filtrate was concentrated in vacuo. to give Intermediate 12D (colorless oil, 127 mg, 0.36 mmol, 53% yield). LC-MS Anal. Calc'd for $C_{19}H_{23}F_3N_2O$ 352.18, found [M+H] 353.2. $T_r$=0.61 min (Method A). $^1$H NMR (400 MHz, METHANOL-$d_4$) δ 8.91 (d, J=4.6 Hz, 1H), 8.51 (s, 1H), 8.20 (d, J=8.8 Hz, 1H), 7.96 (dd, J=9.0, 1.8 Hz, 1H), 7.64 (d, J=4.6 Hz, 1H), 3.60 (dd, J=9.1, 3.0 Hz, 2H), 3.39 (s, 3H), 3.30-3.09 (m, 1H), 2.14-1.60 (m, 10H).

Example 12, two Isomers 6-Methoxy-N-(2-methoxy-1-((1s,4s)-4-(6-(trifluoromethyl)quinolin-4-yl)cyclohexyl)ethyl)nicotinamide To a solution of 6-methoxynicotinic acid (17 mg, 0.111 mmol) in DMF (1 mL) was added HATU (42 mg, 0.111 mmol). The reaction mixture was stirred at rt for 5 min, followed by addition of a solution of 2-methoxy-1-((1s,4s)-4-(6-(trifluoromethyl)quinolin-4-yl)cyclohexyl)ethanamine (30 mg, 0.085 mmol) in THF (0.4 mL) and DIPEA (0.030 mL, 0.170 mmol). The reaction mixture was stirred at rt for 1 h. The reaction mixture was concentrated in vacuo to small amount and dissolved in MeOH, filtered, and purified via preparative HPLC to give a mixture of two isomers. The isomers were further separated by preparative SFC (Method E) to give two isolates. (absolute stereochemistry was not determined).

First elute (11 mg, 0.022 mmol, 26.2% yield). LC-MS Anal. Calc'd for $C_{26}H_{28}F_3N_3O_3$ 487.21, found [M+H] 488.3. $T_r$=1.55 min (Method B). $T_r$=10.8 min over 20 min run (Method F). $^1$H NMR (500 MHz, DMSO-$d_6$) δ 9.00 (d, J=4.5 Hz, 1H), 8.67 (d, J=2.1 Hz, 1H), 8.55 (s, 1H), 8.30 (d, J=8.9 Hz, 1H), 8.23 (d, J=8.8 Hz, 1H), 8.14 (dd, J=8.8, 2.3 Hz, 1H), 7.99 (d, J=8.8 Hz, 1H), 7.59 (d, J=4.5 Hz, 1H), 6.87 (d, J=8.7 Hz, 1H), 4.53 (t, J=9.8 Hz, 1H), 3.88 (s, 3H), 3.52 (br. s., 1H), 3.27 (s, 3H), 2.54 (s, 4H), 2.02 (d, J=10.6 Hz, 1H), 1.92-1.54 (m, 8H).

Second elute (10 mg, 0.020 mmol, 23.9% yield). LC-MS Anal. Calc'd for $C_{26}H_{28}F_3N_3O_3$ 487.21, found [M+H] 488.3. $T_r$=1.55 min (Method B). $T_r$=13.2 min over 20 min run (Method F). $^1$H NMR (500 MHz, DMSO-$d_6$) δ 9.00 (d, J=4.5 Hz, 1H), 8.67 (d, J=2.1 Hz, 1H), 8.55 (s, 1H), 8.30 (d, J=8.9 Hz, 1H), 8.23 (d, J=8.8 Hz, 1H), 8.14 (dd, J=8.8, 2.3 Hz, 1H), 7.99 (d, J=8.8 Hz, 1H), 7.59 (d, J=4.5 Hz, 1H), 6.87 (d, J=8.7 Hz, 1H), 4.53 (t, J=9.8 Hz, 1H), 3.88 (s, 3H), 3.52 (br. s., 1H), 3.27 (s, 3H), 2.54 (s, 4H), 2.02 (d, J=10.6 Hz, 1H), 1.92-1.54 (m, 8H).

Example 13, Four Isomers

N-(2-Ethoxy-1-(4-(6-(trifluoromethyl)quinolin-4-yl)cyclohexyl)ethyl)-6-methoxynicotinamide

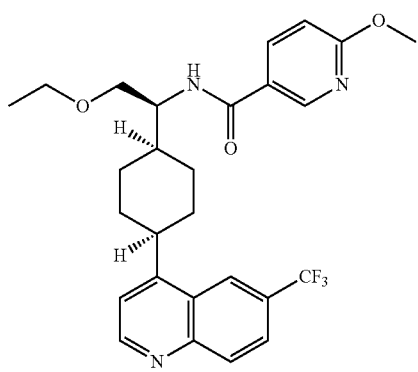

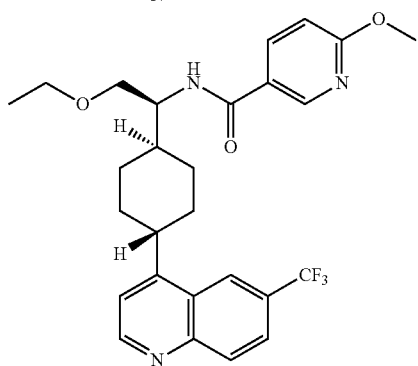

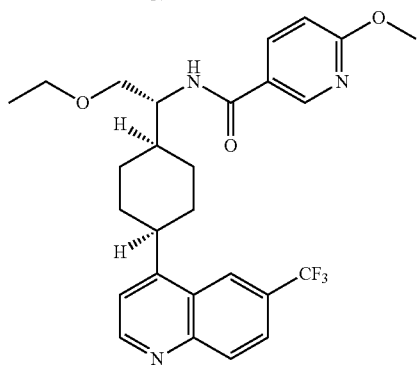

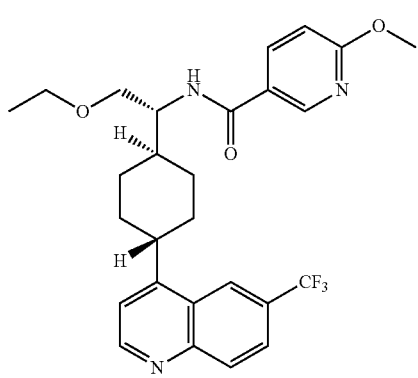

13A. Ethyl 3-ethoxy-2-(4-(6-(trifluoromethyl)quinolin-4-yl)cyclohex-3-en-1-yl)propanoate To a flask containing THF (15 mL) was added LDA (1.5 M solution in cyclohexane) (8.44 mL, 12.66 mmol) and DMPU (0.995 mL, 8.26 mmol) at −78° C., followed by addition of a solution of ethyl 2-(4-(6-(trifluoromethyl)quinolin-4-yl)cyclohex-3-en-1-yl)acetate (2.0 g, 5.50 mmol) in THF (15 mL) dropwise at −78° C. The resulting mixture was stirred at −78° C. for 1 h, then chloromethyl ethyl ether (1.030 mL, 11.01 mmol) was added. The reaction mixture was stirred at −78° C. for 1 h, then warmed up to rt for 3 h. More chloromethyl ethyl ether (1.030 mL, 11.01 mmol) (0.3 mL) was added and the reaction mixture was stirred at −78° C. for another 1 h and warmed up gradually over night. To the reaction mixture was added NH$_4$Cl solution and the resulting mixture was extracted with ethyl acetate twice. The organic layer was separated and washed with saturated NaHCO$_3$ solution, dried over MgSO$_4$. The filtrate was concentrated in vacuo. The residue was dissolved in DCM and purified by silica gel flash chromatography, eluting with 0-50% ethyl acetate in hexane to give Intermediate 13A (brown solid, 0.55 g, 1.305 mmol, 24% yield). LC-MS Anal. Calc'd for C$_{23}$H$_{26}$F$_3$NO$_3$ 421.19 found [M+H] 422.1. T$_r$=0.95 min (Method A). $^1$H NMR (400 MHz, chloroform-d) δ 8.94 (d, J=4.6 Hz, 1H), 8.30 (s, 1H), 8.22 (d, J=8.8 Hz, 1H), 7.87 (dd, J=8.8, 2.0 Hz, 1H), 7.28 (m, 1H), 5.93-5.81 (m, 1H), 4.33-4.19 (m, 2H), 3.83-3.64 (m, 2H), 3.60-3.43 (m, 2H), 2.84-1.59 (m, 8H), 1.33 (td, J=7.2, 0.9 Hz, 3H), 1.24-1.13 (m, 3H).

13B. Ethyl 3-ethoxy-2-(4-(6-(trifluoromethyl)quinolin-4-yl)cyclohexyl)propanoate The reaction mixture of ethyl 3-ethoxy-2-(4-(6-(trifluoromethyl)quinolin-4-yl)cyclohex-3-en-1-yl)propanoate (0.55 g, 1.305 mmol) and Pd—C (0.056 g, 0.052 mmol) in MeOH (15 mL) was evacuated and then hydrogenated with hydrogen balloon for 8 h. The reaction mixture was filtered through a celite pad and the pad was washed with MeOH, ethyl acetate. The filtrate was concentrated in vacuo to give Intermediate 13B (light brown solid, 0.5 g, 1.18 mmol, 90% yield). LC-MS Anal. Calc'd for C$_{23}$H$_{28}$F$_3$NO$_3$ 423.20 found [M+H] 424.2. T$_r$=0.94 min (Method A).

13C. 3-Ethoxy-2-(4-(6-(trifluoromethyl)quinolin-4-yl)cyclohexyl)propanoic Acid To the reaction mixture of ethyl 3-ethoxy-2-(4-(6-(trifluoromethyl)quinolin-4-yl)cyclohexyl)propanoate (0.55 g, 1.299 mmol) in THF (8 mL) and MeOH (5 mL) was added LiOH aqueous solution (2 M) (5.20 mL, 10.39 mmol). The reaction mixture was stirred at rt over weekend. To the reaction mixture was added more LiOH aqueous solution (2M) (5.20 mL, 10.39 mmol) and THF (3 mL). The resulting mixture was stirred at rt for another 25 h. To the reaction mixture was added 1 N HCl solution to adjust pH to 6 and added HOAc (1 mL) to adjust pH to 4-5. The resulting mixture was extracted with ethyl acetate twice. The organic layer was separated and dried over MgSO$_4$. The filtrate was concentrated in vacuo to give brown solid, dried on high vacuum over night to give Intermediate 13C (brown solid, 0.5 g, 1.264 mmol, 97% yield). LC-MS Anal. Calc'd for C$_{21}$H$_{24}$F$_3$NO$_3$ 395.17 found [M+H] 396.2. T$_r$=0.77-0.78 min (Method A).

13D. 2-Ethoxy-1-(4-(6-(trifluoromethyl)quinolin-4-yl)cyclohexyl)ethan-1-amine To a suspension of 3-ethoxy-2-(4-(6-(trifluoromethyl)quinolin-4-yl)cyclohexyl)propanoic acid (0.27 g, 0.683 mmol) in Toluene (10 mL) were added TEA (0.19 mL, 1.366 mmol) and DPPA (0.18 mL, 0.96 mmol). The reaction mixture was stirred at 70° C. for 4 h. The reaction mixture was concentrated in vacuo. The residue was dissolved in THF (5 mL) and to the mixture was added LiOH aqueous solution (2 M solution) (2.73 mL, 5.46 mmol). The reaction mixture was stirred at rt over night. The reaction mixture was diluted with water and 1 N HCl solution. The organic layer was separated. To the aqueous layer was added 1 N NaOH solution to adjust pH to 9-10 and the resulting mixture was extracted with ethyl acetate three times. The organic layer was separated and dried over $MgSO_4$. The filtrate was concentrated in vacuo to give Intermediate 13D (light yellow oily solid, 108 mg, 0.295 mmol, 43% yield). LC-MS Anal. Calc'd for $C_{20}H_{25}F_3N_2O$ 366.19, found [M+H] 367.1. $T_r$=0.63 min, 0.65 min (Method A).

Example 13, Four Isomers, N-(2-Ethoxy-1-(4-(6-(trifluoromethyl)quinolin-4-yl)cyclohexyl)ethyl)-6-methoxynicotinamide To a solution of 6-methoxynicotinic acid (20.5 mg, 0.134 mmol) in DMF (1 mL) was added HATU (47.2 mg, 0.124 mmol). The reaction mixture was stirred at rt for 5 min, followed by addition of a solution of 2-ethoxy-1-(4-(6-(trifluoromethyl)quinolin-4-yl)cyclohexyl)ethanamine (35 mg, 0.096 mmol) in THF (1 mL) and DIPEA (0.050 mL, 0.287 mmol). The reaction mixture was stirred at rt for 1 h. The reaction mixture was concentrated in vacuo and the residue was dissolved in MeOH, filtered, and purified via preparative HPLC to give a mixture of four isomers. The isomers were further separated by preparative SFC (Method 10% MeOH-DEA on OD) to give four isolates. (absolute stereochemistry was not determined).

First elute (5 mg, 9.87 µmol, 10.3% yield). LC-MS Anal. Calc'd for $C_{27}H_{30}F_3N_3O_3$ 501.22, found [M+H] 502.0. $T_r$=1.75 min (Method B). $T_r$=4.5 min over 9 min run (Method 10% MeOH-DEA on OD). $^1$H NMR (500 MHz, DMSO-$d_6$) δ 9.01 (d, J=4.3 Hz, 1H), 8.68 (s, 1H), 8.55 (s, 1H), 8.23 (d, J=8.5 Hz, 2H), 8.14 (d, J=8.9 Hz, 1H), 8.00 (d, J=8.5 Hz, 1H), 7.59 (d, J=4.3 Hz, 1H), 6.88 (d, J=8.5 Hz, 1H), 4.51 (br. s., 1H), 3.89 (s, 3H), 3.66-3.26 (m, 5H), 2.02 (br. s., 1H), 1.94-1.57 (m, 8H), 1.09 (t, J=7.0 Hz, 3H).

Second elute (5.4 mg, 10.5 µmol, 11% yield). LC-MS Anal. Calc'd for $C_{27}H_{30}F_3N_3O_3$ 501.22, found [M+H] 502.0. $T_r$=1.75 min (Method B). $T_r$=5.14 min over 9 min run (Method 10% MeOH-DEA on OD). $^1$H NMR (500 MHz, DMSO-$d_6$) δ 9.01 (d, J=4.3 Hz, 1H), 8.68 (s, 1H), 8.55 (s, 1H), 8.23 (d, J=8.5 Hz, 2H), 8.14 (d, J=8.9 Hz, 1H), 8.00 (d, J=8.5 Hz, 1H), 7.59 (d, J=4.3 Hz, 1H), 6.88 (d, J=8.5 Hz, 1H), 4.51 (br. s., 1H), 3.89 (s, 3H), 3.66-3.26 (m, 5H), 2.02 (br. s., 1H), 1.94-1.57 (m, 8H), 1.09 (t, J=7.0 Hz, 3H).

Third elute (2.4 mg, 4.74 µmol, 5% yield). LC-MS Anal. Calc'd for $C_{27}H_{30}F_3N_3O_3$ 501.22, found [M+H] 502.0. $T_r$=1.75 min (Method B). $T_r$=6.73 min over 9 min run (Method 10% MeOH-DEA on OD). $^1$H NMR (500 MHz, DMSO-$d_6$) δ 8.97 (d, J=4.3 Hz, 1H), 8.70 (br. s., 1H), 8.57 (br. s., 1H), 8.28-8.10 (m, 3H), 7.99 (d, J=8.5 Hz, 1H), 7.57 (d, J=4.3 Hz, 1H), 6.89 (d, J=8.5 Hz, 1H), 4.08 (br. s., 1H), 3.91 (s, 3H), 3.62-3.27 (m, 5H), 1.99-1.84 (m, 4H), 1.73 (br. s., 1H), 1.66-1.37 (m, 4H), 1.10 (t, J=6.9 Hz, 3H).

Fourth elute (5.4 mg, 10.6 µmol, 11.2% yield). LC-MS Anal. Calc'd for $C_{27}H_{30}F_3N_3O_3$ 501.22, found [M+H] 502.0. $T_r$=1.75 min (Method B). $T_r$=7.8 min over 9 min run (Method 10% MeOH-DEA on OD). $^1$H NMR (500 MHz, DMSO-$d_6$) δ 8.97 (d, J=4.3 Hz, 1H), 8.70 (br. s., 1H), 8.57 (br. s., 1H), 8.28-8.10 (m, 3H), 7.99 (d, J=8.5 Hz, 1H), 7.57 (d, J=4.3 Hz, 1H), 6.89 (d, J=8.5 Hz, 1H), 4.08 (br. s., 1H), 3.91 (s, 3H), 3.62-3.27 (m, 5H), 1.99-1.84 (m, 4H), 1.73 (br. s., 1H), 1.66-1.37 (m, 4H), 1.10 (t, J=6.9 Hz, 3H).

Example 14, Two Isomers

N-(1-((1s,4s)-4-(6-Fluoroquinolin-4-yl)cyclohexyl)-2-methoxyethyl)-6-methoxynicotinamide

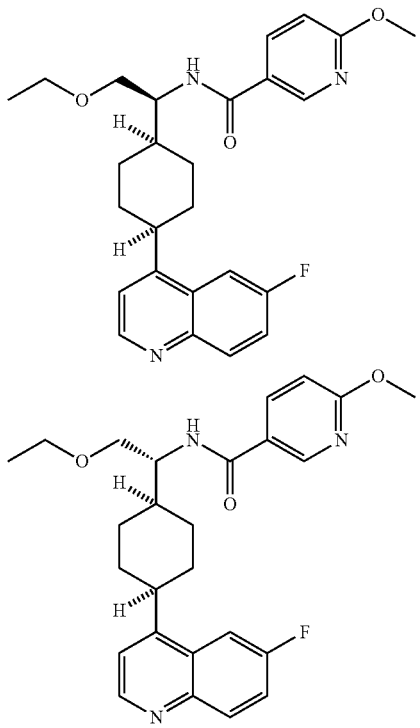

14A. Ethyl 2-(4-(6-fluoroquinolin-4-yl)cyclohex-3-en-1-yl)acetate

Ethyl 2-(4-(4,4,5,5-tetramethyl-1,3,2-dioxaborolan-2-yl)cyclohex-3-en-1-yl)acetate (WO 2016/073774, PCT/US 2015/059316 Intermediate 164E) (5.0 g, 17.00 mmol) was taken up in dioxane (28.3 ml) and water (7.08 ml). 4-chloro-6-fluoroquinoline (2.57 g, 14.15 mmol) was added followed by $K_2CO_3$ (5.87 g, 42.5 mmol). Mixture was bubble with nitrogen gas for 5 minutes before the addition of $Pd(Ph_3P)_4$ (0.327 g, 0.283 mmol). After addition, reaction was vacated and backfilled with $N_2$ three times and then sealed (sealed vial parafilmed) and heated to 100° C. for 16 hours. The reaction was concentrated in vacuo and purified directly via silica gel flash column chromatography to give Intermediate 14A (4.22 g, 13.47 mmol, 95% yield). LC-MS Anal. Calc'd for $C_{19}H_{20}FNO_2$ 313.15, found [M+H] 314.1 $T_r$=0.75 min (Method A). $^1$H NMR (400 MHz, chloroform-d) δ: 8.80 (d, J=4.4 Hz, 1H), 8.10 (dd, J=9.2, 5.6 Hz, 1H), 7.60 (dd, J=10.2, 2.9 Hz, 1H), 7.46 (ddd, J=9.2, 8.1, 2.8 Hz, 1H), 7.19

(d, J=4.4 Hz, 1H), 5.82 (dd, J=2.9, 1.7 Hz, 1H), 4.19 (q, J=7.2 Hz, 2H), 2.60-2.20 (m, 6H), 2.10-1.94 (m, 2H), 1.67-1.51 (m, 1H), 1.37-1.28 (m, 3H).

14B. Ethyl 2-(4-(6-fluoroquinolin-4-yl)cyclohex-3-enyl)-3-methoxypropanoate

To the flask containing THF (8 mL) was added LDA (1.5 M solution in hexane) (4.89 mL, 7.34 mmol) at −78° C., followed by addition of 1,3-dimethyltetrahydropyrimidin-2(1H)-one (0.54 mL, 4.47 mmol) and a solution of ethyl 2-(4-(6-fluoroquinolin-4-yl)cyclohex-3-en-1-yl)acetate (1.0 g, 3.19 mmol) in THF (3 mL) dropwise at −78° C. The resulting mixture turned into green and stirred at −78° C. for 1 h, then MOMCl (0.39 mL, 5.11 mmol) was added slowly. The reaction mixture was stirred at −78° C. for 0.5 h, then warmed up to about −20° C. for 4 h, then warmed to rt over night. The reaction mixture was quenched with water and the resulting mixture was extracted with ethyl acetate. The organic layer was separated and washed with brine, dried over $MgSO_4$. The filtrate was concentrated in vacuo. The residue was dissolved in DCM, purified via silica gel flash column chromatography, eluting with 0-30% ethyl acetate in DCM to give Intermediate 14B (light brown oil, 0.8 g, 2.238 mmol, 70% yield). LC-MS Anal. Calc'd for $C_{21}H_{24}FNO_3$ 357.17, found [M+H] 358.2. $T_r$=0.78 min (Method A). $^1$H NMR (400 MHz, chloroform-d) δ 8.80 (d, J=4.4 Hz, 1H), 8.10 (dd, J=9.2, 5.5 Hz, 1H), 7.60 (dt, J=10.1, 2.9 Hz, 1H), 7.47 (ddd, J=9.1, 8.0, 2.9 Hz, 1H), 7.18 (d, J=4.4 Hz, 1H), 5.97-5.69 (m, 1H), 4.45-4.13 (m, 2H), 3.92-3.59 (m, 2H), 3.39 (s, 3H), 2.83-2.63 (m, 1H), 2.57-1.83 (m, 6H), 1.70-1.59 (m, 1H), 1.33 (td, J=7.2, 1.8 Hz, 3H).

14C. Ethyl 2-((1s,4s)-4-(6-fluoroquinolin-4-yl)cyclohexyl)-3-methoxypropanoate To a solution of ethyl 2-(4-(6-fluoroquinolin-4-yl)cyclohex-3-en-1-yl)-3-methoxypropanoate (1.08 g, 3.02 mmol) in methanol (20 mL) was added Pd—C (10% wt. wet) (0.64 g, 0.30 mmol). The reaction mixture was evacuated and then filled with hydrogen, evacuated again and under hydrogenation with a hydrogen balloon at rt over night. The reaction mixture was filtered through a celite pad and the pad was washed with ethyl acetate and MeOH. The filtrate was concentrated in vacuo. The crude product was separated out for SFC purification (Method: 10% IPA on Waters BEH 2-ethylpyridine column). Fractions with the major product peak were collected and concentrated in vacuo to give Intermediate 14C (colorless oil, 0.44 g, 1.224 mmol, 40.5% yield). The cis configuration was confirmed by NMR experimentals. LC-MS Anal. Calc'd for $C_{21}H_{26}FNO_3$, 359.19, found [M+H] 360.2. $T_r$=0.74 min (Method A). $^1$H NMR (400 MHz, chloroform-d) δ 8.83 (d, J=4.6 Hz, 1H), 8.13 (dd, J=9.2, 5.7 Hz, 1H), 7.65 (dd, J=10.6, 2.6 Hz, 1H), 7.48 (ddd, J=9.2, 7.9, 2.8 Hz, 1H), 7.35 (d, J=4.6 Hz, 1H), 4.22 (dd, J=12.0, 7.2 Hz, 2H), 3.74-3.48 (m, 2H), 3.37 (s, 3H), 3.32-3.19 (m, 1H), 3.06 (ddd, J=10.9, 9.2, 5.0 Hz, 1H), 2.12 (d, J=10.6 Hz, 1H), 1.98-1.64 (m, 8H), 1.29 (t, J=7.2 Hz, 3H).

14D. 2-((1s,4s)-4-(6-Fluoroquinolin-4-yl)cyclohexyl)-3-methoxypropanoic Acid To a solution of ethyl 2-((1s,4s)-4-(6-fluoroquinolin-4-yl)cyclohexyl)-3-methoxypropanoate (0.44 g, 1.22 mmol) in THF (5 mL) and MeOH (5 mL) was added LiOH solution (2.0 m) (3.67 mL, 7.34 mmol). The reaction mixture was stirred at rt over night. To the reaction mixture was added more MeOH (2 mL) and LiOH aqueous solution (2.0 M) (4 mL) and the reaction mixture was heated at 65° C. for 6 h, then stirred at 40° C. over weekend. The reaction mixture was cooled down and diluted with water, and 1 N HCl solution to adjust pH to 4-5 and the resulting mixture was extracted with ethyl acetate twice. The organic layer was separated and dried over $MgSO_4$. The filtrate was concentrated in vacuo to give Intermediate 14D (light brown oil, 0.38 g, 1.147 mmol, 94% yield). LC-MS Anal. Calc'd for $C_{19}H_{22}FNO_3$ 331.15, found [M+H] 332.2. $T_r$=0.62 min (Method A). $^1$H NMR (400 MHz, METHANOL-$d_4$) δ 8.99 (d, J=5.5 Hz, 1H), 8.32-8.16 (m, 2H), 7.95 (d, J=5.5 Hz, 1H), 7.89 (ddd, J=9.2, 7.9, 2.6 Hz, 1H), 3.82-3.54 (m, 3H), 3.36 (s, 3H), 3.07 (ddd, J=11.1, 9.0, 4.8 Hz, 1H), 2.09 (d, J=11.0 Hz, 1H), 2.03-1.74 (m, 8H).

14E. 1-((1s,4s)-4-(6-Fluoroquinolin-4-yl)cyclohexyl)-2-methoxyethan-1-amine

To a suspension of 2-((1s,4s)-4-(6-fluoroquinolin-4-yl)cyclohexyl)-3-methoxypropanoic acid (0.29 g, 0.875 mmol) in Toluene (8 mL) were added DPPA (0.23 mL, 1.05 mmol) and TEA (0.18 mL, 1.31 mmol). The reaction mixture in a sealed vial turned into clear solution after addition of TEA. The reaction mixture was heated to 70° C. for 2 h. The reaction mixture was concentrated under reduced pressure. To the residue was added THF (6 mL) and LiOH aqueous solution (2.0 M solution) (2.2 mL, 4.38 mmol) and the resulting mixture was stirred at rt for 18 h. The reaction mixture was acidified with 1N HCl and extracted with EtOAc to remove DPPA related impurities. Then the aqueous layer was basified with 1N NaOH and extracted with EtOAc 3 times. The basic extracts were combined, dried over $MgSO_4$ and the filtrate was concentrated in vacuo to give Intermediate 14E (colorless oil, 160 mg, 0.529 mmol, 60.5% yield). LC-MS Anal. Calc'd for $C_{18}H_{23}FN_2O$ 302.18, found [M+H] 303.5. $T_r$=0.49 min (Method A).

Example 14, Two Isomers, N-(1-((1s,4s)-4-(6-Fluoroquinolin-4-yl)cyclohexyl)-2-methoxyethyl)-6-methoxynicotinamide To a solution of 6-methoxynicotinic acid (21.0 mg, 0.138 mmol) in DMF (1 mL) was added HATU (52.3 mg, 0.138 mmol). The reaction mixture was stirred at rt for 5 min, followed by addition of a solution of 1-((1s,4s)-4-(6-fluoroquinolin-4-yl)cyclohexyl)-2-methoxyethanamine (32 mg, 0.106 mmol) in THF (0.5 mL) and DIPEA (0.055 mL, 0.317 mmol). The reaction mixture was stirred at rt for 1 h. The reaction mixture was concentrated in vacuo and the residue was dissolved in MeOH, filtered, and purified via preparative HPLC to give a mixture of two isomers. The isomers were further separated by preparative SFC (Method G) to give two isolates. (absolute stereochemistry was not determined). First elute (7.6 mg, 0.017 mmol, 16.3% yield). LC-MS Anal. Calc'd for $C_{25}H_{28}FN_3O_3$ 437.21, found [M+H] 438.3. $T_r$=1.20 min (Method B). $T_r$=2.3 min over 20 min run (Method H). $^1$H NMR (500 MHz, DMSO-$d_6$) δ 8.82 (d, J=4.5 Hz, 1H), 8.67 (d, J=2.0 Hz, 1H), 8.29 (d, J=9.0 Hz, 1H), 8.14 (dd, J=8.8, 2.3 Hz, 1H), 8.08 (dd, J=9.1, 5.8 Hz, 1H), 7.95 (dd, J=10.9, 2.4 Hz, 1H), 7.74-7.59 (m, 1H), 7.46 (d, J=4.5 Hz, 1H), 6.88 (d, J=8.7 Hz, 1H), 4.73-4.32 (m, 1H), 3.89 (s, 3H), 3.53-3.45 (m, 1H), 3.27 (s, 2H), 2.54 (s, 3H), 2.01 (d, J=9.3 Hz, 1H), 1.89-1.53 (m, 8H).

Second elute (7.9 mg, 0.018 mmol, 16.9% yield). LC-MS Anal. Calc'd for $C_{25}H_{28}FN_3O_3$ 437.21, found [M+H] 438.3.

$T_r$=1.20 min (Method B). $T_r$=2.8 min over 20 min run (Method H). $^1$H NMR (500 MHz, DMSO-$d_6$) δ 8.82 (d, J=4.5 Hz, 1H), 8.67 (d, J=2.0 Hz, 1H), 8.29 (d, J=9.0 Hz, 1H), 8.14 (dd, J=8.8, 2.3 Hz, 1H), 8.08 (dd, J=9.1, 5.8 Hz, 1H), 7.95 (dd, J=10.9, 2.4 Hz, 1H), 7.74-7.59 (m, 1H), 7.46 (d, J=4.5 Hz, 1H), 6.88 (d, J=8.7 Hz, 1H), 4.73-4.32 (m, 1H), 3.89 (s, 3H), 3.53-3.45 (m, 1H), 3.27 (s, 2H), 2.54 (s, 3H), 2.01 (d, J=9.3 Hz, 1H), 1.89-1.53 (m, 8H).

Example 15, Two Isomers

N-(1-((1s,4s)-4-(6-Fluoroquinolin-4-yl)cyclohexyl)-2-(2-methoxyethoxy)ethyl)-6-methoxynicotinamide

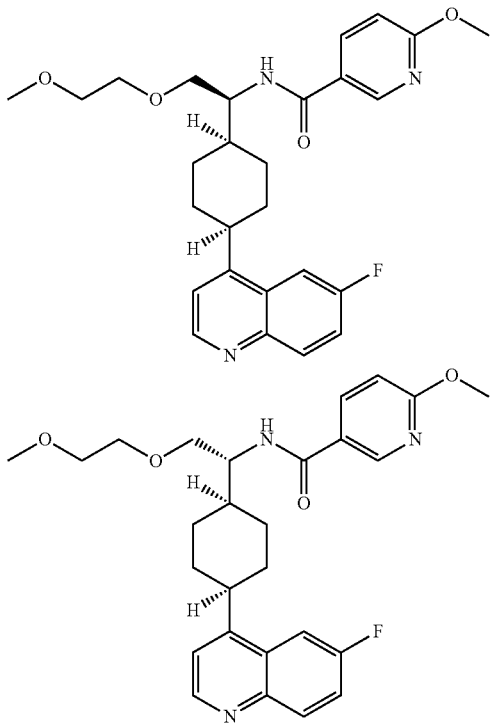

15A. Ethyl 2-((1s,4s)-4-(6-fluoroquinolin-4-yl)cyclohexyl)acetate

The reaction mixture of ethyl 2-(4-(6-fluoroquinolin-4-yl)cyclohex-3-en-1-yl)acetate (1.85 g, 5.90 mmol), ammonium formate (1.303 g, 20.66 mmol) in MeOH (40 mL) was purged with nitrogen stream for 3 min, followed by addition of Pd—C (0.628 g, 0.295 mmol). The resulting mixture was heated at 80° C. for 20 h. The reaction mixture was cooled down and filtered through a celite pad. The filter cake was washed with MeOH. The filtrate was concentrated in vacuo. The residue was diluted with ethyl acetate and water. The organic layer was separated, washed with saturated NaHCO$_3$ solution. The organic layer was dried over MgSO$_4$ and the filtrate was concentrated in vacuo to give a mixture of cis and trans isomers. The isomers were separated by SFC purification (Preparative Columns: Chiralpak AD-H (3×25 cm, 5 m); BPR pressure: 100 bars; Temperature: 40° C.; Flow rate: 160 mL/min; Mobile Phase: CO$_2$/MeOH (81/19); Detector Wavelength: 220 nm) to give the major peak as cis isomer Intermediate 15A (colorless oil, 0.76 g, 2.41 mmol, 40.8% yield). LC-MS Anal. Calc'd for $C_{19}H_{22}FNO_2$ 315.16, found [M+H] 316.2. $T_r$=0.77 min (Method A). $^1$H NMR (400 MHz, chloroform-d) δ 8.84 (d, J=4.6 Hz, 1H), 8.14 (dd, J=9.2, 5.7 Hz, 1H), 7.68 (dd, J=10.6, 2.6 Hz, 1H), 7.49 (ddd, J=9.2, 8.0, 2.6 Hz, 1H), 7.35 (d, J=4.6 Hz, 1H), 4.19 (q, J=7.3 Hz, 2H), 3.40-3.07 (m, 1H), 2.66-2.39 (m, 1H), 2.04-1.69 (m, 9H), 1.40-1.23 (m, 4H).

15B. Ethyl 2-((1s,4s)-4-(6-fluoroquinolin-4-yl)cyclohexyl)-3-(2-methoxyethoxy) propanoate To the flask containing THF (8 mL) was added LDA (1.5 M solution in hexane) (2.79 mL, 4.19 mmol) at −78° C., followed by addition of 1,3-dimethyltetrahydropyrimidin-2(1H)-one (0.482 mL, 4.00 mmol) and a solution of ethyl 2-((1s,4s)-4-(6-fluoroquinolin-4-yl)cyclohexyl)acetate (0.6 g, 1.902 mmol) in THF (8 mL) dropwise at −78° C. The resulting mixture turned into brown and stirred at −78° C. for 1 h, then chloro(methoxy)methane (0.32 g, 4.00 mmol) was added slowly. The reaction mixture was warmed to rt and stirred for 3 h. The reaction mixture was quenched by pouring into water and extracting with EtOAc. The combined organics were washed with brine, dried with MgSO$_4$, filtered and concentrated in vacuo. The residue was purified directly via silica gel flash column chromatography, eluting with 0-50% ethyl acetate in hexane to give Intermediate 15B (oily solid, 0.6 g, 1.487 mmol, 78% yield). LC-MS Anal. Calc'd for $C_{23}H_{30}FNO_4$ 403.22, found [M+H] 404.2. $T_r$=0.80 min (Method A). $^1$H NMR (400 MHz, chloroform-d) δ 8.83 (d, J=4.6 Hz, 1H), 8.13 (dd, J=9.2, 5.7 Hz, 1H), 7.65 (dd, J=10.6, 2.9 Hz, 1H), 7.47 (ddd, J=9.2, 8.0, 2.6 Hz, 1H), 7.35 (d, J=4.4 Hz, 1H), 4.21 (qd, J=7.1, 2.0 Hz, 2H), 3.82-3.48 (m, 6H), 3.38 (s, 3H), 3.32-3.18 (m, 1H), 3.11 (ddd, J=10.9, 9.2, 5.2 Hz, 1H), 2.17-2.06 (m, 1H), 1.94-1.63 (m, 8H), 1.35-1.20 (m, 3H).

15C. 2-((1s,4s)-4-(6-Fluoroquinolin-4-yl)cyclohexyl)-3-(2-methoxyethoxy)propanoic Acid To a solution of ethyl 2-(4-(6-fluoroquinolin-4-yl)cyclohexyl)-3-(2-methoxyethoxy) propanoate (0.4 g, 0.991 mmol) in THF (6 mL) and MeOH (5 mL) was added LiOH aqueous solution (2.0 M solution) (7.44 mL, 14.87 mmol). The resulting mixture was stirred at rt over night. The reaction mixture was heated at 67° C. for 3.5 h. The reaction mixture was cooled down and to the reaction mixture was added ice and 1 N HCl solution to adjust pH to 6-7. The reaction mixture became cloudy and the resulting mixture was extracted with ethyl acetate. The organic layer was separated and dried over MgSO$_4$. The filtrate was concentrated in vacuo give Intermediate 15C (light yellow solid, 0.27 g, 0.719 mmol, 72.5% yield). LC-MS Anal. Calc'd for $C_{21}H_{26}FNO_4$ 375.19, found [M+H] 376.2. $T_r$=0.65 min (Method A). $^1$H NMR (400 MHz, METHANOL-d4) δ 9.00 (d, J=5.5 Hz, 1H), 8.37-8.15 (m, 2H), 7.95 (d, J=5.5 Hz, 1H), 7.89 (ddd, J=9.2, 7.9, 2.6 Hz, 1H), 3.82-3.51 (m, 7H), 3.36 (s, 3H), 3.15-3.01 (m, 1H), 2.13-1.76 (m, 9H).

15D. 1-((1s,4s)-4-(6-Fluoroquinolin-4-yl)cyclohexyl)-2-(2-methoxyethoxy)ethan-1-amine To a suspension of 2-((1s,4s)-4-(6-fluoroquinolin-4-yl)cyclohexyl)-3-(2-methoxyethoxy)propanoic acid (0.16 g, 0.426 mmol) in Toluene (6 mL) were added DPPA (0.111 mL, 0.511 mmol) and triethylamine (0.074 mL, 0.639 mmol). The reaction mixture in a sealed vial turned into clear solution after addition of TEA. The reaction mixture was heated to 70° C. for 2 h. The reaction mixture was concentrated under reduced pressure. To the residue was added THF (8 mL) and lithium hydroxide aqueous solution (2.13 mL, 4.26 mmol) and the resulting mixture was stirred at rt for 1 h. The reaction mixture acidified with 1N HCl and extracted with EtOAc to remove DPPA related impurities. Then the aqueous layer was basified with 1N NaOH and extracted with EtOAc 3 times. The basic extracts were combined, dried over MgSO$_4$ and the filtrate was concentrated in vacuo to give Intermediate 15D (colorless oil, 0.13 g, 0.375 mmol, 88% yield). LC-MS Anal. Calc'd for $C_{20}H_{27}FN_2O_2$ 346.21, found [M+H] 347.2. T$_r$=0.54 min (Method A). $^1$H NMR (400 MHz, METHANOL-d4) δ 9.02 (d, J=5.5 Hz, 1H), 8.28 (dd, J=9.2, 5.1 Hz, 1H), 8.22 (dd, J=10.0, 2.5 Hz, 1H), 7.97 (d, J=5.5 Hz, 1H), 7.94-7.86 (m, 1H), 3.89-3.58 (m, 8H), 3.41 (s, 3H), 2.25-1.74 (m, 9H).

Example 15, Two Isomers N-(1-((1s,4s)-4-(6-Fluoroquinolin-4-yl)cyclohexyl)-2-(2-methoxyethoxy)ethyl)-6-methoxynicotinamide To a solution of 6-methoxynicotinic acid (5.6 mg, 0.036 mmol) in DMF (1.5 mL) was added HATU (13.87 mg, 0.036 mmol). The reaction mixture was stirred at rt for 5 min, followed by addition of a solution of crude 1-((1 s,4s)-4-(6-fluoroquinolin-4-yl)cyclohexyl)-2-(2-methoxyethoxy)ethanamine, TFA (14 mg, 0.024 mmol) in THF (1 mL) and DIPEA (0.025 mL, 0.146 mmol). The resulting mixture was stirred at rt for 1 h. The reaction mixture was concentrated in vacuo and the residue was dissolved in MeOH, filtered, and purified via preparative HPLC to give a mixture of two isomers. The isomers were further separated by preparative SFC (Method I) to give two isolates. (absolute stereochemistry was not determined).

First elute (3.2 mg, 6.58 μmol, 27% yield). LC-MS Anal. Calc'd for $C_{27}H_{32}FN_3O_4$ 481.24, found [M+H] 482.3. T$_r$=1.25 min (Method B). T$_r$=2.42 min over 20 min run (Method J). $^1$H NMR (500 MHz, DMSO-d$_6$) δ 8.82 (d, J=4.4 Hz, 1H), 8.67 (s, 1H), 8.26 (d, J=8.9 Hz, 1H), 8.14 (dd, J=8.7, 1.9 Hz, 1H), 8.08 (dd, J=9.1, 5.9 Hz, 1H), 7.96 (d, J=8.8 Hz, 1H), 7.75-7.60 (m, 1H), 7.46 (d, J=4.4 Hz, 1H), 6.88 (d, J=8.7 Hz, 1H), 4.50 (br. s., 1H), 3.89 (s, 3H), 3.70-3.29 (m, 4H), 3.20 (s, 3H), 2.01 (br. s., 1H), 1.92-1.51 (m, 9H), 2H buried in DMSO.

Second elute (3.0 mg, 6.17 μmol, 25.4% yield). LC-MS Anal. Calc'd for $C_{27}H_{32}FN_3O_4$ 481.24, found [M+H] 482.3. T$_r$=1.25 min (Method B). T$_r$=3.3 min over 20 min run (Method J). $^1$H NMR (500 MHz, DMSO-d$_6$) δ 8.82 (d, J=4.4 Hz, 1H), 8.67 (s, 1H), 8.26 (d, J=8.9 Hz, 1H), 8.14 (dd, J=8.7, 1.9 Hz, 1H), 8.08 (dd, J=9.1, 5.9 Hz, 1H), 7.96 (d, J=8.8 Hz, 1H), 7.75-7.60 (m, 1H), 7.46 (d, J=4.4 Hz, 1H), 6.88 (d, J=8.7 Hz, 1H), 4.50 (br. s., 1H), 3.89 (s, 3H), 3.70-3.29 (m, 4H), 3.20 (s, 3H), 2.01 (br. s., 1H), 1.92-1.51 (m, 9H), 2H buried in DMSO.

Example 16, Two Isomers

N-(1-((1s,4s)-4-(6-Fluoroquinolin-4-yl)cyclohexyl)-2-(2-methoxyethoxy)ethyl)-2-methoxypyrimidine-5-carboxamide

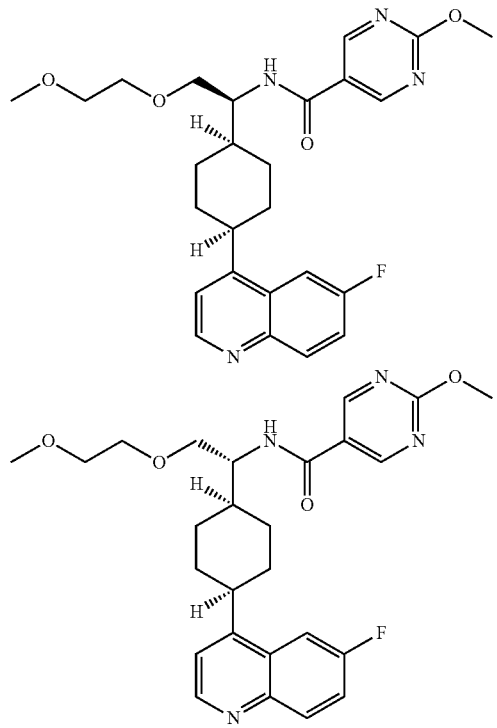

To a solution of 2-methoxypyrimidine-5-carboxylic acid (17.4 mg, 0.113 mmol) in DMF (1.5 mL) was added HATU (42.8 mg, 0.113 mmol). The reaction mixture was stirred at rt for 5 min, then a solution of crude 1-((1s,4s)-4-(6-fluoroquinolin-4-yl)cyclohexyl)-2-(2-methoxyethoxy)ethanamine (30 mg, 0.087 mmol) in THF (1 mL) and DIPEA (0.030 mL, 0.173 mmol) were added. The resulting mixture was stirred at rt for 3 h. The reaction mixture was concentrated in vacuo and the residue was dissolved in MeOH, filtered, and purified via preparative HPLC to give a mixture of two isomers. The isomers were further separated by preparative SFC (Method K) to give two isolates. (absolute stereochemistry was not determined).

First elute (10 mg, 0.021 mmol, 23.7% yield). LC-MS Anal. Calc'd for $C_{26}H_{31}FN_4O_4$ 482.23, found [M+H] 483.0. T$_r$=1.22 min (Method B). T$_r$=9.5 min over 50 min run (Method L). $^1$H NMR (500 MHz, DMSO-d$_6$) δ 9.01 (s, 2H), 8.83 (d, J=4.3 Hz, 1H), 8.44 (d, J=8.8 Hz, 1H), 8.09 (dd, J=8.9, 5.8 Hz, 1H), 7.97 (d, J=9.0 Hz, 1H), 7.66 (t, J=7.4 Hz, 1H), 7.46 (d, J=4.2 Hz, 1H), 4.50 (br. s., 1H), 3.97 (s, 3H), 3.71-3.36 (m, 4H), 3.21 (s, 3H), 2.19-1.47 (m, 10H), 2H buried in DMSO.

Second elute (7.7 mg, 0.016 mmol, 18.1% yield). LC-MS Anal. Calc'd for $C_{26}H_{31}FN_4O_4$ 482.23, found [M+H] 483.0. T$_r$=1.22 min (Method B). T$_r$=39.1 min over 50 min run (Method L). $^1$H NMR (500 MHz, DMSO-d$_6$) δ 9.01 (s, 2H), 8.83 (d, J=4.3 Hz, 1H), 8.44 (d, J=8.8 Hz, 1H), 8.09 (dd, J=8.9, 5.8 Hz, 1H), 7.97 (d, J=9.0 Hz, 1H), 7.66 (t, J=7.4 Hz, 1H), 7.46 (d, J=4.2 Hz, 1H), 4.50 (br. s., 1H), 3.97 (s, 3H), 3.71-3.36 (m, 4H), 3.21 (s, 3H), 2.19-1.47 (m, 10H), 2H buried in DMSO.

Example 17, Four Isomers

6-Methoxy-N-(2-(3-methyloxetan-3-yl)-1-(4-(6-(trifluoromethyl)quinolin-4-yl)cyclohexyl)ethyl) nicotinamide

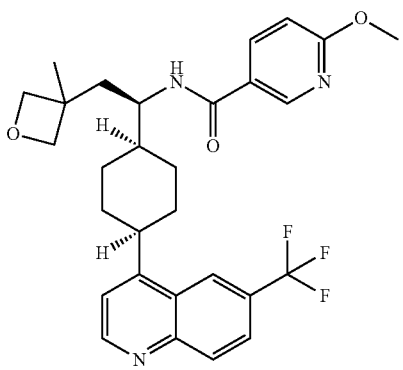

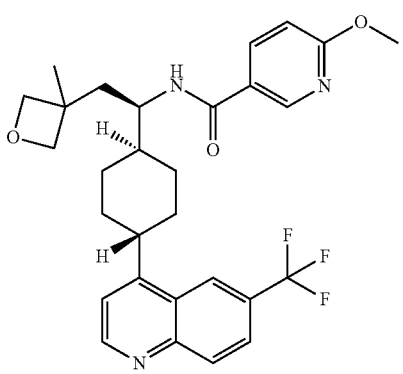

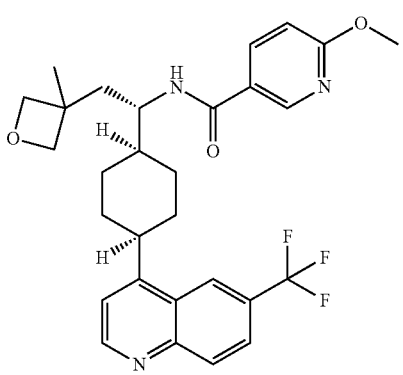

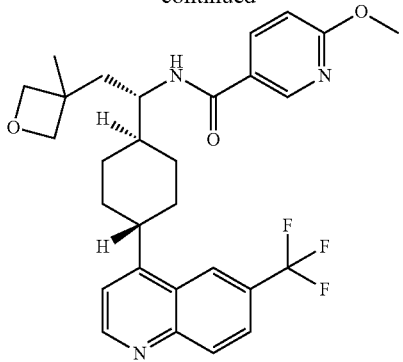

17A. Ethyl 3-(3-methyloxetan-3-yl)-2-(4-(6-(trifluoromethyl)quinolin-4-yl)cyclohexyl) propanoate To the flask containing THF (10 mL) was added LDA (1.5 M solution in hexane) (2.81 mL, 4.21 mmol) at −78° C., followed by addition of 1,3-dimethyltetrahydropyrimidin-2(1H)-one (0.254 mL, 2.107 mmol) and a solution of ethyl 2-((1 s,4s)-4-(6-(trifluoromethyl)quinolin-4-yl)cyclohexyl) acetate (0.7 g, 1.916 mmol) in THF (5 mL) dropwise at −78° C. The resulting mixture turned into brown and stirred at −78° C. for 1 h, then 3-(iodomethyl)-3-methyloxetane (0.609 g, 2.87 mmol) was added slowly. The reaction mixture was stirred at −78° C. for 1 h, then warmed to −20° C. and stirred for 20 h. To the reaction mixture was added more 3-(iodomethyl)-3-methyloxetane (0.1 mL) at −78° C. and the resulting mixture was stored at −20° C. (refridge) over weekend. The reaction mixture was quenched with water and the resulting mixture was extracted with ethyl acetate. The organic layer was separated and washed with brine, dried over MgSO$_4$. The filtrate was concentrated in vacuo and purified via silica gel flash column chromatography, eluting with 0-60% ethyl acetate in hexane to give Intermediate 17A (brown oily solid, 0.34 g, 0.756 mmol, 39.5% yield). LC-MS Anal. Calc'd for $C_{25}H_{30}F_3NO_3$ 449.22, found [M+H] 450.2. T$_r$=0.94 min (Method A). $^1$H NMR (400 MHz, chloroform-d) δ 8.98 (d, J=4.6 Hz, 1H), 8.36 (s, 1H), 8.25 (d, J=8.8 Hz, 1H), 7.88 (dd, J=8.8, 1.8 Hz, 1H), 7.44 (d, J=4.5 Hz, 1H), 4.43 (dd, J=7.9, 5.7 Hz, 2H), 4.35 (d, J=5.6 Hz, 1H), 4.26 (d, J=5.7 Hz, 1H), 4.15 (dtt, J=10.7, 7.1, 3.6 Hz, 2H), 3.62-3.36 (m, 1H), 2.70-2.55 (m, 1H), 2.19 (dd, J=13.9, 11.2 Hz, 1H), 2.07-1.64 (m, 10H), 1.40 (s, 3H), 1.28 (t, J=7.1 Hz, 3H).

17B. 3-(3-Methyloxetan-3-yl)-2-(4-(6-(trifluoromethyl)quinolin-4-yl)cyclohexyl) propanoic acid To a solution of ethyl 3-(3-methyloxetan-3-yl)-2-(4-(6-(trifluoromethyl)quinolin-4-yl)cyclohexyl)propanoate (0.34 g, 0.756 mmol) in THF (3 mL) and MeOH (3 mL) was added LiOH aqueous solution (2.0 M solution) (3.78 mL, 7.56 mmol). The reaction mixture was stirred at rt over night. The reaction mixture was heated at 70° C. over night. To the reaction mixture was added more MeOH (3 mL) and LiOH aqueous solution (2.0 M) (3.78 mL, 7.56 mmol). The reaction mixture was heated at 80° C. for 24 h. The reaction mixture was cooled down and to the mixture was added acetic acid to adjust pH to 5. The reaction mixture was extracted with ethyl acetate and the organic layer was washed with brine, dried over MgSO$_4$. The filtrate was concentrated in vacuo to give Intermediate 17B (yellow solid, 0.29 g, 0.688 mmol, 91% yield). LC-MS Anal. Calc'd for $C_{23}H_{26}F_3NO_3$ 421.19, found [M+H] 422.2. $T_r$=0.78 min (Method A). $^1$H NMR (400 MHz, DMSO-d$_6$) δ 9.00 (d, J=4.6 Hz, 1H), 8.56 (s, 1H), 8.23 (d, J=8.8 Hz, 1H), 8.00 (dd, J=8.8, 1.8 Hz, 1H), 7.62 (d, J=4.6 Hz, 1H), 4.36 (d, J=5.7 Hz, 1H), 4.30 (d, J=5.7 Hz, 1H), 4.20 (d, J=5.5 Hz, 1H), 4.12 (d, J=5.5 Hz, 1H), 3.61 (d, J=7.3 Hz, 1H), 2.05-1.53 (m, 13H), 1.34 (s, 2H).

17C. 2-(3-Methyloxetan-3-yl)-1-(4-(6-(trifluoromethyl)quinolin-4-yl)cyclohexyl)ethan-1-amine To a suspension of 3-(3-methyloxetan-3-yl)-2-((1 s,4s)-4-(6-(trifluoromethyl)quinolin-4-yl)cyclohexyl)propanoic acid (0.21 g, 0.498 mmol) in Toluene (6 mL) were added DPPA (0.13 mL, 0.598 mmol) and triethylamine (0.12 mL, 0.10 mmol). The reaction mixture was heated to 70° C. for 2 h. The reaction mixture was concentrated under reduced pressure. To the residue was added THF (8 mL) and lithium hydroxide aqueous solution (2.5 mL, 5.0 mmol) and the resulting mixture was stirred at rt for 1 h. The reaction mixture acidified with 1N HCl and extracted with EtOAc to remove DPPA related impurities. Then the aqueous layer was basified with 1N NaOH and extracted with EtOAc 3 times. The basic extracts were combined, dried over MgSO$_4$ and the filtrate was concentrated in vacuo to give Intermediate 17C (colorless oil, 0.13 g, 0.331 mmol, 66.5% yield). LC-MS Anal. Calc'd for $C_{22}H_{27}F_3N_2O$ 392.21, found [M+H] 393.2. $T_r$=0.65 min (Method A). $^1$H NMR (400 MHz, methanol-d4) δ 9.19 (br. s., 1H), 8.77 (s, 1H), 8.40 (d, J=8.8 Hz, 1H), 8.25 (d, J=7.7 Hz, 1H), 8.13-8.01 (m, 1H), 4.27-4.12 (m, 1H), 3.83 (br. s., 1H), 3.55-3.38 (m, 3H), 3.04 (d, J=11.9 Hz, 1H), 2.27-1.69 (m, 10H), 1.26-1.14 (m, 3H).

Example 17, Four Isomers

6-Methoxy-N-(2-(3-methyloxetan-3-yl)-1-(4-(6-(trifluoromethyl)quinolin-4-yl)cyclohexyl)ethyl)nicotinamide To a solution of 6-methoxynicotinic acid (15.2 mg, 0.099 mmol) in DMF (1 mL) was added HATU (37.8 mg, 0.099 mmol). The reaction mixture was stirred at rt for 5 min, followed by addition of a solution of crude 2-(3-methyloxetan-3-yl)-1-(4-(6-(trifluoromethyl)quinolin-4-yl)cyclohexyl)ethan-1-amine (30 mg, 0.076 mmol) in THF (1 ML) and DIPEA (0.03 mL, 0.16 mmol). The resulting mixture was stirred at rt for 1 h. The reaction mixture was extracted with ethyl acetate. The organic layer was concentrated in vacuo and the residue was dissolved in MeOH, filtered, and purified via preparative HPLC to give a mixture of isomers. The isomers were further separated by preparative SFC (Method M) to give four isolates. (absolute stereochemistry was not determined).

First elute (3.9 mg, 7.32 μmol, 9.6% yield). LC-MS Anal. Calc'd for $C_{29}H_{32}F_3N_3O_3$ 527.24, found [M+H] 528.1. $T_r$=1.51 min (Method B). $T_r$=7.8 min over 20 min run (Method N). $^1$H NMR (500 MHz, DMSO-d$_6$) δ 9.04 (d, J=4.5 Hz, 1H), 8.64 (d, J=2.0 Hz, 1H), 8.56 (s, 1H), 8.24 (d, J=8.8 Hz, 1H), 8.17-8.07 (m, 2H), 8.01 (br d, J=8.8 Hz, 1H), 7.56 (d, J=4.5 Hz, 1H), 6.90 (d, J=8.7 Hz, 1H), 4.60 (d, J=5.4 Hz, 1H), 4.46 (br d, J=9.8 Hz, 1H), 4.36 (d, J=5.4 Hz, 1H), 4.17 (d, J=5.4 Hz, 1H), 3.93 (d, J=5.3 Hz, 1H), 3.90 (s, 3H), 3.71-3.53 (m, 1H), 2.06-1.54 (m, 11H), 1.39 (s, 3H).

Second elute (6.1 mg, 0.011 mmol, 15.0% yield). LC-MS Anal. Calc'd for $C_{29}H_{32}F_3N_3O_3$ 527.24, found [M+H] 528.1. $T_r$=1.51 min (Method B). $T_r$=9.8 min over 20 min run (Method N). $^1$H NMR (500 MHz, DMSO-d$_6$) δ 9.02 (d, J=4.5 Hz, 1H), 8.56 (s, 1H), 8.35 (d, J=1.8 Hz, 1H), 8.24 (d, J=8.8 Hz, 1H), 8.01 (br d, J=8.8 Hz, 1H), 7.84 (dd, J=8.6, 2.2 Hz, 1H), 7.64 (d, J=4.5 Hz, 1H), 6.88 (d, J=8.5 Hz, 1H), 4.92-4.66 (m, 2H), 3.90 (s, 3H), 3.65 (br s, 1H), 3.37 (br s, 1H), 3.28 (br s, 1H), 3.09 (br d, J=10.7 Hz, 1H), 2.26 (br d, J=9.6 Hz, 1H), 1.96-1.54 (m, 10H), 0.77 (s, 3H).

Third elute (6.2 mg, 0.012 mmol, 15.2% yield). LC-MS Anal. Calc'd for $C_{29}H_{32}F_3N_3O_3$ 527.24, found [M+H] 528.1. $T_r$=1.51 min (Method B). $T_r$=12 min over 20 min run (Method N). $^1$H NMR (500 MHz, DMSO-d$_6$) δ 9.02 (d, J=4.5 Hz, 1H), 8.56 (s, 1H), 8.35 (d, J=1.8 Hz, 1H), 8.24 (d, J=8.8 Hz, 1H), 8.01 (br d, J=8.8 Hz, 1H), 7.84 (dd, J=8.6, 2.2 Hz, 1H), 7.64 (d, J=4.5 Hz, 1H), 6.88 (d, J=8.5 Hz, 1H), 4.92-4.66 (m, 2H), 3.90 (s, 3H), 3.65 (br s, 1H), 3.37 (br s, 1H), 3.28 (br s, 1H), 3.09 (br d, J=10.7 Hz, 1H), 2.26 (br d, J=9.6 Hz, 1H), 1.96-1.54 (m, 10H), 0.77 (s, 3H).

Fourth elute (4.1 mg, 7.31 μmol, 9.6% yield). LC-MS Anal. Calc'd for $C_{29}H_{32}F_3N_3O_3$ 527.24, found [M+H] 528.1. $T_r$=1.51 min (Method B). $T_r$=16.4 min over 20 min run (Method N). $^1$H NMR (500 MHz, DMSO-d$_6$) δ 9.04 (d, J=4.5 Hz, 1H), 8.64 (d, J=2.0 Hz, 1H), 8.56 (s, 1H), 8.24 (d, J=8.8 Hz, 1H), 8.17-8.07 (m, 2H), 8.01 (br d, J=8.8 Hz, 1H), 7.56 (d, J=4.5 Hz, 1H), 6.90 (d, J=8.7 Hz, 1H), 4.60 (d, J=5.4 Hz, 1H), 4.46 (br d, J=9.8 Hz, 1H), 4.36 (d, J=5.4 Hz, 1H), 4.17 (d, J=5.4 Hz, 1H), 3.93 (d, J=5.3 Hz, 1H), 3.90 (s, 3H), 3.71-3.53 (m, 1H), 2.06-1.54 (m, 11H), 1.39 (s, 3H).

Example 18, Two Isomers

6-Methoxy-N-(1-((1s,4s)-4-(8-(trifluoromethyl)quinolin-4-yl)cyclohexyl)propyl)nicotinamide

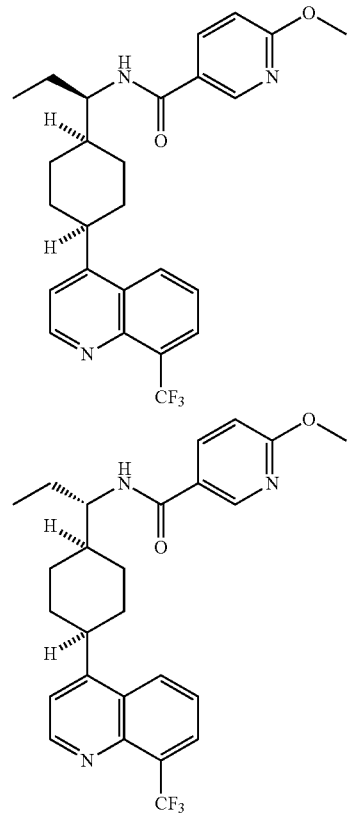

18A. Ethyl 2-(4-(8-(trifluoromethyl)quinolin-4-yl)cyclohex-3-enyl)butanoate

To a solution of 4-chloro-8-(trifluoromethyl)quinoline (0.8 g, 3.45 mmol), ethyl 2-(4-(4,4,5,5-tetramethyl-1,3,2-dioxaborolan-2-yl)cyclohex-3-en-1-yl)butanoate (1.135 g, 3.52 mmol) (Intermediate 24C) in 1,4-Dioxane (25 mL) was added potassium carbonate (1.193 g, 8.64 mmol) and Water (5 mL). The reaction mixture was purged with nitrogen stream for 3 min, followed by addition of Pd(Ph$_3$P)$_4$ (0.16 g, 0.14 mmol). The resulting mixture was heated at 100° C. under nitrogen stream for over night. The reaction mixture was cooled down and diluted with ethyl acetate and saturated NaHCO$_3$ solution. The organic layer was separated, and dried over MgSO$_4$. The filtrate was concentrated in vacuo. The extract was purified via silica gel flash column chromatography, eluting with 0-25% ethyl acetate in hexane to give Intermediate 18A (oil, 0.98 g, 2.504 mmol, 72.5% yield). LC-MS Anal. Calc'd for C$_{22}$H$_{24}$F$_3$NO$_2$ 391.17, found [M+H] 392.1. T$_r$=1.15 min (Method A). $^1$H NMR (400 MHz, chloroform-d) δ 9.00 (d, J=4.4 Hz, 1H), 8.21 (dd, J=7.6, 4.5 Hz, 1H), 8.07 (d, J=7.3 Hz, 1H), 7.56 (t, J=7.8 Hz, 1H), 7.28 (br. s., 1H), 5.82 (br. s., 1H), 4.22 (q, J=7.0 Hz, 2H), 2.59-1.85 (m, 8H), 1.78-1.68 (m, 2H), 1.32 (td, J=7.1, 1.9 Hz, 3H), 0.97 (t, J=7.4 Hz, 3H).

18B. Ethyl 2-(4-(8-(trifluoromethyl)-1,2,3,4-tetrahydroquinolin-4-yl)cyclohexyl) butanoate The reaction mixture of ethyl 2-(4-(8-(trifluoromethyl)quinolin-4-yl)cyclohex-3-en-1-yl)butanoate (0.95 g, 2.427 mmol) in MeOH (20 mL) was purged with nitrogen stream for 3 min, followed by addition of Pd—C (10% wt., wet) (0.155 g, 0.146 mmol). The resulting mixture was evacuated and then hydrogenated with hydrogen balloon at rt for 20 h. The reaction mixture was filtered and the filter cake was washed with MeOH. The filtrate was concentrated in vacuo. and the residue was dissolved in DCM, purified via silica gel flash column chromatography, eluting with 0-15% ethyl acetate in hexane to give Intermediate 18B (oil, 0.85 g, 2.139 mmol, 88% yield). LC-MS Anal. Calc'd for C$_{22}$H$_{30}$F$_3$NO$_2$ 397.22, found [M+H] 398.2. T$_r$=1.22 min (Method A).

18C. Ethyl 2-((1s,4s)-4-(8-(trifluoromethyl)quinolin-4-yl)cyclohexyl)butanoate To a solution of ethyl 2-(4-(8-(trifluoromethyl)-1,2,3,4-tetrahydroquinolin-4-yl)cyclohexyl)butanoate (0.8 g, 2.013 mmol) in Toluene (20 mL) was added DDQ (0.55 g, 2.415 mmol). The dark purple-red reaction mixture was heated at 100° C. for 2 h. The reaction mixture turned into light brown mixture. The reaction mixture was diluted with ethyl acetate and filtered. The filtrate was concentrated in vacuo. and the residue was purified via silica gel flash column chromatography, eluting with 0-20% ethyl acetate in hexane to give product isomer mixture (oil, 0.69 g, 1.754 mmol, 87% yield). The isomers was further separated by SFC (Method 10% MeOH on chiral IC column) to give major isomer as Intermediate 18C (oil, 0.29 g, 0.737 mmol, 36.6% yield). LC-MS Anal. Calc'd for C$_{22}$H$_{26}$F$_3$NO$_2$ 393.19, found [M+H] 394.1. T$_r$=1.20 min (Method A). $^1$H NMR (400 MHz, chloroform-d) δ 9.02 (d, J=4.6 Hz, 1H), 8.30 (d, J=8.6 Hz, 1H), 8.08 (d, J=7.3 Hz, 1H), 7.61 (t, J=7.9 Hz, 1H), 7.46 (d, J=4.6 Hz, 1H), 4.19 (q, J=7.0 Hz, 2H), 3.57-3.30 (m, 1H), 2.64 (td, J=10.8, 4.0 Hz, 1H), 2.17-1.56 (m, 11H), 1.29 (t, J=7.2 Hz, 3H), 0.95 (t, J=7.5 Hz, 3H).

18D. 2-(4-(8-(Trifluoromethyl)quinolin-4-yl)cyclohexyl)butanoic Acid

To a solution of ethyl 2-(4-(8-(trifluoromethyl)quinolin-4-yl)cyclohexyl)butanoate (0.29 g, 0.737 mmol) in THF (5 mL) and MeOH (5 mL) was added LiOH aqueous solution (2.0 M) (3.6 mL, 7.12 mmol). The resulting mixture was heated at 70° C. over night. To the reaction mixture was added more LiOH aqueous solution (2.0 M) (3.56 mL, 7.12 mmol) and THF (4 mL). The reaction mixture was heated at 70° C. for 30 h. The reaction mixture was cooled down and diluted with water, and 1 N HCl solution to adjust pH to 7, then 2 mL of HOAc was added to adjust pH to 5-6. The resulting mixture was extracted with ethyl acetate twice. The organic layer was separated and dried over MgSO$_4$. The filtrate was concentrated in vacuo. to give Intermediate 18D (light brown solid, 0.24 g, 0.657 mmol, 89% yield). LC-MS Anal. Calc'd for C$_{20}$H$_{22}$F$_3$NO$_2$ 365.16, found [M+H] 366.1. T$_r$=0.98 min (Method A). $^1$H NMR (400 MHz, METHANOL-d$_4$) δ 8.90 (d, J=4.8 Hz, 1H), 8.50 (d, J=8.4 Hz, 1H), 8.12 (d, J=7.3 Hz, 1H), 7.71 (t, J=7.9 Hz, 1H), 7.60 (d, J=4.8 Hz, 1H), 3.62-3.49 (m, 1H), 2.73-2.59 (m, 1H), 1.98-1.34 (m, 11H), 0.98 (t, J=7.4 Hz, 3H).

18E. 1-((1s,4s)-4-(8-(Trifluoromethyl)quinolin-4-yl)cyclohexyl)propan-1-amine To a solution of 2-(4-(8-(trifluoromethyl)quinolin-4-yl)cyclohexyl)butanoic acid (0.18 g, 0.493 mmol) in Toluene (6 mL) were added TEA (0.137 mL, 0.985 mmol) and DPPA (0.133 mL, 0.616 mmol). The reaction mixture was heated at 70° C. for 1.5 h. The reaction mixture was concentrated in vacuo. The residue was dissolved in THF (5 mL) and LiOH aqueous solution (2.0 M solution) (1.23 mL, 2.46 mmol) was added to the mixture. The resulting reaction mixture was stirred at rt for 2 h. To the reaction mixture was added water and 1 N HCl solution to adjust pH to 1. The resulting mixture was extracted with ethyl acetate. The aqueous layer was basified with 1 N NaOH solution to adjust pH to 11 and the resulting mixture was extracted with ethyl acetate two times and the organic layer was separated and dried over MgSO$_4$. The filtrate was concentrated in vacuo to give Intermediate 18E (colorless oil, 95 mg, 0.282 mmol, 57.2% yield). LC-MS Anal. Calc'd for C$_{19}$H$_{23}$F$_3$N$_2$ 336.18, found [M+H] 337.2. T$_r$=0.76 min (Method A). 1H NMR (400 MHz, chloroform-d) δ 9.01 (d, J=4.6 Hz, 1H), 8.31 (d, J=8.6 Hz, 1H), 8.08 (d, J=7.3 Hz, 1H), 7.61 (t, J=7.9 Hz, 1H), 7.45 (d, J=4.6 Hz, 1H), 3.55-3.45 (m, 1H), 2.90 (td, J=8.6, 3.2 Hz, 1H), 2.18-1.54 (m, 10H), 1.32-1.18 (m, 1H), 1.00 (t, J=7.4 Hz, 3H).

Example 18, Two Isomers 6-Methoxy-N-(1-((1s,4s)-4-(8-(trifluoromethyl)quinolin-4-yl)cyclohexyl)propyl)nicotinamide To a solution of 6-methoxynicotinic acid (21.2 mg, 0.138 mmol) in DMF (1 mL) was added HATU (52.6 mg, 0.138 mmol). The reaction mixture was stirred at rt for 5 min, followed by addition of a solution of 1-((1s,4s)-4-(8-(trifluoromethyl)quinolin-4-yl)cyclohexyl)propan-1-amine (31 mg, 0.092 mmol) in THF (1 mL) and DIPEA (0.03 mL, 0.184 mmol). The reaction mixture was stirred at rt over night. The reaction mixture was concentrated in vacuo and the residue was dissolved in MeOH, filtered, and purified via preparative HPLC to give a mixture of isomers. The isomers were further separated by preparative SFC (Method 40%

MeOH-DEA on IC) to give two isolates. (absolute stereochemistry was not determined).

First elute (14 mg, 0.029 mmol, 31.6% yield). LC-MS Anal. Calc'd for $C_{26}H_{28}F_3N_3O_2$ 471.21, found [M+H] 472.1. $T_r$=2.12 min (Method B). $T_r$=2.71 min over 10 min run (Method 40% MeOH-DEA on IC). $^1$H NMR (500 MHz, DMSO-$d_6$) δ 8.98 (d, J=4.1 Hz, 1H), 8.68 (s, 1H), 8.55 (d, J=8.5 Hz, 1H), 8.31-8.01 (m, 3H), 7.75 (t, J=7.8 Hz, 1H), 7.58 (d, J=4.1 Hz, 1H), 6.88 (d, J=8.6 Hz, 1H), 4.30 (d, J=9.6 Hz, 1H), 3.89 (s, 3H), 3.62-3.35 (m, 1H), 1.99-1.56 (m, 10H), 1.48-1.29 (m, 1H), 0.88 (t, J=7.0 Hz, 3H).

Second elute (13.9 mg, 0.029 mmol, 31.7% yield). LC-MS Anal. Calc'd for $C_{26}H_{28}F_3N_3O_2$ 471.21, found [M+H] 472.1. $T_r$=2.12 min (Method B). $T_r$=4.24 min over 10 min run (Method 40% MeOH-DEA on IC). $^1$H NMR (500 MHz, DMSO-$d_6$) δ 8.98 (d, J=4.1 Hz, 1H), 8.68 (s, 1H), 8.55 (d, J=8.5 Hz, 1H), 8.31-8.01 (m, 3H), 7.75 (t, J=7.8 Hz, 1H), 7.58 (d, J=4.1 Hz, 1H), 6.88 (d, J=8.6 Hz, 1H), 4.30 (d, J=9.6 Hz, 1H), 3.89 (s, 3H), 3.62-3.35 (m, 1H), 1.99-1.56 (m, 10H), 1.48-1.29 (m, 1H), 0.88 (t, J=7.0 Hz, 3H).

Example 19, Two Isomers

6-Methoxy-N-(1-((1s,4s)-4-(7-(trifluoromethyl)quinolin-4-yl)cyclohexyl)propyl)nicotinamide

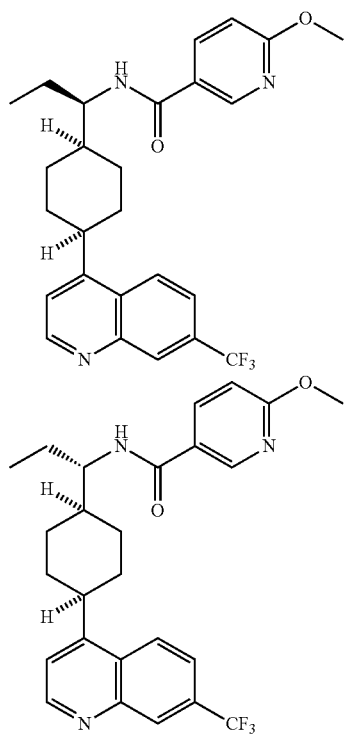

19A. Ethyl 2-(4-(7-(trifluoromethyl)quinolin-4-yl)cyclohex-3-enyl)butanoate

To a solution of 4-chloro-7-(trifluoromethyl)quinoline (0.7 g, 3.02 mmol), ethyl 2-(4-(4,4,5,5-tetramethyl-1,3,2-dioxaborolan-2-yl)cyclohex-3-en-1-yl)butanoate (1.07 g, 3.32 mmol) in 1,4-Dioxane (25 mL) was added potassium carbonate (1.193 g, 8.64 mmol) and Water (5 mL). The reaction mixture was purged with nitrogen stream for 3 min, followed by addition of Pd(Ph$_3$P)$_4$ (0.16 g, 0.14 mmol). The resulting mixture was heated at 100° C. under nitrogen stream for over night. The reaction mixture was cooled down and diluted with ethyl acetate and saturated NaHCO$_3$ solution. The organic layer was separated, and dried over MgSO$_4$. The filtrate was concentrated in vacuo. The extract was purified via silica gel flash column chromatography, eluting with 0-25% ethyl acetate in hexane to give Intermediate 19A (oil, 0.98 g, 2.504 mmol, 83% yield). LC-MS Anal. Calc'd for $C_{22}H_{24}F_3NO_2$ 391.17, found [M+H] 392.1. $T_r$=1.02 min (Method A). $^1$H NMR (400 MHz, chloroform-d) δ 8.93 (d, J=4.6 Hz, 1H), 8.41 (s, 1H), 8.13 (dd, J=8.8, 3.7 Hz, 1H), 7.69 (dd, J=8.8, 1.8 Hz, 1H), 7.31-7.27 (m, 1H), 5.93-5.76 (m, 1H), 4.22 (q, J=7.2 Hz, 2H), 2.62-1.86 (m, 8H), 1.79-1.65 (m, 2H), 1.32 (td, J=7.1, 1.9 Hz, 3H), 0.97 (t, J=7.4 Hz, 3H).

19B. Ethyl 2-((1s,4s)-4-(7-(trifluoromethyl)quinolin-4-yl)cyclohexyl)butanoate

The reaction mixture of ethyl 2-(4-(7-(trifluoromethyl)quinolin-4-yl)cyclohex-3-en-1-yl)butanoate (0.97 g, 2.478 mmol) and Pd—C (0.079 g, 0.074 mmol) (10% wt. wet) in MeOH (30 mL) was evacuated and hydrogenated with hydrogen balloon for 6 h. The reaction mixture was filtered through a celite pad and the pad was washed with MeOH, ethyl acetate. The filtrate was concentrated in vacuo. The residue was separated by SFC (Method 10% MeOH on chiral cellulose-4 column) to give major isomer as Intermediate 19B (oil, 0.46 g, 1.169 mmol, 47.2% yield). LC-MS Anal. Calc'd for $C_{22}H_{26}F_3NO_2$ 393.19, found [M+H] 394.1. $T_r$=0.99 min (Method A). $^1$H NMR (400 MHz, chloroform-d) δ 8.95 (d, J=4.6 Hz, 1H), 8.43 (s, 1H), 8.20 (d, J=9.0 Hz, 1H), 7.73 (dd, J=8.9, 1.9 Hz, 1H), 7.46 (d, J=4.6 Hz, 1H), 4.20 (q, J=7.1 Hz, 2H), 3.43 (br. s., 1H), 2.63 (td, J=10.7, 3.9 Hz, 1H), 2.10-1.58 (m, 11H), 1.29 (t, J=7.2 Hz, 3H), 0.95 (t, J=7.4 Hz, 3H).

19C. 2-((1s,4s)-4-(7-(Trifluoromethyl)quinolin-4-yl)cyclohexyl)butanoic Acid

To the reaction mixture of ethyl 2-((1s,4s)-4-(7-(trifluoromethyl)quinolin-4-yl)cyclohexyl)butanoate (0.45 g, 1.144 mmol) in THF (16 mL) was added LiOH aqueous solution (2.0 M) (8.01 mL, 16.01 mmol). The resulting mixture was heated at 70° C. for overnight. To the reaction mixture was added more LiOH aqueous solution (2.0 M) (3 mL), THF (10 mL) and MeOH (8 mL). The reaction mixture was heated at 82° C. for another 3 days. The reaction mixture was cooled down and diluted with water, acidified with 6 N HCl to adjust pH to 7 and then added acetic acid to adjust pH to 5. The resulting mixture was extracted with ethyl acetate twice. The organic layer was separated, and dried over MgSO$_4$. The filtrate was concentrated in vacuo to give Intermediate 19C (light yellow solid, 0.42 g, 1.126 mmol, 98% yield). LC-MS Anal. Calc'd for $C_{20}H_{22}F_3NO_2$ 365.16, found [M+H] 366.1, $T_r$=0.83 min (Method A). $^1$H NMR (400 MHz, chloroform-d) δ 8.96 (d, J=4.6 Hz, 1H), 8.45 (s, 1H), 8.20 (d, J=9.0 Hz, 1H), 7.74 (dd, J=8.9, 1.9 Hz, 1H), 7.47 (d, J=4.4 Hz, 1H), 3.58-3.39 (m, 1H), 2.68 (td, J=10.6, 3.7 Hz, 1H), 2.11-1.25 (m, 14H), 1.02 (t, J=7.4 Hz, 3H).

19D. 1-((1s,4s)-4-(7-(Trifluoromethyl)quinolin-4-yl)cyclohexyl)propan-1-amine

To a solution of 2-((1s,4s)-4-(7-(Trifluoromethyl)quinolin-4-yl)cyclohexyl)butanoic acid (0.27 g, 0.739 mmol) in Toluene (8 mL) were added TEA (0.206 mL, 1.478 mmol) and DPPA (0.20 mL, 0.924 mmol). The reaction mixture was heated at 70° C. for 1.5 h. The reaction mixture was concentrated in vacuo. The residue was dissolved in THF (6 mL) and LiOH aqueous solution (2.0 M solution) (1.9 mL, 3.8 mmol) was added to the mixture. The resulting reaction mixture was stirred at rt for 2 h. To the reaction mixture was added water and 1 N HCl solution to adjust pH to 1. The resulting mixture was extracted with ethyl acetate. The aqueous layer was basified with 1 N NaOH solution to adjust pH to 11 and the resulting mixture was extracted with ethyl acetate two times and the organic layer was separated and dried over MgSO$_4$. The filtrate was concentrated in vacuo to give Intermediate 19D (colorless oil, 0.195 g, 0.58 mmol, 78% yield). LC-MS Anal. Calc'd for $C_{19}H_{23}F_3N_2$ 336.18, found [M+H] 337.2, T$_r$=0.66 min (Method A). $^1$H NMR (400 MHz, chloroform-d) δ 8.94 (d, J=4.6 Hz, 1H), 8.43 (s, 1H), 8.21 (d, J=8.8 Hz, 1H), 7.73 (dd, J=9.0, 1.8 Hz, 1H), 7.45 (d, J=4.4 Hz, 1H), 3.58-3.43 (m, 1H), 2.89 (td, J=8.6, 3.2 Hz, 1H), 2.15-2.02 (m, 1H), 1.96-1.47 (m, 9H), 1.34-1.19 (m, 1H), 1.04-0.96 (m, 3H).

Example 19, Two Isomers 6-Methoxy-N-(1-((1s, 4s)-4-(7-(trifluoromethyl)quinolin-4-yl)cyclohexyl) propyl)nicotinamide To a solution of 6-methoxynicotinic acid (17.8 mg, 0.116 mmol) in DMF (1 mL) was added HATU (44 mg, 0.116 mmol). The reaction mixture was stirred at rt for 5 min, followed by addition of a solution of 1-((1s,4s)-4-(7-(trifluoromethyl)quinolin-4-yl)cyclohexyl)propan-1-amine (30 mg, 0.089 mmol) in THF (0.6 mL) and DIPEA (0.05 mL, 0.27 mmol). The reaction mixture was stirred at rt for 1 h. The reaction mixture was concentrated in vacuo and the residue was dissolved in MeOH, filtered, and purified via preparative HPLC to give a mixture of isomers. The isomers were further separated by preparative SFC (Method 25% MeOH-DEA on IC) to give two isolates. (absolute stereochemistry was not determined).

First elute (12.3 mg, 0.026 mmol, 29% yield). LC-MS Anal. Calc'd for $C_{26}H_{28}F_3N_3O_2$ 471.21, found [M+H] 472.3. T$_r$=1.79 min (Method B). T$_r$=4.20 min over 10 min run (Method 25% MeOH-DEA on IC). $^1$H NMR (500 MHz, DMSO-d$_6$) δ 8.97 (d, J=4.6 Hz, 1H), 8.65 (s, 1H), 8.45 (d, J=9.2 Hz, 1H), 8.34 (s, 1H), 8.12 (d, J=8.8 Hz, 2H), 7.86 (d, J=8.5 Hz, 1H), 7.60 (d, J=4.6 Hz, 1H), 6.87 (d, J=8.9 Hz, 1H), 4.28 (d, J=7.6 Hz, 1H), 3.88 (s, 3H), 3.49 (br. s., 1H), 1.98-1.55 (m, 10H), 1.46-1.30 (m, 1H), 0.87 (t, J=7.2 Hz, 3H).

Second elute (12.6 mg, 0.026 mmol, 29.7% yield). LC-MS Anal. Calc'd for $C_{26}H_{28}F_3N_3O_2$ 471.21, found [M+H] 472.3. T$_r$=1.79 min (Method B). T$_r$=6.68 min over 10 min run (Method 25% MeOH-DEA on IC). $^1$H NMR (500 MHz, DMSO-d$_6$) δ 8.97 (d, J=4.6 Hz, 1H), 8.65 (s, 1H), 8.45 (d, J=9.2 Hz, 1H), 8.34 (s, 1H), 8.12 (d, J=8.8 Hz, 2H), 7.86 (d, J=8.5 Hz, 1H), 7.60 (d, J=4.6 Hz, 1H), 6.87 (d, J=8.9 Hz, 1H), 4.28 (d, J=7.6 Hz, 1H), 3.88 (s, 3H), 3.49 (br. s., 1H), 1.98-1.55 (m, 10H), 1.46-1.30 (m, 1H), 0.87 (t, J=7.2 Hz, 3H).

Example 20, Four Isomers

6-Methoxy-N-(1-(4-(quinolin-3-yl)cyclohexyl)propyl)nicotinamide

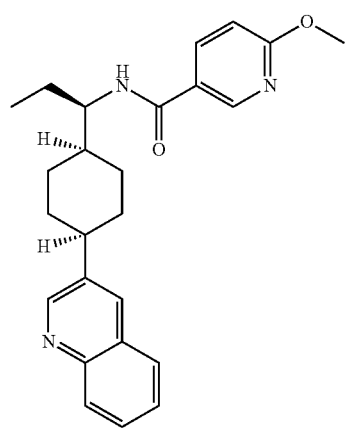

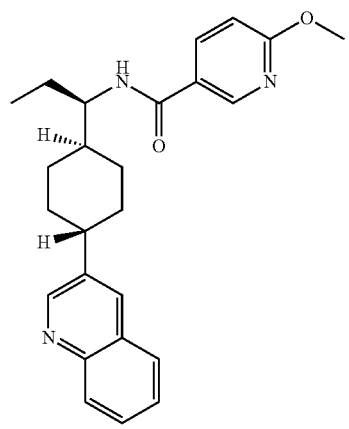

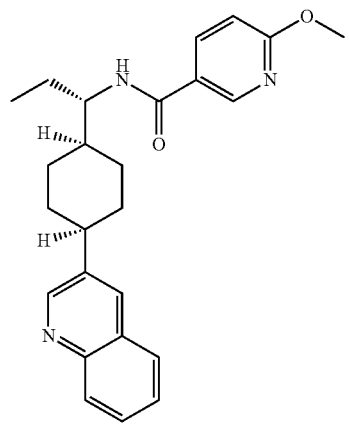

-continued

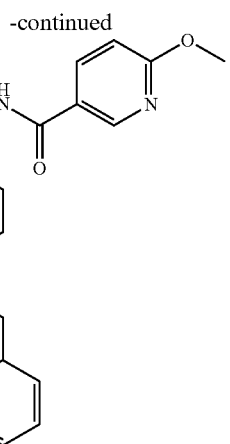

To a solution of 6-methoxynicotinic acid (29.7 mg, 0.194 mmol) in DMF (1 mL) was added HATU (73.7 mg, 0.194 mmol). The reaction mixture was stirred at rt for 10 min, followed by addition of a solution of 1-(4-(quinolin-3-yl)cyclohexyl)propan-1-amine (40 mg, 0.149 mmol) (WO 2016/073774, PCT/US 2015/059316 Intermediate 200 E) in THF (1 mL) and DIPEA (0.052 mL, 0.298 mmol). The resulting mixture was a stirred at rt for 1 h. The reaction mixture was concentrated in vacuo. The residue was the residue was dissolved in MeOH, filtered, and purified via preparative HPLC to give a mixture of isomers. The isomers were further separated by preparative SFC (17% MeOH-DEA on OJ) to give four isolates (absolute stereochemistry was not determined).

First elute (8.9 mg, 0.021 mmol, 14.4% yield). LC-MS Anal. Calc'd for $C_{25}H_{29}N_3O_2$ 403.23, found [M+H] 404.3, $T_r$=1.31 min (Method B). $T_r$=1.76 min over 10 min run (17% MeOH-MeCN-DEA on OJ). $^1$H NMR (500 MHz, DMSO-d6) δ 8.82 (s, 1H), 8.63 (s, 1H), 8.16 (s, 1H), 8.09 (d, J=8.5 Hz, 2H), 7.95 (dd, J=13.0, 8.4 Hz, 2H), 7.69 (t, J=7.5 Hz, 1H), 7.57 (t, J=7.5 Hz, 1H), 6.85 (d, J=8.5 Hz, 1H), 4.19 (d, J=7.9 Hz, 1H), 3.88 (s, 3H), 2.89 (br. s., 1H), 1.97-1.61 (m, 9H), 1.54 (br. s., 1H), 1.45-1.28 (m, 1H), 0.86 (t, J=7.2 Hz, 3H).

Second elute (9.2 mg, 0.022 mmol, 14.8% yield). LC-MS Anal. Calc'd for $C_{25}H_{29}N_3O_2$ 403.23, found [M+H] 404.3, $T_r$=1.31 min (Method B). $T_r$=2.06 min over 10 min run (17% MeOH-MeCN-DEA on OJ). $^1$H NMR (500 MHz, DMSO-d6) δ 8.82 (s, 1H), 8.69 (s, 1H), 8.21-8.10 (m, 2H), 8.07 (d, J=9.2 Hz, 1H), 7.99-7.86 (m, 2H), 7.68 (t, J=7.3 Hz, 1H), 7.56 (t, J=7.5 Hz, 1H), 6.89 (d, J=8.5 Hz, 1H), 3.90 (s, 3H), 3.80 (br. s., 1H), 2.77-2.63 (m, 1H), 2.01-1.82 (m, 4H), 1.72-1.44 (m, 5H), 1.31-1.15 (m, 2H), 0.87 (t, J=7.2 Hz, 3H).

Third elute (8.1 mg, 0.020 mmol, 13.3% yield). LC-MS Anal. Calc'd for $C_{25}H_{29}N_3O_2$ 403.23, found [M+H] 404.3, $T_r$=1.31 min (Method B). $T_r$=3.42 min over 10 min run (17% MeOH-MeCN-DEA on OJ). $^1$H NMR (500 MHz, DMSO-d6) δ 8.82 (s, 1H), 8.63 (s, 1H), 8.16 (s, 1H), 8.09 (d, J=8.5 Hz, 2H), 7.95 (dd, J=13.0, 8.4 Hz, 2H), 7.69 (t, J=7.5 Hz, 1H), 7.57 (t, J=7.5 Hz, 1H), 6.85 (d, J=8.5 Hz, 1H), 4.19 (d, J=7.9 Hz, 1H), 3.88 (s, 3H), 2.89 (br. s., 1H), 1.97-1.61 (m, 9H), 1.54 (br. s., 1H), 1.45-1.28 (m, 1H), 0.86 (t, J=7.2 Hz, 3H).

Fourth elute (9.5 mg, 0.023 mmol, 15.6% yield). LC-MS Anal. Calc'd for $C_{25}H_{29}N_3O_2$ 403.23, found [M+H] 404.3, $T_r$=1.31 min (Method B). $T_r$=5.06 min over 10 min run (17% MeOH-MeCN-DEA on OJ). $^1$H NMR (500 MHz, DMSO-d6) δ 8.82 (s, 1H), 8.69 (s, 1H), 8.21-8.10 (m, 2H), 8.07 (d, J=9.2 Hz, 1H), 7.99-7.86 (m, 2H), 7.68 (t, J=7.3 Hz, 1H), 7.56 (t, J=7.5 Hz, 1H), 6.89 (d, J=8.5 Hz, 1H), 3.90 (s, 3H), 3.80 (br. s., 1H), 2.77-2.63 (m, 1H), 2.01-1.82 (m, 4H), 1.72-1.44 (m, 5H), 1.31-1.15 (m, 2H), 0.87 (t, J=7.2 Hz, 3H).

Example 21, Four Isomers

N-(1-(4-(3-Fluoro-2-methoxypyridin-4-yl)cyclohexyl)propyl)-2-methoxypyrimidine-5-carboxamide

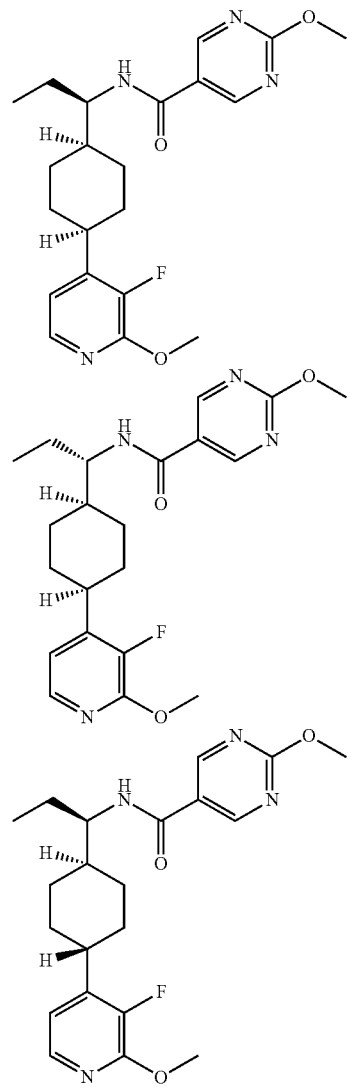

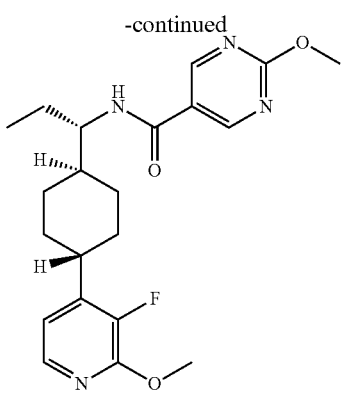

1H), 6.30-6.12 (m, 1H), 4.19 (qd, J=7.1, 5.3 Hz, 2H), 2.60-2.36 (m, 3H), 2.32-1.77 (m, 4H), 1.71-1.62 (m, 2H), 1.51-1.37 (m, 1H), 1.33-1.27 (m, 3H), 0.94 (td, J=7.4, 2.9 Hz, 3H).

21C. Ethyl 2-(4-(3-fluoro-2-methoxypyridin-4-yl)cyclohex-3-en-1-yl)butanoate To a solution of ethyl 2-(4-(2,3-difluoropyridin-4-yl)cyclohex-3-en-1-yl)butanoate (1.1 g, 3.56 mmol) in MeOH (10 mL) was added NaOMe (25% wt in MeOH solution) (3.84 mL, 14.22 mmol). The reaction mixture was stirred at rt over night. To the reaction mixture was added ice water and the resulting mixture was stirred for 5 min and extracted with ethyl acetate. The organic layer was separated and washed with brine, dried over MgSO$_4$. The filtrate was concentrated in vacuo. The residue was dissolved in DCM and hexane, purified by silica gel flash column chromatography, eluting with 0-15% ethyl acetate in hexane to give Intermediate 21C (oil, 1.0 g, 3.11 mmol, 88% yield). LC-MS Anal. Calc'd for $C_{18}H_{24}FNO_3$ 321.17, found [M+H] 322.2. $T_r$=1.10 min (Method A).

21D. Ethyl 2-(4-(3-fluoro-2-methoxypyridin-4-yl)cyclohexyl)butanoate

To a solution of ethyl 2-(4-(3-fluoro-2-methoxypyridin-4-yl)cyclohex-3-en-1-yl)butanoate (1.05 g, 3.27 mmol) in MeOH (20 mL) was added Pd—C(on activated C, 10% wt.) (0.278 g, 0.261 mmol) under nitrogen stream. The reaction mixture was evacuated and then hydrogenated with hydrogen balloon over night. The reaction mixture was filtered through a celite pad and the pad was washed with additional MeOH, ethyl acetate. The filtrate was concentrated in vacuo to give Intermediate 21D as a mixture of isomers (oil, 1.0 g, 3.09 mmol, 95% yield). LC-MS Anal. Calc'd for $C_{18}H_{26}FNO_3$ 323.19, found [M+H]324.2. $T_r$=1.17-1.18 min (Method A).

21E. 2-(4-(3-Fluoro-2-methoxypyridin-4-yl)cyclohexyl)butanoic Acid

To a solution of ethyl 2-(4-(3-fluoro-2-methoxypyridin-4-yl)cyclohexyl)butanoate (1.08 g, 3.34 mmol) in THF (15 mL) and MeOH (15 mL) was added LiOH aqueous solution (3.0 M solution) (22.26 mL, 66.8 mmol). The reaction mixture was heated at 80° C. for 2 days. The reaction mixture was stirred at 40° C. over weekend. The reaction mixture was cooled down and to the reaction mixture was added 1 N HCl solution to adjust pH to about 7 and then added acetic acid to adjust pH to 5. The resulting mixture was extracted with ethyl acetate twice. The organic layer was separated, washed with brine, dried over MgSO$_4$. The filtrate was concentrated in vacuo to give colorless oil. It solidified upon standing at rt over night. Intermediate 21E (white solid, 1.0 g, 3.09 mmol, 95% yield). LC-MS Anal. Calc'd for $C_{16}H_{22}FNO_3$ 295.16, found [M+H]296.2. $T_r$=0.91 min (Method A).

21F. 1-(4-(3-Fluoro-2-methoxypyridin-4-yl)cyclohexyl)propan-1-amine

To a solution of 2-(4-(3-fluoro-2-methoxypyridin-4-yl)cyclohexyl)butanoic acid (1.0 g, 3.39 mmol) in Toluene (15 mL) were added TEA (0.755 mL, 5.42 mmol) and DPPA (0.92 mL, 4.23 mmol). The resulting mixture was heated at 70° C. for 2 h. To the reaction mixture was added more TEA

21A. 2,3-Difluoro-4-iodopyridine

To a flask containing THF (35 mL) was added LDA (1.0 M solution in hexane) (26.1 mL, 26.1 mmol) at −78° C., then a solution of 2,3-difluoropyridine (2.5 g, 21.72 mmol) in THF (6 mL) was added dropwise at −78° C. The reaction mixture turned into bright yellow suspension after addition of pyridine. The resulting mixture was stirred at −78° C. for 1 h, then iodine (6.62 g, 26.1 mmol) was added in several batches at −78° C. The reaction mixture was stirred at −78° C. for 1 h. To the reaction mixture was added NH$_4$Cl solution and the reaction mixture was stirred for 10 min. The resulting mixture was extracted with ethyl acetate. The organic layer was separated and washed with saturated NaHCO$_3$ solution, dried over MgSO$_4$. The filtrate was concentrated in vacuo. The extract was purified via silica gel flash column chromatography, eluting with 0-15% ethyl acetate in hexane to give Intermediate 21A (yellow solid, 3.3 g, 13.69 mmol, 63% yield). LC-MS Anal. Calc'd for $C_5H_2F_2IN$ 240.92, found [M+H] 242.1. $T_r$=0.82 min (Method A). $^1$H NMR (499 MHz, chloroform-d) δ 7.68 (dd, J=5.2, 0.9 Hz, 1H), 7.57 (dd, J=5.2, 3.5 Hz, 1H).

21B. Ethyl 2-(4-(2,3-difluoropyridin-4-yl)cyclohex-3-en-1-yl)butanoate

To a solution of 2,3-difluoro-4-iodopyridine (1.0 g, 4.15 mmol)), ethyl 2-(4-(4,4,5,5-tetramethyl-1,3,2-dioxaborolan-2-yl)cyclohex-3-en-1-yl)butanoate (1.404 g, 4.36 mmol) in 1,4-Dioxane (15 mL) and Water (4 mL) was added K$_2$CO$_3$ (1.204 g, 8.71 mmol) in a sealed tube. The reaction mixture was purged with nitrogen stream for 3 min, followed by addition of Pd(Ph$_3$P)$_4$ (0.24 g, 0.207 mmol). The resulting mixture was heated at 90° C. under nitrogen stream over night. The reaction mixture was transferred to a 100 mL flask and to the reaction mixture were added more 2,3-difluoro-4-iodopyridine (0.2 g) and K$_2$CO$_3$ (0.8 g), dioxane (4 mL) and water (1 mL). The reaction mixture was purged with nitrogen stream for 5 min, followed by addition of more Pd(Ph$_3$P)$_4$ (0.3 g) and the resulting mixture was heated at 100° C. for another 5 h. The reaction mixture was cooled down and diluted with ethyl acetate and saturated NaHCO$_3$ solution. The organic layer was separated, and dried over MgSO$_4$. The filtrate was concentrated in vacuo. The residue was purified by silica gel flash column chromatography, eluting with 0-20% ethyl acetate in hexane to give Intermediate 21B (yellow oil, 1.15 g, 3.72 mmol, 90% yield). LC-MS Anal. Calc'd for $C_{17}H_{21}F_2NO_2$ 309.15, found [M+H] 310.2. $T_r$=1.11 min (Method A). $^1$H NMR (499 MHz, chloroform-d) δ 7.86 (d, J=5.2 Hz, 1H), 7.10-6.93 (m, (0.5 mL) and DPPA (0.4 mL) and the resulting mixture was heated at 70° C. for another 1 h. The reaction mixture was concentrated in vacuo. To the residue was added THF (10 mL) and LiOH aqueous solution (3 M solution) (7.90 mL, 23.70 mmol). The resulting mixture was stirred at rt for 18 h. The reaction mixture was diluted with 1 N HCl solution to adjust pH to 2. The resulting mixture was extracted with ethyl acetate to remove DPPA related impurity. The aqueous layer was basified with 1 N NaOH to adjust pH to 9-10 and the resulting mixture was extracted with ethyl acetate three times. The organic layer was combined and dried over $MgSO_4$. The filtrate was concentrated in vacuo to give Intermediate 21F (oil, 0.48 g, 1.802 mmol, 53% yield). LC-MS Anal. Calc'd for $C_{15}H_{23}FN_2O$ 266.18, found [M+H] 267.3. $T_r$=0.67 min (Method A).

Example 21, Four Isomers of N-(1-(4-(3-Fluoro-2-methoxypyridin-4-yl)cyclohexyl)propyl)-2-methoxy-pyrimidine-5-carboxamide To a solution of 2-methoxypyrimidine-5-carboxylic acid (45.1 mg, 0.293 mmol) in DMF (2 mL) was added HATU (111 mg, 0.293 mmol) at rt. The reaction mixture was stirred at rt for 20 min, followed by addition of a solution of 1-(4-(3-fluoro-2-methoxypyridin-4-yl)cyclohexyl)propan-1-amine (60 mg, 0.225 mmol) in THF (1.5 mL) and DIPEA (0.12 mL, 0.68 mmol). The resulting mixture was stirred at rt for 1 h. The reaction mixture was concentrated in vacuo and the residue was dissolved in MeOH, filtered, and purified via preparative HPLC to give a mixture of four isomers. The isomers were further separated by preparative SFC (Method 80% $CO_2$/20% MeOH-0.1% DEA (isocratic) on Chiralpak IC column) to give four isolates.

First elute (14.2 mg, 0.035 mmol, 15.1% yield). LC-MS Anal. Calc'd for $C_{21}H_{27}FN_4O_3$ 402.21, found [M+H] 402.9. $T_r$=6.33 min over 15 min run (Method O). $^1$H NMR (500 MHz, DMSO-$d_6$) δ 9.00 (s, 1H), 8.22 (d, J=8.8 Hz, 1H), 7.90 (d, J=5.2 Hz, 1H), 6.96 (t, J=4.7 Hz, 1H), 4.24 (d, J=9.2 Hz, 1H), 3.97 (s, 3H), 3.90 (s, 3H), 2.92 (br. s., 1H), 1.86-1.55 (m, 8H), 1.50 (br. s., 2H), 1.43-1.30 (m, 1H), 0.87 (t, J=7.3 Hz, 3H).

Second elute (13.8 mg, 0.034 mmol, 15.1% yield). LC-MS Anal. Calc'd for $C_{21}H_{27}FN_4O_3$ 402.21, found [M+H] 402.9. $T_r$=8.11 min over 15 min run (Method O). $^1$H NMR (500 MHz, DMSO-$d_6$) δ 9.00 (s, 1H), 8.22 (d, J=8.8 Hz, 1H), 7.90 (d, J=5.2 Hz, 1H), 6.96 (t, J=4.7 Hz, 1H), 4.24 (d, J=9.2 Hz, 1H), 3.97 (s, 3H), 3.90 (s, 3H), 2.92 (br. s., 1H), 1.86-1.55 (m, 8H), 1.50 (br. s., 2H), 1.43-1.30 (m, 1H), 0.87 (t, J=7.3 Hz, 3H).

Third elute (12.7 mg, 0.031 mmol, 13.9% yield). LC-MS Anal. Calc'd for $C_{21}H_{27}FN_4O_3$ 402.21, found [M+H] 402.9. $T_r$=10.84 min over 15 min run (Method O). $^1$H NMR (500 MHz, DMSO-$d_6$) δ 1H NMR (500 MHz, DMSO-d6) δ 9.00 (s, 1H), 8.20 (d, J=8.9 Hz, 1H), 7.86 (d, J=5.2 Hz, 1H), 6.94 (t, J=4.7 Hz, 1H), 3.97 (s, 3H), 3.89 (s, 3H), 3.77 (d, J=8.5 Hz, 1H), 2.79 (t, J=12.1 Hz, 1H), 1.93-1.72 (m, 4H), 1.69-1.36 (m, 5H), 1.18 (br. s., 2H), 0.85 (t, J=7.2 Hz, 3H).

Fourth elute (12.8 mg, 0.031 mmol, 14% yield). LC-MS Anal. Calc'd for $C_{21}H_{27}FN_4O_3$ 402.21, found [M+H] 402.9. $T_r$=12.01 min over 15 min run (Method O). $^1$H NMR (500 MHz, DMSO-$d_6$) δ 9.00 (s, 1H), 8.20 (d, J=8.9 Hz, 1H), 7.86 (d, J=5.2 Hz, 1H), 6.94 (t, J=4.7 Hz, 1H), 3.97 (s, 3H), 3.89 (s, 3H), 3.77 (d, J=8.5 Hz, 1H), 2.79 (t, J=12.1 Hz, 1H), 1.93-1.72 (m, 4H), 1.69-1.36 (m, 5H), 1.18 (br. s., 2H), 0.85 (t, J=7.2 Hz, 3H).

Examples 22-23

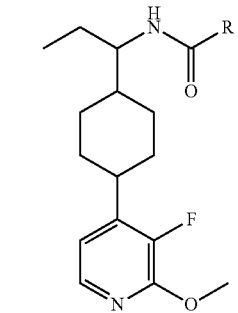

Examples 22-23 were prepared from Intermediate 21F following the procedure for Example 21 using the corresponding acid

| Ex. No. | Name | R | Tr (min) Method B * | [M + H]$^+$ |
|---|---|---|---|---|
| Example 22 | N-(1-(4-(3-Fluoro-2-methoxypyridin-4-yl)cyclohexyl)propyl)-6-methoxynicotinamide | | 1.94 | 402.2 |
| Example 23 | N-(1-(4-(3-Fluoro-2-methoxypyridin-4-yl)cyclohexyl)propyl)-2-methylpyrimidine-5-carboxamide | | 1.65 | 387.3 |

* unless otherwise noted

Example 24, Two Isomers

N-(1-((1s,4s)-4-(3-(Difluoromethyl)-2-methoxypyridin-4-yl)cyclohexyl)propyl)-6-methoxynicotinamide

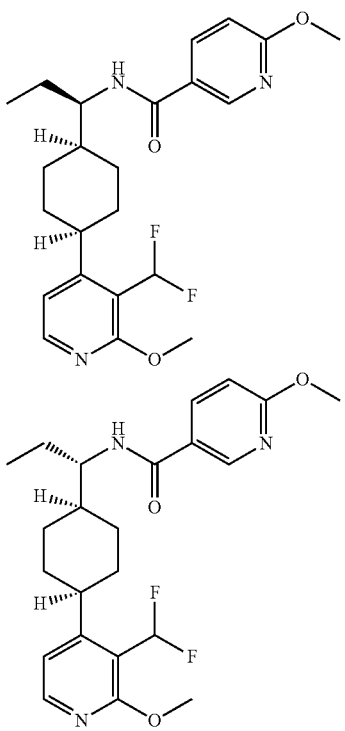

24A. 4-Chloro-2-methoxynicotinaldehyde

To a solution of LDA (1.0 M solution in hexane) (29.3 mL, 29.3 mmol) in THF (45 mL) was added a solution of 4-chloro-2-methoxypyridine (3.5 g, 24.38 mmol) in THF (8 mL) dropwise at −78° C. The reaction mixture turned into light yellow solution and was stirred at −78° C. for 1 h, then DMF (3.78 mL, 48.8 mmol) was added dropwise. The reaction mixture was stirred at −78° C. for 1 h. The reaction mixture was quenched with saturated NH$_4$Cl solution at −78° C. and the resulting mixture was stirred for 10 min and warmed up to rt. The resulting mixture was mixed with saturated NaHCO$_3$ solution and ethyl acetate. The organic layer was separated and washed with saturated NaHCO$_3$ solution, dried over MgSO$_4$. The filtrate was concentrated in vacuo. The residue was dissolved in DCM, purified via silica gel flash column chromatography, eluting with 0-25% ethyl acetate in hexane to give Intermediate 24A (white solid, 2.6 g, 15.15 mmol, 60% yield). LC-MS Anal. Calc'd for C$_7$H$_6$C$_1$NO$_2$ 171.01, found [M+H] 172.1. T$_r$=0.71 min (Method A). $^1$H NMR (499 MHz, chloroform-d) δ 10.47 (s, 1H), 8.20 (d, J=5.5 Hz, 1H), 7.01 (d, J=5.5 Hz, 1H), 4.08 (s, 3H)

24B. 4-Chloro-3-(difluoromethyl)-2-methoxypyridine

To a solution of 4-chloro-2-methoxynicotinaldehyde (2.8 g, 16.32 mmol) in DCM (25 mL) was added DAST (7.55 mL, 57.1 mmol) slowly at 0° C. The reaction mixture was stirred at 0° C. for 1 h, then at rt over night. The reaction mixture was cooled down with ice bath and to the reaction mixture was added ice cold saturated NaHCO$_3$ solution very slowly. Bubbles evoluted. The reaction mixture was stirred for 30 min, then extracted with ethyl acetate. The organic layer was separated and dried over MgSO$_4$. The filtrate was concentrated in vacuo. The residue was dissolved in DCM, purified via silica gel flash column chromatography, eluting with 0-15% ethyl acetate in hexane to give Intermediate 24B (colorless oil, 2.35 g, 12.14 mmol, 82% yield). LC-MS Anal. Calc'd for C$_7$H$_6$ClF$_2$NO 193.01, found [M+H] 194. T$_r$=0.88 min (Method A). $^1$H NMR (499 MHz, chloroform-d) δ 8.13 (dt, J=5.5, 1.1 Hz, 1H), 7.23-6.99 (m, 1H), 6.97 (d, J=5.5 Hz, 1H), 4.03 (s, 3H).

24C. Ethyl 2-(4-(4,4,5,5-tetramethyl-1,3,2-dioxaborolan-2-yl)cyclohex-3-enyl)butanoate To the flask containing THF (136 ml) was added diisopropylamine (5.81 ml, 40.8 mmol) at −78° C., followed by addition of nBuLi (15.64 ml, 39.1 mmol). After 30 minutes, 1,3-dimethyl tetrahydropyrimidin-2(1H)-one (4.92 ml, 40.8 mmol) was added as well as a solution of ethyl 2-(4-(4,4,5,5-tetramethyl-1,3,2-dioxaborolan-2-yl)cyclohex-3-en-1-yl)acetate (10 g, 34.0 mmol) in THF (136 ml) dropwise at −78° C. The resulting mixture turned into brown and stirred at −78° C. for 1 h, then iodoethane (3.26 ml, 40.8 mmol) was added slowly. After 1 hour, the reaction mixture was warmed to rt and stirred for 16 hours. The reaction mixture was quenched with water, extracted with EtOAc. The combined organics were dried with sodium sulfate, filtered, and concentrated in vacuo. The residue was dissolved in DCM, purified via silica gel flash column chromatography, eluting with 0-40% ethyl acetate in hexane to give Intermediate 24C (colorless oil, 9.12 g, 28.3 mmol, 83% yield). LC-MS Anal. Calc'd for C$_{18}$H$_{31}$BO$_4$ 322.23, found [M+H] 323.3. T$_r$=1.21 min (Method A). $^1$H NMR (400 MHz, chloroform-d) δ 6.58-6.47 (m, 1H), 4.21-4.10 (m, 2H), 2.39-2.00 (m, 4H), 1.96-1.60 (m, 5H), 1.31-1.22 (m, 16H), 0.88 (td, J=7.4, 2.1 Hz, 3H).

24D. Ethyl 2-(4-(3-(difluoromethyl)-2-methoxypyridin-4-yl)cyclohex-3-enyl)butanoate To a solution of 4-chloro-3-(difluoromethyl)-2-methoxypyridine (2.0 g, 10.33 mmol)), ethyl 2-(4-(4,4,5,5-tetramethyl-1,3,2-dioxaborolan-2-yl)cyclohex-3-en-1-yl)butanoate (3.50 g, 10.85 mmol) in 1,4-Dioxane (40 mL) were added K$_2$CO$_3$ (3.57 g, 25.8 mmol) and Water (10 mL). The reaction mixture was purged with nitrogen stream for 3 min, followed by addition of Pd(Ph$_3$P)$_4$ (0.836 g, 0.723 mmol). The resulting mixture was heated at 100° C. under nitrogen stream for over night. The reaction mixture was cooled down and diluted with ethyl acetate and saturated NaHCO$_3$ solution. The organic layer was separated, dried over MgSO$_4$. The filtrate was concentrated in vacuo. The residue was dissolved in DCM, purified via silica gel flash column chromatography, eluting with 0-30% ethyl acetate in hexane to give Intermediate 24D (colorless oil, 2.60 g, 7.36 mmol, 71% yield). LC-MS Anal. Calc'd for C$_{19}$H$_{25}$F$_2$NO$_3$ 353.18, found [M+H] 354.2. T$_r$=1.10 min (Method A). $^1$H NMR (400 MHz, chloroform-d) δ 8.13 (d, J=5.1 Hz, 1H), 7.05-6.71 (m, 1H), 6.69 (d, J=5.3 Hz, 1H), 5.87-5.52 (m, 1H), 4.31-4.12 (m, 2H), 4.02 (s, 3H), 2.45-2.14 (m, 4H), 2.09-1.76 (m, 3H), 1.67 (sxt, J=7.4 Hz, 2H), 1.52-1.35 (m, 1H), 1.33-1.25 (m, 3H), 0.93 (td, J=7.4, 2.0 Hz, 3H).

24E. Ethyl 2-((1s,4s)-4-(3-(difluoromethyl)-2-methoxypyridin-4-yl)cyclohexyl)butanoate To a solution of ethyl 2-(4-(3-(difluoromethyl)-2-methoxypyridin-4-yl)cyclohex-3-en-1-yl)butanoate (2.60 g, 7.36 mmol) in MeOH (35 mL) was added Pd—C (10% wt.) (0.313 g, 0.294 mmol). The reaction mixture was evacuated and then filled with hydrogen, evacuated again and hydrogenated at rt with hydrogen balloon for 18 h. The reaction mixture was filtered through a celite pad and washed with additional MeOH, ethyl acetate. The filtrate was concentrated in vacuo to give colorless oil. The sample was submitted for SFC purification (Method P) to give the major peak as the cis product peak 24E (colorless oil, 1.33 g, 3.74 mmol, 50.9% yield). The cis isomer was confirmed by NMR experimentals. LC-MS Anal. Calc'd for $C_{19}H_{27}F_2NO_3$ 355.19, found [M+H] 356.2. $T_r$=1.13 min (Method A). $^1$H NMR (499 MHz, METHANOL-$d_4$) δ 8.17 (d, J=5.5 Hz, 1H), 7.39-7.01 (m, 2H), 4.18 (qd, J=7.1, 0.8 Hz, 2H), 3.95 (s, 3H), 3.28-3.19 (m, 1H), 2.76 (td, J=11.0, 3.8 Hz, 1H), 2.04-1.90 (m, 2H), 1.82-1.44 (m, 9H), 1.27 (t, J=7.1 Hz, 3H), 0.94 (t, J=7.5 Hz, 3H).

24F. 2-((1s,4s)-4-(3-(Difluoromethyl)-2-methoxypyridin-4-yl)cyclohexyl)butanoic Acid To the reaction mixture of ethyl 2-(4-(3-(difluoromethyl)-2-methoxypyridin-4-yl)cyclohexyl)butanoate (0.235 g, 0.661 mmol) in THF (7 mL) and MeOH (5 mL) was added aqueous LiOH solution (2.0 M solution) (4.96 mL, 9.92 mmol). The reaction mixture was heated at 80° C. for 30 h. To the reaction mixture was added more LiOH solution (2.0 M solution) (4.96 mL, 9.92 mmol) and the reaction mixture was heated at 80° C. for another 30 h. The reaction mixture was cooled down and diluted with water. To the mixture was added 1 N HCl solution to adjust pH to 6-7. White solid crashed out and to the mixture was added about 0.5 mL of acetaic acid to adjust pH to 5. The resulting mixture was extracted with ethyl acetate three times. The organic layers were combined and dried over MgSO$_4$. The filtrate was concentrated in vacuo. to give Intermediate 24F (white solid, 0.23 g, 0.646 mmol, 98% yield). LC-MS Anal. Calc'd for $C_{17}H_{23}F_2NO_3$ 327.16, found [M+H] 328.1. $T_r$=1.00 min (Method A). $^1$H NMR (400 MHz, methanol-$d_4$) δ 8.17 (d, J=5.5 Hz, 1H), 7.09 (d, J=5.5 Hz, 1H), 7.37-6.95 (m, 1H), 3.95 (s, 3H), 3.28-3.14 (m, 1H), 2.71 (td, J=10.9, 3.7 Hz, 1H), 2.03-1.39 (m, 11H), 0.98 (d, J=14.7 Hz, 3H).

24G. 1-((1s,4s)-4-(3-(Difluoromethyl)-2-methoxypyridin-4-yl)cyclohexyl)propan-1-amine To a solution of 2-(4-(3-(difluoromethyl)-2-methoxypyridin-4-yl)cyclohexyl)butanoic acid (1.18 g, 3.60 mmol) in Toluene (12 mL) were added TEA (0.804 mL, 5.77 mmol) and DPPA (0.935 mL, 4.33 mmol). The reaction mixture was heated at 70° C. for 1 h. The reaction mixture was concentrated in vacuo. To the residue was added THF (10 mL) and LiOH aqueous solution (2.0 M solution) (12.62 mL, 25.2 mmol). The reaction mixture was stirred at rt for 4 h. The reaction mixture was diluted with water and 1 N HCl solution was added to adjust pH to 1-2. The resulting mixture was extracted with ethyl acetate to remove DPPA related impurity. The aqueous layer was separated and to the aqueous layer was added 1 N NaOH solution to adjust pH to 10. The resulting mixture was extracted with ethyl acetate two times. The organic layers were combined, dried over MgSO$_4$. The filtrate was concentrated in vacuo to give Intermediate 24G (colorless oil, 0.69 g, 2.31 mmol, 64% yield). LC-MS Anal. Calc'd for $C_{16}H_{24}F_2N_2O$ 298.19, found [M+H] 299.2. $T_r$=0.74 min (Method A). $^1$H NMR (499 MHz, chloroform-d) δ 8.14 (d, J=5.3 Hz, 1H), 7.18-6.88 (m, 2H), 3.96 (s, 3H), 3.34-3.18 (m, 1H), 3.08-2.87 (m, 1H), 2.15-2.07 (m, 1H), 1.89 (dt, J=13.3, 2.7 Hz, 1H), 1.79-1.38 (m, 10H), 1.33-1.20 (m, 1H), 1.00 (t, J=7.5 Hz, 3H).

Example 24, N-(1-((1s,4s)-4-(3-(Difluoromethyl)-2-methoxypyridin-4-yl)cyclohexyl)propyl)-6-methoxynicotinamide To a solution of 6-methoxynicotinic acid (203 mg, 1.329 mmol) in DMF (8 mL) was added HATU (505 mg, 1.329 mmol) at ice bath temperature. The reaction mixture was stirred at 0° C. for 5 min, followed by addition of a solution of 1-((1s,4s)-4-(3-(difluoromethyl)-2-methoxypyridin-4-yl)cyclohexyl)propan-1-amine (305 mg, 1.022 mmol) in THF (3 mL) and DIPEA (0.536 mL, 3.07 mmol) at 0° C. The resulting mixture was stirred at rt over night. The reaction mixture was diluted with ethyl acetate and saturated NaHCO$_3$ solution. The organic layer was separated and washed with brine twice, dried over MgSO$_4$. The filtrate was concentrated in vacuo. The residue was submitted for chiral separation. The isomers was separated by SFC (Method Q) to give two isolates. (absolute stereochemistry was not determined).

First elute (175 mg, 0.40 mmol, 39% yield). LC-MS Anal. Calc'd for $C_{23}H_{29}F_2N_3O_3$ 433.22, found [M+H] 434.3, $T_r$=2.31 min (Method B). $T_r$=2.8 min over 15 min run (Method R).

$^1$H NMR (499 MHz, METHANOL-$d_4$) δ 8.65 (dd, J=2.4, 0.6 Hz, 1H), 8.17 (d, J=5.5 Hz, 1H), 8.11 (dd, J=8.8, 2.5 Hz, 1H), 7.33-7.03 (m, 2H), 6.85 (dd, J=8.8, 0.7 Hz, 1H), 4.48 (td, J=10.3, 3.3 Hz, 1H), 3.97 (s, 3H), 3.95 (s, 3H), 3.26 (t, J=10.6 Hz, 1H), 2.07-1.80 (m, 5H), 1.77-1.38 (m, 6H), 0.99 (t, J=7.4 Hz, 3H).

Second elute (175 mg, 0.40 mmol, 39% yield). LC-MS Anal. Calc'd for $C_{23}H_{29}F_2N_3O_3$ 433.22, found [M+H] 434.3, $T_r$=2.31 min (Method B). $T_r$=3.8 min over 15 min run (Method R).

$^1$H NMR (499 MHz, METHANOL-$d_4$) δ 8.65 (dd, J=2.4, 0.6 Hz, 1H), 8.17 (d, J=5.5 Hz, 1H), 8.11 (dd, J=8.8, 2.5 Hz, 1H), 7.33-7.03 (m, 2H), 6.85 (dd, J=8.8, 0.7 Hz, 1H), 4.48 (td, J=10.3, 3.3 Hz, 1H), 3.97 (s, 3H), 3.95 (s, 3H), 3.26 (t, J=10.6 Hz, 1H), 2.07-1.80 (m, 5H), 1.77-1.38 (m, 6H), 0.99 (t, J=7.4 Hz, 3H).

Example 25, Two Isomers

N-(1-((1s,4s)-4-(3-(Difluoromethyl)-2-methoxypyridin-4-yl)cyclohexyl)propyl)-2-methoxypyrimidine-5-carboxamide

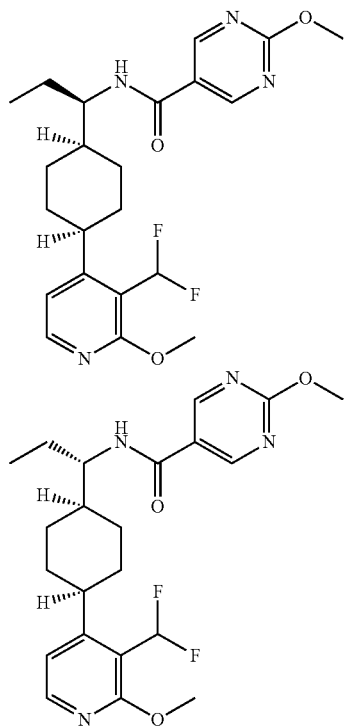

Example 26, Two Isomers

N-(1-((1s,4s)-4-(3-(Difluoromethyl)-2-methoxypyridin-4-yl)cyclohexyl)propyl)-2-morpholinoisonicotinamide

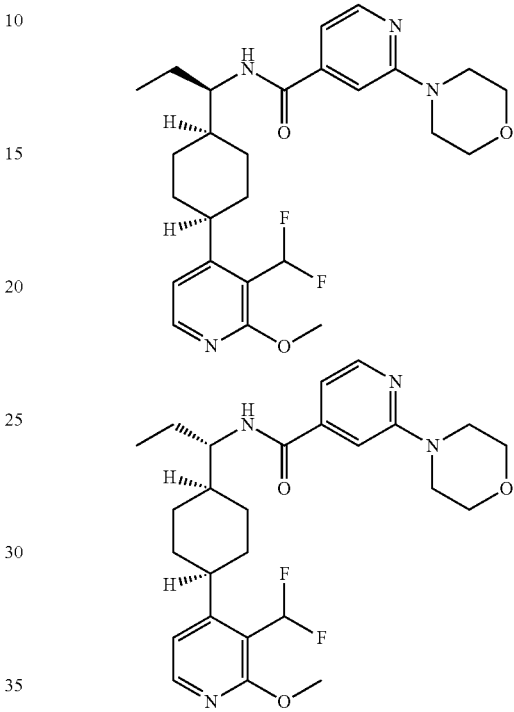

To a solution of 2-methoxypyrimidine-5-carboxylic acid (18.8 mg, 0.122 mmol) in DMF (1 mL) was added HATU (46.4 mg, 0.122 mmol) at rt. The reaction mixture was stirred at rt for 5 min, followed by addition of a solution of 1-((1s,4s)-4-(3-(difluoromethyl)-2-methoxypyridin-4-yl)cyclohexyl)propan-1-amine (28 mg, 0.094 mmol) (prepared in the above example) in THF (3 mL) and DIPEA (0.049 mL, 0.282 mmol). The resulting mixture was stirred at rt for 1 h. The reaction mixture was concentrated in vacuo. The residue was the residue was dissolved in MeOH, filtered, and purified via preparative HPLC to give a mixture of two isomers. The isomers were further separated by preparative SFC (Method: 15% IPA-DEA on AD column) to give two isolates. (absolute stereochemistry was not determined).

First elute (12 mg, 0.027 mmol, 29% yield). LC-MS Anal. Calc'd for $C_{22}H_{28}F_2N_4O_3$ 434.21, found [M+H] 435.4, $T_r$=1.89 min (Method B). $T_r$=3.94 min over 8 min run (Method: 15% IPA-DEA on AD). $^1$H NMR (500 MHz, DMSO-$d_6$) δ 8.98 (s, 2H), 8.31 (d, J=9.5 Hz, 1H), 8.23 (d, J=5.5 Hz, 1H), 7.41-7.12 (m, 1H), 7.10 (d, J=5.5 Hz, 1H), 4.32 (d, J=8.2 Hz, 1H), 3.96 (s, 3H), 3.87 (s, 3H), 3.09 (br. s., 1H), 1.95-1.26 (m, 11H), 0.86 (t, J=7.2 Hz, 3H).

Second elute (12.1 mg, 0.027 mmol, 29% yield). LC-MS Anal. Calc'd for $C_{22}H_{28}F_2N_4O_3$ 434.21, found [M+H] 435.4, $T_r$=1.89 min (Method B). $T_r$=6.15 min over 8 min run (Method: 15% IPA-DEA on AD). $^1$H NMR (500 MHz, DMSO-$d_6$) δ 8.98 (s, 2H), 8.31 (d, J=9.5 Hz, 1H), 8.23 (d, J=5.5 Hz, 1H), 7.41-7.12 (m, 1H), 7.10 (d, J=5.5 Hz, 1H), 4.32 (d, J=8.2 Hz, 1H), 3.96 (s, 3H), 3.87 (s, 3H), 3.09 (br. s., 1H), 1.95-1.26 (m, 11H), 0.86 (t, J=7.2 Hz, 3H).

To a solution of 2-morpholin-4-yl-isonictinic acid (20 mg, 0.095 mmol) was added HATU (46.4 mg, 0.122 mmol) at rt. The reaction mixture was stirred at rt for 5 min, followed by addition of a solution of 1-((1s,4s)-4-(3-(difluoromethyl)-2-methoxypyridin-4-yl)cyclohexyl)propan-1-amine (28 mg, 0.094 mmol) in THF (1 mL) and DIPEA (0.049 mL, 0.282 mmol). The resulting mixture was stirred at rt for 1 h. The reaction mixture was concentrated in vacuo. The residue was the residue was dissolved in MeOH, filtered, and purified via preparative HPLC to give a mixture of two isomers. The isomers were further separated by preparative SFC (Method: 15% MeOH-DEA on AD) to give two isolates. (absolute stereochemistry was not determined).

First elute (9.2 mg, 0.019 mmol, 19.9% yield). LC-MS Anal. Calc'd for $C_{26}H_{34}F_2N_4O_3$ 488.26, found [M+H] 489.5, $T_r$=1.63 min (Method B). $T_r$=2.52 min over 8 min run (Method: 15% MeOH-DEA on AD). $^1$H NMR (500 MHz, DMSO-$d_6$) δ 8.26 (d, J=5.2 Hz, 1H), 8.24-8.16 (m, 2H), 7.39-7.12 (m, 2H), 7.08 (dd, J=15.1, 5.0 Hz, 2H), 4.33 (d, J=10.4 Hz, 1H), 3.89 (s, 3H), 3.70 (br. s., 4H), 3.11 (br. s., 1H), 2.01-1.23 (m, 11H), 0.87 (t, J=7.0 Hz, 3H), 4H of morphline buried in DMSO.

Second elute (10.3 mg, 0.021 mmol, 22.2% yield). LC-MS Anal. Calc'd for $C_{26}H_{34}F_2N_4O_3$ 488.26, found [M+H] 489.5, $T_r$=1.63 min (Method B). $T_r$=6.33 min over 8 min run (Method: 15% MeOH-DEA on AD). $^1$H NMR (500 MHz, DMSO-$d_6$) δ 8.26 (d, J=5.2 Hz, 1H), 8.24-8.16 (m, 2H), 7.39-7.12 (m, 2H), 7.08 (dd, J=15.1, 5.0 Hz, 2H), 4.33 (d, J=10.4 Hz, 1H), 3.89 (s, 3H), 3.70 (br. s., 4H), 3.11 (br. s., 1H), 2.01-1.23 (m, 11H), 0.87 (t, J=7.0 Hz, 3H), 4H of morphline buried in DMSO.

Example 27, Two Isomers

N-(1-((1s,4s)-4-(2-Fluoro-3-methylpyridin-4-yl) cyclohexyl)propyl)-6-methoxynicotinamide

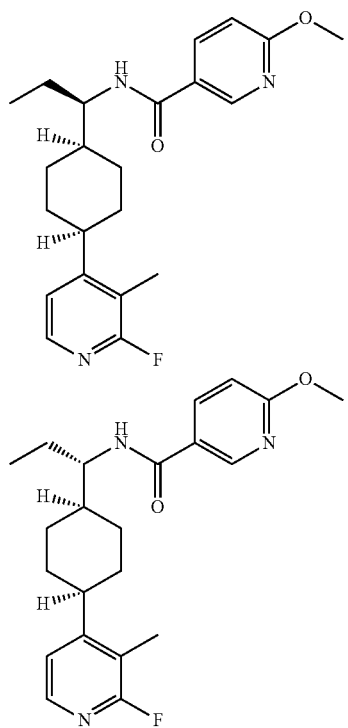

27A. 4-Bromo-2-fluoro-3-methylpyridine

To a solution of LDA (2.0 M solution in THF) (12.79 mL, 25.6 mmol) in THF (20 mL) was added a solution of 4-bromo-2-fluoropyridine (3.0 g, 17.05 mmol) in THF (5 mL) dropwise at −78° C. The reaction mixture was stirred at −78° C. for 1 h, then methyl iodide (1.599 mL, 25.6 mmol) was added. The reaction mixture was stirred at −78° C. for 30 min, then stirred at rt for 0.2 h. The reaction mixture was diluted with water and the resulting mixture was extracted with ethyl acetate. The organic layer was separated and washed with brine, dried over MgSO$_4$. The filtrate was concentrated in vacuo.

The residue was dissolved in DCM, purified via silica gel flash column chromatography, eluting with 0-15% ethyl acetate in hexane to give Intermediate 27A (colorless oil, 2.3 g, 12.1 mmol, 71% yield). LC-MS Anal. Calc'd for C$_6$H$_5$BrFN 188.96, found [M+H] 190, 192.1. T$_r$=0.83 min (Method A). $^1$H NMR (400 MHz, DMSO-d$_6$) δ 7.97 (d, J=5.4 Hz, 1H), 7.63 (d, J=5.4 Hz, 1H), 2.30-2.29 (m, 3H).

27B. Ethyl 2-(4-(2-fluoro-3-methylpyridin-4-yl) cyclohex-3-en-1-yl)acetate

To a reaction flask containing a solution of ethyl 2-(4-(4, 4,5,5-tetramethyl-1,3,2-dioxaborolan-2-yl)cyclohex-3-en-1-yl)acetate (5.93 g, 20.17 mmol) in Dioxane (120 mL) were added 4-bromo-2-fluoro-3-methylpyridine (3.72 g, 19.58 mmol), Water (40.0 mL) and Na$_2$CO$_3$ (8.30 g, 78 mmol). After the mixture was degassed with Ar for 10 min, Pd(Ph$_3$P)$_4$ (1.131 g, 0.979 mmol) was added. The flask was sealed and the mixture was heated to 100° C. over night. The reaction mixture was cooled down and diluted with EtOAc and water, plus sonication to break up solids, then transferred to a separation funnel. The layers were separated and the aqueous layer was extracted once more with EtOAc. The organic layers were combined, washed with brine, dried over anhyd Na$_2$SO$_4$, filtered and concentrated in vacuo to afford a white precipitate in a pale gold residue. The extract was purified via silica gel flash column chromatography, eluting with 0-25% ethyl acetate in hexane to give Intermediate 27B (gold pale oil, 5.01 g, 17.72 mmol, 91% yield). LC-MS Anal. Calc'd for C$_{16}$H$_{20}$FNO$_2$ 277.15, found [M+H] 278.1. T$_r$=1.02 min (Method A). $^1$H NMR (400 MHz, chloroform-d) δ 7.94 (d, J=5.0 Hz, 1H), 6.89 (dd, J=5.1, 0.9 Hz, 1H), 5.79-5.49 (m, 1H), 4.18 (q, J=7.1 Hz, 2H), 2.55-2.28 (m, 4H), 2.26-2.11 (m, 5H), 2.00-1.86 (m, 2H), 1.55-1.41 (m, 1H), 1.29 (t, J=7.2 Hz, 3H).

27C. Ethyl 2-((1s,4s)-4-(2-fluoro-3-methylpyridin-4-yl)cyclohexyl)butanoate

To a flak containing a homogeneous mixture of ethyl 2-(4-(2-fluoro-3-methylpyridin-4-yl)cyclohex-3-en-1-yl)acetate (7.23 g, 26.1 mmol) in MeOH (100 mL) was added ammonium formate (8.22 g, 130 mmol). The resulting mixture was sparged with Argon for 5 min, before being evacuated then purged with nitrogen (×3). To this mixture was then added Pd—C (10% Pd/C, wet) (2.77 g, 2.61 mmol) and the reaction was heated to reflux for 3 hours then allowed to cool slowly to rt. Stir bar was removed before reaction concentrated to remove volatiles. The residue was then treated with DCM and filtered through a pad of celite which was thoroughly rinsed with DCM. The combined filtrates were concentrated in vacuo to afford a clear oil. The cis and trans isomers were separated by preparative SFC (Method S) to give the peak 2 as the cis isomer based on NMR and NOE experiment. Intermediate 27C (gold pale oil, 2.18 g, 7.80 mmol, 29.9% yield). LC-MS Anal. Calc'd for C$_{16}$H$_{22}$FNO$_2$ 279.16, found [M+H] 280.2. T$_r$=1.01 min (Method A). $^1$H NMR (400 MHz, BENZENE-d$_6$) δ 7.89 (d, J=5.1 Hz, 1H), 6.46 (d, J=5.0 Hz, 1H), 4.01 (q, J=7.1 Hz, 2H), 2.40-2.12 (m, 4H), 1.82 (d, J=1.1 Hz, 3H), 1.59-1.46 (m, 2H), 1.41-1.13 (m, 6H), 1.01 (t, J=7.2 Hz, 3H).

27D. Ethyl 2-((1s,4s)-4-(2-fluoro-3-methylpyridin-4-yl)cyclohexyl)butanoate

To a flask containing THF (15 mL) was added LDA (1.5 M solution in cyclohexane) (11.0 mL, 16.54 mmol) and DMPU (1.36 mL, 11.28 mmol) at −78° C., followed by addition of a solution of ethyl 2-((1s,4s)-4-(2-fluoro-3-methylpyridin-4-yl)cyclohexyl)acetate (2.1 g, 7.52 mmol) in THF (8 mL) dropwise at −78° C. The resulting orange solution mixture was stirred at −78° C. for 1 h, then iodoethane (0.97 mL, 12.03 mmol) was added. The reaction mixture was stirred at −78° C., then gradually warmed up to rt for 4 h. The reaction mixture turned into a cloudy yellow mixture. The reaction mixture was quenched with NH$_4$Cl aqueous solution. The resulting mixture was extracted with ethyl acetate. The organic layers of extract were combined, washed with brine, dried over MgSO$_4$. The filtrate was concentrated in vacuo. The extract was purified via silica gel flash column chromatography, eluting with 0-20% ethyl acetate in hexane to give Intermediate 27D (oil, 1.31 g, 4.26 mmol, 56.7% yield). LC-MS Anal. Calc'd for $C_{18}H_{26}FNO_2$ 307.1, found [M+H] 308.2. $T_r$=1.08 min (Method A). $^1$H NMR (400 MHz, chloroform-d) δ 7.98 (d, J=5.1 Hz, 1H), 7.08 (d, J=5.3 Hz, 1H), 4.19 (q, J=7.1 Hz, 2H), 2.93-2.74 (m, 1H), 2.62 (td, J=10.8, 3.9 Hz, 1H), 2.23 (d, J=1.1 Hz, 3H), 2.04-1.86 (m, 2H), 1.77-1.43 (m, 9H), 1.28 (t, J=7.2 Hz, 3H), 0.94 (t, J=7.4 Hz, 3H).

27E. 2-((1s,4s)-4-(2-Fluoro-3-methylpyridin-4-yl) cyclohexyl)butanoic Acid

To the reaction mixture of ethyl 2-((1s,4s)-4-(2-fluoro-3-methylpyridin-4-yl)cyclohexyl)butanoate (0.9 g, 2.93 mmol) in THF (10 mL) and MeOH (6 mL) was added LiOH aqueous solution (2 M) (14.64 mL, 29.3 mmol). The reaction mixture was heated at 70° C. for over night. The reaction was not complete. To the reaction mixture was added more LiOH solution (2 M) (4 mL) and MeOH (6 mL). The reaction mixture was heated at 70° C. for another 20 h. The reaction mixture was cooled down and to the reaction mixture was added 2 mL of acetic acid to adjust pH to about 5. The resulting mixture was extracted with ethyl acetate twice and the organic layers was washed with brne, dried over $MgSO_4$. The filtrate was concentrated in vacuo. and the residue was dissolved in MeOH, filtered, and purified via preparative HPLC to give Intermediate 27E (425 mg, 1.506 mmol, 51.4% yield). LC-MS Anal. Calc'd for $C_{16}H_{22}FNO_2$ 279.16, found [M+H] 280.1. $T_r$=0.89 min (Method A). $^1$H NMR (400 MHz, METHANOL-$d_4$) δ 7.94 (d, J=5.3 Hz, 1H), 7.24 (d, J=5.3 Hz, 1H), 2.93 (d, J=4.2 Hz, 1H), 2.65 (td, J=10.8, 3.7 Hz, 1H), 2.25 (d, J=0.9 Hz, 3H), 1.95 (br. s., 2H), 1.83-1.40 (m, 9H), 0.97 (t, J=7.4 Hz, 3H).

27F. 1-((1s,4s)-4-(2-Fluoro-3-methylpyridin-4-yl) cyclohexyl)propan-1-amine

To a suspension of 2-(4-(2-fluoro-3-methylpyridin-4-yl)cyclohexyl)butanoic acid (0.24 g, 0.859 mmol) in Toluene (8 mL) were added diphenylphosphoryl azide (0.23 mL, 1.03 mmol) and TEA (0.42 mL, 3.01 mmol). The reaction mixture in a sealed vial turned into clear solution after addition of TEA. The reaction mixture was heated to 70° C. for 2 h. The reaction was cooled to rt. and concentrated under reduced pressure. To the residue was added THF (8 mL) and LiOH aqueous solution (2.0 M) (3.0 mL, 6.0 mmol) and the resulting mixture was stirred at rt for 2 h. The reaction mixture acidified with 1N HCl and extracted with EtOAc to remove DPPA related impurities. Then the aqueous layer was basified with 1N NaOH and extracted with EtOAc 3 times. The basic extracts were combined, dried over $MgSO_4$ and the filtrate was concentrated in vacuo to give Intermediate 27F (colorless oil, 167 mg, 0.667 mmol, 78% yield). LC-MS Anal. Calc'd for $C_{15}H_{23}FN_2$ 250.18, found [M+H] 251.1. $T_r$=0.66 min (Method A). $^1$H NMR (400 MHz, chloroform-d) δ 7.97 (d, J=5.3 Hz, 1H), 7.05 (d, J=5.1 Hz, 1H), 2.98-2.77 (m, 2H), 2.24 (d, J=1.3 Hz, 3H), 2.14-2.03 (m, 1H), 1.95-1.81 (m, 1H), 1.77-1.46 (m, 8H), 1.31-1.17 (m, 1H), 0.99 (d, J=14.7 Hz, 3H).

Example 27, Two Isomers N-(1-((1s,4s)-4-(2-Fluoro-3-methylpyridin-4-yl)cyclohexyl)propyl)-6-methoxynicotinamide The reaction mixture of 6-methoxynicotinic acid (23 mg, 0.150 mmol) and HATU (57.0 mg, 0.150 mmol) in DMF (1 mL) was stirred at rt for 5 min, followed by addition of a solution of 1-((1 s,4s)-4-(2-fluoro-3-methylpyridin-4-yl)cyclohexyl)propan-1-amine (30 mg, 0.120 mmol) in THF (1 ML) and DIPEA (0.04 mL, 0.24 mmol). The resulting mixture was stirred at rt over night. The reaction mixture was concentrated in vacuo. The residue was the residue was dissolved in MeOH, filtered, and purified via preparative HPLC to give a mixture of two isomers. The isomers were further separated by preparative SFC (Method: 40% MeOH on IC column) to give two isolates. (absolute stereochemistry was not determined).

First elute (14.7 mg, 0.037 mmol, 31.2% yield). LC-MS Anal. Calc'd for $C_{22}H_{28}FN_3O_2$ 385.22, found [M+H] 386.2, $T_r$=1.91 min (Method B). $T_r$=2.7 min over 10 min run (Method: 40% MeOH on IC column). $^1$H NMR (500 MHz, DMSO-d6) δ 8.64 (s, 1H), 8.11 (d, J=8.9 Hz, 2H), 7.98 (d, J=4.9 Hz, 1H), 7.20 (d, J=5.2 Hz, 1H), 6.87 (d, J=8.8 Hz, 1H), 4.26 (d, J=8.9 Hz, 1H), 3.88 (s, 3H), 2.83 (br. s., 1H), 2.17 (s, 3H), 1.90-1.27 (m, 11H), 0.85 (t, J=7.2 Hz, 3H).

Second elute (14.3 mg, 0.036 mmol, 29.7% yield). LC-MS Anal. Calc'd for $C_{22}H_{28}FN_3O_2$ 385.22, found [M+H] 386.2, $T_r$=1.91 min (Method B). $T_r$=3.3 min over 10 min run (Method: 40% MeOH on IC column). $^1$H NMR (500 MHz, DMSO-d6) δ 8.64 (s, 1H), 8.11 (d, J=8.9 Hz, 2H), 7.98 (d, J=4.9 Hz, 1H), 7.20 (d, J=5.2 Hz, 1H), 6.87 (d, J=8.8 Hz, 1H), 4.26 (d, J=8.9 Hz, 1H), 3.88 (s, 3H), 2.83 (br. s., 1H), 2.17 (s, 3H), 1.90-1.27 (m, 11H), 0.85 (t, J=7.2 Hz, 3H).

Example 28, Two Isomers

6-Methoxy-N-(1-((1s,4s)-4-(2-methoxy-3-methylpyridin-4-yl)cyclohexyl)propyl)nicotinamide

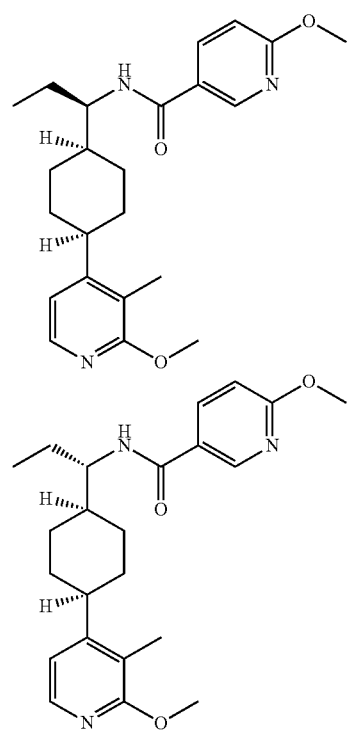

To a solution of ethyl 2-((1s,4s)-4-(2-fluoro-3-methylpyridin-4-yl)cyclohexyl)butanoate (0.38 g, 1.236 mmol) (Intermediate 27D) in MeOH (6 mL) was added NaOMe solution (0.5 M solution in MeOH) (17.31 mL, 8.65 mmol). The reaction mixture was heated at 80° C. for 3 h. To the reaction mixture was added more NaOMe solution (0.5 M solution in MeOH) (17.31 mL, 8.65 mmol) and the reaction mixture was heated at 80° C. over night. The reaction mixture was quenched with ice water and the resulting mixture was extracted with ethyl acetate. The organic layer was separated and dried over MgSO$_4$. The filtrate was concentrated in vacuo to give Intermediate 28A (brown oil, 0.34 g, 1.113 mmol, 90% yield). LC-MS Anal. Calc'd for $C_{18}H_{27}NO_3$ 305.20, found [M+H] 306.3. $T_r$=0.94 min (Method A). $^1$H NMR (400 MHz, chloroform-d) δ 7.96 (d, J=5.5 Hz, 1H), 6.81 (d, J=5.5 Hz, 1H), 3.95 (s, 3H), 3.71 (s, 3H), 2.80 (d, J=3.7 Hz, 1H), 2.67 (td, J=10.9, 4.0 Hz, 1H), 2.16 (s, 3H), 2.03-1.84 (m, 2H), 1.77-1.42 (m, 9H), 0.92 (t, J=7.4 Hz, 3H).

28B. 2-((1s,4s)-4-(2-Methoxy-3-methylpyridin-4-yl)cyclohexyl)butanoic Acid

To the reaction mixture of methyl 2-((1s,4s)-4-(2-methoxy-3-methylpyridin-4-yl)cyclohexyl)butanoate (0.35 g, 1.146 mmol) in THF (5 mL) and MeOH (8 mL) was added LiOH aqueous solution (3 M) (7.64 mL, 22.92 mmol). The reaction mixture was heated at 80° C. over night. More LiOH aqueous solution (3 M) (3 mL) was added and the reaction mixture was heated at 80° C. over night. To the reaction mixture was added 1 N HCl solution to adjust pH to 6 and then added 1 mL of HOAc to adjust pH to 5. The resulting mixture was extracted with ethyl acetate twice. The organic layers were combined and dried ove MgSO$_4$. The filtrate was concentrated in vacuo to give Intermediate 28B (white solid, 0.32 g, 1.098 mmol, 96% yield). LC-MS Anal. Calc'd for $C_{17}H_{25}NO_3$ 291.18, found [M+H] 292.3. $T_r$=0.85 min (Method A). $^1$H NMR (400 MHz, METHANOL-d4) δ 7.94 (d, J=5.7 Hz, 1H), 7.10 (d, J=5.9 Hz, 1H), 4.04 (s, 3H), 3.06-2.86 (m, 1H), 2.65 (td, J=10.8, 3.7 Hz, 1H), 2.22 (s, 3H), 2.03-1.88 (m, 2H), 1.82-1.40 (m, 9H), 0.97 (t, J=7.4 Hz, 3H).

28C. 1-((1s,4s)-4-(2-Methoxy-3-methylpyridin-4-yl)cyclohexyl)propan-1-amine

To a suspension of 2-(4-(2-methoxy-3-methylpyridin-4-yl)cyclohexyl)butanoic acid (0.33 g, 1.133 mmol) inToluene (8 mL) were added DPPA (0.29 mL, 1.359 mmol) and TEA (0.55 mL, 3.96 mmol). The reaction mixture turned into clear solution after addition of TEA. The reaction mixture was heated to 70° C. for 1.5 h. The reaction mixture was concentrated under reduced pressure. To the residue was added THF (8 mL) and LiOH aqueous solution (2.0 M solution) (3.96 mL, 7.93 mmol) and the resulting mixture was stirred at rt for 20 h. The reaction mixture acidified with 1N HCl and extracted with EtOAc to remove DPPA related impurities. Then the aqueous layer was basified with 1N NaOH and extracted with EtOAc 3 times. The basic extracts were combined, dried over MgSO$_4$ and the filtrate was concentrated in vacuo to give Intermediate 28C (colorless oil, 0.18 g, 0.686 mmol, 60.6% yield). LC-MS Anal. Calc'd for $C_{16}H_{26}N_2O$ 262.21, found [M+H]263.3. $T_r$=0.63 min (Method A).
$^1$H NMR (400 MHz, chloroform-d) δ7.94 (d, J=5.3 Hz, 1H), 6.77 (d, J=5.3 Hz, 1H), 3.94 (s, 3H), 3.02-2.71 (m, 2H), 2.16 (s, 3H), 2.09-1.15 (m, 11H), 0.98 (t, J=7.4 Hz, 3H).

Example 28, Two Isomers 6-Methoxy-N-(1-((1s,4s)-4-(2-methoxy-3-methylpyridin-4-yl)cyclohexyl)propyl)nicotinamide To a solution of 6-methoxynicotinic acid (23.3 mg, 0.152 mmol) in DMF (1 mL) was added HATU (61.6 mg, 0.162 mmol). The reaction mixture was stirred at rt for 5 min, followed by addition of a solution of crude 1-((1s,4s)-4-(2-methoxy-3-methylpyridin-4-yl)cyclohexyl)propan-1-amine (25 mg, 0.095 mmol) in THF (1 mL) and DIPEA (0.050 mL, 0.286 mmol). The yellow reaction mixture was stirred at rt for 1 h. The reaction mixture was concentrated in vacuo. The residue was the residue was dissolved in MeOH, filtered, and purified via preparative HPLC to give a mixture of two isomers. The isomers were further separated by preparative SFC (Method: 30% IPA-DEA on AD column) to give two isolates. (absolute stereochemistry was not determined).

First elute (4.1 mg, 10.11 μmol, 10.6% yield). LC-MS Anal. Calc'd for $C_{23}H_{31}N_3O_3$ 397.24, found [M+H] 397.9, $T_r$=1.76 min (Method B). $T_r$=2.54 min over 10 min run (Method: 30% IPA-DEA on AD). $^1$H NMR (500 MHz, DMSO-d6) δ 8.66 (d, J=1.8 Hz, 1H), 8.26-8.03 (m, 2H), 7.92 (d, J=5.2 Hz, 1H), 6.95-6.77 (m, 2H), 4.27 (d, J=8.2 Hz, 1H), 3.88 (s, 3H), 3.84-3.73 (m, 3H), 2.89-2.69 (m, 1H), 2.09 (s, 3H), 1.88-1.29 (m, 11H), 0.86 (t, J=7.2 Hz, 3H).

Second elute (4.0 mg, 9.56 μmol, 10.0% yield). LC-MS Anal. Calc'd for $C_{23}H_{31}N_3O_3$ 397.24, found [M+H] 397.9, $T_r$=1.76 min (Method B). $T_r$=5.70 min over 10 min run (Method: 30% IPA-DEA on AD). $^1$H NMR (500 MHz, DMSO-d6) δ 8.66 (d, J=1.8 Hz, 1H), 8.26-8.03 (m, 2H), 7.92 (d, J=5.2 Hz, 1H), 6.95-6.77 (m, 2H), 4.27 (d, J=8.2 Hz, 1H), 3.88 (s, 3H), 3.84-3.73 (m, 3H), 2.89-2.69 (m, 1H), 2.09 (s, 3H), 1.88-1.29 (m, 11H), 0.86 (t, J=7.2 Hz, 3H).

Example 29, Two Isomers

6-Amino-N-(1-((1s,4s)-4-(2-methoxy-3-methylpyridin-4-yl)cyclohexyl)propyl)nicotinamide

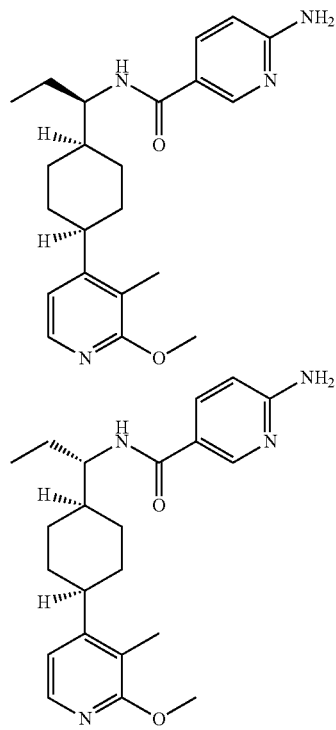

To a suspension of 6-aminonicotinic acid (13.7 mg, 0.099 mmol) in DMF (1 mL) was added HATU (37.7 mg, 0.099 mmol). The reaction mixture was stirred at rt for 5 min, followed by addition of a solution of 1-((1s,4s)-4-(2-methoxy-3-methylpyridin-4-yl)cyclohexyl)propan-1-amine (20 mg, 0.076 mmol) in THF (1 mL) and DIPEA (0.040 mL, 0.229 mmol). The reaction mixture was stirred at rt for 1 h. The reaction mixture was concentrated in vacuo. The residue was dissolved in MeOH, filtered, and purified via preparative HPLC to give a mixture of two isomers. The isomers were further separated by preparative SFC (Method: 30% MeOH-DEA on IC) to give two isolates. (absolute stereochemistry was not determined).

First elute (6.3 mg, 0.016 mmol, 21.4% yield). LC-MS Anal. Calc'd for $C_{22}H_{30}N_4O_2$ 382.24, found [M+H] 383.3, $T_r$=1.21 min (Method B). $T_r$=4.3 min over 10 min run (Method: 30% MeOH-DEA on IC). $^1$H NMR (500 MHz, DMSO-$d_6$) δ 8.42 (br. s., 1H), 7.90 (d, J=5.1 Hz, 1H), 7.82 (dd, J=8.6, 2.1 Hz, 2H), 6.86 (d, J=5.3 Hz, 1H), 6.56-6.32 (m, 3H), 4.23 (d, J=9.5 Hz, 1H), 3.79 (br. s., 3H), 2.83-2.69 (m, 1H), 2.07 (s, 3H), 1.85-1.21 (m, 11H), 0.82 (t, J=7.2 Hz, 3H).

Second elute (5.6 mg, 0.014 mmol, 18.8% yield). LC-MS Anal. Calc'd for $C_{22}H_{30}N_4O_2$ 382.24, found [M+H] 383.3, $T_r$=1.21 min (Method B). $T_r$=5.85 min over 10 min run (Method: 30% MeOH-DEA on IC). $^1$H NMR (500 MHz, DMSO-$d_6$) δ 8.42 (br. s., 1H), 7.90 (d, J=5.1 Hz, 1H), 7.82 (dd, J=8.6, 2.1 Hz, 2H), 6.86 (d, J=5.3 Hz, 1H), 6.56-6.32 (m, 3H), 4.23 (d, J=9.5 Hz, 1H), 3.79 (br. s., 3H), 2.83-2.69 (m, 1H), 2.07 (s, 3H), 1.85-1.21 (m, 11H), 0.82 (t, J=7.2 Hz, 3H).

Example 30, Four Isomers

N-(1-(4-(2-(Difluoromethoxy)pyridin-4-yl)cyclohexyl)propyl)-6-methoxynicotinamide

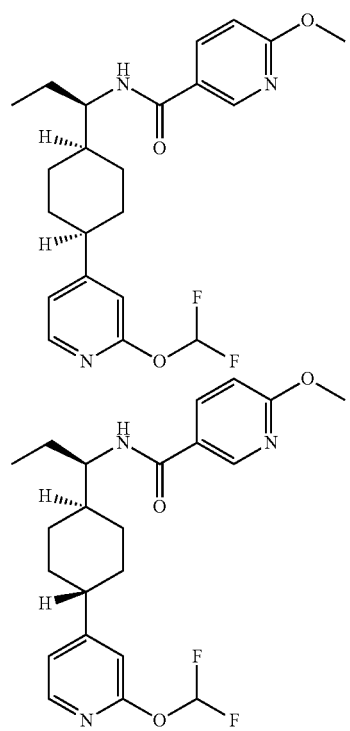

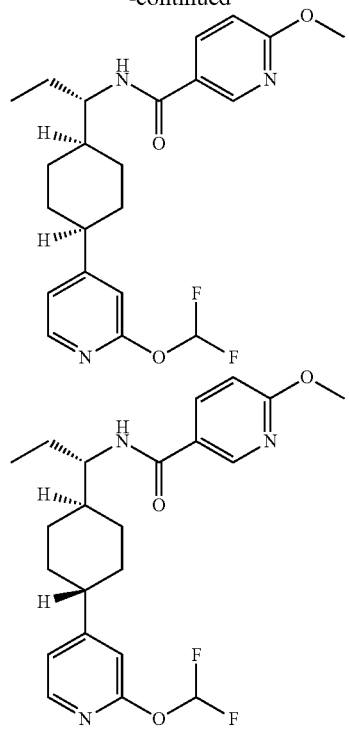

30A. 4-Bromo-2-(difluoromethoxy)pyridine

To a suspension of 4-bromo-2-hydroxypyridine (3.0 g, 17.24 mmol) in Acetonitrile (35 mL) was added sodium chlorodifluoroacetate (3.15 g, 20.69 mmol). The reaction mixture was heated at 90° C. over night. To the reaction mixture was added more $CH_3CN$ (35 ML), $K_2CO_3$ (3.57 g, 25.9 mmol) and sodium chlorodifluoroacetate (2 g). The reaction mixture was heated at 70° C. over night. The reaction mixture was diluted with water and ethyl acetate. The organic layer was separated, washed with brine, dried over $MgSO_4$. The filtrate was concentrated in vacuo. The extract was purified via silica gel flash column chromatography, eluting with 0-25% ethyl acetate in hexane to give the latter came out peak as N-alkylated product and the first flushed out peak as Intermediate 30A (oil, 0.77 g, 3.44 mmol, 19.9% yield). LC-MS Anal. Calc'd for $C_6H_4BrF_2NO$ 222.94, found [M+H] 224, 226. $T_r$=0.91 min (Method A). $^1$H NMR (400 MHz, chloroform-d) δ 8.05 (d, J=5.3 Hz, 1H), 7.67-7.29 (m, 1H), 7.29-7.27 (m, 1H), 7.13 (d, J=1.3 Hz, 1H).

30B. Ethyl 2-(4-(2-(difluoromethoxy)pyridin-4-yl)cyclohex-3-en-1-yl)butanoate

To a solution of 4-bromo-2-(difluoromethoxy)pyridine (0.62 g, 2.77 mmol)), ethyl 2-(4-(4,4,5,5-tetramethyl-1,3,2-dioxaborolan-2-yl)cyclohex-3-en-1-yl)butanoate (0.981 g, 3.04 mmol) (Intermediate 24C) in 1,4-Dioxane (15 mL) was added potassium carbonate (0.956 g, 6.92 mmol) and Water (4 mL). The reaction mixture was purged with nitrogen stream for 3 min, followed by addition of $Pd(Ph_3P)_4$ (0.160 g, 0.138 mmol). The resulting mixture in a sealed tube was heated at 100° C. under nitrogen stream over night. The reaction mixture was cooled down and diluted with ethyl acetate and saturated $NaHCO_3$ solution. The organic layer was separated, dried over MgSO$_4$. The filtrate was concentrated in vacuo. The extract was purified via silica gel flash column chromatography, eluting with 0-15% ethyl acetate in hexane to give Intermediate 30B (oil, 0.93 g, 2.74 mmol, 99% yield). LC-MS Anal. Calc'd for C$_{18}$H$_{23}$F$_2$NO$_3$ 339.16, found [M+H] 340.2. T$_r$=1.1 min (Method A). $^1$H NMR (400 MHz, chloroform-d) δ 8.08 (d, J=5.3 Hz, 1H), 7.68-7.28 (m, 1H), 7.08 (dd, J=5.5, 1.5 Hz, 1H), 6.83 (s, 1H), 6.44-6.23 (m, 1H), 4.19 (qd, J=7.1, 5.7 Hz, 2H), 2.51-2.34 (m, 2H), 2.29-1.82 (m, 4H), 1.71-1.61 (m, 2H), 1.49-1.36 (m, 1H), 1.33-1.25 (m, 4H), 0.93 (td, J=7.4, 2.6 Hz, 3H).

30C. Ethyl 2-(4-(2-(difluoromethoxy)pyridin-4-yl)cyclohexyl)butanoate

To the reaction mixture of ethyl 2-(4-(2-(difluoromethoxy)pyridin-4-yl)cyclohex-3-en-1-yl)butanoate (0.93 g, 2.74 mmol) in MeOH (20 mL) was added Pd—C (10% wt.) (0.233 g, 0.219 mmol). The reaction mixture was evacuated and then hydrogenated with hydrogen balloon over night. The reaction mixture was filtered through a celite pad and the filtrate was concentrated in vacuo to give Intermediate 30C (oil, 0.93 g, 2.72 mmol, 99% yield). LC-MS Anal. Calc'd for C$_{18}$H$_{25}$F$_2$NO$_3$ 341.18, found [M+H] 342.2. T$_r$=1.12 min (Method A).

30D. 2-(4-(2-(Difluoromethoxy)pyridin-4-yl)cyclohexyl)butanoic Acid

To the reaction mixture of ethyl 2-(4-(2-(difluoromethoxy)pyridin-4-yl)cyclohexyl) butanoate (0.93 g, 2.72 mmol) in THF (10 mL) and MeOH (10 mL) was added LiOH aqueous solution (4 M) (17.03 mL, 68.1 mmol). The resulting mixture was heated at 70° C. over weekend. The reaction mixture was cooled down and to the mixture was added 1 N HCl solution to adjust pH to 7 and then 2 mL of acetic acid was added to adjust pH to 5. White solid crashed out. The resulting mixture was extracted with ethyl acetate twice. The organic layer was separated, washed with brine and dried over MgSO$_4$. The filtrate was concentrated in vacuo to give Intermediate 30D (oil, 0.86 g, 2.74 mmol, 100% yield). LC-MS Anal. Calc'd for C$_{16}$H$_{21}$F$_2$NO$_3$ 313.15, found [M+H] 314.2. T$_r$=0.97 min (Method A). $^1$H NMR (400 MHz, chloroform-d) δ 8.08 (t, J=5.5 Hz, 1H), 7.73-7.27 (m, 1H), 7.04-6.89 (m, 1H), 6.84-6.67 (m, 1H), 2.85-2.39 (m, 2H), 2.22-1.12 (m, 11H), 0.97 (td, J=7.4, 2.2 Hz, 3H).

30E. 1-(4-(2-(Difluoromethoxy)pyridin-4-yl)cyclohexyl)propan-1-amine

To a solution of 2-(4-(2-(difluoromethoxy)pyridin-4-yl)cyclohexyl)butanoic acid (0.6 g, 1.915 mmol) in Toluene (12 mL) were added TEA (0.267 mL, 1.915 mmol) and DPPA (0.497 mL, 2.298 mmol). The reaction mixture was heated at 75° C. for 2 h. The reaction mixture was concentrated in vacuo and to the residue was added THF (8 mL) and LiOH aqueous solution (2 M solution) (5.74 mL, 11.49 mmol). The reaction mixture was stirred at rt over night. To the reaction mixture was added 1 N HCl solution to adjust pH to 2-3. The resulting mixture was extracted with ethyl acetate. The aqueous layer was basified with 1 N NaOH solution to adjust pH to 10. The resulting mixture was extracted with ethyl acetate three times. The organic layer was separated and dried over MgSO$_4$. The filtrate was concentrated in vacuo to give colorless oil. The first acidic extracted organic layer still contained product. It was mixed with 1 N HCl solution again. The aqueous layer was separated and basified with 1 N NaOH solution. The resulting mixture was extracted with ethyl acetate. The organic layers were dried over MSO$_4$. The filtrate was concentrated in vacuo and combined to give Intermediate 30E (colorless oil, 0.28 g, 0.985 mmol, 51.4% yield). LC-MS Anal. Calc'd for C$_{15}$H$_{22}$F$_2$N$_2$O 284.17, found [M+H] 285.2. T$_r$=0.72 min (Method A).

Example 30, Four Isomers, N-(1-(4-(2-(Difluoromethoxy)pyridin-4-yl)cyclohexyl)propyl)-6-methoxynicotinamide To a solution of 6-methoxynicotinic acid (33.6 mg, 0.219 mmol) in DMF (1 mL) was added HATU (83 mg, 0.219 mmol). The reaction mixture was stirred at rt for 10 min, followed by addition of a solution of 1-(4-(2-(difluoromethoxy)pyridin-4-yl)cyclohexyl)propan-1-amine (48 mg, 0.169 mmol) in THF (1 mL) and DIPEA (0.059 mL, 0.338 mmol). The resulting mixture was stirred at rt for 1 h. The reaction mixture was concentrated in vacuo and the residue was dissolved in MeOH, filtered, and purified via preparative HPLC to give a mixture of four isomers. The isomers were further separated by preparative SFC (Method 18% MeOH-DEA on IC) to give four isolates. (absolute stereochemistry was not determined).

First elute (12 mg, 0.028 mmol, 16.8% yield). LC-MS Anal. Calc'd for C$_{22}$H$_{27}$F$_2$N$_3$O$_3$ 419.20, found [M+H] 420.2. T$_r$=2.08 min (Method B). T$_r$=3.44 min over 10 min run (Method 18% MeOH-DEA on IC). $^1$H NMR (500 MHz, DMSO-d$_6$) δ 8.64 (br. s., 1H), 8.24-7.99 (m, 3H), 7.88-7.44 (m, 1H), 7.17 (d, J=5.1 Hz, 1H), 6.93 (s, 1H), 6.87 (d, J=8.7 Hz, 1H), 4.11 (d, J=9.4 Hz, 1H), 3.89 (s, 3H), 2.72 (d, J=7.9 Hz, 1H), 1.91-1.27 (m, 11H), 0.84 (t, J=7.2 Hz, 3H).

Second elute (12.6 mg, 0.030 mmol, 17.6% yield). LC-MS Anal. Calc'd for C$_{22}$H$_{27}$F$_2$N$_3$O$_3$ 419.20, found [M+H] 420.2. T$_r$=2.08 min (Method B). T$_r$=4.23 min over 10 min run (Method 18% MeOH-DEA on IC). $^1$H NMR (500 MHz, DMSO-d$_6$) δ 8.64 (br. s., 1H), 8.24-7.99 (m, 3H), 7.88-7.44 (m, 1H), 7.17 (d, J=5.1 Hz, 1H), 6.93 (s, 1H), 6.87 (d, J=8.7 Hz, 1H), 4.11 (d, J=9.4 Hz, 1H), 3.89 (s, 3H), 2.72 (d, J=7.9 Hz, 1H), 1.91-1.27 (m, 11H), 0.84 (t, J=7.2 Hz, 3H).

Third elute (13 mg, 0.031 mmol, 18.2% yield). LC-MS Anal. Calc'd for C$_{22}$H$_{27}$F$_2$N$_3$O$_3$ 419.20, found [M+H] 420.2. T$_r$=2.08 min (Method B). T$_r$=4.75 min over 10 min run (Method 18% MeOH-DEA on IC). $^1$H NMR (500 MHz, DMSO-d$_6$) δ 8.67 (d, J=1.9 Hz, 1H), 8.23-8.09 (m, 2H), 8.05 (d, J=7.9 Hz, 1H), 7.86-7.48 (m, 1H), 7.15 (d, J=5.0 Hz, 1H), 6.99-6.82 (m, 2H), 3.75 (br. s., 1H), 2.53 (d, J=6.8 Hz, 1H), 1.93-1.73 (m, 4H), 1.69-1.31 (m, 5H), 1.19-1.07 (m, 2H), 0.85 (t, J=7.2 Hz, 3H).

Fourth elute (12.7 mg, 0.030 mmol, 17.8% yield). LC-MS Anal. Calc'd for C$_{22}$H$_{27}$F$_2$N$_3$O$_3$ 419.20, found [M+H] 420.2. T$_r$=2.08 min (Method B). T$_r$=5.22 min over 10 min run (Method 18% MeOH-DEA on IC). $^1$H NMR (500 MHz, DMSO-d$_6$) δ 8.67 (d, J=1.9 Hz, 1H), 8.23-8.09 (m, 2H), 8.05 (d, J=7.9 Hz, 1H), 7.86-7.48 (m, 1H), 7.15 (d, J=5.0 Hz, 1H), 6.99-6.82 (m, 2H), 3.75 (br. s., 1H), 2.53 (d, J=6.8 Hz, 1H), 1.93-1.73 (m, 4H), 1.69-1.31 (m, 5H), 1.19-1.07 (m, 2H), 0.85 (t, J=7.2 Hz, 3H).

Example 31, Four Isomers

6-Methoxy-N-(1-(4-(1-methyl-2-oxo-1,2-dihydro-pyridin-4-yl)cyclohexyl)propyl)nicotinamide

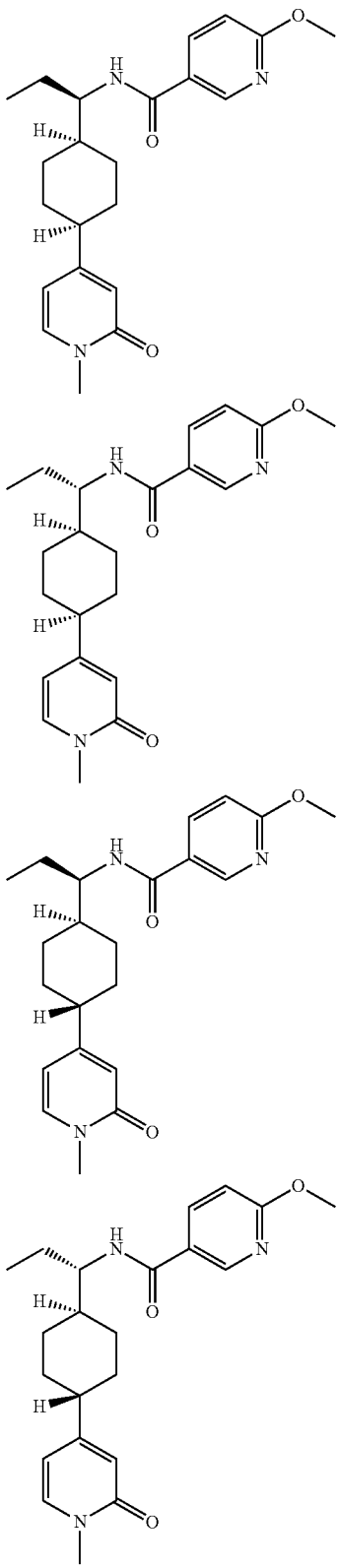

31A. 4-Bromo-1-methylpyridin-2(1H)-one

To a solution of 4-bromo-2-hydroxypyridine (0.55 g, 3.16 mmol) in DMF (8 mL) were added $K_2CO_3$ (0.874 g, 6.32 mmol) and MeI (0.23 mL, 3.64 mmol). The reaction mixture was stirred at rt over night. The reaction mixture was diluted with ethyl acetate and water. The organic layer was separated and washed with brine, dried over $MgSO_4$. The filtrate was concentrated in vacuo to give Intermediate 31A (white solid, 0.35 g, 1.89 mmol, 58% yield). LC-MS Anal. Calc'd for $C_6H_6BrNO$ 188.96, found [M+H] 188, 190.1. $T_r$=0.58 min (Method A).

31B. Ethyl 2-(4-(1-methyl-2-oxo-1,2-dihydropyridin-4-yl)cyclohex-3-en-1-yl)butanoate To a solution of 4-bromo-1-methylpyridin-2(1H)-one (0.35 g, 1.861 mmol)), ethyl 2-(4-(4,4,5,5-tetramethyl-1,3,2-dioxaborolan-2-yl)cyclohex-3-en-1-yl)butanoate (0.690 g, 2.141 mmol) in 1,4-Dioxane (10 mL) in a sealed tube were added potassium carbonate (0.643 g, 4.65 mmol) and Water (3 mL). The reaction mixture was purged with nitrogen stream for 3 min, followed by addition of $Pd(Ph_3P)_4$ (0.108 g, 0.093 mmol). The resulting mixture was heated at 100° C. under nitrogen stream over night. The reaction mixture was cooled down and diluted with ethyl acetate and saturated $NaHCO_3$ solution. The organic layer was separated, dried over $MgSO_4$. The filtrate was concentrated in vacuo. The extract was dissolved in DCM, purified via silica gel flash column chromatography, eluting with 0-50% ethyl acetate in DCM to give Intermediate 31B (oil, 0.52 g, 1.71 mmol, 92% yield). LC-MS Anal. Calc'd for $C_{18}H_{25}NO_3$ 303.18, found [M+H] 304.2. $T_r$=0.89 min (Method A). $^1$H NMR (400 MHz, chloroform-d) δ 7.16 (d, J=7.3 Hz, 1H), 6.49 (s, 1H), 6.35-6.17 (m, 2H), 4.29-4.14 (m, 2H), 3.52 (s, 3H), 2.57-1.59 (m, 9H), 1.48-1.33 (m, 1H), 1.29 (td, J=7.2, 3.3 Hz, 3H), 0.92 (td, J=7.4, 2.6 Hz, 3H).

31C. Ethyl 2-(4-(1-methyl-2-oxo-1,2-dihydropyridin-4-yl)cyclohexyl)butanoate To the reaction mixture of ethyl 2-(4-(1-methyl-2-oxo-1,2-dihydropyridin-4-yl)cyclohex-3-en-1-yl)butanoate (0.52 g, 1.714 mmol) in Methanol (12 mL) was added Pd—C (10% wt., wet) (0.091 g, 0.086 mmol). The reaction mixture was evacuated and then hydrogenated with a hydrogen balloon for 4 h. The reaction mixture was filtered through a celite pad and the pad was washed with MeOH and ethyl acetate. The filtrate was concentrated in vacuo to give Intermediate 31C (oil, 0.52 g, 1.70 mmol, 99% yield). LC-MS Anal. Calc'd for $C_{18}H_{27}NO_3$ 305.20, found [M+H] 306.2. $T_r$=0.89 min, 0.91 min (Method A).

31D. 2-(4-(1-Methyl-2-oxo-1,2-dihydropyridin-4-yl)cyclohexyl)butanoic acid

To a solution of ethyl 2-(4-(1-methyl-2-oxo-1,2-dihydropyridin-4-yl)cyclohexyl)butanoate (0.52 g, 1.703 mmol) in THF (10 mL) and MeOH (5 mL) was added LiOH aqueous solution (2.0 M) (10.22 mL, 20.43 mmol) in a sealed tube. The reaction mixture was heated at 80° C. for 3 days.

More LiOH solution (2.0 M) (5 mL), THF (5 mL) and MeOH (5 mL) were added and the reaction mixture was heated at 80° C. for another day. LC-MS showed the reaction was almost complete. The reaction mixture was cooled down and diluted with water and 1 N HCl solution to adjust pH to 7, then added 1 mL of acetic acid to adjust pH to 5.

The resulting mixture was extracted with ethyl acetate. The organic layer was separated and dried over MgSO$_4$. The filtrate was concentrated in vacuo to give Intermediate 31D (light brown solid, 0.46 g, 1.66 mmol, 97% yield). LC-MS Anal. Calc'd for C$_{16}$H$_{23}$NO$_3$ 277.17, found [M+H] 278.2. T$_r$=0.71 min (Method A). $^1$H NMR (400 MHz, chloroform-d) δ 7.21 (dd, J=6.8, 1.8 Hz, 1H), 6.57-6.45 (m, 1H), 6.21-6.01 (m, 1H), 3.79-3.62 (m, 1H), 3.58-3.49 (m, 3H), 2.65-2.07 (m, 2H), 2.03-1.48 (m, 8H), 1.29-1.10 (m, 2H), 0.96 (td, J=7.4, 2.3 Hz, 3H).

31E. 4-(4-(1-Aminopropyl)cyclohexyl)-1-methylpyridin-2(1H)-one

To a solution of 2-(4-(1-methyl-2-oxo-1,2-dihydropyridin-4-yl)cyclohexyl)butanoic acid (0.25 g, 0.901 mmol) in Toluene (12 mL) were added TEA (0.201 mL, 1.442 mmol) and DPPA (0.224 mL, 1.172 mmol). The reaction mixture was heated at 70° C. for 1.5 h. The reaction mixture was concentrated in vacuo. To the residue was added THF (8 mL) and LiOH aqueous solution (2.0 M solution) (3.15 mL, 6.31 mmol). The reaction mixture was stirred at rt for 2 h. The reaction mixture was diluted with water and 1 N HCl solution was added to adjust pH to 1-2. The resulting mixture was extracted with ethyl acetate to remove DPPA related impurity. The aqueous layer was separated and to the aqueous layer was added 1 N NaOH solution to adjust pH to 10-11. The resulting mixture was extracted with ethyl acetate three times. The organic layers were combined, dried over MgSO$_4$. The filtrate was concentrated in vacuo to give Intermediate 31E (oil, 0.105 g, 0.423 mmol, 46.9% yield). LC-MS Anal. Calc'd for C$_{15}$H$_{24}$N$_2$O 248.19, found [M+H] 249.2. T$_r$=0.55 min (Method A).

Example 31, Four Isomers

6-Methoxy-N-(1-(4-(1-methyl-2-oxo-1,2-dihydropyridin-4-yl)cyclohexyl)propyl)nicotinamide To a solution of 6-methoxynicotinic acid (26.5 mg, 0.173 mmol) in DMF (1 mL) was added HATU (65.7 mg, 0.173 mmol). The reaction mixture was stirred at rt for 5 min, followed by addition of a solution of crude 4-(4-(1-aminopropyl)cyclohexyl)-1-methylpyridin-2(1H)-one (33 mg, 0.133 mmol) in THF (1 mL) and DIPEA (0.046 mL, 0.266 mmol). The reaction mixture was stirred at rt for 1 h. The reaction mixture was concentrated in vacuo and the residue was dissolved in MeOH, filtered, and purified via preparative HPLC to give a mixture of four isomers. The isomers were further separated by preparative SFC (Method 40% MeOH-DEA on AD) to give four isolates. (absolute stereochemistry was not determined).

First elute (4.5 mg, 0.012 mmol, 8.7% yield). LC-MS Anal. Calc'd for C$_{22}$H$_{29}$N$_3$O$_3$ 383.22, found [M+H] 384.2. T$_r$=1.29 min (Method B). T$_r$=1.57 min over 10 min run (Method 40% MeOH-DEA on AD). $^1$H NMR (500 MHz, DMSO-d$_6$) δ 8.63 (s, 1H), 8.19-7.98 (m, 2H), 7.56 (d, J=6.7 Hz, 1H), 6.87 (d, J=8.5 Hz, 1H), 6.21 (s, 1H), 6.16 (d, J=7.0 Hz, 1H), 4.08 (d, J=9.8 Hz, 1H), 3.89 (s, 3H), 3.36 (s, 3H), 2.45 (br. s., 1H), 1.79-1.28 (m, 11H), 0.83 (t, J=7.3 Hz, 3H).

Second elute (4.9 mg, 0.013 mmol, 9.5% yield). LC-MS Anal. Calc'd for C$_{22}$H$_{29}$N$_3$O$_3$ 383.22, found [M+H] 384.2. T$_r$=1.29 min (Method B). T$_r$=2.13 min over 10 min run (Method 18% MeOH-DEA on IC). $^1$H NMR (500 MHz, DMSO-d$_6$) δ 8.63 (s, 1H), 8.19-7.98 (m, 2H), 7.56 (d, J=6.7 Hz, 1H), 6.87 (d, J=8.5 Hz, 1H), 6.21 (s, 1H), 6.16 (d, J=7.0 Hz, 1H), 4.08 (d, J=9.8 Hz, 1H), 3.89 (s, 3H), 3.36 (s, 3H), 2.45 (br. s., 1H), 1.79-1.28 (m, 11H), 0.83 (t, J=7.3 Hz, 3H).

Third elute (7.0 mg, 0.018 mmol, 13.6% yield). LC-MS Anal. Calc'd for C$_{22}$H$_{29}$N$_3$O$_3$ 383.22, found [M+H] 384.2. T$_r$=1.29 min (Method B). T$_r$=3.61 min over 10 min run (Method 18% MeOH-DEA on IC). $^1$H NMR (500 MHz, DMSO-d$_6$) δ 8.65 (s, 1H), 8.12 (d, J=8.5 Hz, 1H), 8.04 (d, J=8.9 Hz, 1H), 7.53 (d, J=6.7 Hz, 1H), 6.87 (d, J=8.9 Hz, 1H), 6.27-6.07 (m, 2H), 3.89 (s, 3H), 3.74 (br. s., 1H), 3.35 (s, 3H), 2.26 (t, J=11.9 Hz, 1H), 1.90-1.70 (m, 4H), 1.61 (br. s., 1H), 1.53-1.39 (m, 2H), 1.38-1.20 (m, 2H), 1.10 (br. s., 2H), 0.83 (t, J=7.2 Hz, 3H).

Fourth elute (6.9 mg, 0.018 mmol, 13.4% yield). LC-MS Anal. Calc'd for C$_{22}$H$_{29}$N$_3$O$_3$ 383.22, found [M+H] 384.2. T$_r$=1.29 min (Method B). T$_r$=4.74 min over 10 min run (Method 18% MeOH-DEA on IC). $^1$H NMR (500 MHz, DMSO-d$_6$) δ 8.65 (s, 1H), 8.12 (d, J=8.5 Hz, 1H), 8.04 (d, J=8.9 Hz, 1H), 7.53 (d, J=6.7 Hz, 1H), 6.87 (d, J=8.9 Hz, 1H), 6.27-6.07 (m, 2H), 3.89 (s, 3H), 3.74 (br. s., 1H), 3.35 (s, 3H), 2.26 (t, J=11.9 Hz, 1H), 1.90-1.70 (m, 4H), 1.61 (br. s., 1H), 1.53-1.39 (m, 2H), 1.38-1.20 (m, 2H), 1.10 (br. s., 2H), 0.83 (t, J=7.2 Hz, 3H).

Example 32, Four Isomers

6-Methoxy-N-(1-(4-(1-methyl-6-oxo-1,6-dihydropyridin-2-yl)cyclohexyl)propyl)nicotinamide

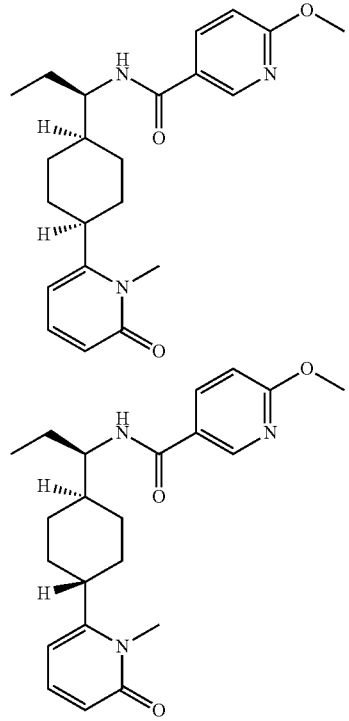

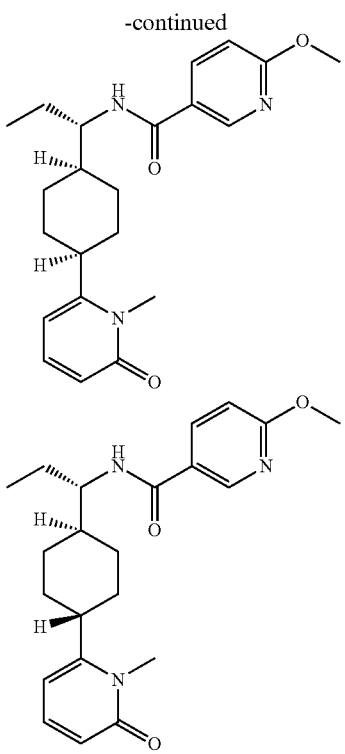

32A. 6-Bromo-1-methylpyridin-2(1H)-one

To a solution of 6-bromopyridin-2-ol (0.6 g, 3.45 mmol) in THF (8 mL) were added $K_2CO_3$ (0.953 g, 6.90 mmol) and MeI (0.323 mL, 5.17 mmol). The reaction mixture was stirred at rt for 3 h. The reaction mixture was diluted with ethyl acetate and water. The organic layer was separated and washed with brine, dried over $MgSO_4$. The filtrate was concentrated in vacuo. The extract was purified via silica gel flash column chromatography, eluting with 0-45% ethyl acetate in hexane to give Intermediate 32A (white solid, 0.40 g, 2.127 mmol, 61.7% yield). LC-MS Anal. Calc'd for $C_6H_6BrNO$ 186.96, found [M+H] 188, 190. $T_r$=0.57 min (Method A). $^1$H NMR (400 MHz, chloroform-d) δ 7.15 (dd, J=9.2, 7.3 Hz, 1H), 6.60-6.34 (m, 2H), 3.75 (s, 3H).

32B. Ethyl 2-(4-(1-methyl-6-oxo-1,6-dihydropyridin-2-yl)cyclohex-3-en-1-yl)butanoate To a solution of 6-bromo-1-methylpyridin-2(1H)-one (0.35 g, 1.861 mmol)), ethyl 2-(4-(4,4,5,5-tetramethyl-1,3,2-dioxaborolan-2-yl)cyclohex-3-en-1-yl)butanoate (0.660 g, 2.048 mmol) in 1,4-Dioxane (10 mL) in a sealed tube were added $K_2CO_3$ (0.643 g, 4.65 mmol) and Water (3 mL). The reaction mixture was purged with nitrogen stream for 3 min, followed by addition of Pd(Ph$_3$P)$_4$ (0.108 g, 0.093 mmol). The resulting mixture was heated at 100° C. under nitrogen stream over night. The reaction mixture was cooled down and diluted with ethyl acetate and saturated NaHCO$_3$ solution. The organic layer was separated, dried over MgSO$_4$. The filtrate was concentrated in vacuo. The extract was purified via silica gel flash column chromatography, eluting with 0-50% ethyl acetate in DCM to give Intermediate 32B (brown oil, 0.4 g, 1.318 mmol, 70.8% yield). LC-MS Anal. Calc'd for $C_{18}H_{25}NO_3$ 303.18, found [M+H] 304.2. $T_r$=0.90 min (Method A).

32C. Ethyl 2-(4-(1-methyl-6-oxo-1,6-dihydropyridin-2-yl)cyclohexyl)butanoate To the reaction mixture of ethyl 2-(4-(1-methyl-6-oxo-1,6-dihydropyridin-2-yl)cyclohex-3-en-1-yl)butanoate (0.4 g, 1.318 mmol) in MeOH (15 mL) was added Pd—C (10% wt. wet) (0.070 g, 0.066 mmol). The reaction mixture was evacuated and hydrogenated with hydrogen balloon for 24 h. The reaction mixture was filtered through a celite pad and the pad was washed with MeOH and ethyl acetate. The filtrate was concentrated in vacuo. The residue was purified via silica gel flash column chromatography, eluting with 0-60% ethyl acetate in DCM to give Intermediate 32C (colorless oil, 0.3 g, 0.985 mmol, 74.5% yield). LC-MS Anal. Calc'd for $C_{18}H_{27}NO_3$ 305.20, found [M+H]306.2. $T_r$=0.88-0.89 min (Method A).

32D. 2-(4-(1-Methyl-6-oxo-1,6-dihydropyridin-2-yl)cyclohexyl)butanoic Acid

To a solution of ethyl 2-(4-(1-methyl-6-oxo-1,6-dihydropyridin-2-yl)cyclohexyl)butanoate (0.3 g, 0.982 mmol) in THF (6 mL) and MeOH (6 mL) was added lithium hydroxide (2M aqueous solution) (7.86 mL, 15.72 mmol). The resulting mixture was heated at 68° C. for 4 days. The reaction mixture was cooled down and to the reaction mixture was added 1 N HCl solution to adjust pH to 3. The resulting mixture was extracted with ethyl acetate. The organic layer was separated and washed with brine, and dried over MgSO$_4$. The filtrate was concentrated in vacuo to give Intermediate 32D (white solid, 0.22 g, 0.793 mmol, 81% yield). LC-MS Anal. Calc'd for $C_{16}H_{23}NO_3$ 277.17, found [M+H] 278.3. $T_r$=0.72-0.74 min (Method A).

32E. 6-(4-(1-Aminopropyl)cyclohexyl)-1-methylpyridin-2(1H)-one

To a solution of 2-(4-(1-methyl-6-oxo-1,6-dihydropyridin-2-yl)cyclohexyl)butanoic acid (0.22 g, 0.793 mmol) in Toluene (6 mL) were added TEA (0.177 mL, 1.269 mmol) and DPPA (0.197 mL, 1.031 mmol). The reaction mixture was heated at 70° C. for 1.5 h. The reaction mixture was concentrated in vacuo. To the residue was added THF (4 mL) and LiOH aqueous solution (2.0 M solution) (2.78 mL, 5.55 mmol). The reaction mixture was stirred at rt for 20 h. The reaction mixture was diluted with water and 1 N HCl solution was added to adjust pH to 1-2. The resulting mixture was extracted with ethyl acetate to remove DPPA related impurity. The aqueous layer was separated and to the aqueous layer was added 1 N NaOH solution to adjust pH to 10-11. The resulting mixture was extracted with ethyl acetate three times. The organic layers were combined and dried over MgSO$_4$. The filtrate was concentrated in vacuo to give Intermediate 32E (colorless oil, 0.103 g, 0.415 mmol, 52.3% yield). LC-MS Anal. Calc'd for $C_{15}H_{24}N_2O$ 248.19, found [M+H] 249.3. $T_r$=0.52-0.53 min (Method A).

Example 32, Four Isomers

6-Methoxy-N-(1-(4-(1-methyl-6-oxo-1,6-dihydropyridin-2-

To a solution of 6-methoxynicotinic acid (27.3 mg, 0.178 mmol) in DMF (1 mL) was added HATU (72.9 mg, 0.192 mmol). The reaction mixture was stirred at rt for 5 min, followed by addition of a solution of 6-(4-(1-aminopropyl)cyclohexyl)-1-methylpyridin-2(1H)-one (34 mg, 0.137 mmol) in THF (1 mL) and DIPEA (0.072 mL, 0.411 mmol). The reaction mixture was stirred at rt for 50 min. The reaction mixture was concentrated in vacuo. and the residue was dissolved in MeOH, filtered, and purified via preparative HPLC to give a mixture of four isomers. The isomers were further separated by preparative SFC (Method 32% IPA-DEA on AD) to give four isolates. (absolute stereochemistry was not determined).

First elute (5.9 mg, 0.015 mmol, 11.0% yield). LC-MS Anal. Calc'd for $C_{22}H_{29}N_3O_3$ 383.22, found [M+H] 383.9. $T_r$=1.41 min (Method B). $T_r$=2.09 min over 10 min run (Method 32% IPA-DEA on AD). $^1$H NMR (500 MHz, DMSO-$d_6$) δ 8.66 (br s, 1H), 8.26-7.96 (m, 2H), 7.55-7.26 (m, 1H), 6.89 (d, J=8.7 Hz, 1H), 6.27 (br d, J=8.9 Hz, 1H), 6.21-6.11 (m, 1H), 4.20 (br d, J=9.8 Hz, 1H), 3.89 (s, 3H), 2.97-2.69 (m, 1H), 2.55 (s, 3H), 1.86-1.29 (m, 11H), 0.85 (br t, J=6.8 Hz, 3H).

Second elute (6.1 mg, 0.016 mmol, 11.5% yield). LC-MS Anal. Calc'd for $C_{22}H_{29}N_3O_3$ 383.22, found [M+H] 383.9. $T_r$=1.41 min (Method B). $T_r$=2.36 min over 10 min run (Method 32% IPA-DEA on AD). $^1$H NMR (500 MHz, DMSO-$d_6$) δ 8.66 (br s, 1H), 8.26-7.96 (m, 2H), 7.55-7.26 (m, 1H), 6.89 (d, J=8.7 Hz, 1H), 6.27 (br d, J=8.9 Hz, 1H), 6.21-6.11 (m, 1H), 4.20 (br d, J=9.8 Hz, 1H), 3.89 (s, 3H), 2.97-2.69 (m, 1H), 2.55 (s, 3H), 1.86-1.29 (m, 11H), 0.85 (br t, J=6.8 Hz, 3H).

Third elute (2.4 mg, 6.2 µmol, 4.5% yield). LC-MS Anal. Calc'd for $C_{22}H_{29}N_3O_3$ 383.22, found [M+H] 383.9. $T_r$=1.41 min (Method B). $T_r$=3.32 min over 10 min run (Method 32% IPA-DEA on AD). $^1$H NMR (500 MHz, DMSO-$d_6$) δ 8.66 (br s, 1H), 8.25-8.00 (m, 2H), 7.35 (br t, J=8.0 Hz, 1H), 6.89 (d, J=8.7 Hz, 1H), 6.26 (br d, J=8.9 Hz, 1H), 6.14 (br d, J=6.1 Hz, 1H), 3.89 (s, 3H), 3.81-3.74 (m, 1H), 2.68 (br t, J=10.9 Hz, 1H), 2.55 (s, 3H), 1.97-1.76 (m, 4H), 1.68-1.12 (m, 7H), 0.84 (br t, J=6.5 Hz, 3H).

Fourth elute (2.6 mg, 6.7 µmol, 4.9% yield). LC-MS Anal. Calc'd for $C_{22}H_{29}N_3O_3$ 383.22, found [M+H] 383.9. $T_r$=1.41 min (Method B). $T_r$=5.18 min over 10 min run (Method 32% IPA-DEA on AD). $^1$H NMR (500 MHz, DMSO-$d_6$) δ 8.66 (br s, 1H), 8.25-8.00 (m, 2H), 7.35 (br t, J=8.0 Hz, 1H), 6.89 (d, J=8.7 Hz, 1H), 6.26 (br d, J=8.9 Hz, 1H), 6.14 (br d, J=6.1 Hz, 1H), 3.89 (s, 3H), 3.81-3.74 (m, 1H), 2.68 (br t, J=10.9 Hz, 1H), 2.55 (s, 3H), 1.97-1.76 (m, 4H), 1.68-1.12 (m, 7H), 0.84 (br t, J=6.5 Hz, 3H).

Example 33

N—((R)-1-((cis)-4-(6-fluoroquinolin-4-yl)cyclohexyl)ethyl)nicotinamide

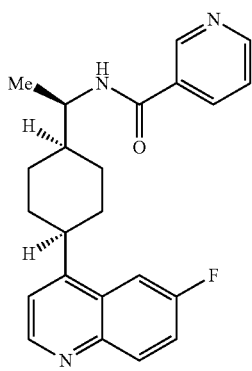 [SMILES: C[C@@H](NC(=O)c1cccnc1)[C@H]1CC[C@@H](c2ccnc3ccc(F)cc32)CC1]

Example 33. N—((R)-1-((cis)-4-(6-fluoroquinolin-4-yl)cyclohexyl)ethyl)nicotinamide The procedures found in WO 2016/073774 were utilized to prepare (R)-1-((1 s,4S)-4-(6-fluoroquinolin-4-yl)cyclohexyl)ethan-1-amine (20 mg, 0.073 mmol) was dissolved in 0.26 mL of DMF. To this was added a solution of HOBT (16.87 mg, 0.110 mmol) and EDC (21.12 mg, 0.110 mmol) in 0.26 mL of DMF. To this, nicotinic acid (18 mg, 0.147 mmol) was added and the reaction was stirred at room temperature overnight. After 16 hours, the reaction was diluted with DMF to bring the total reaction volume to 2 mL, filtered, and purified via preparative HPLC (method C) to give Example 33 (12.4 mg, 45% yield). LC-MS Anal. Calc'd for $C_{23}H_{24}FN_3O$ 377.19, found [M+H] 378.3 $T_r$=1.592 min (Method B). $^1$H NMR (500 MHz, DMSO-$d_6$) δ 9.00 (d, J=1.5 Hz, 1H), 8.83 (d, J=4.5 Hz, 1H), 8.69 (dd, J=4.7, 1.2 Hz, 1H), 8.48 (br d, J=8.8 Hz, 1H), 8.18 (br d, J=8.0 Hz, 1H), 8.08 (dd, J=9.2, 5.9 Hz, 1H), 7.96 (dd, J=10.9, 2.5 Hz, 1H), 7.66 (td, J=8.7, 2.6 Hz, 1H), 7.53-7.43 (m, 2H), 4.52-4.38 (m, 1H), 3.51-3.31 (m, 1H), 1.92-1.76 (m, 5H), 1.75-1.59 (m, 4H), 1.21 (d, J=6.5 Hz, 3H).

Examples 34-40

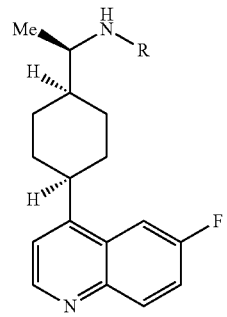

Examples 34-36 were prepared from intermediate 33A following the procedure for Example 33 using the corresponding benzoic acids.

| Ex. No. | Name | R | Tr (min) (Method B) | [M + H]⁺ |
|---|---|---|---|---|
| 34 | N-((R)-1-((cis)-4-(6-fluoroquinolin-4-yl)cyclohexyl)ethyl) isonicotinamide | ![structure] | 1.599 | 378.3 |
| 35 | N-((R)-1-((cis)-4-(6-fluoroquinolin-4-yl)cyclohexyl)ethyl)pyrazine-2-carboxamide | ![structure] | 1.763 | 379.3 |
| 36 | N-((R)-1-((cis)-4-(6-fluoroquinolin-4-yl)cyclohexyl)ethyl)pyrimidine-5-carboxamide | ![structure] | 1.521 | 379.3 |

Example 44

(±)-6-methoxy-N-(1-((cis)-4-(8-methoxy-6-(trifluoromethyl)quinolin-4-yl)cyclohexyl)propyl)nicotinamide

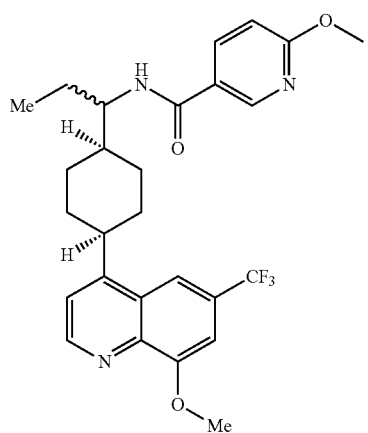 [SMILES: CCC(NC(=O)c1ccc(OC)nc1)[C@H]1CC[C@@H](c2ccnc3c(OC)cc(C(F)(F)F)cc32)CC1]

Intermediate 44A: ethyl 8-fluoro-4-hydroxy-6-(trifluoromethyl)quinoline-3-carboxylate Diethyl 2-(ethoxymethylene)malonate (13.54 ml, 67.0 mmol) and 2-fluoro-4-(trifluoromethyl)aniline (10 g, 55.8 mmol) were stirred at 100° C. for 2 hours. The reaction was then concentrated in vacuo to remove EtOH formed in first step. The crude residue taken up in diphenyl ether (55.8 ml) and refluxed at 250° C. for 6 hours. Reaction was then cooled to room temperature and a precipitate forms. The resulting solid was filtered off and rinsed with 1:1 hexanes: EtOAc to give ethyl 8-fluoro-4-hydroxy-6-(trifluoromethyl)quinoline-3-carboxylate Intermediate 44A (7.79 g, 25.7 mmol, 46.0% yield) as an off white solid. LC-MS Anal. Calc'd for $C_{13}H_9F_4NO_3$ 303.05, found [M+H]304.1, $T_r$=0.75 min (Method A). $^1$H NMR (400 MHz, DMSO-$d_6$) δ 12.80 (br s, 1H), 8.46 (s, 1H), 8.22 (s, 1H), 8.12 (dd, J=10.6, 1.8 Hz, 1H), 4.24 (q, J=7.1 Hz, 2H), 1.29 (t, J=7.1 Hz, 3H)

Intermediate 44B: 8-fluoro-4-hydroxy-6-(trifluoromethyl)quinoline-3-carboxylic Acid To a flask containing ethyl 8-fluoro-4-hydroxy-6-(trifluoromethyl)quinoline-3-carboxylate Intermediate 44A (7.79 g, 25.7 mmol) was added water (42.8 ml) followed by NaOH (4.26 g, 107 mmol). This mixture was heated to reflux (100° C.) for 1 hour. The resulting mixture was cooled to 5° C. and to this one was added 1 N hydrochloric acid (190 ml). The precipitates were collected by filtration and the filter cake was washed with water and dried under high vacuum to give 8-fluoro-4-hydroxy-6-(trifluoromethyl)quinoline-3-carboxylic acid Intermediate 44B (6.97 g, 25.3 mmol, 99% yield). LC-MS Anal. Calc'd for $C_{11}H_5F_4NO_3$ 275.02, found [M+H] 276.0, $T_r$=0.78 min (Method A).

Intermediate 44C: give 8-fluoro-6-(trifluoromethyl)quinolin-4-ol 8-fluoro-4-hydroxy-6-(trifluoromethyl)quinoline-3-carboxylic acid Intermediate 44B (5 g, 18.17 mmol) was taken up in diphenylether (36.3 ml) and refluxed for 4 hours. The resulting mixture was cooled to room temperature and to this was added hexane (100 ml). After the mixture was stirred for 1 hour, the precipitates were collected by filtration and the filter cake was washed with a mixture of hexane and ethyl acetate (1:1), followed by drying on high vacuum, to give 8-fluoro-6-(trifluoromethyl)quinolin-4-ol Intermediate 44C (3.84 g, 16.61 mmol, 91% yield). LC-MS Anal. Calc'd for $C_{10}H_5F_4NO$ 231.03, found [M+H] 232.1, $T_r$=0.76 min (Method A). $^1$H NMR (400 MHz, DMSO-$d_6$) δ 12.22 (br s, 1H), 8.17 (s, 1H), 8.03 (dd, J=10.9, 1.8 Hz, 1H), 7.95 (dd, J=7.5, 5.9 Hz, 1H), 6.27-6.18 (m, 1H)

Intermediate 44D: 4-chloro-8-fluoro-6-(trifluoromethyl)quinoline 8-fluoro-6-(trifluoromethyl)quinolin-4-ol Intermediate 44C (3.84 g, 16.61 mmol) was taken up in $POCl_3$ (16.61 ml) and heated to 90° C. for 1 hour. The reaction was cooled and the resulting mixture was evaporated under reduced pressure. The residue was dissolved in tetrahydrofuran and the solution was poured into 28% ammonium hydroxide and the mixture was cooled to 5° C. The aqueous mixture was extracted with ethyl acetate. The organic layer was washed successively with water (×2) and brine, dried over anhydrous sodium sulfate, filtered, and evaporated under reduced pressure. Drying on high vacuum gave 4-chloro-8-fluoro-6-(trifluoromethyl)quinoline Intermediate 44D (4.14 g, 16.59 mmol, 100% yield). LC-MS Anal. Calc'd for $C_{10}H_4Cl_4N$ 249.00, found [M+H]250.1, $T_r$=0.98 min (Method A). $^1$H NMR (400 MHz, chloroform-d) δ 8.97 (d, J=4.6 Hz, 1H), 8.44-8.34 (m, 1H), 7.73-7.64 (m, 2H).

Intermediate 44E: ethyl 2-(4-(8-fluoro-6-(trifluoromethyl)quinolin-4-yl)cyclohex-3-en-1-yl)butanoate To a reaction mixture of 4-chloro-8-fluoro-6-(trifluoromethyl)quinoline Intermediate 44D (0.668 g, 2.68 mmol) and ethyl 2-(4-(4,4,5,5-tetramethyl-1,3,2-dioxaborolan-2-yl)cyclohex-3-en-1-yl)butanoate (Intermediate 24C) (0.75 g, 2.327 mmol) in 1,4-Dioxane (9.31 ml) was added $K_2CO_3$ (0.965 g, 6.98 mmol) solution and the resulting mixture was purged with nitrogen stream for 3 min, followed by addition of $Pd(Ph_3P)_4$ (0.134 g, 0.116 mmol) and the reaction mixture was further purged with nitrogen stream and then heated at 100° C. under nitrogen for 20 h. The reaction mixture was diluted with water and ethyl acetate. The organic layer was separated, dried over $Na_2SO_4$. The filtrate was concentrated in vacuo. The residue was purified by silica gel flash column chromatography to give ethyl 2-(4-(8-fluoro-6-(trifluoromethyl)quinolin-4-yl)cyclohex-3-en-1-yl)butanoate Intermediate 44E (860 mg, 2.101 mmol, 90% yield) as a mixture of diastereomers. LC-MS Anal. Calc'd for $C_{22}H_{23}F_4NO_2$ 409.17, found [M+H] 409.9, $T_r$=1.15 min (Method A).

Intermediate 44F: ethyl 2-(4-(8-fluoro-6-(trifluoromethyl)quinolin-4-yl)cyclohexyl) butanoate Ethyl 2-(4-(8-fluoro-6-(trifluoromethyl)quinolin-4-yl)cyclohex-3-en-1-yl)butanoate Intermediate 44E (860 mg, 2.101 mmol) was dissolved in MeOH (11.600 mL) and Ammonium formate (662 mg, 10.50 mmol) was added. The vessel was equipt with a reflux condenser and vacated and flushed with $N_2$ 3 times. Then, 10% Pd/C (224 mg, 0.210 mmol) (wet, degussa type) was added and the reaction was heated to reflux for 2 hours. LCMS shows good conversion to two peaks corresponding to loss of fluorine and over reduction. 1H NMR consistent with a mixture of diastereomers resulting from over reduction to tetrahydroisoquinoline. The reaction was cooled, concentrated in vacuo, diluted with DCM and filtered over celite. This crude mixture was carried forward.

The crude reaction mixture was taken up in toluene (18 mL) and DDQ (488 mg, 2.152 mmol) was added. The dark purple-red reaction mixture was heated at 100° C. for 2 h. The reaction mixture was then cooled and diluted with ethyl acetate and filtered. The filtrate was concentrated in vacuo. The crude product was purified by silica gel flash column to give ethyl 2-(4-(8-fluoro-6-(trifluoromethyl)quinolin-4-yl)cyclohexyl)butanoate Intermediate 44F (350 mg, 0.681 mmol, 38.0% yield over 2 steps) as a mixture of 4 isomers (cis/trans and R/S). LC-MS Anal. Calc'd for $C_{22}H_{25}F_4NO_2$ 411.18, found [M+H]412.2, $T_r$=1.16 min (Method A).

Intermediate 44G: 2-(4-(8-fluoro-6-(trifluoromethyl)quinolin-4-yl)cyclohexyl)butanoic Acid Ethyl 2-(4-(8-fluoro-6-(trifluoromethyl)quinolin-4-yl)cyclohexyl)butanoate Intermediate 44F (350 mg, 0.851 mmol) taken up in THF (1418 μl), Water (1418 μl), and MeOH (1418 μl). Lithium hydroxide (204 mg, 8.51 mmol) added and reaction stirred at 60° C. for three days. LCMS shows complete displacement of fluorine with methanol. The reaction was concentrated in vacuo, acetic acid was added (until a precipitate forms), and the aqueous layer was extracted with EtOAc followed by CHCl$_3$/iPrOH 7:3. Organics were combined, dried with sodium sulfate, filtered and concentrated to give 2-(4-(8-methoxy-6-(trifluoromethyl)quinolin-4-yl)cyclohexyl)butanoic acid Intermediate 44G (320 mg, 0.809 mmol, 95%) as a mixture of 4 stereoisomers. LC-MS Anal. Calc'd for $C_{21}H_{24}F_3NO_3$ 395.17, found [M+H] 396.2, $T_r$=0.77 min (Method A).

Intermediate 44H: 1-(4-(8-methoxy-6-(trifluoromethyl)quinolin-4-yl)cyclohexyl)propan-1-amine 2-(4-(8-methoxy-6-(trifluoromethyl)quinolin-4-yl)cyclohexyl)butanoic acid Intermediate 44G (320 mg, 0.809 mmol) taken up in Toluene (2698 μl) and diphenyl phosphorazidate (245 mg, 0.890 mmol) and TEA (135 μl, 0.971 mmol) added and the reaction was heated to 70° C. for 1 hour. 0.5 eq DPPA added and heated for an additional hour. Reaction was then concentrated in vacuo, taken up in THF (7 mL) and water (7 mL) and LiOH (97 mg, 4.05 mmol) was added. The reaction stirred at room temperature for 1 hour. The reaction was acidified with 1 N HCl, and extracted with EtOAc to remove DPPA related impurities. Aqueous was then treated in 1 N NaOH and a white precipitate forms. Extracted with 7:3 chloroform isopropanol twice to give an organic fraction containing product (2 diast present by LCMS). Organics dried with sodium sulfate, filtered, and concentrated in vacuo to give 1-(4-(8-methoxy-6-(trifluoromethyl)quinolin-4-yl)cyclohexyl)propan-1-amine Intermediate 44H (222 mg, 0.454 mmol, 56.1% yield) as a mixture of 4 stereoisomers. LC-MS Anal. Calc'd for $C_{20}H_{25}F_3N_2O$ 366.19, found [M+H]366.9, $T_r$=0.61 and 0.63 min (cis and trans diastereomers) (Method A).

Example 44: (±)-6-methoxy-N-(1-((cis)-4-(8-methoxy-6-(trifluoromethyl)quinolin-4-yl)cyclohexyl)propyl)nicotinamide 1-(4-(8-methoxy-6-(trifluoromethyl)quinolin-4-yl)cyclohexyl)propan-1-amine Intermediate 44H (70 mg, 0.191 mmol) was taken up in DMF (955 μl) and HOBT (35.1 mg, 0.229 mmol), EDC (43.9 mg, 0.229 mmol), 6-methoxynicotinic acid (38.0 mg, 0.248 mmol) and TEA (133 μl, 0.955 mmol) were added and reaction stirred at room temperature for 4 hours. The reaction was diluted with DMF to bring overall volume to 2 mL, filtered, and purified via preparative HPLC. The cis-diastereomer was successfully separated to give (±)-6-methoxy-N-(1-((cis)-4-(8-methoxy-6-(trifluoromethyl)quinolin-4-yl)cyclohexyl)propyl)nicotinamide Example 44 (26.2 mg, 0.052 mmol, 27.1%). LC-MS Anal. Calc'd for $C_{27}H_{30}F_3N_3O_3$ 501.22, found [M+H] 502.1 $T_r$=1.996 min (Method B). $^1$H NMR (500 MHz, DMSO-d$_6$) δ 8.92 (d, J=4.3 Hz, 1H), 8.66 (d, J=2.1 Hz, 1H), 8.18-8.08 (m, 2H), 8.04 (s, 1H), 7.60 (d, J=4.6 Hz, 1H), 7.31 (s, 1H), 6.87 (d, J=8.9 Hz, 1H), 4.28 (br d, J=9.2 Hz, 1H), 4.02 (s, 3H), 3.88 (s, 3H), 2.5 (m, 1H), 1.92-1.55 (m, 10H), 1.47-1.32 (m, 1H), 0.87 (br t, J=7.2 Hz, 3H)

Examples 45A and B (±)-6-methoxy-N-(1-(4-(4-methylpyridin-2-yl)cyclohexyl)propyl)nicotinamide (Cis/Trans Isomers Prepared, Relative Stereochemistry not Determined)

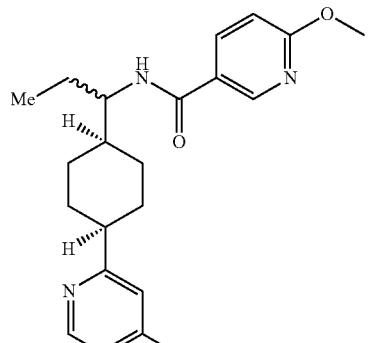

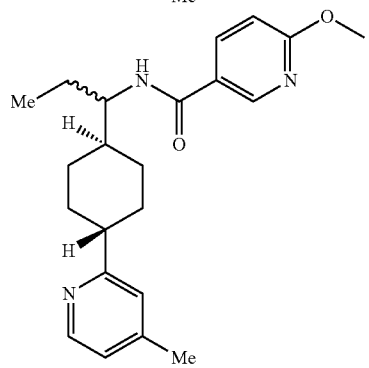

Intermediate 45A: Ethyl 2-(4-(4-methylpyridin-2-yl)cyclohex-3-en-1-yl)butanoate

To a reaction mixture of 2-bromo-4-methylpyridine (307 mg, 1.784 mmol) and ethyl 2-(4-(4,4,5,5-tetramethyl-1,3,2-dioxaborolan-2-yl)cyclohex-3-en-1-yl)butanoate (Intermediate 24C) (500 mg, 1.552 mmol) in 1,4-Dioxane (6206 μl) was added K$_2$CO$_3$ (643 mg, 4.65 mmol) solution in 1.5 mL water and the resulting mixture was purged with nitrogen stream for 3 min, followed by addition of Pd(Ph$_3$P)$_4$ (90 mg, 0.078 mmol) and the reaction mixture was further purged with nitrogen stream and then heated at 100° C. under nitrogen for 20 h. The reaction mixture was diluted with water and ethyl acetate. The organic layer was separated, dried over $Na_2SO_4$ and filtered. The filtrate was concentrated in vacuo. The residue was purified by silica gel flash column chromatography to give ethyl 2-(4-(4-methylpyridin-2-yl)cyclohex-3-en-1-yl)butanoate Intermediate 45A (236 mg, 0.821 mmol, 52.9% yield) as a mixture of diastereomers. LC-MS Anal. Calc'd for $C_{18}H_{25}NO_2$ 287.19, found [M+H] 288.1, $T_r$=0.74 min (Method A).

Intermediate 45B: Ethyl 2-(4-(4-methylpyridin-2-yl)cyclohexyl)butanoate

Ethyl 2-(4-(4-methylpyridin-2-yl)cyclohex-3-en-1-yl)butanoate Intermediate 45A (236 mg, 0.821 mmol) was dissolved in MeOH (3285 μl) and ammonium formate (259 mg, 4.11 mmol) was added. The vessel was equipt with a reflux condenser and vacated and flushed with $N_2$ 3 times. Then, PALLADIUM ON CARBON (87 mg, 0.082 mmol) (wet, degussa type) was added and the reaction was heated to reflux for 1 hour. The reaction was cooled, concentrated in vacuo, diluted with DCM and filtered over celite. The filtrate was concentrated in vacuo to give ethyl 2-(4-(4-methylpyridin-2-yl)cyclohexyl)butanoate Intermediate 145B (216 mg, 0.746 mmol, 91% yield) as a mixture of cis and trans diastereomers. LC-MS Anal. Calc'd for $C_{18}H_{27}NO_2$ 289.20, found [M+H] 290.2, $T_r$=0.73 and 0.75 min for each diastereomer (Method A).

Intermediate 45C: 2-(4-(4-methylpyridin-2-yl)cyclohexyl)butanoic Acid

Ethyl 2-(4-(4-methylpyridin-2-yl)cyclohexyl)butanoate Intermediate 45B (216 mg, 0.746 mmol) taken up in THF (1244 μl), Water (1244 μl), and MeOH (1244 μl). Lithium hydroxide (179 mg, 7.46 mmol) added and reaction stirred at 60° C. for 2 days. The reaction was concentrated in vacuo and acetic acid was added (until a precipitate forms). The aqueous layer was extracted with EtOAc followed by CHCl3/iPrOH 7:3. The combined organics were dried with sodium sulfate, filtered and concentrated to give 2-(4-(4-methylpyridin-2-yl)cyclohexyl)butanoic acid Intermediate 45C (200 mg, 0.765 mmol, ~quant.) as a mixture of cis and trans diastereomers. LC-MS Anal. Calc'd for $C_{16}H_{23}NO_2$ 261.17, found [M+H] 262.2, $T_r$=0.55 and 0.56 min for each diastereomer (Method A).

Intermediate 45D: 1-(4-(4-methylpyridin-2-yl)cyclohexyl)propan-1-amine 2-(4-(4-methylpyridin-2-yl)cyclohexyl)butanoic acid Intermediate 45C (200 mg, 0.765 mmol) taken up in toluene (2551 μl) and diphenyl phosphorazidate (232 mg, 0.842 mmol) and TEA (128 μl, 0.918 mmol) were added. The reaction was heated to 70° C. for 1 hour. Another equivalent of DPPA was added and the reaction was heated another hour. The reaction was then concentrated in vacuo, taken up in THF (3 mL) and water (3 mL) and LiOH (92 mg, 3.83 mmol) was added. Reaction stirred at room temperature overnight. The reaction was acidified with 1 N HCl, and extracted with EtOAc to remove DPPA related impurities. The aqueous was then treated in 1 N NaOH and a white precipitate formed. The aqueous layer was extracted with 7:3 chloroform isopropanol twice to give an organic fraction containing product. The combined organics were dried with sodium sulfate, filtered, and concentrated in vacuo to give 1-(4-(4-methylpyridin-2-yl)cyclohexyl)propan-1-amine Intermediate 45C (95 mg, 0.409 mmol, 53.4% yield) as a mixture of cis and trans diastereomers. LC-MS Anal. Calc'd for $C_{15}H_{24}N_2$ 232.19, found [M+H] 233.1, $T_r$=0.44 and 0.46 min for each diastereomer (Method A).

Examples 45A and B: (±)-6-methoxy-N-(1-(4-(4-methylpyridin-2-yl)cyclohexyl)propyl)nicotinamide (Cis/Trans Isomers Prepared, Relative Stereochemistry not Determined)

1-(4-(4-methylpyridin-2-yl)cyclohexyl)propan-1-amine Intermediate 45B (32 mg, 0.138 mmol) was taken up in DMF (689 μl) and HOBT (25.3 mg, 0.165 mmol), EDC (31.7 mg, 0.165 mmol), 6-methoxynicotinic acid (27.4 mg, 0.179 mmol) and TEA (96 μl, 0.689 mmol) were added and reaction stirred at room temperature overnight. The reaction was diluted with DMF to bring overall volume to 2 mL, filtered, and purified via preparative HPLC. Cis and trans diastereomers were successfully separated to give Example 45A (12.5 mg, 0.031 mmol, 22.72%) LC-MS Anal. Calc'd for $C_{22}H_{29}N_3O_2$ 367.23, found [M+H] 368.3 $T_r$=1.693 min (Method B). $^1$H NMR (500 MHz, DMSO-$d_6$) δ 8.65 (br s, 1H), 8.26 (br d, J=4.4 Hz, 1H), 8.12 (br d, J=8.6 Hz, 2H), 7.05 (s, 1H), 7.00 (br d, J=4.7 Hz, 1H), 6.88 (d, J=8.6 Hz, 1H), 3.88 (s, 3H), 3.72 (m, 1H) 2.25 (s, 3H), 1.82 (br d, J=9.7 Hz, 5H), 1.62 (br d, J=3.7 Hz, 1H), 1.51-1.39 (m, 4H), 1.12 (br d, J=12.0 Hz, 2H), 0.83 (br t, J=7.0 Hz, 3H) and Example 45B (16.5 mg, 0.045 mmol, 32.6%) LC-MS Anal. Calc'd for $C_{22}H_{29}N_3O_2$ 367.23, found [M+H] 368.0 $T_r$=1.761 min (Method B). $^1$H NMR (500 MHz, DMSO-$d_6$) δ 8.62 (br s, 1H), 8.32 (br d, J=4.8 Hz, 1H), 8.13-8.07 (m, 1H), 8.03 (br d, J=8.7 Hz, 1H), 7.09 (s, 1H), 7.00 (d, J=4.8 Hz, 1H), 6.87 (d, J=8.7 Hz, 1H), 4.16-4.01 (m, 1H), 3.88 (s, 3H), 2.73 (br s, 1H), 2.27 (s, 3H), 2.00-1.79 (m, 2H), 1.76-1.51 (m, 7H), 1.46 (br d, J=11.1 Hz, 1H), 1.40-1.30 (m, 1H), 0.83 (br t, J=7.2 Hz, 3H)

Examples 46A-D 6-methoxy-N-(1-(4-(6-methylpyridin-2-yl)cyclohexyl)propyl)nicotinamide (Homochiral, Relative and Absolute Stereochemistry not Determined)

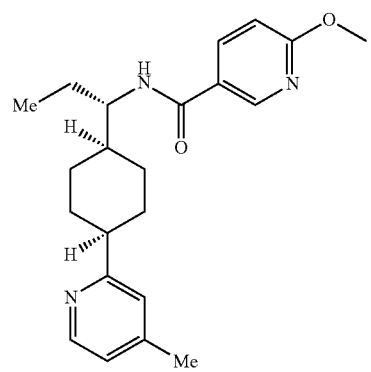

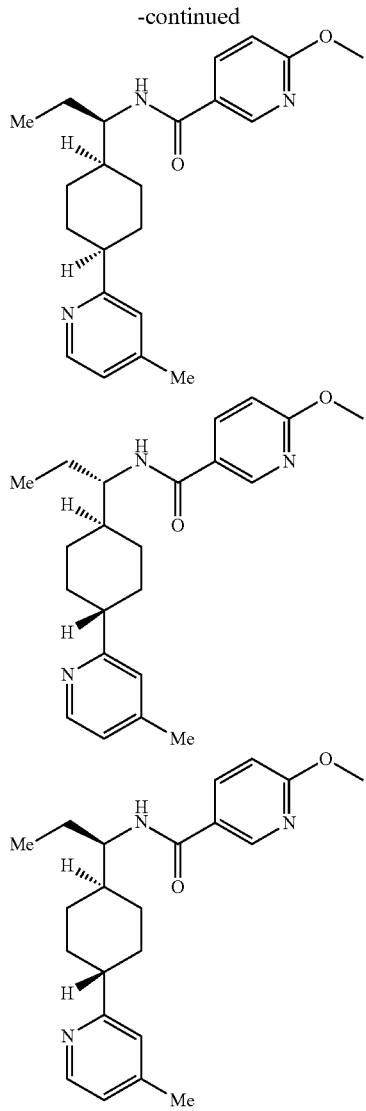

Intermediate 46A: ethyl 2-(4-(6-methylpyridin-2-yl)cyclohex-3-en-1-yl)butanoate

To a reaction mixture of 2-bromo-6-methylpyridine (307 mg, 1.784 mmol) and ethyl 2-(4-(4,4,5,5-tetramethyl-1,3,2-dioxaborolan-2-yl)cyclohex-3-en-1-yl)butanoate (Intermediate 24C) (500 mg, 1.552 mmol) in 1,4-Dioxane (6206 μl) was added $K_2CO_3$ (643 mg, 4.65 mmol) solution and the resulting mixture was purged with nitrogen stream for 3 min, followed by addition of Pd(Ph$_3$P)$_4$ (90 mg, 0.078 mmol) and the reaction mixture was further purged with nitrogen stream and then heated at 100° C. under nitrogen for 20 hours. The reaction mixture was diluted with water and ethyl acetate. The organic layer was separated and dried over $Na_2SO_4$. The filtrate was concentrated in vacuo. The residue was purified by silica gel flash column chromatography to give ethyl 2-(4-(6-methylpyridin-2-yl)cyclohex-3-en-1-yl)butanoate Intermediate 46A (575 mg, 1.200 mmol, 77% yield) as a mixture of diastereomers. LC-MS Anal. Calc'd for $C_{18}H_{25}NO_2$ 287.19, found [M+H] 288.2, $T_r$=0.71 (Method A).

Intermediate 46B: ethyl 2-(4-(6-methylpyridin-2-yl)cyclohexyl)butanoate

Ethyl 2-(4-(6-methylpyridin-2-yl)cyclohex-3-en-1-yl)butanoate Intermediate 46A (575 mg, 2.001 mmol) was dissolved in MeOH (8003 μl) and ammonium formate (631 mg, 10.00 mmol) was added. The vessel was equipt with a reflux condenser and vacated and flushed with $N_2$ 3 times. Then, 10% Pd/C (213 mg, 0.200 mmol) was added and the reaction was heated to reflux for 1 hour. The reaction was cooled, concentrated in vacuo, diluted with DCM and filtered over celite to give ethyl 2-(4-(6-methylpyridin-2-yl)cyclohexyl) butanoate Intermediate 46B (372 mg, 1.285 mmol, 64.2% yield) as a mixture cis- and trans- of diastereomers. LC-MS Anal. Calc'd for $C_{18}H_{27}NO_2$ 289.20, found [M+H] 290.2, $T_r$=0.71 and 0.72 for each diastereomer (Method A).

Intermediate 46C: give 2-(4-(6-methylpyridin-2-yl)cyclohexyl)butanoic Acid

Ethyl 2-(4-(6-methylpyridin-2-yl)cyclohexyl)butanoate Intermediate 46B (372 mg, 1.285 mmol) taken up in THF (2142 μl), Water (2142 μl), and MeOH (2142 μl). Lithium hydroxide (308 mg, 12.85 mmol) added and reaction stirred at 60° C. for 2 days. The reaction was concentrated in vacuo and acetic acid added until a white precipitate formed. The aqueous layer was extracted with EtOAc. The combined organic extracts were dried with sodium sulfate, filtered, and concentrated to give 2-(4-(6-methylpyridin-2-yl)cyclohexyl)butanoic acid Intermediate 46C (360 mg, 1.377 mmol, 107% yield) as a mixture cis- and trans- of diastereomers. LC-MS Anal. Calc'd for $C_{16}H_{23}NO_2$ 261.17, found [M+H] 262.2, $T_r$=0.57 and 0.58 for each diastereomer (Method A).

Intermediate 46D: 1-(4-(6-methylpyridin-2-yl)cyclohexyl)propan-1-amine 2-(4-(6-methylpyridin-2-yl)cyclohexyl)butanoic acid Intermediate 46C (360 mg, 1.377 mmol) taken up in toluene (4591 μl) and diphenyl phosphorazidate (417 mg, 1.515 mmol) and TEA (480 μl, 3.44 mmol) added. heated to 70° C. for 1 hour. The reaction was concentrated in vacuo, raken up in THF (3 mL) and water (3 mL) and LiOH (165 mg, 6.89 mmol) was added. The reaction was stirred at room temperature overnight. The reaction was acidified with 1 N HCl and extracted with EtOAc to remove DPPA related impurities. The aqueous layer was then treated in 1 N NaOH and extracted with 7:3 chloroform isopropanol twice to give an organic fraction containing product. The combined organic extracts were dried with sodium sulfate, filtered, and concentrated in vacuo to give 1-(4-(6-methylpyridin-2-yl)cyclohexyl)propan-1-amine Intermediate 46D (190 mg, 0.818 mmol, 59.4% yield) as a mixture cis- and trans- of diastereomers. LC-MS Anal. Calc'd for $C_{15}H_{24}N_2$ 232.19, found [M+H] 233.2, $T_r$=0.45 (Method A).

Examples 46A-D 6-methoxy-N-(1-(4-(6-methylpyridin-2-yl)cyclohexyl)propyl)nicotinamide (Homochiral, Relative and Absolute Stereochemistry not Determined)

1-(4-(6-methylpyridin-2-yl)cyclohexyl)propan-1-amine Intermediate 46D (40 mg, 0.172 mmol) was taken up in DMF (861 μl) and HOBT (31.6 mg, 0.207 mmol), EDC (39.6 mg, 0.207 mmol), 6-methoxynicotinic acid (34.3 mg, 0.224 mmol) and TEA (120 µl, 0.861 mmol) were added and reaction stirred at room temperature for 3 days. After weekend LCMS shows new peak with M+1 of desired product has formed. The reaction diluted with DMF to bring overall volume to 2 mL, filtered, and purified via preparative SFC (Preparative Method: Column: Chiralpak AD, 30×250 mm, 5 micron; Flow Rate: 100 mL/min; Oven Temperature: 40 C; BPR Setting: 120 bar; UV wavelength: 220 nm; Mobile Phase: 85% CO2/15% Methanol-0.1% DEA (isocratic); Injection: 500 uL of 28.9 mg/2 mL Methanol) All four stereoisomers were successfully separated as homochiral compounds (Analytical Method: Column: Chiralpak AD, 4.6×100 mm, 5 micron (analytical); Flow Rate: 2 mL/min.; Oven Temperature: 40 C; BPR setting: 1700 psi; UV wavelength: 220 nm; Mobile Phase: 83% CO2/17% Methanol-0.1% DEA (isocratic)). Retention times for Examples 46A-D respectively=1.852 min, 2.182 min, 4.067 min, and 5.199 min. Relative and absolute stereochemistry was not determined.

Example 46A: (5.1 mg, 0.014 mmol, 7.98%) LC-MS Anal. Calc'd for $C_{22}H_{29}N_3O_2$ 367.23, found [M+H] 368.3, $T_r$=1.713 (Method B). $^1$H NMR (500 MHz, DMSO-d$_6$) δ 8.62 (s, 1H), 8.12-8.01 (m, 2H), 7.57 (t, J=7.7 Hz, 1H), 7.06 (d, J=7.8 Hz, 1H), 7.02 (d, J=7.6 Hz, 1H), 6.87 (d, J=8.7 Hz, 1H), 4.15-4.00 (m, 1H), 3.88 (s, 3H), 2.72 (br s, 1H), 2.40 (s, 3H), 1.99-1.77 (m, 2H), 1.75-1.51 (m, 7H), 1.49-1.40 (m, 1H), 1.39-1.29 (m, 1H), 0.83 (br t, J=7.2 Hz, 3H)

Example 46B: (4.9 mg, 0.013 mmol, 7.75%) LC-MS Anal. Calc'd for $C_{22}H_{29}N_3O_2$ 367.23, found [M+H] 368.3, $T_r$=1.713 (Method B). $^1$H NMR (500 MHz, DMSO-d$_6$) δ 8.61 (d, J=1.9 Hz, 1H), 8.13-8.03 (m, 2H), 7.57 (t, J=7.7 Hz, 1H), 7.06 (d, J=7.7 Hz, 1H), 7.02 (d, J=7.6 Hz, 1H), 6.87 (d, J=8.7 Hz, 1H), 4.13-4.01 (m, 1H), 3.88 (s, 3H), 2.76-2.66 (m, 1H), 2.40 (s, 3H), 1.94-1.76 (m, 2H), 1.74-1.50 (m, 7H), 1.50-1.40 (m, 1H), 1.40-1.28 (m, 1H), 0.82 (t, J=7.3 Hz, 3H)

Example 46C: (5.9 mg, 0.016 mmol, 9.33%) LC-MS Anal. Calc'd for $C_{22}H_{29}N_3O_2$ 367.23, found [M+H] 368.3, $T_r$=1.703 (Method B). $^1$H NMR (500 MHz, DMSO-d$_6$) δ 8.65 (s, 1H), 8.18-8.05 (m, 2H), 7.55 (t, J=7.7 Hz, 1H), 7.01 (dd, J=7.3, 5.4 Hz, 2H), 6.88 (d, J=8.7 Hz, 1H), 3.88 (s, 3H), 3.74 (m, 1H), 2.54 (br s, 1H), 2.39 (s, 3H), 1.82 (br d, J=8.1 Hz, 4H), 1.70-1.58 (m, 1H), 1.55-1.36 (m, 4H), 1.12 (br d, J=11.9 Hz, 2H), 0.83 (br t, J=7.2 Hz, 3H)

Example 46D: (5.8 mg, 0.015 mmol, 8.71%) LC-MS Anal. Calc'd for $C_{22}H_{29}N_3O_2$ 367.23, found [M+H] 368.3, $T_r$=1.693 (Method B). $^1$H NMR (500 MHz, DMSO-d$_6$) δ 8.65 (d, J=2.1 Hz, 1H), 8.12 (dd, J=8.6, 2.2 Hz, 1H), 8.08 (br d, J=8.8 Hz, 1H), 7.55 (t, J=7.7 Hz, 1H), 7.01 (dd, J=7.4, 5.1 Hz, 2H), 6.88 (d, J=8.7 Hz, 1H), 3.89 (s, 3H), 3.73 (br s, 1H), 2.56-2.52 (m, 1H), 2.39 (s, 3H), 1.84 (br t, J=7.5 Hz, 4H), 1.68-1.59 (m, 1H), 1.56-1.37 (m, 4H), 1.12 (br dd, J=7.2, 3.4 Hz, 2H), 0.83 (t, J=7.2 Hz, 3H)

Examples 47A-D 6-methoxy-N-(1-(4-(6-(trifluoromethyl)pyridin-2-yl) cyclohexyl)propyl)nicotinamide (Homochiral, Relative and Absolute Stereochemistry not Determined)

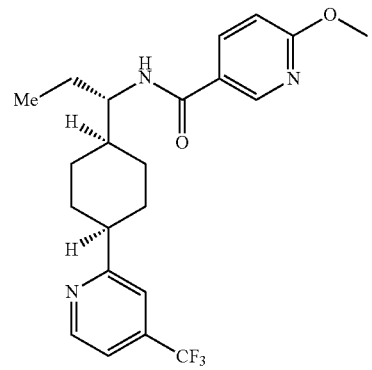

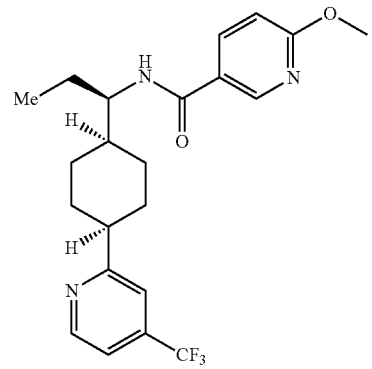

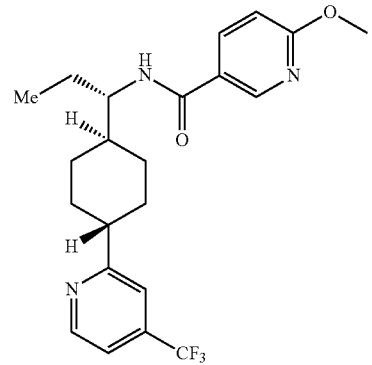

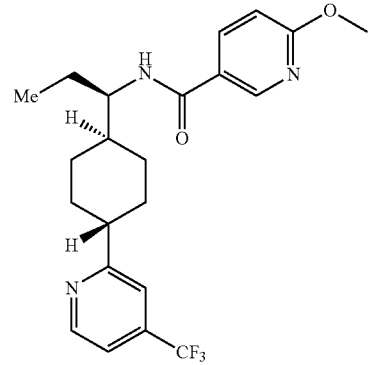

Intermediate 47A: ethyl 2-(4-(6-(trifluoromethyl)pyridin-2-yl)cyclohex-3-en-1-yl)butanoate To a reaction mixture of 2-bromo-6-(trifluoromethyl)pyridine (403 mg, 1.784 mmol) and ethyl 2-(4-(4,4,5,5-tetramethyl-1,3,2-dioxaborolan-2-yl)cyclohex-3-en-1-yl)butanoate (Intermediate 24C) (500 mg, 1.552 mmol) in 1,4-Dioxane (6206 µl) was added $K_2CO_3$ (643 mg, 4.65 mmol) solution and the resulting mixture was purged with nitrogen stream for 3 min, followed by addition of $Pd(Ph_3P)_4$ (90 mg, 0.078 mmol) and the reaction mixture was further purged with nitrogen stream and then heated at 100° C. under nitrogen for 20 h. The reaction mixture was diluted with water and ethyl acetate. The organic layer was separated and dried over $Na_2SO_4$. The filtrate was concentrated in vacuo. The residue was purified by silica gel flash column chromatography to give ethyl 2-(4-(6-(trifluoromethyl)pyridin-2-yl)cyclohex-3-en-1-yl)butanoate Intermediate 47A (524 mg, 1.535 mmol, 99% yield) as a mixture of diastereomers. LC-MS Anal. Calc'd for $C_{18}H_{22}F_3NO_2$ 341.16, found [M+H] 342.2, $T_r$=1.19 (Method A).

Intermediate 47B: ethyl 2-(4-(6-(trifluoromethyl)pyridin-2-yl)cyclohexyl)butanoate Ethyl 2-(4-(6-(trifluoromethyl)pyridin-2-yl)cyclohex-3-en-1-yl)butanoate Intermediate 47A (524 mg, 1.535 mmol) was dissolved in MeOH (6140 µl) and ammonium formate (484 mg, 7.68 mmol) was added. The vessel was equipt with a reflux condenser and vacated and flushed with $N_2$ 3 times. Then, 10% Pd/C (163 mg, 0.154 mmol) was added and the reaction was heated to reflux for 1 hour. The reaction was cooled, concentrated in vacuo, diluted with DCM and filtered over celite to give ethyl 2-(4-(6-(trifluoromethyl)pyridin-2-yl)cyclohexyl)butanoate Intermediate 47B (448 mg, 1.305 mmol, 85% yield) as a mixture of cis- and trans-diastereomers. LC-MS Anal. Calc'd for $C_{18}H_{24}F_3NO_2$ 343.18, found [M+H] 344.2, $T_r$=1.18 (Method A).

Intermediate 47C: 2-(4-(6-(trifluoromethyl)pyridin-2-yl)cyclohexyl)butanoic Acid Ethyl 2-(4-(6-(trifluoromethyl)pyridin-2-yl)cyclohexyl)butanoate Intermediate 47 B (448 mg, 1.305 mmol) was taken up in THF (2174 µl), Water (2174 µl), and MeOH (2174 µl). Lithium hydroxide (312 mg, 13.05 mmol) added and reaction stirred at 60° C. for 2 days. The reaction was concentrated in vacuo and acetic acid added until a white precipitate forms. The aqueous layer was extracted with EtOAc. The combined organic extracts were dried with sodium sulfate, filtered, and concentrated to give 2-(4-(6-(trifluoromethyl)pyridin-2-yl)cyclohexyl)butanoic acid Intermediate 47C (425 mg, 1.348 mmol, ~quant. yield) as a mixture of cis- and trans-diastereomers. LC-MS Anal. Calc'd for $C_{16}H_{20}F_3NO_2$ 315.15, found [M+H] 316.2, $T_r$=1.00 (Method A).

Intermediate 47D: 1-(4-(6-(trifluoromethyl)pyridin-2-yl)cyclohexyl)propan-1-amine 2-(4-(6-(trifluoromethyl)pyridin-2-yl)cyclohexyl)butanoic acid Intermediate 47C (425 mg, 1.348 mmol) taken up in toluene (4493 µl) and diphenyl phosphorazidate (408 mg, 1.483 mmol) and TEA (470 µl, 3.37 mmol) added. heated to 70 C for 1 hour. The reaction was concentrated in vacuo, taken up in THF (3 mL) and water (3 mL) and LiOH (161 mg, 6.74 mmol) was added. Reaction stirred at room temperature overnight. Then, the reaction was acidified with 1 N HCl, and extracted with EtOAc to remove DPPA related impurities. The aqueous layer was then treated in 1 N NaOH and extracted with 7:3 chloroform isopropanol twice to give an organic fraction containing product. The combined organic extracts were dried with sodium sulfate, filtered, and concentrated in vacuo to give 1-(4-(6-(trifluoromethyl)pyridin-2-yl)cyclohexyl)propan-1-amine Intermediate 47D (223 mg, 0.779 mmol, 57.8% yield) as a mixture of cis- and trans-diastereomers. LC-MS Anal. Calc'd for $C_{15}H_{21}F_3N_2$ 286.17, found [M+H] 287.2, $T_r$=0.74 (Method A).

Examples 447A-D 6-methoxy-N-(1-(4-(6-(trifluoromethyl)pyridin-2-yl)cyclohexyl)propyl)nicotinamide (Homochiral, Relative and Absolute Stereochemistry not Determined)

(4-(6-(trifluoromethyl)pyridin-2-yl)cyclohexyl)propan-1-amine Intermediate 47D (40 mg, 0.140 mmol) was taken up in DMF (698 µl) and HOBT (25.7 mg, 0.168 mmol), EDC (32.1 mg, 0.168 mmol), 6-methoxynicotinic acid (27.8 mg, 0.182 mmol) and TEA (97 µl, 0.698 mmol) were added and reaction stirred at room temperature for 3 days. The reaction was then diluted with DMF to bring overall volume to 2 mL, filtered, and purified via preparative SFC (preparative method: Column: Chiralpak AD, 30×250 mm, 5 micron; Flow Rate: 100 mL/min; Oven Temperature: 40 C; BPR Setting: 120 bar; UV wavelength: 220 nm; Mobile Phase: 90% CO2/10% Methanol-0.1% DEA (isocratic); Injection: 400 uL of 19.7 mg/1.5 mL Methanol). All four stereoisomers were successfully separated a homochiral compounds (analytical method: Column: Chiralpak AD, 4.6×100 mm, 5 micron (analytical); Flow Rate: 2 mL/min.; Oven Temperature: 40 C; BPR setting: 1700 psi; UV wavelength: 220 nm; Mobile Phase: 90% CO2/10% Methanol-0.1% DEA (isocratic). Retention times for Examples 47A-D respectively=2.911 min, 3.321 min, 6.272 min, 9.499 min. Relative and absolute stereochemistry were not determined.

Example 47A: (3.3 mg, 7.67 µmol, 5.49%) LC-MS Anal. Calc'd for $C_{22}H_{26}F_3N_3O_2$ 421.20, found [M+H] 422.3, $T_r$=2.085 (Method B). $^1$H NMR (500 MHz, DMSO-$d_6$) δ 8.60 (br d, J=2.0 Hz, 1H), 8.13-8.02 (m, 2H), 8.01-7.96 (m, 1H), 7.71-7.64 (m, 1H), 7.63 (br d, J=7.9 Hz, 1H), 6.86 (d, J=8.7 Hz, 1H), 3.99 (br d, J=9.1 Hz, 1H), 3.88 (s, 3H), 2.92 (br s, 1H), 1.92 (br d, J=5.3 Hz, 2H), 1.79-1.57 (m, 6H), 1.50 (br s, 2H), 1.37 (dt, J=14.2, 7.3 Hz, 1H), 0.88-0.78 (m, 3H)

Example 47B: (3.4 mg, 7.58 µmol, 5.43%) LC-MS Anal. Calc'd for $C_{22}H_{26}F_3N_3O_2$ 421.20, found [M+H] 422.3, $T_r$=2.085 (Method B). $^1$H NMR (500 MHz, DMSO-$d_6$) δ 8.60 (br s, 1H), 8.07 (br d, J=8.8 Hz, 2H), 7.99 (br t, J=7.7 Hz, 1H), 7.68 (br d, J=7.6 Hz, 1H), 7.63 (br d, J=8.0 Hz, 1H), 6.86 (d, J=8.6 Hz, 1H), 3.99 (br d, J=8.8 Hz, 1H), 3.88 (s, 3H), 2.92 (br s, 1H), 2.00-1.86 (m, 2H), 1.82-1.57 (m, 6H), 1.50 (br s, 2H), 1.36 (dt, J=14.3, 7.2 Hz, 1H), 0.82 (br t, J=7.1 Hz, 3H)

Example 47C: (4.1 mg, 9.34 µmol, 6.69%) LC-MS Anal. Calc'd for $C_{22}H_{26}F_3N_3O_2$ 421.20, found [M+H] 422.3, $T_r$=2.075 (Method B). $^1$H NMR (500 MHz, DMSO-$d_6$) δ 8.67 (br s, 1H), 8.16-8.02 (m, 2H), 8.01-7.93 (m, 1H), 7.68 (br d, J=7.6 Hz, 1H), 7.59 (br d, J=7.4 Hz, 1H), 6.88 (d, J=8.7 Hz, 1H), 3.89 (br s, 3H), 3.75 (m, 1H), 2.70 (br s, 1H), 1.97-1.80 (m, 4H), 1.71-1.60 (m, 1H), 1.58-1.41 (m, 4H), 1.26-1.09 (m, 2H), 0.90-0.78 (m, 3H)

Example 47D: (3.8 mg, 8.48 µmol, 6.07%) LC-MS Anal. Calc'd for $C_{22}H_{26}F_3N_3O_2$ 421.20, found [M+H] 422.3, $T_r$=2.075 (Method B). $^1$H NMR (500 MHz, DMSO-$d_6$) δ 8.66 (br s, 1H), 8.22-8.05 (m, 2H), 7.97 (br t, J=7.7 Hz, 1H), 7.68 (br d, J=7.7 Hz, 1H), 7.58 (br d, J=7.7 Hz, 1H), 6.88 (d, J=8.6 Hz, 1H), 3.89 (d, J=1.8 Hz, 3H), 3.75 (m, 1H), 2.77-2.65 (m, 1H), 1.98-1.79 (m, 4H), 1.63 (br d, J=4.0 Hz, 1H), 1.57-1.41 (m, 4H), 1.17 (br s, 2H), 0.84 (br t, J=6.9 Hz, 3H)

Examples 48A-D

N-(1-(4-(6-(difluoromethoxy)pyridin-2-yl)cyclohexyl)propyl)-6-methoxynicotinamide (Homochiral, Relative and Absolute Stereochemistry not Determined)

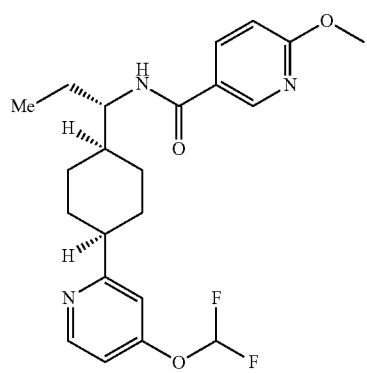

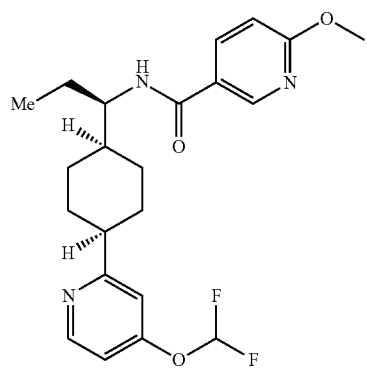

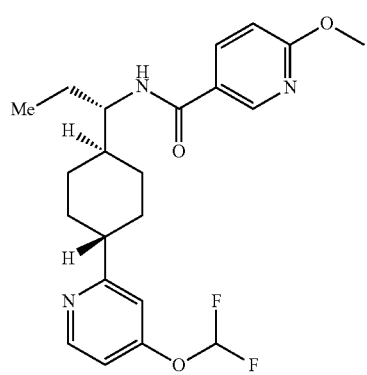

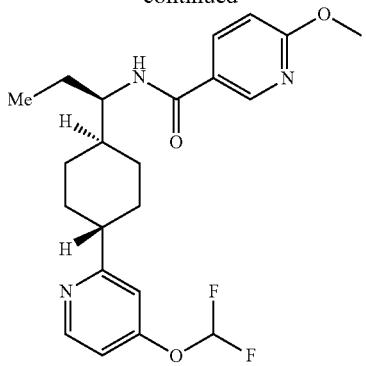

Intermediate 48A: give ethyl 2-(4-(6-(difluoromethoxy)pyridin-2-yl)cyclohex-3-en-1-yl)butanoate To a reaction mixture of 2-bromo-6-(difluoromethoxy)pyridine (125 mg, 0.558 mmol) and ethyl 2-(4-(4,4,5,5-tetramethyl-1,3,2-dioxaborolan-2-yl)cyclohex-3-en-1-yl)butanoate (Intermediate 24C) (500 mg, 1.552 mmol) in 1,4-Dioxane (6206 μl) was added $K_2CO_3$ (643 mg, 4.65 mmol) solution in 1.5 mL water and the resulting mixture was purged with nitrogen stream for 3 min, followed by addition of $Pd(Ph_3P)_4$ (90 mg, 0.078 mmol) and the reaction mixture was further purged with nitrogen stream and then heated at 100° C. under nitrogen for 20 h. The reaction mixture was then diluted with water and ethyl acetate. The organic layer was separated and dried over sodium sulfate and filtered. The filtrate was concentrated in vacuo. The residue was purified by via silica gel flash column chromatography to give ethyl 2-(4-(6-(difluoromethoxy)pyridin-2-yl)cyclohex-3-en-1-yl)butanoate Intermediate 48A (392 mg, 0.381 mmol, 24.57% yield) as a mixture of diastereomers. LC-MS Anal. Calc'd for $C_{18}H_{23}F_2NO_3$ 339.17, found [M+H] 340.2, $T_r$=1.17 (Method A).

Intermediate 48B: ethyl 2-(4-(6-(difluoromethoxy)pyridin-2-yl)cyclohexyl)butanoate Ethyl 2-(4-(6-(difluoromethoxy)pyridin-2-yl)cyclohex-3-en-1-yl)butanoate Intermediate 48A (392 mg, 1.155 mmol) was dissolved in MeOH (4620 μl) and ammonium formate (364 mg, 5.78 mmol) was added. The vessel was equipt with a reflux condenser and vacated and flushed with $N_2$ three times. Then, 10% Pd/C (123 mg, 0.116 mmol) (wet, degussa type) was added and the reaction was heated to reflux for 1 hour. The reaction was cooled, concentrated in vacuo, diluted with DCM and filtered over celite to give ethyl 2-(4-(6-(difluoromethoxy)pyridin-2-yl)cyclohexyl)butanoate Intermediate 48B (377 mg, 1.104 mmol, 96% yield) as a mixture cis- and trans- of diastereomers. LC-MS Anal. Calc'd for $C_{18}H_{25}F_2NO_3$ 341.18, found [M+H] 342.2, $T_r$=1.18 and 1.19 for each diastereomer (Method A).

Intermediate 48C: 2-(4-(6-(difluoromethoxy)pyridin-2-yl)cyclohexyl)butanoic Acid Ethyl 2-(4-(6-(difluoromethoxy)pyridin-2-yl)cyclohexyl)butanoate Intermediate 48B (377 mg, 1.104 mmol) taken up in THF (1840 μl), Water (1840 μl), and MeOH (1840 μl). Lithium hydroxide (264 mg, 11.04 mmol) added and reaction stirred at 60° C. for 2 days. The reaction was concentrated in vacuo and acetic acid added until white precipitate forms. The aqueous layer was extracted with EtOAc. The combined organic extracts were dried with sodium sulfate, filtered, and concentrated to give 2-(4-(6-(difluoromethoxy) pyridin-2-yl)cyclohexyl)butanoic acid Intermediate 48C (255 mg, 0.814 mmol, 73.7% yield) as a mixture cis- and trans- of diastereomers. LC-MS Anal. Calc'd for $C_{16}H_{21}F_2NO_3$ 313.15, found [M+H] 314.2, $T_r$=1.01 (Method A).

Intermediate 48D: 1-(4-(6-(difluoromethoxy)pyridin-2-yl)cyclohexyl)propan-1-amine 2-(4-(6-(difluoromethoxy)pyridin-2-yl)cyclohexyl)butanoic acid Intermediate 48C (255 mg, 0.814 mmol) taken up in toluene (2713 µl) and diphenyl phosphorazidate (246 mg, 0.895 mmol) and TEA (284 µl, 2.035 mmol) were added. heated to 70° C. for 1 hour. The reaction was concentrated in vacuo, taken up in THF (3 mL) and water (3 mL) and LiOH (97 mg, 4.07 mmol) was added. The reaction was stirred at room temperature overnight. Then, the reaction was acidified with 1 N HCl, and extracted with EtOAc. The crude organic extracts were dried with sodium sulfate, filtered, and concentrated in vacuo to give crude 1-(4-(6-(difluoromethoxy)pyridin-2-yl)cyclohexyl)propan-1-amine Intermediate 48D (135 mg, 0.475 mmol, 58.3% yield, ~25% pure) as a mixture cis- and trans- of diastereomers and other impurities related to DPPA. The material was carried forward crude without further purification. LC-MS Anal. Calc'd for $C_{15}H_{22}F_2N_2O$ 284.17, found [M+H] 285.2, $T_r$=0.77 (Method A).

Examples 48A-D N-(1-(4-(6-(difluoromethoxy)pyridin-2-yl)cyclohexyl)propyl)-6-methoxynicotinamide (Homochiral, Relative and Absolute Stereochemistry not Determined)

1-(4-(6-(difluoromethoxy)pyridin-2-yl)cyclohexyl)propan-1-amine Intermediate 48D (45 mg, 0.158 mmol) was taken up in DMF (791 µl) and HOBT (29.1 mg, 0.190 mmol), 1-(4-(6-(difluoromethoxy)pyridin-2-yl)cyclohexyl) propan-1-amine (45 mg, 0.158 mmol), EDC (36.4 mg, 0.190 mmol) and TEA (110 µl, 0.791 mmol) were added and reaction stirred at room temperature overnight. The reaction was diluted with DMF to bring overall volume to 2 mL, filtered, and purified via preparative chiral SFC (preparative method: Column: Chiralpak AD, 30×250 mm, 5 micron; Flow Rate: 100 mL/min; Oven Temperature: 40 C; BPR Setting: 120 bar; UV wavelength: 220 nm; Mobile Phase: 85% CO2/15% Isopropanol-Acetonitrile-0.1% DEA (isocratic)

Injection: 1000 uL of 7.3 mg/1 mL Methanol). Each stereoisomer was successfully separated as a homochiral compound (analytic method: Column: Chiralpak AD, 4.6× 100 mm, 5 micron (analytical); Flow Rate: 2 mL/min.; Oven Temperature: 40 C; BPR setting: 1700 psi; UV wavelength: 220 nm; Mobile Phase: 85% CO2/15% Isopropanol-Acetonitrile-0.1% DEA (isocratic)). Retention times for Examples 48A-D respectively=3.324 min, 3.781 min, 5.937 min, 7.623 min. Relative and absolute stereochemistry were not determined.

Example 48A: (1.4 mg, 3.20 µmol, 2.025%) LC-MS Anal. Calc'd for $C_{22}H_{27}F_2N_3O_3$ 419.20, found [M+H] 420.2, $T_r$=2.163 (Method B). $^1$H NMR (500 MHz, DMSO-d$_6$) δ 8.59 (s, 1H), 8.06 (br dd, J=8.5, 2.3 Hz, 2H), 7.83-7.50 (m, 2H), 7.15 (d, J=7.5 Hz, 1H), 6.86 (d, J=8.7 Hz, 1H), 6.83 (d, J=8.2 Hz, 1H), 3.98 (br d, J=9.8 Hz, 1H), 3.87 (s, 3H), 2.81-2.73 (m, 1H), 1.98-1.83 (m, 2H), 1.71-1.52 (m, 6H), 1.47 (br d, J=5.2 Hz, 2H), 1.40-1.30 (m, 1H), 0.81 (t, J=7.2 Hz, 3H)

Example 48B: (1.4 mg, 3.20 µmol, 2.025%) LC-MS Anal. Calc'd for $C_{22}H_{27}F_2N_3O_3$ 419.20, found [M+H] 420.3, $T_r$=2.126 (Method B). $^1$H NMR (500 MHz, DMSO-d$_6$) δ 8.61 (br d, J=1.3 Hz, 1H), 8.12-8.01 (m, 2H), 7.87-7.51 (m, 2H), 7.15 (d, J=7.5 Hz, 1H), 6.90-6.81 (m, 2H), 3.99 (br d, J=8.8 Hz, 1H), 3.88 (s, 3H), 2.78 (br s, 1H), 1.99-1.82 (m, 2H), 1.75-1.43 (m, 8H), 1.41-1.29 (m, 1H), 0.82 (br t, J=7.0 Hz, 3H)

Example 48C: (1.2 mg, 2.75 µmol, 1.735%) LC-MS Anal. Calc'd for $C_{22}H_{27}F_2N_3O_3$ 419.20, found [M+H] 420.3, $T_r$=2.116 (Method B). $^1$H NMR (500 MHz, DMSO-d$_6$) δ 8.66 (br s, 1H), 8.13 (br d, J=8.5 Hz, 1H), 8.08 (br s, 1H), 7.87-7.51 (m, 2H), 7.10 (d, J=7.4 Hz, 1H), 6.88 (d, J=8.7 Hz, 1H), 6.83 (br d, J=8.0 Hz, 1H), 3.89 (s, 3H), 3.74 (m, 1H), 2.60-2.52 (m, 1H), 1.86 (br s, 4H), 1.62 (br dd, J=10.7, 6.4 Hz, 1H), 1.56-1.38 (m, 4H), 1.14 (br d, J=10.1 Hz, 2H), 0.84 (br t, J=7.1 Hz, 3H)

Example 48D: (1.2 mg, 2.75 µmol, 1.735%) LC-MS Anal. Calc'd for $C_{22}H_{27}F_2N_3O_3$ 419.20, found [M+H] 420.3, $T_r$=2.116 (Method B). $^1$H NMR (500 MHz, DMSO-d$_6$) δ 8.65 (br s, 1H), 8.12 (br d, J=8.6 Hz, 1H), 8.07 (br d, J=8.6 Hz, 1H), 7.85-7.50 (m, 2H), 7.10 (br d, J=7.4 Hz, 1H), 6.88 (d, J=8.7 Hz, 1H), 6.83 (br d, J=8.0 Hz, 1H), 3.89 (s, 3H), 3.73 (m, 1H), 2.61-2.51 (m, 1H), 1.92-1.76 (m, 4H), 1.69-1.57 (m, 1H), 1.55-1.38 (m, 4H), 1.25-1.05 (m, 2H), 0.84 (br t, J=7.0 Hz, 3H)

Examples 49A and B (±)-6-methoxy-N-(1-(4-(4-methylpyrimidin-2-yl) cyclohexyl)propyl)nicotinamide (Relative Stereochemistry not Determined)

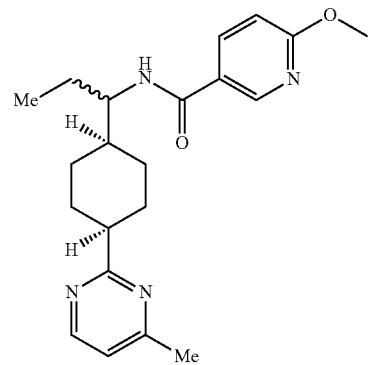

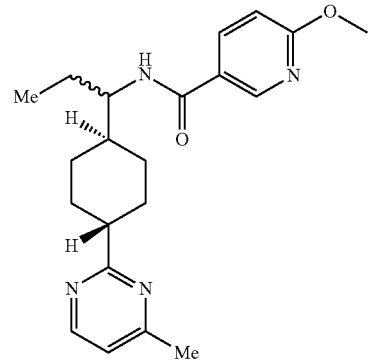

Examples 49A and B: (±)-6-methoxy-N-(1-(4-(4-methylpyrimidin-2-yl)cyclohexyl)propyl)nicotinamide (Relative Stereochemistry not Determined)

Examples 49A and 49B were synthesized using the same route outlined in Examples 45A and 45B except 2-chloro-4-methylpyrimidine was employed in the synthesis. Example 49A (24.5 mg, 0.064 mmol, 45.1%) LC-MS Anal. Calc'd for $C_{21}H_{28}N_4O_2$ 368.22, found [M+H] 369.3 $T_r$=1.441 min (Method B). $^1$H NMR (500 MHz, DMSO-$d_6$) δ 8.64 (d, J=1.8 Hz, 1H), 8.51 (d, J=5.2 Hz, 1H), 8.12 (dd, J=8.8, 2.1 Hz, 1H), 8.07 (br d, J=9.2 Hz, 1H), 7.15 (d, J=4.9 Hz, 1H), 6.87 (d, J=8.5 Hz, 1H), 3.88 (s, 3H), 3.74 (br d, J=6.7 Hz, 1H), 2.66 (br t, J=11.9 Hz, 1H), 2.39 (s, 3H), 1.96-1.78 (m, 4H), 1.69-1.58 (m, 1H), 1.57-1.38 (m, 4H), 1.12 (q, J=12.4 Hz, 2H), 0.83 (br t, J=7.2 Hz, 3H) and Example 49B (29.1 mg, 0.079 mmol, 55.8%) LC-MS Anal. Calc'd for $C_{21}H_{28}N_4O_2$ 368.22, found [M+H] 368.9 $T_r$=1.445 min (Method B). $^1$H NMR (500 MHz, DMSO-$d_6$) δ 8.58 (d, J=1.8 Hz, 1H), 8.53 (d, J=4.9 Hz, 1H), 8.08-8.00 (m, 2H), 7.15 (d, J=5.2 Hz, 1H), 6.85 (d, J=8.5 Hz, 1H), 3.92 (br d, J=9.5 Hz, 1H), 3.87 (s, 3H), 2.90 (br s, 1H), 2.39 (s, 3H), 2.13-1.97 (m, 2H), 1.71-1.28 (m, 9H), 0.80 (br t, J=7.3 Hz, 3H)

Examples 150A-D 6-methoxy-N-(1-(4-(5-methoxypyridin-3-yl)cyclohexyl)propyl)nicotinamide (Homochiral, Relative and Absolute Stereochemistry not Determined)

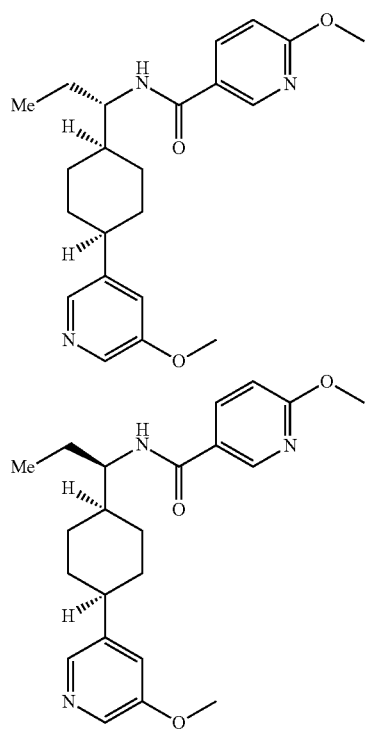

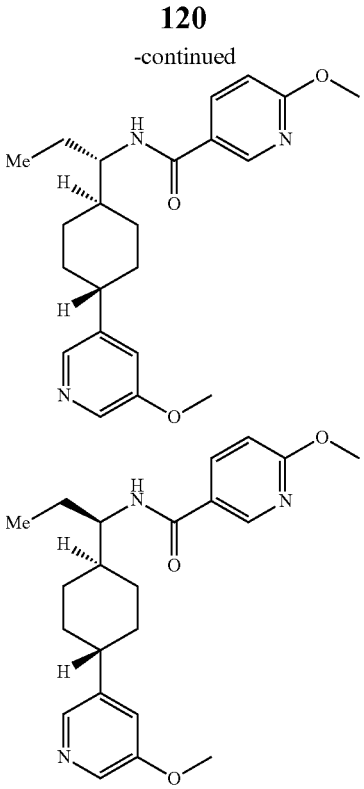

Examples 50A-D: 6-methoxy-N-(1-(4-(5-methoxypyridin-3-yl)cyclohexyl)propyl)nicotinamide (Homochiral, Relative and Absolute Stereochemistry not Determined)

Examples 50 A-D were synthesized using the same route outlined in Examples 48A-D except 3-bromo-5-methoxypyridine was employed in the synthesis. Crude product was purified via chiral SFC (Preparative Method: Column: Chiralpak IC, 21×250 mm, 5 micron; Flow Rate: 60 mL/min; Oven Temperature: 40 C; BPR Setting: 120 bar; UV wavelength: 220 nm; Mobile Phase: 75% CO2/25% MeOH-0.1% DEA (isocratic); Injection: 700 uL of 33.6 mg/4.5 mL Methanol). All four stereoisomers were successfully separated as homochiral compounds (Analytical Method: Column: Chiralpak IC, 4.6×100 mm, 5 micron (analytical); Flow Rate: 2 mL/min.; Oven Temperature: 40 C; BPR setting: 1700 psi; UV wavelength: 220 nm; Mobile Phase: 75% CO2/25% MeOH-0.1% DEA (isocratic). Retention times for Examples 50A-D respectively=5.991 min, 6.530 min, 9.359 min, 11.308 min. Relative and absolute stereochemistry were not determined.

Example 50A: (5.7 mg, 0.015 mmol, 11.19%) LC-MS Anal. Calc'd for $C_{22}H_{29}N_3O_3$ 383.22, found [M+H] 383.9, $T_r$=1.636 (Method B). $^1$H NMR (500 MHz, DMSO-$d_6$) δ 8.64 (d, J=1.8 Hz, 1H), 8.16-7.99 (m, 4H), 7.20 (br s, 1H), 6.87 (d, J=8.5 Hz, 1H), 4.22-4.09 (m, 1H), 3.89 (s, 3H), 3.80 (s, 3H), 2.72-2.60 (m, 1H), 1.84-1.30 (m, 11H), 0.85 (br t, J=7.3 Hz, 3H)

Example 50B: (6.2 mg, 0.016 mmol, 12.17%) LC-MS Anal. Calc'd for $C_{22}H_{29}N_3O_3$ 383.22, found [M+H] 383.9, $T_r$=1.636 (Method B). $^1$H NMR (500 MHz, DMSO-$d_6$) δ 8.64 (s, 1H), 8.18-8.01 (m, 4H), 7.19 (br s, 1H), 6.87 (d, J=8.5 Hz, 1H), 4.16 (br d, J=8.9 Hz, 1H), 3.89 (s, 3H), 3.80 (s, 3H), 2.67 (br s, 1H), 1.84-1.30 (m, 11H), 0.85 (br t, J=7.2 Hz, 3H)

Example 50C: (5.3 mg, 0.014 mmol, 10.19%) LC-MS Anal. Calc'd for $C_{22}H_{29}N_3O_3$ 383.22, found [M+H] 384.2, $T_r$=1.624 (Method B). $^1$H NMR (500 MHz, DMSO-$d_6$) δ 8.66 (s, 1H), 8.17-7.98 (m, 4H), 7.19 (br s, 1H), 6.88 (d, J=8.5 Hz, 1H), 3.89 (s, 3H), 3.79 (s, 3H), 3.75 (m, 1H), 2.46 (m, 1H), 1.92-1.76 (m, 4H), 1.70-1.58 (m, 1H), 1.58-1.33 (m, 4H), 1.22-1.07 (m, 2H), 0.85 (br t, J=7.2 Hz, 3H)

Example 50D: (4.6 mg, 0.012 mmol, 9.03%) LC-MS Anal. Calc'd for $C_{22}H_{29}N_3O_3$ 383.22, found [M+H] 383.9, $T_r$=1.624 (Method B). $^1$H NMR (500 MHz, DMSO-$d_6$) δ 8.67 (s, 1H), 8.18-8.00 (m, 4H), 7.19 (br s, 1H), 6.88 (d, J=8.5 Hz, 1H), 3.90 (s, 3H), 3.79 (s, 3H), 3.77 (m, 1H), 2.47 (m, 1H), 1.94-1.72 (m, 4H), 1.70-1.36 (m, 5H), 1.28-1.06 (m, 2H), 0.85 (br t, J=7.2 Hz, 3H)

Examples 51A-D

N-(1-(4-(3-(difluoromethyl)-2-methoxypyridin-4-yl)cyclohexyl)-2-methoxyethyl)-6-methoxynicotinamide (Homochiral, Relative and Absolute Stereochemistry not Determined)

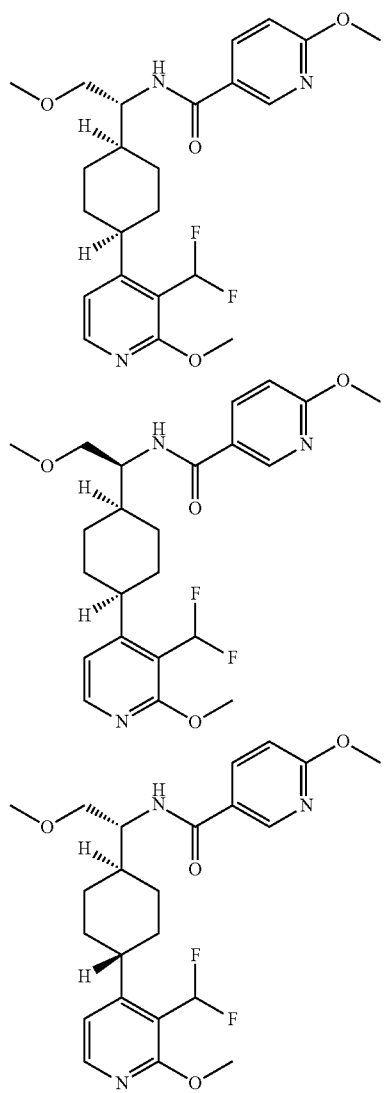

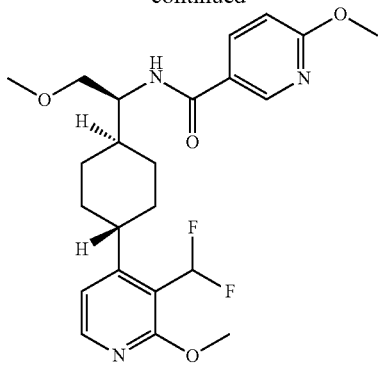

Intermediate 51A

To the flask containing THF (68.0 ml) was added LDA (1.5 M solution in hexane) (28.3 ml, 42.5 mmol) at −78° C., followed by addition of 1,3-dimethyltetrahydropyrimidin-2(1H)-one (3.07 ml, 25.5 mmol) and a solution of ethyl 2-(4-(4,4,5,5-tetramethyl-1,3,2-dioxaborolan-2-yl)cyclohex-3-en-1-yl)acetate (WO 2016/073770) (5.0 g, 17.00 mmol) in THF (5 mL) dropwise at −78° C. The resulting mixture turned yellow. After 30 minutes chloromethyl methylether (1.936 ml, 25.5 mmol) was added slowly. The reaction mixture was stirred at −78° C. for 2 hours, then the bath removed and reaction warmed to room temperature and stirred for 4 hours. The reaction was then quenched with saturated ammonium hydroxide and extracted with EtOAc. Combined organics were concentrated in vacuo and purified via silica gel flash column chromatography to give ethyl 3-methoxy-2-(4-(4,4,5,5-tetramethyl-1,3,2-dioxaborolan-2-yl)cyclohex-3-en-1-yl)propanoate Intermediate 51A (3.51 g, 10.38 mmol, 61.1% yield) as a mixture of diastereomers. LC-MS Anal. Calc'd for $C_{18}H_{31}BO_5$ 338.23, found [M+H] 338.9, $T_r$=1.06 (Method A).

Examples 51A-D

N-(1-(4-(3-(difluoromethyl)-2-methoxypyridin-4-yl)cyclohexyl)-2-methoxyethyl)-6-methoxynicotinamide (Homochiral, Relative and Absolute Stereochemistry not Determined)

Examples 51A-D were synthesized using the same route outlined in Examples 48 A-D except Intermediate 51A and 4-chloro-3-(difluoromethyl)-2-methoxypyridine (Intermediate 24C) was employed in the synthesis. Crude product was purified via chiral SFC (Preparative Conditions: Column: Chiralpak IC, 21×250 mm, 5 micron; Flow Rate: 60 mL/min; Oven Temperature: 40 C; BPR Setting: 120 bar; UV wavelength: 220 nm; Mobile Phase: 85% CO2/15% MeOH-0.1% DEA (isocratic); Injection: 400 uL of 36 mg/2 mL Methanol). All four stereoisomers were successfully separated as homochiral compounds. (Analytical Method: Column: Chiralpak IC, 4.6×100 mm, 5 micron (analytical); Flow Rate: 2 mL/min.; Oven Temperature: 40 C; BPR setting: 1700 psi; UV wavelength: 220 nm Mobile Phase: 85% CO2/15% MeOH-0.1% DEA (isocratic)). Retention times for Examples 51A-D respectively=4.649 min, 5.264 min, 6.967 min, 8.108 min. Relative and absolute stereochemistry were not determined.

Example 51A: (7.7 mg, 0.017 mmol, 8.80%) LC-MS Anal. Calc'd for $C_{23}H_{29}F_2N_3O_4$ 449.21, found [M+H]

450.0, $T_r$=1.937 (Method B). $^1$H NMR (500 MHz, DMSO-$d_6$) δ 8.67 (s, 1H), 8.30-8.22 (m, 2H), 8.14 (br d, J=8.5 Hz, 1H), 7.25 (t, J=55 Hz, 1H), 7.09 (br d, J=5.2 Hz, 1H), 6.87 (d, J=8.5 Hz, 1H), 4.62-4.51 (m, 1H), 3.89 (s, 6H), 3.49 (br d, J=8.5 Hz, 1H), 3.26 (s, 3H), 3.18-3.03 (m, 1H), 1.96 (br d, J=9.8 Hz, 2H), 1.89-1.75 (m, 2H), 1.73-1.35 (m, 6H)

Example 51B: (7.6 mg, 0.016 mmol, 8.59%) LC-MS Anal. Calc'd for $C_{23}H_{29}F_2N_3O_4$ 449.21, found [M+H] 450.3, $T_r$=1.936 (Method B). $^1$H NMR (500 MHz, DMSO-$d_6$) δ 8.67 (d, J=1.5 Hz, 1H), 8.28 (br d, J=8.9 Hz, 1H), 8.25 (br d, J=5.2 Hz, 1H), 8.14 (dd, J=8.8, 1.8 Hz, 1H), 7.24 (t, J=55.0 Hz, 1H), 7.10 (d, J=5.2 Hz, 1H), 6.87 (d, J=8.9 Hz, 1H), 4.56 (br t, J=9.6 Hz, 1H), 3.89 (s, 6H), 3.26 (s, 3H), 3.10 (br t, J=9.9 Hz, 1H), 2.54 (s, 2H), 1.96 (br d, J=10.4 Hz, 1H), 1.85 (br d, J=12.2 Hz, 1H), 1.77 (br d, J=13.4 Hz, 1H), 1.72-1.35 (m, 6H)

Example 51C: (6.7 mg, 0.015 mmol, 7.73%) LC-MS Anal. Calc'd for $C_{23}H_{29}F_2N_3O_4$ 449.21, found [M+H] 450.2, $T_r$=1.880 (Method B). $^1$H NMR (500 MHz, DMSO-$d_6$) δ 8.66 (d, J=1.5 Hz, 1H), 8.26-8.17 (m, 2H), 8.13 (dd, J=8.5, 2.1 Hz, 1H), 7.24 (t, J=52.0 Hz, 1H), 7.10 (d, J=5.2 Hz, 1H), 6.88 (d, J=8.5 Hz, 1H), 4.09-4.00 (m, 1H), 3.89 (s, 3H), 3.88 (s, 3H), 3.25 (s, 3H), 3.00 (br t, J=11.6 Hz, 1H), 2.54 (s, 2H), 1.84 (br t, J=11.6 Hz, 2H), 1.71 (br d, J=12.2 Hz, 3H), 1.57-1.39 (m, 2H), 1.23-1.10 (m, 2H)

Example 51D: (6.5 mg, 0.014 mmol, 7.50%) LC-MS Anal. Calc'd for $C_{23}H_{29}F_2N_3O_4$ 449.21, found [M+H] 450.1, $T_r$=1.880 (Method B). $^1$H NMR (500 MHz, DMSO-$d_6$) δ 8.66 (d, J=1.5 Hz, 1H), 8.23-8.17 (m, 2H), 8.13 (dd, J=8.5, 1.8 Hz, 1H), 7.24 (t, J=52.0 Hz, 1H), 7.10 (d, J=5.2 Hz, 1H), 6.88 (d, J=8.9 Hz, 1H), 4.03 (br d, J=6.1 Hz, 1H), 3.90 (s, 3H), 3.88 (s, 3H), 3.25 (s, 3H), 3.00 (br t, J=11.3 Hz, 1H), 2.54 (s, 2H), 1.85 (br t, J=11.9 Hz, 2H), 1.78-1.63 (m, 3H), 1.58-1.39 (m, 2H), 1.17 (q, J=12.3 Hz, 2H)

Example 52

(+/−)-Cis and trans N-(1-(4-(1,8-naphthyridin-4-yl)cyclohexyl)propyl)-6-methoxynicotinamide

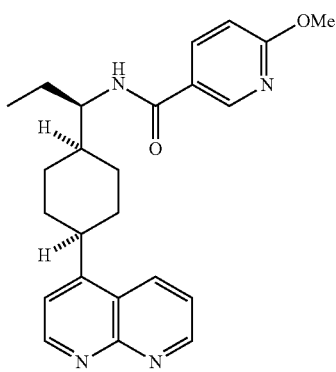

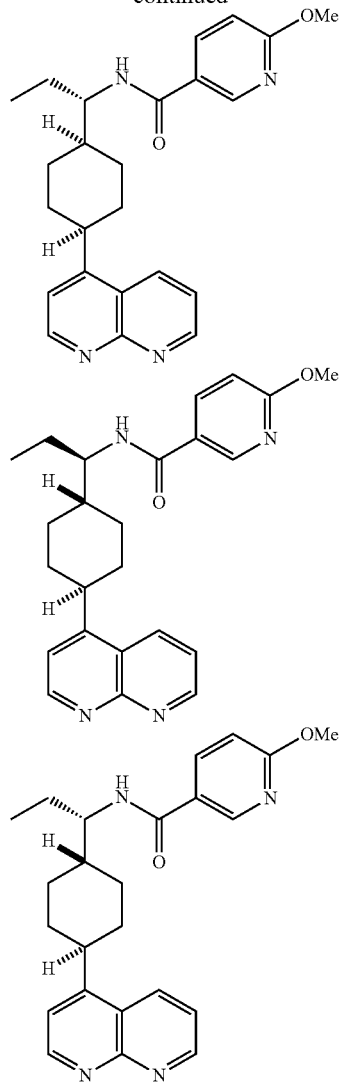

Preparation 52A. ethyl 2-(4-(1,8-naphthyridin-4-yl)cyclohex-3-en-1-yl)acetate

A mixture of 4-bromo-1,8-naphthyridine (1.02 g, 4.88 mmol), ethyl 2-(4-(4,4,5,5-tetramethyl-1,3,2-dioxaborolan-2-yl)cyclohex-3-en-1-yl)acetate (1.479 g, 5.03 mmol), $Na_2CO_3$ (2.069 g, 19.52 mmol), and Pd(Ph$_3$P)$_4$ (0.282 g, 0.244 mmol) in dioxane (45.2 ml) and water (15.06 ml) was heated at 100° C. overnight. The reaction was quenched with water and diluted with EtOAc. Layers were separated. The aqueous phase was extracted with EtOAc (2×). The organics were combined, dried over $Na_2SO_4$, filtered, and concentrated to afford a brown residue. Purification of the crude material by silica gel chromatography using an ISCO machine (80 g column, 60 mL/min, 0-10% MeOH in $CH_2Cl_2$ over 14 min, $t_r$=8.5 min) gave ethyl 2-(4-(1,8-naphthyridin-4-yl)cyclohex-3-en-1-yl)acetate as an orange residue. ESI MS (M+H)$^+$=297.2. HPLC Peak $t_r$=0.69 minutes. HPLC conditions: A.

Preparation 52B. ethyl 2-(4-(1,8-naphthyridin-4-yl)cyclohexyl)acetate

To a solution of ethyl 2-(4-(1,8-naphthyridin-4-yl)cyclohex-3-en-1-yl)acetate (1.446 g, 4.88 mmol) in MeOH (24.40 ml) was added ammonium formate (1.538 g, 24.40 mmol) followed by Pd/C (0.140 g, 1.317 mmol). The reaction was heated at 70° C. for 1 h. The reaction was filtered through Celite and the filter cake washed with MeOH. The filtrate was concentrated. Additional ammonium formate (1.538 g, 24.40 mmol), Pd/C (0.140 g, 1.317 mmol), and MeOH (24.40 ml) were added. The reaction was heated at 70° C. for 1 h. The reaction was filtered through Celite and the filter cake washed with MeOH. The filtrate was concentrated. Additional ammonium formate (1.538 g, 24.40 mmol), Pd/C (0.140 g, 1.317 mmol), and MeOH (24.40 ml) were added. The reaction was heated for 1.5 h at 70° C., then allowed to cool to rt. The reaction was subjected to the reaction conditions two more times. The reaction was filtered through Celite and the filter cake washed with MeOH. The filtrate was concentrated. The crude material was taken up in $CH_2Cl_2$ and loaded directly onto an ISCO column. Purification of the crude material by silica gel chromatography using an ISCO machine (80 g column, 60 mL/min, 0-20% MeOH in $CH_2Cl_2$ over 15 min, $t_r$=7.5 min) gave ethyl 2-(4-(1,8-naphthyridin-4-yl)cyclohexyl)acetate. ESI MS $(M+H)^+$=299.1. HPLC Peak $t_r$=0.68 minutes. HPLC conditions: A.

Preparation 52C. ethyl 2-(4-(1,8-naphthyridin-4-yl)cyclohexyl)butanoate

A solution of ethyl 2-(4-(1,8-naphthyridin-4-yl)cyclohexyl)acetate (0.782 g, 2.62 mmol) and DMPU (0.316 ml, 2.62 mmol) in THF (17.47 ml) was cooled to −78° C. To this solution was added KHMDS (1M solution in THF) (5.50 ml, 5.50 mmol). After 1 h, ethyl iodide (0.445 ml, 5.50 mmol) was added dropwise. The reaction was covered with Al foil and stirred at −78° C. for 3.5 h, then allowed to warm to rt overnight. The reaction was quenched with a sat. aq. soln. of $NH_4Cl$ and diluted with EtOAc. Layers were separated. The aqueous phase was extracted with EtOAc (2×). The organic phases were combined, dried over $Na_2SO_4$, filtered, and concentrated to afford an orange residue. Purification of the crude material by silica gel chromatography using an ISCO machine (80 g column, 60 mL/min, 0-20% MeOH in $CH_2Cl_2$ over 15 min, $t_r$=8.5 min) gave ethyl 2-(4-(1,8-naphthyridin-4-yl)cyclohexyl)butanoate as a brown residue. ESI MS (M+H)+=327.2. HPLC Peak $t_r$=0.78 minutes. HPLC conditions: A.

Preparation 53D. 2-(4-(1,8-naphthyridin-4-yl)cyclohexyl)butanoic Acid, TFA

To a solution of ethyl 2-(4-(1,8-naphthyridin-4-yl)cyclohexyl)butanoate (2.81 g, 8.61 mmol) in THF (6.89 ml), MeOH (3.44 ml), and water (6.89 ml) was added lithium hydroxide (2.062 g, 86 mmol). The reaction was heated at 80° C. overnight, then cooled to rt. The reaction was adjusted to pH 7 with 1N HCl, then the solvent was evaporated. The crude material was dissolved in a minimal amount of water containing 2% TFA and loaded directly onto a reverse phase ISCO column. Purification by a C18 GOLD column using an ISCO machine (100 g column, 60 mL/min, 0-100% water/ACN+0.5% TFA over 35 min, $t_r$=21 min) gave 2-(4-(1,8-naphthyridin-4-yl)cyclohexyl)butanoic acid, TFA. ESI MS (M+H)+=298.9. HPLC Peak $t_r$=0.59 minutes. HPLC conditions: A.

Preparation 53E. 1-(4-(1,8-naphthyridin-4-yl)cyclohexyl)propan-1-amine 2-(4-(1,8-naphthyridin-4-yl)cyclohexyl)butanoic acid, TFA (0.1345 g, 0.326 mmol) was taken up in toluene (1.087 ml) and diphenyl phosphorazidate (0.077 ml, 0.359 mmol) and triethylamine (0.100 ml, 0.718 mmol) added. The vial was sealed and heated to 80° C. After about 3.5 h, the reaction was cooled to rt. More diphenyl phosphorazidate (0.077 ml, 0.359 mmol) and triethylamine (0.05 mL) were added. The reaction was heated an additional 3 h, then allowed to cool to rt. The reaction was concentrated under reduced pressure. The crude residue was taken up in 1 mL THF and 1 mL of water and lithium hydroxide (0.078 g, 3.26 mmol) were added. The reaction was stirred at rt. After 4 h, the reaction was neutralized to pH=7 with 1N HCl. The water was evaporated and the crude material was dried under high vacuum to give 1-(4-(1,8-naphthyridin-4-yl)cyclohexyl)propan-1-amine as a brown residue. Will carry forward crude. ESI MS (M+H)+=270.2. HPLC Peak $t_r$=0.46 minutes. HPLC conditions: A.

Example 53. (+/−)-Cis and trans N-(1-(4-(1,8-naphthyridin-4-yl)cyclohexyl)propyl)-6-methoxynicotinamide To a solution of 1-(4-(1,8-naphthyridin-4-yl)cyclohexyl)propan-1-amine (0.088 g, 0.327 mmol) in THF (3.27 ml) at rt was added Hunig's base (0.342 ml, 1.960 mmol), followed by 6-methoxynicotinoyl chloride (0.224 g, 1.307 mmol). The reaction was stirred at rt for 2 h. The reaction was quenched with MeOH and then concentrated. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 3-minute hold at 100% B; Flow: 20 mL/min. Fractions containing the desired product were combined and dried via centrifugal evaporation to afford the title compound as a mixture of 4 isomers (25.3 mg, 36%). ESI MS (M+H)+=405.0. HPLC Peak $t_r$=1.411 minutes. Purity=100%. HPLC conditions: U.

Example 54

2-(4-(1,8-naphthyridin-4-yl)cyclohexyl)-N-(4-chlorophenyl)propanamide

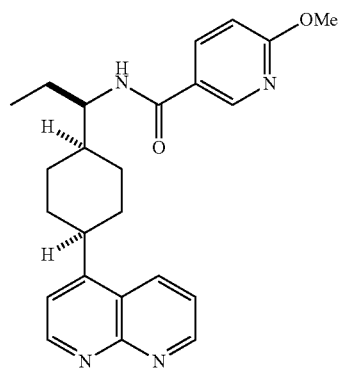

2

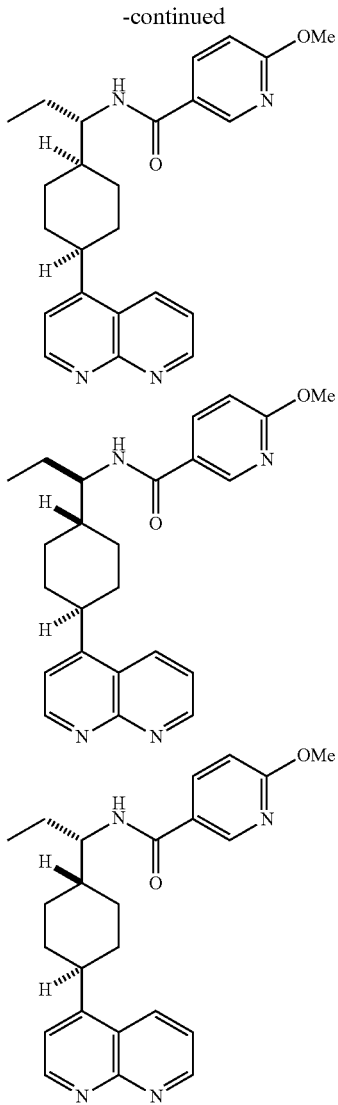

Approximately 24 mg of diastereomeric and racemic Example 53 was resolved. The isomeric mixture was purified via preparative SFC with the following conditions: Column: Phenomenex Lux Cellulose-4 25×3 cm ID, 5p m; Mobile Phase A: 50/50 CO$_2$/MeOH; Detector Wavelength: 220 nm; Flow: 85 mL/min. The fractions ("Peak-1" $t_r$=7.325, "Peak-2" $t_r$=9.082, "Peak-3" $t_r$=11.179, "Peak-4" $t_r$=13.726; analytical conditions: Column: Phenomenex Lux Cellulose-4 250×4.6 mm ID, 5 m; Mobile Phase A: 50/50 CO$_2$/MeOH; Flow: 2.0 mL/min) were collected in MeOH. The stereoisomeric purity of each fraction was estimated to be greater than 99% based on the prep-SFC chromatograms. Each diasteromers or enantiomer was further purified via preparative LC/MS:

Second eluting isomer: The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 19 minutes, then a 5-minute hold at 100% B; Flow: 20 mL/min. Fractions containing the desired product were combined and dried via centrifugal evaporation to afford Isomer 2 (2.8 mg, 2.0%). ESI MS (M+H)+=405.0. HPLC Peak $t_r$=1.430 minutes. Purity=95%. HPLC conditions: U. Absolute stereochemistry not determined.

Third eluting isomer: The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 19 minutes, then a 5-minute hold at 100% B; Flow: 20 mL/min. Fractions containing the desired product were combined and dried via centrifugal evaporation to afford Isomer 3 (7.5 mg, 5.7%). ESI MS (M+H)+=405.0. HPLC Peak $t_r$=1.411 minutes. Purity=100%. HPLC conditions: U. Absolute stereochemistry not determined.

Fourth eluting isomer: The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-70% B over 19 minutes, then a 5-minute hold at 100% B; Flow: 20 mL/min. Fractions containing the desired product were combined and dried via centrifugal evaporation to afford Isomer 4 (7.5 mg, 5.6%). ESI MS (M+H)+=405.0. HPLC Peak $t_r$=1.412 minutes. Purity=99%. HPLC conditions: U. Absolute stereochemistry not determined.

Example 54

(+/−)-Cis and trans-2-(4-(1H-pyrazolo[4,3-b]pyridin-7-yl)cyclohexyl)-N-(4-chlorophenyl)propanamide

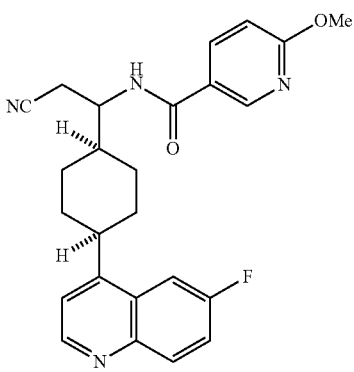

Preparation 54A. ethyl 2-(4-(6-fluoroquinolin-4-yl) cyclohex-3-en-1-yl)acetate

A mixture of 4-chloro-6-fluoroquinoline (6.75 g, 37.2 mmol), ethyl 2-(4-(4,4,5,5-tetramethyl-1,3,2-dioxaborolan-2-yl)cyclohex-3-en-1-yl)acetate (11.26 g, 38.3 mmol), Na$_2$CO$_3$ (15.76 g, 149 mmol), and Pd(Ph$_3$P)$_4$ (2.148 g, 1.859 mmol) in dioxane (232 ml) and water (77 ml) was heated at 100° C. overnight. The reaction was quenched with water and diluted with EtOAc. Layers were separated. The aqueous phase was extracted with EtOAc (3×). The organics were combined, dried over Na$_2$SO$_4$, filtered, and concentrated to afford a yellow residue. Purification of the crude material by silica gel chromatography using an ISCO machine (750 g column, 300 mL/min, 0-30% EtOAc in hexanes over 15 min, $t_r$=12.5 min) gave ethyl 2-(4-(6-fluoroquinolin-4-yl)cyclohex-3-en-1-yl)acetate (9.82 g, 29.8 mmol, 80% yield) as a colorless residue. NMR showed pure desired product. ESI MS (M+H)+=313.6. HPLC Peak $t_r$=0.79 minutes. HPLC conditions: A.

Preparation 54B. ethyl 2-(4-(6-fluoroquinolin-4-yl)cyclohexyl)acetate

To a solution of ethyl 2-(4-(6-fluoroquinolin-4-yl)cyclohex-3-en-1-yl)acetate (9.82 g, 31.3 mmol) in MeOH (157 ml) was added ammonium formate (9.39 g, 149 mmol) followed by Pd/C (0.900 g, 8.46 mmol). The reaction was heated at 70° C. for 1 h. The reaction was filtered through Celite, the filter cake washed with MeOH, and the filtrate was concentrated. The crude material was re-dissolved in MeOH and ammonium formate (9.39 g, 149 mmol) and Pd/C (0.900 g, 8.46 mmol) were added. The reaction was heated at 70° C. for 1.5 h. The reaction was heated for an additional 1 h. The reaction was filtered through Celite and the filter cake washed with $CH_2Cl_2$. The filtrate was concentrated. The crude material was taken up in $CH_2Cl_2$ and washed with a sat. aq. solution of $NaHCO_3$ (1×). The organic phase was dried over $Na_2SO_4$, filtered, and concentrated to afford a yellow residue. Purification of the crude material by silica gel chromatography using an ISCO machine (330 g column, 200 mL/min, 0-35% EtOAc in hexanes over 16 min, $t_r$=13.5 min) gave ethyl 2-(4-(6-fluoroquinolin-4-yl)cyclohexyl)acetate as a yellow residue. ESI MS (M+H)+=315.7. HPLC Peak $t_r$=0.78 minutes. HPLC conditions: A.

Preparation 54C. (+/−)-Cis- and trans-ethyl 3-cyano-2-(4-(6-fluoroquinolin-4-yl)cyclohexyl) propanoate A solution of ethyl 2-(4-(6-fluoroquinolin-4-yl)cyclohexyl)acetate (6 g, 19.02 mmol) and DMPU (2.294 ml, 19.02 mmol) in THF (127 ml) was cooled to −78° C. To this solution was added KHMDS (1M solution in THF) (40.0 ml, 40.0 mmol). After 30 min, 2-bromoacetonitrile (2.78 ml, 40.0 mmol) (filtered through basic alumina) was added dropwise. The reaction was covered with Al foil and stirred at −78° C., then allowed to warm to rt overnight. The reaction was quenched with a sat. aq. soln. of $NH_4Cl$ and diluted with EtOAc. Layers were separated. The aqueous phase was extracted with EtOAc (3×). The organic phases were combined, dried over $Na_2SO_4$, filtered, and concentrated to afford a purple residue. Purification of the crude material by silica gel chromatography using an ISCO machine (220 g column, 150 mL/min, 0-60% EtOAc in hexanes over 30 min, $t_r$=23 min) gave ethyl 3-cyano-2-(4-(6-fluoroquinolin-4-yl)cyclohexyl)propanoate as an orange residue. ESI MS (M+H)+=355.1. HPLC Peak $t_r$=0.73 minutes. HPLC conditions: A.

Preparation 54D. Cis- or trans-ethyl 3-cyano-2-(4-(6-fluoroquinolin-4-yl)cyclohexyl)propanoate Approximately 920 mg of diastereomeric and racemic Preparation 3C was resolved. The isomeric mixture was purified via preparative SFC with the following conditions: Phenomenex Cellulose-4 25×3 cm, 5 m; Mobile Phase A: 90/10 $CO_2$/MeOH/ACN 50:50; Detector Wavelength: 220 nm; Flow: 85 mL/min. The fractions ("Peak-1" $t_r$=22.454, "Peak-2" $t_r$=24.761, "Peak-3" $t_r$=27.250, "Peak-4" $t_r$=29.771; analytical conditions: Phenomenex Cellulose-4 250×4.6 mm ID, 5 m; Mobile Phase A: 90/10 $CO_2$/MeOH/ACN 50:50; Flow: 2.0 mL/min) were collected in MeOH. The stereoisomeric purity of Peak 1, 2, 3, and 4 were estimated to be greater than 95% based on the prep-SFC chromatograms. Peak 2 was re-purified via preparative SFC with the following conditions: Column: Chiral AS, 25×3 cm ID, 5-µm particles; Mobile Phase A: 80/20 $CO_2$/MeOH; Detector Wavelength: 220 nm; Flow: 85 mL/min. The fractions ("Peak-1" $t_r$=3.391 and "Peak-2" $t_r$=4.071; analytical conditions: Column: Chiral AS, 250×4.6 mm ID, 5-µm particles; Mobile Phase A: 80/20 CO2/MeOH; Flow: 2.0 mL/min) was collected in MeOH. The stereoisomeric purity of the fractions was estimated to be greater than 95% based on the prep-SFC chromatogram.

First eluting isomer: ESI MS (M+H)+=355.1. HPLC Peak $t_r$=0.73 minutes. HPLC conditions: A. Absolute stereochemistry not determined.

Preparation 54E. 3-cyano-2-(4-(6-fluoroquinolin-4-yl)cyclohexyl)propanoic Acid

To a solution of ethyl 3-cyano-2-(4-(6-fluoroquinolin-4-yl)cyclohexyl)propanoate (0.280 g, 0.790 mmol) in THF (0.632 ml), MeOH (0.316 ml), and water (0.632 ml) was added lithium hydroxide (0.189 g, 7.90 mmol). The reaction was stirred at rt for 5 h. The reaction was adjusted to pH 7 with 1N HCl, then diluted with EtOAc. A white solid precipitated and was filtered. Layers were separated. The aqueous phase was extracted with EtOAc (3×). Then the pH was adjusted to 6, 4, and 1. Each time the aqueous layer was extracted with EtOAc (3×). The combined organic phases were combined, dried over $Na_2SO_4$, filtered, and concentrated to afford a yellow residue. NMR of the solid and the residue was taken. Will carry forward crude. ESI MS (M+H)+=327.2. HPLC Peak $t_r$=0.62 minutes. HPLC conditions: A.

Preparation 54F. 3-amino-3-((1s,4s)-4-(6-fluoroquinolin-4-yl)cyclohexyl)propanenitrile 3-cyano-2-((1s,4s)-4-(6-fluoroquinolin-4-yl)cyclohexyl)propanoic acid (0.158 g, 0.484 mmol) taken up in toluene (1.614 ml) and diphenyl phosphorazidate (0.115 ml, 0.533 mmol) and triethylamine (0.081 ml, 0.581 mmol) added. The vial was sealed and heated to 80° C. After about 3 h, the reaction was cooled to rt and concentrated under reduced pressure. The crude residue was taken up in 1 mL THF and 1 mL of water and lithium hydroxide (0.116 g, 4.84 mmol) was added. The reaction was stirred at rt. The reaction was neutralized to pH=7 with 1N HCl. The water was evaporated and the crude material was dried under high vacuum to give 3-amino-3-((1s,4s)-4-(6-fluoroquinolin-4-yl)cyclohexyl)propanenitrile as a brown solid. Will carry forward crude. ESI MS (M+H)+=298.1. HPLC Peak $t_r$=0.50 minutes. HPLC conditions: A.

Example 54. Cis or trans-N-(2-cyano-1-((1s,4s)-4-(6-fluoroquinolin-4-yl)cyclohexyl)ethyl)-6-methoxynicotinamide To a solution of 3-amino-3-((1s,4s)-4-(6-fluoroquinolin-4-yl)cyclohexyl)propanenitrile (29 mg, 0.098 mmol) in THF (975 µl) at rt was added Hunig's Base (102 µl, 0.585 mmol), followed by 6-methoxynicotinoyl chloride (66.9 mg, 0.390 mmol). The reaction was stirred at rt for 48 h. The reaction was quenched with MeOH and the solvent was evaporated. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 19 minutes, then a 5-minute hold at 100% B; Flow: 20 mL/min. Fractions containing the desired product were combined and dried via centrifugal evaporation to afford the title compound (2.1 mg, 98%). ESI MS (M+H)+=433.1. HPLC Peak $t_r$=1.653 minutes. Purity=99%. HPLC conditions: U.

Example 55

(+/−)-Cis and trans-N-(1-(4-(2-fluoro-3-methylpyridin-4-yl)cyclohexyl)propyl)-6-methoxynicotinamide

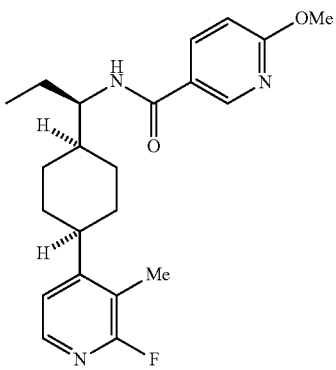

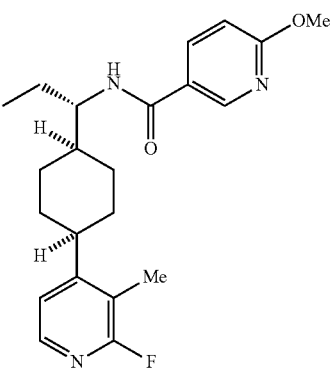

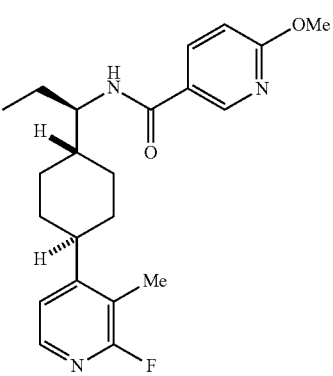

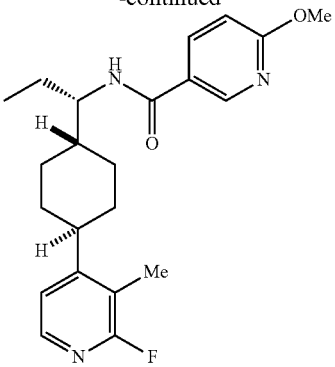

Preparation 55A.
4-bromo-2-fluoro-3-methylpyridine

To a solution of 4-bromo-2-fluoropyridine (6 g, 34.1 mmol) in THF (50 ml) at −70° C. was added 4-chloropyridine (11.3 g) in solution in THF (20 ml) keeping the temperature below −65° C. The reaction was allowed to stir for 4 hours at −70° C. and methyl iodide (15 g) was added keeping the temperature below −65° C. The reaction was then allowed to warm at room temperature and water was added. The aqueous phase was extracted with ether and the desired compound was obtained by distillation under reduced pressure after removal of the solvent. $^1$H NMR (400 MHz, chloroform-d) δ 7.27 (s, 1H), 7.22-7.11 (m, 1H), 2.48-2.26 (m, 3H).

Preparation 55B. ethyl 2-(4-(2-fluoro-3-methylpyridin-4-yl)cyclohex-3-en-1-yl)acetate To a solution of ethyl 2-(4-(4,4,5,5-tetramethyl-1,3,2-dioxaborolan-2-yl)cyclohex-3-en-1-yl)acetate (4.5 g, 15.30 mmol) in dioxane (10 mL) was added 4-bromo-2-fluoro-3-methylpyridine (3.20 g, 16.83 mmol), water (2 mL) and Na$_2$CO$_3$ (6.48 g, 61.2 mmol). The mixture was degassed with N$_2$ for 10 min, Pd(Ph$_3$P)$_4$ (0.884 g, 0.765 mmol) was added. The mixture was heated to 100° C. for 16 h. The mixture was diluted with EtOAc, washed with water, brine, dried over Na$_2$SO$_4$. The mixture was concentrated. The crude material was purified by ISCO (0-50% EtOAc/hexane). Fractions containing the desired product were concentrated to yield ethyl 2-(4-(2-fluoro-3-methylpyridin-4-yl)cyclohex-3-en-1-yl)acetate as a yellow oil. ESI MS (M+H)+=278.2. HPLC Peak $t_r$=1.02 minutes. HPLC conditions: A.

Preparation 55C. ethyl 2-(4-(2-fluoro-3-methylpyridin-4-yl)cyclohex-3-en-1-yl)butanoate A solution of ethyl 2-(4-(2-fluoro-3-methylpyridin-4-yl)cyclohex-3-en-1-yl)acetate (3.05 g, 11.00 mmol) and DMPU (1.326 ml, 11.00 mmol) in THF (73.3 ml) was cooled to −78° C. To this solution was added KHMDS (22.00 ml, 22.00 mmol). After 2 h, ethyl iodide (1.866 ml, 23.09 mmol) was added dropwise. The reaction was covered with Al foil and stirred at −78° C. for 3.5 h, then allowed to warm to rt. The reaction was allowed to stir at rt for 4 d. The reaction was quenched with a sat. aq. soln of NaHCO$_3$ and diluted with EtOAc. Layers were separated. The aqueous phase was extracted with EtOAc (3×). The organic phases were combined, dried over Na$_2$SO$_4$, filtered, and concentrated to afford ethyl 2-(4-(2-fluoro-3-methylpyridin-4-yl)cyclohex-3-en-1-yl)butanoate (1.4 g, 4.58 mmol, 41.7% yield) as a clear oil. ESI MS (M+H)+=306.2. HPLC Peak $t_r$=1.12 minutes. HPLC conditions: A.

Preparation 55D. ethyl 2-(4-(2-fluoro-3-methylpyridin-4-yl)cyclohexyl)butanoate

To a solution of ethyl 2-(4-(2-fluoro-3-methylpyridin-4-yl)cyclohex-3-en-1-yl)butanoate (1.4 g, 4.58 mmol) in methanol (9.17 ml) was added ammonium formate (1.445 g, 22.92 mmol) and Pd—C (0.244 g, 0.229 mmol). The mixture was heated to 80° C. for 1 h. The mixture was filtered. The filtrate was diluted with EtOAc, washed with satd. aq. $Na_2CO_3$, water, brine, dried over $Na_2SO_4$, and concentrated. ESI MS (M+H)+=308.2. HPLC Peak $t_r$=1.10 minutes. HPLC conditions: A.

Preparation 55E. 2-(4-(2-fluoro-3-methylpyridin-4-yl)cyclohexyl)butanoic Acid

To a mixture of MeOH (2 mL), THF (2 mL), and water (2 mL) was added ethyl 2-(4-(2-fluoro-3-methylpyridin-4-yl)cyclohexyl)butanoate (1.4 g, 4.55 mmol) and LiOH (1.091 g, 45.5 mmol). The mixture was heated to 80° C. for 3 days. The mixture was cooled to rt, neutralized with 1N HCl until pH~4, then extracted with EtOAc (3×). The combined organic phases were washed with water, brine, dried over $Na_2SO_4$, and concentrated. ESI MS (M+H)+=280.2. HPLC Peak $t_r$=0.90 minutes. HPLC conditions: A.

Preparation 55F. 1-(4-(2-fluoro-3-methylpyridin-4-yl)cyclohexyl)propan-1-amine 2-(4-(2-fluoro-3-methylpyridin-4-yl)cyclohexyl)butanoic acid (600 mg, 2.148 mmol) was taken up in toluene (5 ml), then diphenyl phosphorazidate (0.926 mL, 4.30 mmol) and triethylamine (0.659 mL, 4.73 mmol) were added. The vial was sealed and heated to 70° C. After about 2 h, the reaction was cooled to rt and concentrated under reduced pressure. The crude residue was taken up in 40 mL THF and 40 mL of water and lithium hydroxide (1.589 g, 66.4 mmol) were added. The reaction was stirred at rt. The reaction was acidified with 1N HCl and extracted with EtOAc to remove DPPA related impurities. The reaction was then basified with 1N NaOH and extracted with EtOAc (5×). The basic extracts were combined and concentrated in vacuo to give 1-(4-(2-fluoro-3-methylpyridin-4-yl)cyclohexyl)propan-1-amine as a yellow oil. ESI MS (M+H)+=251.1. HPLC Peak $t_r$=0.71 minutes. HPLC conditions: A.

Example 55. (+/−)-Cis and trans-N-(1-(4-(2-fluoro-3-methylpyridin-4-yl)cyclohexyl)propyl)-6-methoxynicotinamide To a solution of 1-(4-(2-fluoro-3-methylpyridin-4-yl)cyclohexyl)propan-1-amine (80 mg, 0.320 mmol) in THF (1 mL) was added 6-methoxynicotinic acid (48.9 mg, 0.320 mmol), HOBT (98 mg, 0.639 mmol), EDC (123 mg, 0.639 mmol) and TEA (0.089 mL, 0.639 mmol). The mixture was stirred at rt overnight. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 20 minutes, then a 3-minute hold at 100% B; Flow: 20 mL/min. Fractions containing the desired product were combined and dried via centrifugal evaporation to afford the title compound as a mixture of 4 isomers. ESI MS (M+H)+=386.2. HPLC Peak $t_r$=1.964 minutes. HPLC conditions: U.

Example 56

N-(1-(4-(2-fluoro-3-methylpyridin-4-yl)cyclohexyl)propyl)-6-methoxynicotinamide

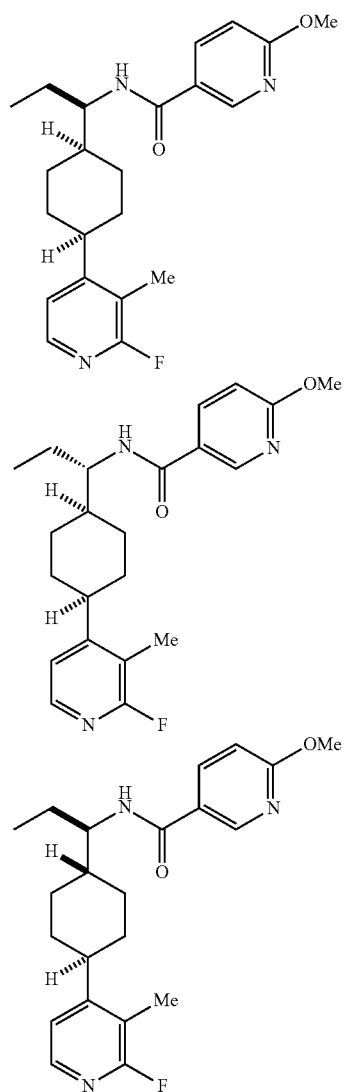

135

-continued

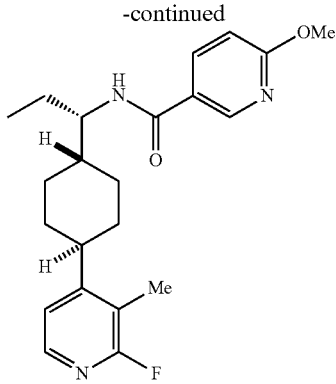

Approximately 123 mg of diastereomeric and racemic Example 55 was resolved. The isomeric mixture was purified via preparative SFC. Each diasteromers or enantiomer was further purified via preparative LC/MS:

Second eluting isomer: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-100% B over 20 minutes, then a 5-minute hold at 100% B; Flow: 20 mL/min. Fractions containing the desired product were combined and dried via centrifugal evaporation to afford Isomer 2 (2.4 mg, 2.0%). ESI MS (M+H)+=386.1. HPLC Peak $t_r$=1.962 minutes. Purity=100%. HPLC conditions: U. Absolute stereochemistry not determined.

Third eluting isomer: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-100% B over 20 minutes, then a 5-minute hold at 100% B; Flow: 20 mL/min. Fractions containing the desired product were combined and dried via centrifugal evaporation to afford Isomer 3 (1.5 mg, 1.2%). ESI MS (M+H)+=386.2. HPLC Peak $t_r$=1.923 minutes. Purity=100%. HPLC conditions: U. Absolute stereochemistry not determined.

Fourth eluting isomer: The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 50-100% B over 20 minutes, then a 5-minute hold at 100% B; Flow: 20 mL/min. Fractions containing the desired product were combined and dried via centrifugal evaporation to afford Isomer 4 (1.6 mg, 1.3%). ESI MS (M+H)+=386.2. HPLC Peak $t_r$=1.954 minutes. Purity=100%. HPLC conditions: U. Absolute stereochemistry not determined.

136

Four Isomers of Example 57

N-(1-4-(6,8-difluoroquinolin-4-yl)cyclohexyl)propyl)-6-methoxynicotinamide (Relative Stereochemistry not Determined)

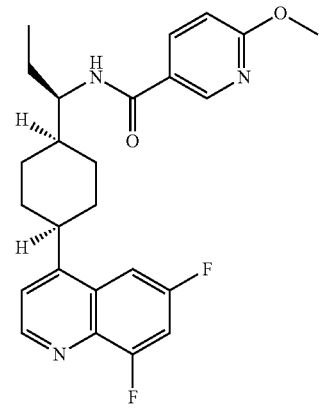

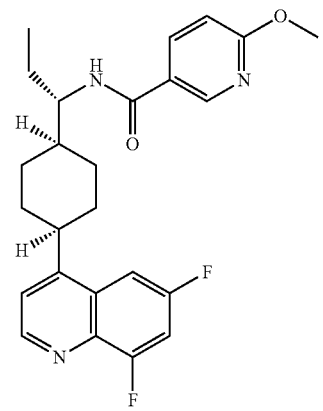

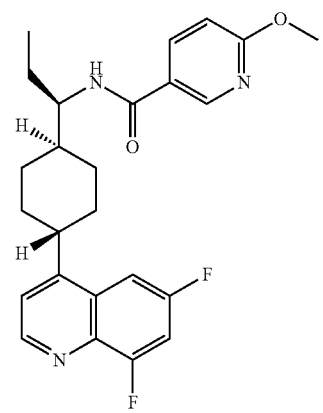

137

-continued

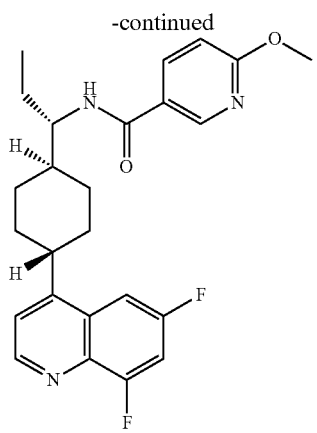

Examples 57 were synthesized using the same route outlined in Examples 10 except 4-chloro-6,8-difluoroquinoline was employed in the synthesis.

First elute (6.8 mg, 0.015 mmol, 10.24% yield). LC-MS Anal. Calc'd for $C_{25}H_{27}F_2N_3O_2$ 439.207, found [M+H] 440.0. $T_r$=1.70 min (Method B). $T_r$=6.69 min (Method N) $^1$H NMR (500 MHz, DMSO-$d_6$) δ 9.00-8.80 (m, 1H), 8.68 (s, 1H), 8.20-8.04 (m, 2H), 7.94-7.80 (m, 1H), 7.77-7.67 (m, 1H), 7.61-7.45 (m, 1H), 6.89 (d, J=8.5 Hz, 1H), 4.38-4.19 (m, 1H), 3.96-3.82 (m, 3H), 3.46-3.30 (m, 1H), 1.92-1.56 (m, 10H), 1.53-1.30 (m, 1H), 1.08-0.95 (m, 1H), 0.94-0.81 (m, 3H)

Second elute (8.0 mg, 0.018 mmol, 12.0% yield). LC-MS Anal. Calc'd for $C_{25}H_{27}F_2N_3O_2$ 439.207, found [M+H] 440.0. $T_r$=1.70 min (Method B). $T_r$=9.32 min (Method N) $^1$H NMR (500 MHz, DMSO-$d_6$) δ 9.00-8.80 (m, 1H), 8.68 (s, 1H), 8.20-8.04 (m, 2H), 7.94-7.80 (m, 1H), 7.77-7.67 (m, 1H), 7.61-7.45 (m, 1H), 6.89 (d, J=8.5 Hz, 1H), 4.38-4.19 (m, 1H), 3.96-3.82 (m, 3H), 3.46-3.30 (m, 1H), 1.92-1.56 (m, 10H), 1.53-1.30 (m, 1H), 1.08-0.95 (m, 1H), 0.94-0.81 (m, 3H)

Third elute (6.8 mg, 0.015 mmol, 10.2% yield). LC-MS Anal. Calc'd for $C_{25}H_{27}F_2N_3O_2$ 439.207, found [M+H] 440.0. $T_r$=1.74 min (Method B). $T_r$=14.67 min (Method N) $^1$H NMR (500 MHz, DMSO-$d_6$) δ 8.94-8.77 (m, 1H), 8.73-8.59 (m, 1H), 8.23-8.02 (m, 2H), 7.93-7.77 (m, 1H), 7.79-7.64 (m, 1H), 7.62-7.44 (m, 1H), 6.96-6.48 (m, 1H), 4.38-4.17 (m, 1H), 4.00-3.82 (m, 3H), 3.50-3.31 (m, 1H), 3.21-3.12 (m, 1H), 3.53-2.82 (m, 1H), 2.99-2.74 (m, 1H), 1.91-1.53 (m, 10H), 1.51-1.29 (m, 1H), 1.24-1.09 (m, 1H), 0.91-0.74 (m, 3H)

Fourth elute (6.2 mg, 0.014 mmol, 9.33% yield). LC-MS Anal. Calc'd for $C_{25}H_{27}F_2N_3O_2$ 439.207, found [M+H] 440.0. $T_r$=1.74 min (Method B). $T_r$=18.71 min (Method N) $^1$H NMR (500 MHz, DMSO-$d_6$) δ 8.94-8.77 (m, 1H), 8.73-8.59 (m, 1H), 8.23-8.02 (m, 2H), 7.93-7.77 (m, 1H), 7.79-7.64 (m, 1H), 7.62-7.44 (m, 1H), 6.96-6.48 (m, 1H), 4.38-4.17 (m, 1H), 4.00-3.82 (m, 3H), 3.50-3.31 (m, 1H), 3.21-3.12 (m, 1H), 3.53-2.82 (m, 1H), 2.99-2.74 (m, 1H), 1.91-1.53 (m, 10H), 1.51-1.29 (m, 1H), 1.24-1.09 (m, 1H), 0.91-0.74 (m, 3H)

138

Four Isomers of Example 58

N-(1-4-(6,8-difluoroquinolin-4-yl)cyclohexyl)propyl)-2-methoxypyrimidine-5-carboxamide (Relative Stereochemistry not Determined)

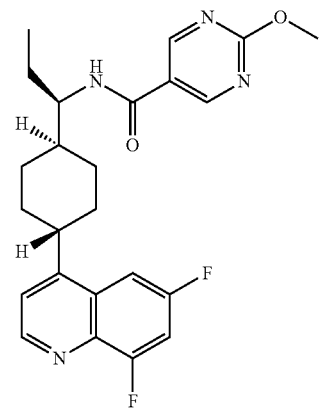

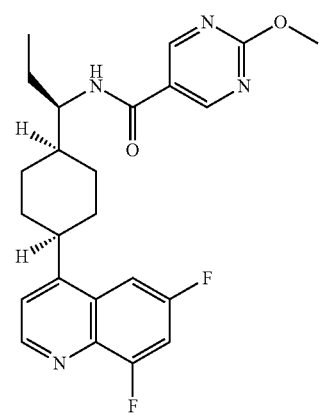

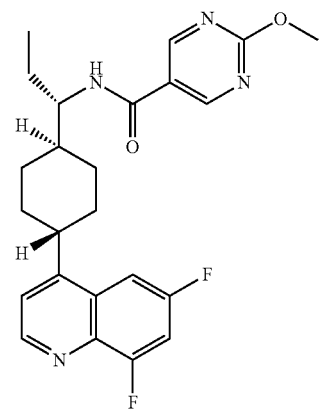

-continued

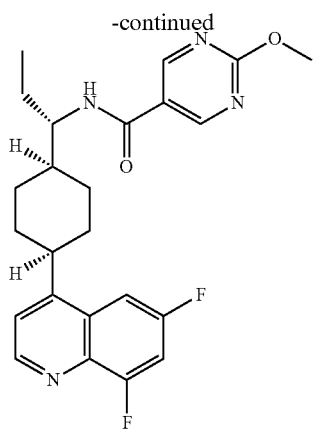

Examples 58 were synthesized using the same route outlined in Examples 10 except 4-chloro-6,8-difluoroquinoline and 2-methoxypyrimidine-5-carboxylic acid were employed in the synthesis.

First elute (5.1 mg, 0.012 mmol, 8.81% yield). LC-MS Anal. Calc'd for $C_{24}H_{26}F_2N_4O_2$ 440.202, found [M+H] 441.1. $T_r$=1.66 min (Method B). $T_r$=2.93 min (25% IPA-DEA on AD)$^1$H NMR (500 MHz, DMSO-$d_6$) δ 9.12-8.95 (m, 2H), 8.84-8.64 (m, 1H), 8.41-8.18 (m, 1H), 7.93-7.73 (m, 1H), 7.75-7.58 (m, 1H), 7.61-7.23 (m, 1H), 4.07-3.95 (m, 3H), 3.90-3.72 (m, 1H), 3.36-3.12 (m, 2H), 2.00-1.79 (m, 4H), 1.74-1.23 (m, 8H)

Second elute (2.9 mg, 0.0066 mmol, 5.01% yield). $C_{24}H_{26}F_2N_4O_2$ 440.202, found [M+H] 441.1. $T_r$=1.57 min (Method B). $T_r$=3.35 min (25% IPA-DEA on AD)$^1$H NMR (500 MHz, DMSO-$d_6$) δ 9.04-8.87 (m, 2H), 8.92-8.72 (m, 1H), 8.46-8.19 (m, 1H), 7.88-7.79 (m, 1H), 7.74-7.64 (m, 1H), 7.61-7.37 (m, 1H), 4.41-4.17 (m, 1H), 4.04-3.89 (m, 3H), 3.40-3.24 (m, 1H), 1.99-1.56 (m, 10H), 1.47-1.31 (m, 1H), 0.92-0.53 (m, 3H)

Third elute (5.1 mg, 0.012 mmol, 8.81% yield). LC-MS Anal. Calc'd for $C_{24}H_{26}F_2N_4O_2$ 440.202, found [M+H] 441.1. $T_r$=1.66 min (Method B). $T_r$=3.93 min (25% IPA-DEA on AD)$^1$H NMR (500 MHz, DMSO-$d_6$) δ 9.12-8.95 (m, 2H), 8.84-8.64 (m, 1H), 8.41-8.18 (m, 1H), 7.93-7.73 (m, 1H), 7.75-7.58 (m, 1H), 7.61-7.23 (m, 1H), 4.07-3.95 (m, 3H), 3.90-3.72 (m, 1H), 3.36-3.12 (m, 2H), 2.00-1.79 (m, 4H), 1.74-1.23 (m, 8H)

Fourth elute (2.9 mg, 0.0066 mmol, 5.01% yield). $C_{24}H_{26}F_2N_4O_2$ 440.202, found [M+H] 441.1. $T_r$=1.57 min (Method B). $T_r$=5.46 min (25% IPA-DEA on AD)$^1$H NMR (500 MHz, DMSO-$d_6$) δ 9.04-8.87 (m, 2H), 8.92-8.72 (m, 1H), 8.46-8.19 (m, 1H), 7.88-7.79 (m, 1H), 7.74-7.64 (m, 1H), 7.61-7.37 (m, 1H), 4.41-4.17 (m, 1H), 4.04-3.89 (m, 3H), 3.40-3.24 (m, 1H), 1.99-1.56 (m, 10H), 1.47-1.31 (m, 1H), 0.92-0.53 (m, 3H)

Four Isomers of Example 59

N-(1-(4-(8-fluoroquinolin-4-yl)cyclohexyl)propyl)-6-methoxynicotinamide (Relative Stereochemistry not Determined)

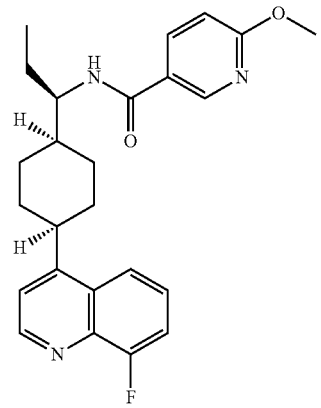

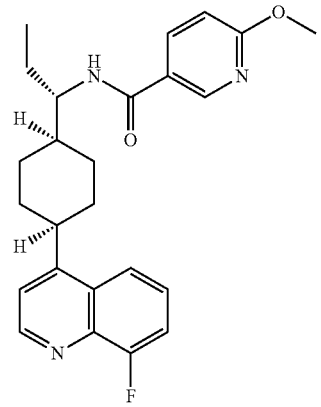

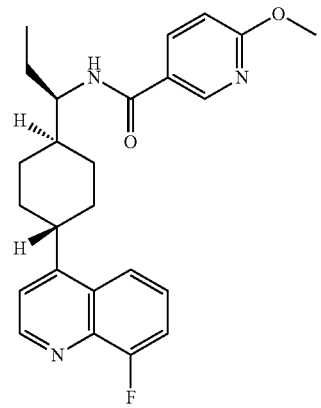

141

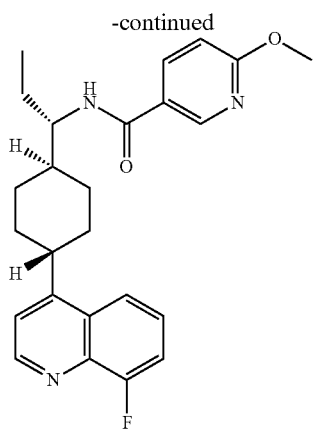

Examples 59 were synthesized using the same route outlined in Examples 10 except 4-chloro-8-fluoroquinoline was employed in the synthesis.

First elute (8.4 mg, 0.020 mmol, 11.2% yield). LC-MS Anal. Calc'd for $C_{25}H_{28}FN_3O_2$ 421.217, found [M+H] 422.0. $T_r$=1.41 min (Method B). $^1$H NMR (500 MHz, DMSO-$d_6$) δ 8.99-8.78 (m, 1H), 8.73-8.49 (m, 1H), 8.24-8.05 (m, 2H), 8.07-7.93 (m, 1H), 7.66-7.37 (m, 3H), 6.97-6.65 (m, 1H), 4.38-4.17 (m, 1H), 4.00-3.83 (m, 3H), 1.94-1.59 (m, 10H), 1.49-1.32 (m, 1H), 1.00-0.78 (m, 3H)

Second elute (7.8 mg, 0.019 mmol, 10.6% yield).). LC-MS Anal. Calc'd for $C_{25}H_{28}FN_3O_2$ 421.217, found [M+H] 422.0. $T_r$=1.41 min (Method B). $^1$H NMR (500 MHz, DMSO-$d_6$) δ 8.99-8.78 (m, 1H), 8.73-8.49 (m, 1H), 8.24-8.05 (m, 2H), 8.07-7.93 (m, 1H), 7.66-7.37 (m, 3H), 6.97-6.65 (m, 1H), 4.38-4.17 (m, 1H), 4.00-3.83 (m, 3H), 1.94-1.59 (m, 10H), 1.49-1.32 (m, 1H), 1.00-0.78 (m, 3H)

Third elute (4.3 mg, 0.010 mmol, 5.8% yield LC-MS Anal. Calc'd for $C_{25}H_{28}FN_3O_2$ 421.217, found [M+H] 422.0. $T_r$=1.38 min (Method B). $^1$H NMR (500 MHz, DMSO-$d_6$) δ 8.89-8.78 (m, 1H), 8.74-8.57 (m, 1H), 8.24-7.99 (m, 3H), 7.65-7.42 (m, 3H), 6.94-6.68 (m, 1H), 3.96-3.88 (m, 3H), 3.85-3.74 (m, 1H), 3.38-3.24 (m, 1H), 2.01-1.79 (m, 4H), 1.72-1.24 (m, 7H), 0.93-0.77 (m, 3H)

Fourth elute (4.4 mg, 0.010 mmol, 5.8% yield). LC-MS Anal. Calc'd for $C_{25}H_{28}FN_3O_2$ 421.217, found [M+H] 422.0. $T_r$=1.38 min (Method B). $^1$H NMR (500 MHz, DMSO-$d_6$) δ 8.89-8.78 (m, 1H), 8.74-8.57 (m, 1H), 8.24-7.99 (m, 3H), 7.65-7.42 (m, 3H), 6.94-6.68 (m, 1H), 3.96-3.88 (m, 3H), 3.85-3.74 (m, 1H), 3.38-3.24 (m, 1H), 2.01-1.79 (m, 4H), 1.72-1.24 (m, 7H), 0.93-0.77 (m, 3H)

Four Isomers of Example 60

N-(1-(4-(8-fluoroquinolin-4-yl)cyclohexyl)propyl)-2-methoxypyrimidine-5-carboxamide (Relative Stereochemistry not Determined)

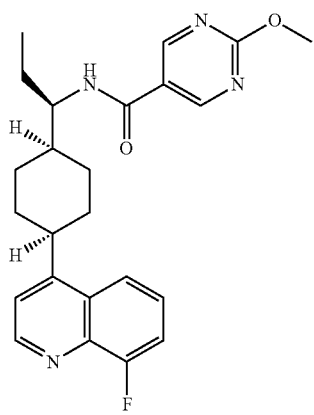

142

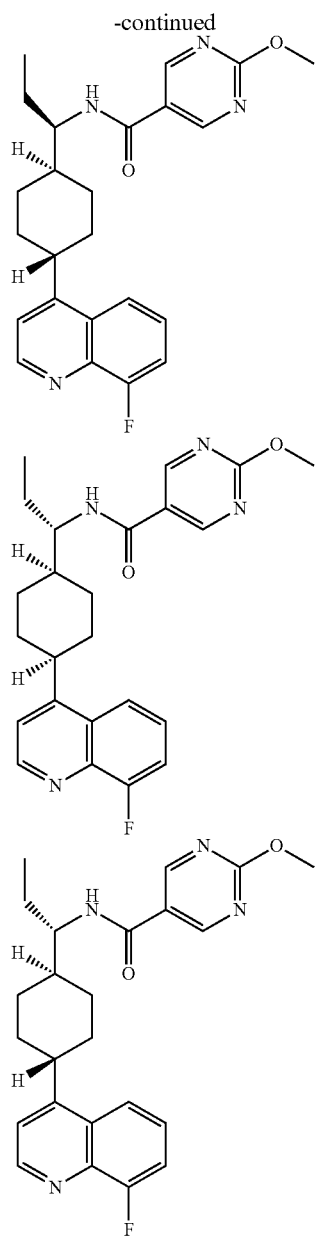

Examples 60 were synthesized using the same route outlined in Examples 10 except 4-chloro-8-fluoroquinoline and 2-methoxypyrimidine-5-carboxylic acid were employed in the synthesis.

First elute (7.9 mg, 0.018 mmol, 10.4% yield). LC-MS Anal. Calc'd for $C_{24}H_{27}FN_4O_2$ 422.212, found [M+H] 423.3. $T_r$=1.28 min (Method B). $T_r$=9.7 min (Method N)$^1$H NMR (500 MHz, DMSO-$d_6$) δ 9.05-8.94 (m, 2H), 8.94-8.73 (m, 1H), 8.40-8.21 (m, 1H), 8.09-7.98 (m, 1H), 7.73-7.38 (m, 3H), 4.36-4.18 (m, 1H), 4.03-3.88 (m, 3H), 3.50-3.28 (m, 1H), 2.00-1.58 (m, 10H), 1.46-1.28 (m, 1H), 0.98-0.75 (m, 3H)

Second elute (4.2 mg, 0.009 mmol, 5.5% yield). LC-MS Anal. Calc'd for $C_{24}H_{27}FN_4O_2$ 422.212, found [M+H] 423.3. $T_r$=1.26 min (Method B). $T_r$=11.8 min (Method N)$^1$H NMR (500 MHz, DMSO-$d_6$) δ 9.06-8.95 (m, 2H), 8.88-8.75 (m, 1H), 8.37-8.19 (m, 1H), 8.10-7.91 (m, 1H), 7.68-7.37 (m, 3H), 4.10-3.89 (m, 3H), 3.88-3.72 (m, 1H), 3.42-3.14 (m, 1H), 2.01-1.82 (m, 4H), 1.75-1.29 (m, 7H), 1.07-0.76 (m, 3H)

Third elute (7.5 mg, 0.017 mmol, 9.8% yield).). LC-MS Anal. Calc'd for $C_{24}H_{27}FN_4O_2$ 422.212, found [M+H] 423.3. $T_r$=1.28 min (Method B). $T_r$=14.7 min (Method N) $^1$H NMR (500 MHz, DMSO-$d_6$) δ 9.05-8.94 (m, 2H), 8.94-8.73 (m, 1H), 8.40-8.21 (m, 1H), 8.09-7.98 (m, 1H), 7.73-7.38 (m, 3H), 4.36-4.18 (m, 1H), 4.03-3.88 (m, 3H), 3.50-3.28 (m, 1H), 2.00-1.58 (m, 10H), 1.46-1.28 (m, 1H), 0.98-0.75 (m, 3H)

Fourth elute (2.4 mg, 0.055 mmol, 3.1% yield). LC-MS Anal. Calc'd for $C_{24}H_{27}FN_4O_2$ 422.212, found [M+H] 423.3. $T_r$=1.26 min (Method B). $T_r$=16.4 min (Method N) $^1$H NMR (500 MHz, DMSO-$d_6$) δ 9.06-8.95 (m, 2H), 8.88-8.75 (m, 1H), 8.37-8.19 (m, 1H), 8.10-7.91 (m, 1H), 7.68-7.37 (m, 3H), 4.10-3.89 (m, 3H), 3.88-3.72 (m, 1H), 3.42-3.14 (m, 1H), 2.01-1.82 (m, 4H), 1.75-1.29 (m, 7H), 1.07-0.76 (m, 3H)

Four Isomers of Example 61

N-(1-(4-(8-fluoroquinolin-4-yl)cyclohexyl)propyl)-2-methylpyrimidine-5-carboxamide (Relative Stereochemistry not Determined)

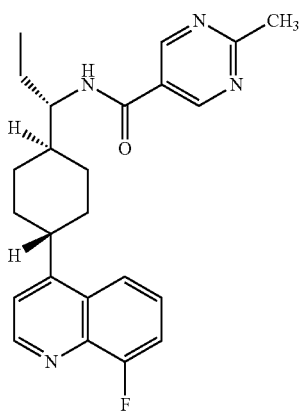

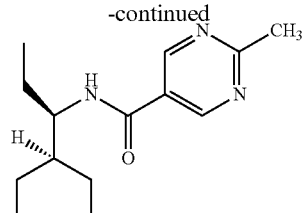

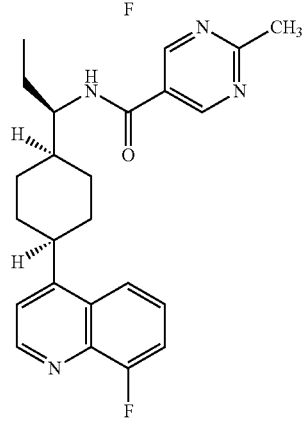

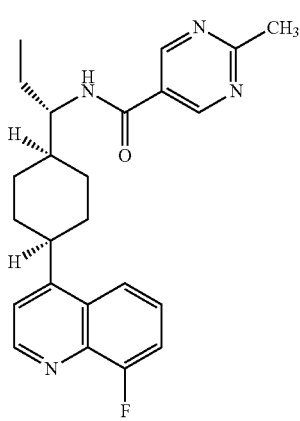

First elute (2.7 mg, 0.0064 mmol, 3.7% yield). LC-MS Anal. Calc'd for $C_{24}H_{27}FN_4O$ 406.217, found [M+H] 407.3. $T_r$=1.14 min (Method B). $^1$H NMR (500 MHz, DMSO-$d_6$) δ 9.15-8.98 (m, 2H), 8.92-8.71 (m, 1H), 8.46-8.31 (m, 1H), 8.10-7.80 (m, 1H), 7.65-7.29 (m, 3H), 3.89-3.69 (m, 1H), 3.38-3.19 (m, 1H), 2.73-2.59 (m, 3H), 2.01-1.83 (m, 4H), 1.74-1.27 (m, 7H), 0.95-0.70 (m, 3H)

Second elute (5.5 mg, 0.013 mmol, 7.5% yield). LC-MS Anal. Calc'd for $C_{24}H_{27}FN_4O$ 406.217, found [M+H] 407.3. $T_r$=1.15 min (Method B). $^1$H NMR (500 MHz, DMSO-$d_6$) δ 9.18-9.01 (m, 2H), 8.94-8.68 (m, 1H), 8.49-8.31 (m, 1H), 8.14-7.94 (m, 1H), 7.72-7.37 (m, 3H), 4.41-4.05 (m, 1H), 3.51-3.33 (m, 1H), 2.71-2.58 (m, 3H), 1.95-1.55 (m, 10H), 1.50-1.27 (m, 1H), 0.95-0.79 (m, 3H)

Third elute (2.1 mg, 0.0049 mmol, 2.8% yield).). LC-MS Anal. Calc'd for $C_{24}H_{27}FN_4O$ 406.217, found [M+H] 407.3. $T_r$=1.14 min (Method B). $^1$H NMR (500 MHz, DMSO-$d_6$) δ 9.15-8.98 (m, 2H), 8.92-8.71 (m, 1H), 8.46-8.31 (m, 1H), 8.10-7.80 (m, 1H), 7.65-7.29 (m, 3H), 3.89-3.69 (m, 1H), 3.38-3.19 (m, 1H), 2.73-2.59 (m, 3H), 2.01-1.83 (m, 4H), 1.74-1.27 (m, 7H), 0.95-0.70 (m, 3H)

Fourth elute (5.1 mg, 0.012 mmol, 7.1% yield). LC-MS Anal. Calc'd for $C_{24}H_{27}FN_4O$ 406.217, found [M+H] 407.3. $T_r$=1.15 min (Method B). $^1$H NMR (500 MHz, DMSO-$d_6$) δ 9.18-9.01 (m, 2H), 8.94-8.68 (m, 1H), 8.49-8.31 (m, 1H), 8.14-7.94 (m, 1H), 7.72-7.37 (m, 3H), 4.41-4.05 (m, 1H), 3.51-3.33 (m, 1H), 2.71-2.58 (m, 3H), 1.95-1.55 (m, 10H), 1.50-1.27 (m, 1H), 0.95-0.79 (m, 3H)

Example 62

N-(1-((1r,4r)-4-(6-fluoroquinolin-4-yl)-1-hydroxycyclohexyl)ethyl)-6-methoxynicotinamide (Relative Stereochemistry not Determined)

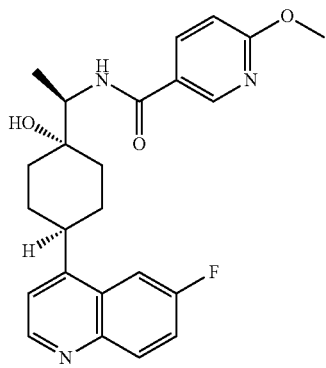

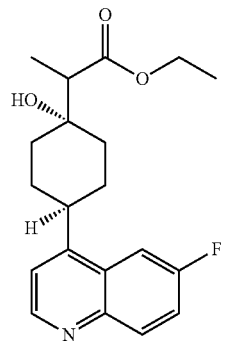

62A: methyl 2-((1r, 4r)-4-(6-fluoroquinolin-4-yl)-1-hydroxycyclohexyl) propanoate

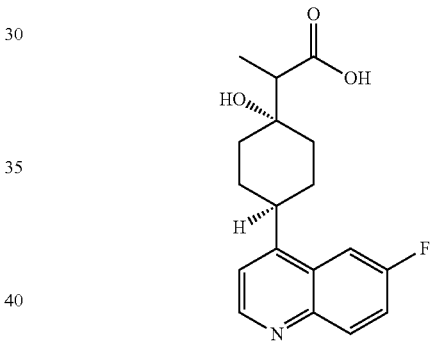

To a solution of 4-(6-fluoroquinolin-4-yl) cyclohexanone (200 mg, 0.822 mmol), methyl 2-bromopropanoate (275 mg, 1.644 mmol) in CH$_3$CN (6 mL) at 0° C. was added tris (triphenylphosphine)rhodium(I) chloride (45.6 mg, 0.049 mmol). The reaction was stirred at 0° C. for 30 min. Then diethylzinc (1.0 M solution in heptane) (1.726 mL, 1.726 mmol) was added. The reaction was stirred at RT for 16 h. The reaction was diluted with EtOAc and saturated NH$_4$Cl. Organic was separated and washed with brine, dried over MgSO$_4$, filtered and concentrated to give a crude material. This crude material was purified with ISCO 24 g, 40 mL/min. 0-100% EtOAc/Hexane in 50 min. The product 62A (87 mg, 0.26 mmol, 32%) was eluted with 50% EtOAc/Hexane. $^1$H NMR (400 MHz, chloroform-d) δ 8.83 (d, J=4.6 Hz, 1H), 8.14 (dd, J=9.2, 5.7 Hz, 1H), 7.67 (dd, J=10.5, 2.8 Hz, 1H), 7.50 (ddd, J=9.2, 8.0, 2.8 Hz, 1H), 7.33 (d, J=4.6 Hz, 1H), 3.78 (s, 3H), 3.65 (s, 1H), 3.36-3.23 (m, 1H), 3.08 (q, J=7.1 Hz, 1H), 2.18-2.08 (m, 1H), 2.06-1.94 (m, 2H), 1.94-1.81 (m, 2H), 1.79-1.68 (m, 3H), 1.68-1.51 (m, 1H), 1.36-1.23 (m, 3H) LC-MS: M+H=332.2 T$_r$=0.59 min. (Method A)

62B: 2-((1r,4r)-4-(6-fluoroquinolin-4-yl)-1-hydroxycyclohexyl)butanoic Acid

To a solution of ethyl 2-((1r,4r)-4-(6-fluoroquinolin-4-yl)-1-hydroxycyclohexyl)butanoate (840 mg, 2.337 mmol) in EtOH (3 mL) and THF (1 mL) was added 2M LiOH (8.18 mL, 16.36 mmol). The reaction was stirred at 50° C. for 16 h. The mixture was cooled to RT and diluted with EtOAc. Organic was separated and washed with 0.5N NaOH. The aqueous layers were combined and pH was adjusted to 5 with concentrated HCl (~0.5 mL). Then it was extracted with EtOAc (3×). The combined EtOAc layers were washed with brine, dried over MgSO$_4$, filtered and concentrated to give 2-((1r,4r)-4-(6-fluoroquinolin-4-yl)-1-hydroxycyclohexyl)butanoic acid (700 mg, 2.007 mmol, 86% yield) as light yellow solid. LC-MS: M+H=332.2 T$_r$=0.56 min. (Method A) $^1$H NMR (400 MHz, chloroform-d) δ 8.87 (d, J=4.6 Hz, 1H), 8.19 (dd, J=9.2, 5.7 Hz, 1H), 7.69 (dd, J=10.4, 2.7 Hz, 1H), 7.52 (ddd, J=9.3, 7.9, 2.8 Hz, 1H), 7.40 (d, J=4.6 Hz, 1H), 3.39-3.24 (m, 1H), 2.95 (dd, J=11.1, 4.2 Hz, 1H), 2.38 (t, J=7.4 Hz, 1H), 2.22 (d, J=13.0 Hz, 1H), 2.05 (d, J=9.2 Hz, 3H), 1.96-1.83 (m, 3H), 1.83-1.53 (m, 5H), 1.09 (t, J=7.5 Hz, 3H), 1.01 (t, J=7.4 Hz, 2H)

62C: (5r,8r)-8-(6-fluoroquinolin-4-yl)-4-methyl-1-oxa-3-azaspiro[4.5]decan-2-one

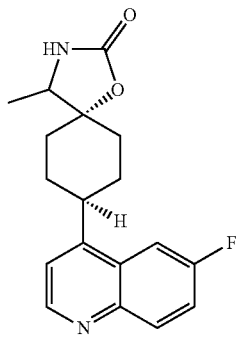

To a solution of 2-((1r,4r)-4-(6-fluoroquinolin-4-yl)-1-hydroxycyclohexyl)propanoic acid (75 mg, 0.236 mmol) in Toluene (2 mL) at Rt was added diphenylphosphoryl azide (0.102 mL, 0.473 mmol), followed by triethylamine (0.066 mL, 0.473 mmol). The reaction was heated at 70° C. for 16 h. The reaction was cooled to RT and concentrated to dryness. The crude material was purified with ISCO 24 g column, 30 mL/min. 0-10% meOH/CH$_2$Cl$_2$ in 20 min. The desired product was eluted with 5% MeOH/CH2Cl2 to give (5r,8r)-8-(6-fluoroquinolin-4-yl)-4-methyl-1-oxa-3-azaspiro[4.5]decan-2-one (74 mg, 0.233 mmol, 99% yield) as white solid. LC-MS: M+H=315.0 T$_r$=0.54 min. (Method A) $^1$H NMR (400 MHz, chloroform-d) δ 8.84 (d, J=4.6 Hz, 1H), 8.16 (dd, J=9.2, 5.7 Hz, 1H), 7.68 (dd, J=10.3, 2.8 Hz, 1H), 7.52 (ddd, J=9.2, 7.9, 2.7 Hz, 1H), 7.32-7.19 (m, 2H), 5.40 (s, 1H), 3.83 (q, J=6.4 Hz, 1H), 3.41-3.28 (m, 1H), 2.37-2.25 (m, 2H), 2.25-2.13 (m, 2H), 2.12-1.91 (m, 2H), 1.81-1.68 (m, 1H), 1.64-1.47 (m, 1H), 1.35 (d, J=6.5 Hz, 3H)

62D: (1r,4r)-1-(1-aminoethyl)-4-(6-fluoroquinolin-4-yl)cyclohexanol

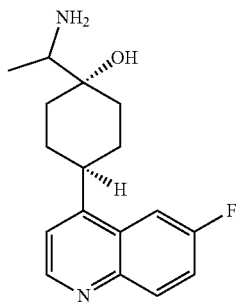 [SMILES: CC(N)[C@]1(O)CC[C@H](c2ccnc3ccc(F)cc32)CC1]

To a solution of (5r,8r)-8-(6-fluoroquinolin-4-yl)-4-methyl-1-oxa-3-azaspiro[4.5]decan-2-one (65 mg, 0.207 mmol) in Dioxane (1 mL) and H$_2$O (1 mL) at RT was added KOH (57.9 mg, 1.034 mmol). The reaction was stirred at 85° C. for 2 days. The mixture was cooled to RT. The reaction was adjusted pH to 10 with concentrated HCl. The aqueous layer was extracted with EtOAc (3×), brine and dried over MgSO$_4$, filtered and concentrated to give (1r,4r)-1-(1-aminoethyl)-4-(6-fluoroquinolin-4-yl)cyclohexanol (35 mg, 0.120 mmol, 58.1% yield) as white solid. LC-MS: M+H=289.1 T$_r$=0.44 min. (Method A)

62: N-(1-((1r,4r)-4-(6-fluoroquinolin-4-yl)-1-hydroxycyclohexyl)ethyl)-6-methoxynicotinamide To a solution of 1-(3-dimethylaminopropyl)-3-ethylcarbodiimide hydrochloride (13.30 mg, 0.069 mmol) in DMF (2 mL) at RT was added 5-methoxypicolinic acid (10.62 mg, 0.069 mmol), 1-(3-dimethylaminopropyl)-3-ethylcarbodiimide hydrochloride (13.30 mg, 0.069 mmol),1-hydroxybenzotriazole (10.61 mg, 0.069 mmol) and Hunig's Base (0.018 mL, 0.104 mmol). The reaction was stirred at RT for 16 h. The reaction mixture was concentrated in vacuo and the residue was dissolved in MeOH, filtered, and purified via preparative SFC (Method E) to give two isolates. (absolute stereochemistry was not determined).

First elute (4.8 mg, 0.011 mmol, 32.4% yield). LC-MS Anal. Calc'd for C$_{24}$H$_{26}$FN$_3$O$_3$423.196, found [M+H] 424.1. T$_r$=1.077 min (Method B). T$_r$=11.397 min (Method O)$^1$H NMR (500 MHz, DMSO-d$_6$) δ 8.85-8.73 (m, 1H), 8.60 (br d, J=10.1 Hz, 1H), 8.19-8.07 (m, 2H), 8.00-7.86 (m, 2H), 7.73-7.57 (m, 1H), 7.53-7.39 (m, 1H), 6.97-6.69 (m, 1H), 4.67-4.47 (m, 1H), 3.88 (s, 3H), 3.22-3.10 (m, 1H), 2.08-1.49 (m, 9H), 1.25-1.00 (m, 3H)

Second elute (4.9 mg, 0.012 mmol, 33.4% yield). LC-MS Anal. Calc'd for C$_{24}$H$_{26}$FN$_3$O$_3$423.196, found [M+H] 424.1. T$_r$=1.078 min (Method B). T$_r$=13.244 min (Method O)$^1$H NMR (500 MHz, DMSO-d$_6$) δ 8.85-8.73 (m, 1H), 8.60 (br d, J=10.1 Hz, 1H), 8.19-8.07 (m, 2H), 8.00-7.86 (m, 2H), 7.73-7.57 (m, 1H), 7.53-7.39 (m, 1H), 6.97-6.69 (m, 1H), 4.67-4.47 (m, 1H), 3.88 (s, 3H), 3.22-3.10 (m, 1H), 2.08-1.49 (m, 9H), 1.25-1.00 (m, 3H).

Examples 63-1 and 63-2

N-(1-((1s,4s)-4-(3-(Difluoromethyl)-2-methoxypyridin-4-yl)cyclohexyl)propyl)-6-oxo-1,6-dihydropyridine-3-carboxamide (Absolute Stereochemistry not Assigned)

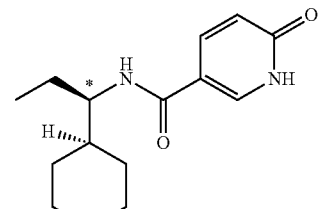

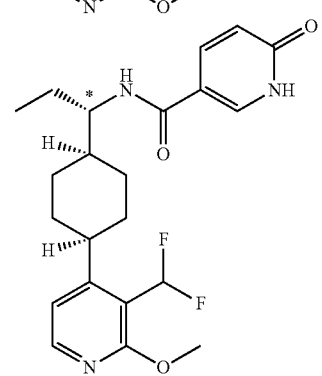

To a mixture of 6-hydroxynicotinic acid (72.7 mg, 0.52 mmol), EDCI (125 mg, 0.65 mmol) and HOBT (100 mg, 0.65 mmol) in anhydrous DMF (4 mL), in a sealable vial, was added a solution of preparation 24G (130 mg, 0.44 mmol) and TEA (0.08 mL, 0.57 mmol) in anhydrous DMF (2 mL). The resulting mixture was stirred at ambient temperature for 50 hours before being diluted with EtOAc then washed with water. The layers were separated and the organic layer was concentrated in vacuo to afford the crude racemic product. Purification by Isco chromatography afforded (±)-N-(1-((1s,4s)-4-(3-(difluoromethyl)-2-methoxypyridin-4-yl)cyclohexyl)propyl)-6-oxo-1,6-dihydropyridine-3-carboxamide as an off-white solid (93.5 mg; 50% yield). MS (ES): m/z=420 [M+H]+. $t_R$=0.90 min (Method A). $^1$H NMR (400 MHz, CDCl$_3$) δ 8.16 (d, J=5.1 Hz, 1H), 8.07 (d, J=1.5 Hz, 1H), 7.84 (dd, J=9.5, 2.1 Hz, 1H), 7.05 (d, J=5.4 Hz, 1H), 7.16 (br t, J=54.3 Hz, 1H), 6.60 (d, J=9.5 Hz, 1H), 5.61 (d, J=9.7 Hz, 1H), 4.61-4.44 (m, 1H), 3.96 (s, 3H), 3.23 (br t, J=11.0 Hz, 1H), 1.93 (br d, J=10.5 Hz, 2H), 1.87-1.78 (m, 2H), 1.76-1.65 (m, 4H), 1.64-1.54 (m, 3H), 1.45-1.31 (m, 1H), 0.97 (br t, J=7.3 Hz, 3H).

Example 63-1 N-(1-((1s,4s)-4-(3-(difluoromethyl)-2-methoxypyridin-4-yl)cyclohexyl)propyl)-6-oxo-1,6-dihydropyridine-3-carboxamide (Enantiomer 1, Absolute Stereochemistry not Assigned)

and

Example 63-2 N-(1-((1s,4s)-4-(3-(difluoromethyl)-2-methoxypyridin-4-yl)cyclohexyl)propyl)-6-oxo-1,6-dihydropyridine-3-carboxamide (Enantiomer 2, Absolute Stereochemistry not Assigned Racemic (±)-N-(1-((1s,4s)-4-(3-(difluoromethyl)-2-methoxypyridin-4-yl)cyclohexyl)propyl)-6-oxo-1,6-dihydropyridine-3-carboxamide (93.5 mg) was purified by chiral SFC (70/30 CO$_2$/MeOH with 0.1% NH$_4$OH mobile phase, Chiralpak IC 3×25 cm, 5 μm column, 170 ml/min, detector wavelength=215 nm). Concentration of the appropriate (earlier eluting) fractions afforded Example 63-1 (34.2 mg) assigned as N-(1-((1s,4s)-4-(3-(difluoromethyl)-2-methoxypyridin-4-yl)cyclohexyl)propyl)-6-oxo-1,6-dihydropyridine-3-carboxamide (Enantiomer 1). MS (ES): m/z=420 [M+H]+. $T_r$=0.86 min (Method A). $^1$H NMR (400 MHz, DMSO-d$_6$) δ 12.09-11.75 (m, 1H), 8.27 (d, J=5.4 Hz, 1H), 8.03 (d, J=2.4 Hz, 1H), 7.90 (dd, J=9.7, 2.7 Hz, 1H), 7.81 (d, J=9.2 Hz, 1H), 7.42-7.11 (m, 1H), 7.07 (d, J=5.5 Hz, 1H), 6.34 (d, J=9.5 Hz, 1H), 4.37-4.22 (m, 1H), 3.90 (s, 3H), 3.19-3.05 (m, 1H), 1.92-1.66 (m, 5H), 1.65-1.48 (m, 3H), 1.46-1.27 (m, 3H), 0.85 (t, J=7.3 Hz, 3H) Concentration of the later eluting fractions afforded Example 63-2 (4.9 mg) assigned as N-(1-((1 s,4s)-4-(3-(difluoromethyl)-2-methoxypyridin-4-yl)cyclohexyl)propyl)-6-oxo-1,6-dihydropyridine-3-carboxamide (Enantiomer 2). MS (ES): m/z=420 [M+H]+. $T_r$=0.86 min (Method A). $^1$H NMR (400 MHz, DMSO-d$_6$) δ 11.93 (br d, J=1.8 Hz, 1H), 8.27 (d, J=5.4 Hz, 1H), 8.03 (d, J=2.4 Hz, 1H), 7.90 (dd, J=9.7, 2.7 Hz, 1H), 7.81 (d, J=9.0 Hz, 1H), 7.42-7.11 (m, 1H), 7.07 (d, J=5.4 Hz, 1H), 6.34 (d, J=9.5 Hz, 1H), 4.41-4.20 (m, 1H), 3.90 (s, 3H), 3.21-3.03 (m, 1H), 1.91-1.66 (m, 5H), 1.66-1.48 (m, 3H), 1.47-1.27 (m, 3H), 0.85 (t, J=7.3 Hz, 3H).

Examples 64-1 and 64-2 N-(1-((1s,4s)-4-(3-(difluoromethyl)-2-oxo-1,2-dihydropyridin-4-yl)cyclohexyl)propyl)-6-methoxynicotinamide Absolute Stereochemistry not Assigned

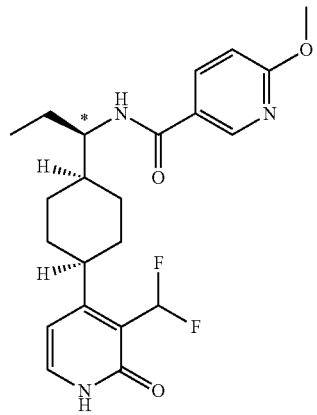

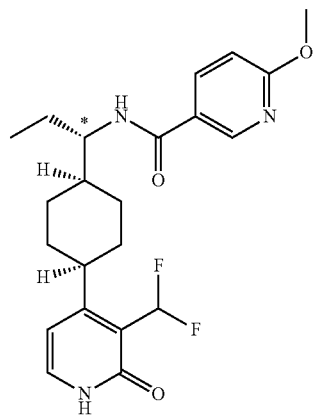

64A. (±)-4-((1s,4s)-4-(1-aminopropyl)cyclohexyl)-3-(difluoromethyl)pyridin-2(1H)-one To a sealable reaction flask, charged with preparation 24G (122 mg, 0.41 mmol) was added HCl (4N in dioxane) (5 mL, 20.0 mmol). The flask was sealed and the mixture was stirred at 85° C. for 4.5 hours before being concentrated in vacuo to afford an off-white solid. Purification by RP Preparative HPLC (Phen Axia C18 5μ 30×100 column. Conditions: 40 mL/min flow rate; 15 minute gradient from 0-70% B (Solvent A=90:10 H2O/MeOH with 0.1% TFA. Solvent B=10:90 H2O/MeOH with 0.1% TFA) afforded the TFA salt of (±)-4-((1s,4s)-4-(1-aminopropyl)cyclohexyl)-3-(difluoromethyl)pyridin-2(1H)-one as a white solid (120.8 mg; 74% yield). MS (ES): m/z=285 [M+H]+. $T_r$=0.54 min (Method A).

64B. (±)-N-(1-((1s,4s)-4-(3-(difluoromethyl)-2-oxo-1,2-dihydropyridin-4-yl)cyclohexyl)propyl)-6-methoxynicotinamide To a mixture of 6-methoxynicotinic acid (55.7 mg, 0.36 mmol), EDCI (87.0 mg, 0.46 mmol) and HOBT (69.7 mg, 0.46 mmol) in anhydrous DMF (4 mL), in a sealable vial, was added a solution of (±)-4-((1s,4s)-4-(1-aminopropyl)cyclohexyl)-3-(difluoromethyl)pyridin-2(1H)-one (120.8 mg, 0.30 mmol) and TEA (0.1 mL, 0.717 mmol) in anhydrous DMF (2 mL). The resulting mixture was stirred at ambient temperature for 64 hours before being diluted with EtOAc then washed with water. The layers were separated and the organic layer was concentrated in vacuo to afford the crude racemic product. Purification by Isco chromatography afforded (±)-N-(1-((1s,4s)-4-(3-(difluoromethyl)-2-oxo-1,2-dihydropyridin-4-yl)cyclohexyl)propyl)-6-methoxynicotinamide as an white solid (93.0 mg; 73% yield). MS (ES): m/z=420 [M+H]$^+$. t$_R$=0.81 min (Method A).

Example 64-1 N-(1-((1s,4s)-4-(3-(difluoromethyl)-2-oxo-1,2-dihydropyridin-4-yl)cyclohexyl)propyl)-6-methoxynicotinamide (Enantiomer 1, Absolute Stereochemistry not Assigned)

and

Example 64-2. N-(1-((1s,4s)-4-(3-(difluoromethyl)-2-oxo-1,2-dihydropyridin-4-yl)cyclohexyl)propyl)-6-methoxynicotinamide (Enantiomer 2, Absolute Stereochemistry not Assigned)

Racemic preparation 64B (93.0 mg) was purified by chiral SFC (84/16 CO$_2$/MeOH with 0.1% NH$_4$OH mobile phase, Chiralpak IC 3×25 cm, 5 µm column, 180 ml/min, detector wavelength=212 nm). Concentration of the appropriate (earlier eluting) fractions afforded Example 64-1 (34.4 mg) assigned as N-(1-((1s,4s)-4-(3-(difluoromethyl)-2-oxo-1,2-dihydropyridin-4-yl)cyclohexyl)propyl)-6-methoxynicotinamide (Enantiomer 1). MS (ES): m/z=420 [M+H]+. T$_r$=0.81 min (Method A). $^1$H NMR (400 MHz, DMSO-d6) δ 11.90 (br s, 1H), 8.68 (d, J=2.2 Hz, 1H), 8.15 (dd, J=8.7, 2.4 Hz, 1H), 8.07 (d, J=9.2 Hz, 1H), 7.54 (d, J=6.8 Hz, 1H), 7.29-6.95 (m, 1H), 6.89 (d, J=8.6 Hz, 1H), 6.28 (d, J=7.0 Hz, 1H), 4.40-4.25 (m, 1H), 3.90 (s, 3H), 3.11-2.97 (m, 1H), 1.92-1.67 (m, 5H), 1.66-1.30 (m, 6H), 0.87 (t, J=7.3 Hz, 3H).

Concentration of the later eluting fractions afforded Example 64-2 (37.2 mg) assigned as N-(1-((1s,4s)-4-(3-(difluoromethyl)-2-oxo-1,2-dihydropyridin-4-yl)cyclohexyl)propyl)-6-methoxynicotinamide (Enantiomer 2). MS (ES): m/z=420 [M+H]+. T$_r$=0.86 min (Method A). $^1$H NMR (400 MHz, DMSO-d$_6$) δ 11.89 (br s, 1H), 8.68 (d, J=2.2 Hz, 1H), 8.15 (dd, J=8.7, 2.4 Hz, 1H), 8.07 (d, J=9.2 Hz, 1H), 7.54 (d, J=7.0 Hz, 1H), 7.30-6.94 (m, 1H), 6.89 (d, J=8.7 Hz, 1H), 6.28 (d, J=7.0 Hz, 1H), 4.39-4.25 (m, 1H), 3.90 (s, 3H), 3.13-2.98 (m, 1H), 1.93-1.65 (m, 5H), 1.64-1.30 (m, 6H), 0.87 (t, J=7.3 Hz, 3H).

Example 65

(±)-N-(1-((1s,4s)-4-(3-(difluoromethyl)-2-methoxypyridin-4-yl)cyclohexyl)propyl)-6-(methoxy-d$_3$)nicotinamide

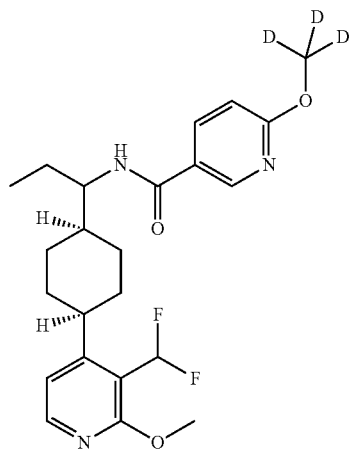 [SMILES: [2H]C([2H])([2H])Oc1ccc(C(=O)NC(CC)[C@H]2CC[C@@H](c3ccnc(OC)c3C(F)F)CC2)cn1]

65A. Methyl-d$_3$ 6-(methoxy-d$_3$)nicotinate

To a flask containing CD$_3$OD (12 mL), under nitrogen atmosphere, was added sodium (735 mg, 32.0 mmol) portionwise. The resulting mixture was stirred until homogenous before methyl 6-chloronicotinate (2.15 mL, 11.42 mmol) was added in one portion. After stirring at ambient temperature for 17 hours, the mixture was concentrated to approximately one fourth of its original volume before being quenched with saturated aqueous ammonium chloride. The resultant mixture was partitioned between EtOAc and 1N HCl (aq). The layers were separated and the aqueous layer was extracted once more with EtOAc. The organic layers were combined, washed with brine, dried (anhydrous Na$_2$SO$_4$), filtered and concentrated in vacuo to afford the crude product. Purification by Isco chromatography afforded methyl-d$_3$ 6-(methoxy-d$_3$)nicotinate as a white solid (1.05 g; 53% yield). MS (ES): m/z=174 [M+H]$^+$. t$_R$=0.75 min (Method A). $^1$H NMR (400 MHz, DMSO-d6) δ 8.75 (d, J=2.3 Hz, 1H), 8.16 (dd, J=8.7, 2.4 Hz, 1H), 6.93 (d, J=8.7 Hz, 1H).

65B. 6-(methoxy-d$_3$)nicotinic Acid

To a homogeneous mixture of methyl-d$_3$ 6-(methoxy-d$_3$)nicotinate (229.0 mg, 1.32 mmol) in anhydrous THF (6 mL), under nitrogen atmosphere, was added LiOH (38.0 mg, 1.59 mmol) followed by H2O (1.5 mL). After stirring at ambient temperature for 19 hours, LiOH (19.0 mg, 0.80 mmol) was added to the mixture and stirring was continued. After 7 hours, the mixture was partially concentrated to remove volatiles then diluted with EtOAc before being washed sequentially with 1N HCl (aq) then brine. The aqueous layers were thoroughly backwashed with EtOAc to remove all product before the organic layers were combined and concentrated in vacuo. The resultant crude product was treated with acetonitrile, frozen then lyophilized overnight to afford 6-(methoxy-d$_3$)nicotinic acid as a white solid (229.0 mg, 90% yield). MS (ES): m/z=157 [M+H]$^+$. t$_R$=0.60 min (Method A). $^1$H NMR (400 MHz, DMSO-d$_6$) δ 13.03 (br s, 1H), 8.72 (d, J=2.2 Hz, 1H), 8.13 (dd, J=8.7, 2.4 Hz, 1H), 6.90 (d, J=8.7 Hz, 1H).

Example 65. (±)-N-(1-((1s,4s)-4-(3-(difluoromethyl)-2-methoxypyridin-4-yl)cyclohexyl)propyl)-6-(methoxy-d₃)nicotinamide To a mixture of 6-(methoxy-d₃)nicotinic acid (82.0 mg, 0.52 mmol), EDCI (125 mg, 0.65 mmol) and HOBT (100 mg, 0.65 mmol) in anhydrous DMF (4 mL), in a sealable vial, was added a solution of preparation 24G (130 mg, 0.44 mmol) and TEA (0.08 mL, 0.57 mmol) in anhydrous DMF (2 mL). The resulting mixture was stirred at ambient temperature for 50 hours before being diluted with EtOAc then washed with water. The layers were separated and the organic layer was concentrated in vacuo to afford the crude racemic product. Purification by Isco chromatography afforded (±)-N-(1-((1s,4s)-4-(3-(difluoromethyl)-2-methoxypyridin-4-yl)cyclohexyl)propyl)-6-(methoxy-d₃)nicotinamide as a white solid (147.9 mg; 78% yield). MS (ES): m/z=437 [M+H]$^+$. t$_R$=1.06 min (Method A). $^1$H NMR (400 MHz, CDCl₃) δ 8.59 (d, J=2.0 Hz, 1H), 8.16 (d, J=5.4 Hz, 1H), 8.01 (dd, J=8.7, 2.6 Hz, 1H), 7.07 (d, J=5.5 Hz, 1H), 7.16 (br t, J=54.4 Hz, 1H), 6.79 (d, J=8.7 Hz, 1H), 5.65 (br d, J=9.8 Hz, 1H), 4.70-4.45 (m, 1H), 3.96 (s, 3H), 3.36-3.10 (m, 1H), 2.02-1.80 (m, 4H), 1.80-1.64 (m, 4H), 1.61-1.52 (m, 2H), 1.48-1.33 (m, 1H), 0.99 (t, J=7.4 Hz, 3H).

Examples 66-1 and 66-2 N-(1-((1s,4s)-4-(3-(difluoromethyl)-2-methoxypyridin-4-yl)cyclohexyl)propyl)-6-(methoxy-d₃)nicotinamide Absolute Stereochemistry not Assigned

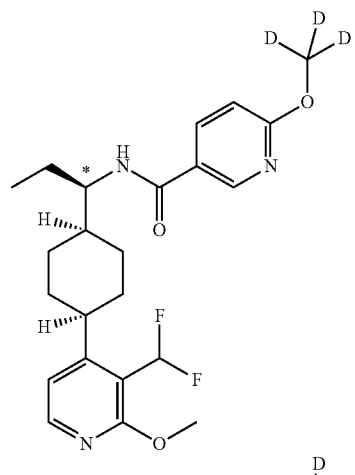

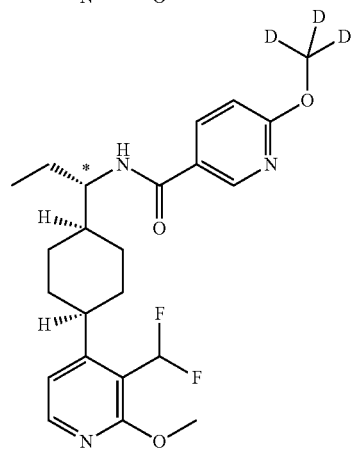

Racemic (±)-N-(1-((1s,4s)-4-(3-(difluoromethyl)-2-methoxypyridin-4-yl)cyclohexyl)propyl)-6-(methoxy-d₃)nicotinamide (147 mg) was purified by chiral SFC (77/23 CO₂/IPA with 0.1% NH₄OH mobile phase, Chiralpak IC 3×25 cm, 5 μm column, 160 ml/min, detector wavelength=220 nm). Concentration of the appropriate (earlier eluting) fractions afforded Example 66-1 (56.3 mg) assigned as N-(1-((1s,4s)-4-(3-(difluoromethyl)-2-methoxypyridin-4-yl)cyclohexyl)propyl)-6-(methoxy-d₃)nicotinamide (Enantiomer 1). MS (ES): m/z=437 [M+H]$^+$. T$_r$=1.01 min (Method A). $^1$H NMR (400 MHz, DMSO-d6) δ 8.69 (d, J=2.0 Hz, 1H), 8.27 (d, J=5.4 Hz, 1H), 8.15 (dd, J=8.7, 2.4 Hz, 1H), 8.06 (d, J=9.3 Hz, 1H), 7.42-7.11 (m, 1H), 7.09 (d, J=5.4 Hz, 1H), 6.88 (d, J=9.0 Hz, 1H), 4.44-4.28 (m, 1H), 3.90 (s, 3H), 3.19-3.05 (m, 1H), 1.92-1.71 (m, 5H), 1.67-1.51 (m, 3H), 1.49-1.35 (m, 3H), 0.88 (t, J=7.3 Hz, 3H).

Concentration of the later eluting fractions afforded Example 66-2 (59.3 mg) assigned as N-(1-((1 s,4s)-4-(3-(difluoromethyl)-2-methoxypyridin-4-yl)cyclohexyl)propyl)-6-(methoxy-d₃)nicotinamide (Enantiomer 2). MS (ES): m/z=437 [M+H]$^+$. T$_r$=1.01 min (Method A). $^1$H NMR (400 MHz, DMSO-d₆) δ 8.69 (d, J=2.2 Hz, 1H), 8.27 (d, J=5.4 Hz, 1H), 8.15 (dd, J=8.6, 2.5 Hz, 1H), 8.06 (d, J=9.3 Hz, 1H), 7.41-7.11 (m, 1H), 7.09 (d, J=5.4 Hz, 1H), 6.88 (d, J=8.6 Hz, 1H), 4.40-4.29 (m, 1H), 3.90 (s, 3H), 3.19-3.06 (m, 1H), 1.92-1.69 (m, 5H), 1.69-1.50 (m, 3H), 1.50-1.31 (m, 3H), 0.88 (t, J=7.3 Hz, 3H).

Example 67

(±)-N-(1-((1r,4r)-4-(2-fluoro-3-methylpyridin-4-yl)cyclohexyl)propyl)-6-methoxynicotinamide

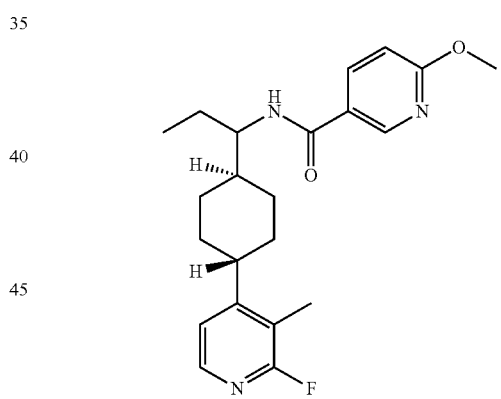

67A. Ethyl 2-(4-(2-fluoro-3-methylpyridin-4-yl)cyclohex-3-en-1-yl)acetate

To a sealable reaction flask containing a solution of ethyl 2-(4-(4,4,5,5-tetramethyl-1,3,2-dioxaborolan-2-yl)cyclohex-3-en-1-yl)acetate (9.90 g, 33.7 mmol) in anhydrous dioxane (195 mL) was added 4-bromo-2-fluoro-3-methylpyridine (prepared as in *J. Organomet. Chem.*, 382 (1990) 319) (6.21 g, 32.7 mmol), water (65 mL) and Na₂CO₃ (13.86 g, 131 mmol). The mixture was sparged with Argon for 15 minutes before Pd(Ph₃P)₄ (1.89 g, 1.63 mmol) was added, the flask was sealed and the mixture was heated at 100° C. After 24 hours the mixture was allowed to slowly cool to room temperature. After an additional 60 hours of stirring at ambient temperature, the mixture was partitioned between EtOAc and water. The layers were separated and the aqueous layer was extracted once more with EtOAc before the organic layers were combined, washed with brine, dried over anhydrous $Na_2SO_4$, filtered and concentrated in vacuo to afford the crude product as a brown residue. Purification by Isco chromatography afforded ethyl 2-(4-(2-fluoro-3-methylpyridin-4-yl)cyclohex-3-en-1-yl)acetate as an oil (7.23 g; 80% yield). MS (ES): m/z=278 [M+H]$^+$. $t_R$=1.02 min (Method A). $^1$H NMR (400 MHz, CDCl$_3$) δ 7.93 (d, J=5.0 Hz, 1H), 6.91-6.85 (m, 1H), 5.61 (dd, J=3.0, 1.8 Hz, 1H), 4.17 (q, J=7.2 Hz, 2H), 2.39-2.31 (m, 4H), 2.23-2.16 (m, 5H), 1.98-1.87 (m, 2H), 1.53-1.42 (m, 1H), 1.28 (t, J=7.2 Hz, 3H).

67B. (trans)-Ethyl 2-((1r,4r)-4-(2-fluoro-3-methylpyridin-4-yl)cyclohexyl)acetate and (cis)-Ethyl 2-((1s,4s)-(4-(2-fluoro-3-methylpyridin-4-yl)cyclohexyl)acetate To a solution of ethyl 2-(4-(2-fluoro-3-methylpyridin-4-yl)cyclohex-3-en-1-yl)acetate (7.23 g, 26.1 mmol) in MeOH (100 mL) was added ammonium formate (8.22 g, 130 mmol). The resulting mixture was sparged with Argon for 10 minutes before being sequentially evacuated then purged with nitrogen three times. 10% Palladium on carbon (wet, 2.77 g, 2.6 mmol) was added and the reaction was heated at reflux for three hours before being allowed to cool to room temperature. After 11 hours, the mixture was concentrated to remove volatiles then treated with DCM and filtered through a pad of Celite to remove any solids. The filtrate was concentrated in vacuo to remove volatiles then resubjected to the original conditions of the reaction. After refluxing for three hours, the mixture was concentrated to remove volatiles then treated with DCM and filtered through a pad of Celite which was thoroughly rinsed with DCM. The combined filtrates were concentrated in vacuo to afford the cis/trans ethyl 2-(4-(2-fluoro-3-methylpyridin-4-yl)cyclohexyl)acetate as a clear oil (7.32 g; 100% yield). MS (ES): m/z=280 [M+H]$^+$. $t_R$=1.02 min (Method A).

Ethyl 2-(4-(2-fluoro-3-methylpyridin-4-yl)cyclohexyl) acetate (7.32 g) was separated by chiral SFC (90/10 CO$_2$/MeOH mobile phase, OJ-H #72156 3×25 cm, 5 μm column, 150 ml/min, 35° C., detector wavelength=220 nm). Concentration of the appropriate (earlier eluting) fractions afforded (trans)-ethyl 2-((1r,4r)-4-(2-fluoro-3-methylpyridin-4-yl) cyclohexyl)acetate (2.68 g). MS (ES): m/z=280 [M+H]$^+$. $T_r$=1.01 min (Method A).

Concentration of the later eluting fractions afforded (cis)-ethyl 2-(4-(2-fluoro-3-methylpyridin-4-yl)cyclohexyl)acetate (2.18 g). MS (ES): m/z=280 [M+H]$^+$. $T_r$=1.01 min (Method A).

67C. (±)-Ethyl 2-((1r,4r)-4-(2-fluoro-3-methylpyridin-4-yl)cyclohexyl)butanoate To a flask charged with anhydrous THF (20 mL), at −78° C. under Argon, was added lithium diisopropylamide (2M in THF/heptane/ethyl benzene, 6 mL, 12.0 mmol). 1,3-Dimethyltetrahydropyrimidin-2(1H)-one (0.94 mL, 7.80 mmol) was slowly added to the resulting mixture, followed by dropwise addition of a solution of ethyl 2-((1r,4r)-4-(2-fluoro-3-methylpyridin-4-yl)cyclohexyl)acetate (1.45 g, 5.2 mmol) in anhydrous THF (5 mL) over 20 minutes, maintaining a temperature of −78° C. The mixture was stirred at that temperature for one hour before iodoethane (0.83 mL, 10.4 mmol) was added slowly dropwise. The resultant mixture was stirred at −78° C. for three hours before being allowed to slowly warm to room temperature. After 15.5 hours, the reaction was quenched with water then thoroughly extracted with EtOAc. The organic layers were combined, washed with brine, dried (Na2SO4), filtered and concentrated in vacuo to afford the crude product. Purification by Isco chromatography afforded (±)-ethyl 2-((1r,4r)-4-(2-fluoro-3-methylpyridin-4-yl)cyclohexyl)butanoate as a colorless oil (0.47 g; 29% yield). MS (ES): m/z=308 [M+H]$^+$. $t_R$=1.11 min (Method A).

67D. (±)-2-((1r,4r)-4-(2-Fluoro-3-methylpyridin-4-yl)cyclohexyl)butanoic Acid To a mixture of (+)-ethyl 2-((1r,4r)-4-(2-fluoro-3-methylpyridin-4-yl)cyclohexyl)butanoate (863.8 mg, 2.8 mmol) in THF (2 mL), MeOH (1 mL) and water (2 mL), under nitrogen atmosphere, was added LiOH (673.0 mg, 28.1 mmol). The resulting mixture was stirred at 80° C. for six hours before THF (2 mL), MeOH (1 mL) and Water (2 mL) were added and the mixture was allowed to cool slowly to room temperature overnight. MeOH (2 mL) and LiOH (2N aqueous, 2 mL) were added and the reaction was heated at 70° C. for 5.5 hours before MeOH (1 mL) was added. After 1.5 hours, the reaction was cooled to room temperature then acidified with HCl (6N aqueous) until pH 6 (pH test strips). The mixture was extracted with EtOAc and the combined organic layers were concentrated to afford the crude product (675.8 mg; 86%) which was used in the next step without further purification. MS (ES): m/z=280 [M+H]$^+$. $t_R$=0.90 min (Method A).

67E. (±)-1-((1r,4r)-4-(2-Fluoro-3-methylpyridin-4-yl)cyclohexyl)propan-1-amine To a mixture of (±)-2-((1r,4r)-4-(2-fluoro-3-methylpyridin-4-yl)cyclohexyl)butanoic acid (785 mg, 2.8 mmol) in toluene (40 mL), under nitrogen atmosphere, was added diphenylphosphoryl azide (0.73 mL, 3.4 mmol) followed by TEA (0.78 mL, 5.6 mmol). The flask was sealed and the mixture was heated at 70° C. for two hours. After cooling to room temperature, the reaction was filtered to remove solids before the filtrate was concentrated in vacuo to afford a pale gold oil. The oil was dissolved in THF (20 mL) then treated with LiOH (2M aqueous solution, 10 mL, 20 mmol). After stirring at ambient temperature for 1.5 hours, the mixture was acidified with 1N HCl (aq) until pH 1 to pH test strips. EtOAc was added to the mixture and the layers were separated. The aqueous layer was then treated with 2N NaOH (aq) until the mixture became cloudy (pH 14 to pH test strips) before being thoroughly extracted with EtOAc. The combined organic layers were concentrated in vacuo to afford the crude product as an off-white solid (357.1 mg; 51%). MS (ES): m/z=251 [M+H]$^+$. $t_R$=0.65 min (Method A). $^1$H NMR (400 MHz, CDCl$_3$) δ 7.96 (d, J=5.0 Hz, 1H), 6.99 (d, J=4.7 Hz, 1H), 5.14-4.78 (m, 2H), 2.76-2.65 (m, 1H), 2.51 (dt, J=8.6, 4.4 Hz, 1H), 2.22 (s, 3H), 1.96-1.81 (m, 5H), 1.44-1.21 (m, 6H), 0.96 (t, J=7.4 Hz, 3H).

Example 67. (±)-N-(1-((1r,4r)-4-(2-Fluoro-3-methylpyridin-4-yl)cyclohexyl)propyl)-6-methoxynicotinamide To a mixture of 6-methoxynicotinic acid (22.0 mg, 0.14 mmol) in anhydrous DMF (1 mL), at room temperature in a sealable reaction vial, was added PyBOP (62.4 mg, 0.12 mmol) followed by DIPEA (0.1 mL, 0.57 mmol). The resulting mixture was stirred at ambient temperature for 10 minutes before (±)-1-((1r,4r)-4-(2-fluoro-3-methylpyridin- 4-yl)cyclohexyl)propan-1-amine (30.0 mg, 0.12 mmol) was added. The vial was sealed and the reaction stirred at ambient temperature for 70 hours, before being diluted with DMF, passed through a syringe filter, then purified via preparative HPLC/MS to afford the title compound as a racemate (3.7 mg; 8% yield). MS (ES): m/z=386 [M+H]$^+$. t$_R$=1.90 min (Method B).

Examples 68-1 and 68-2 N-(1-((1r,4r)-4-(2-Fluoro-3-methylpyridin-4-yl)cyclohexyl)propyl)-6-methoxynicotinamide Absolute Stereochemistry not Assigned

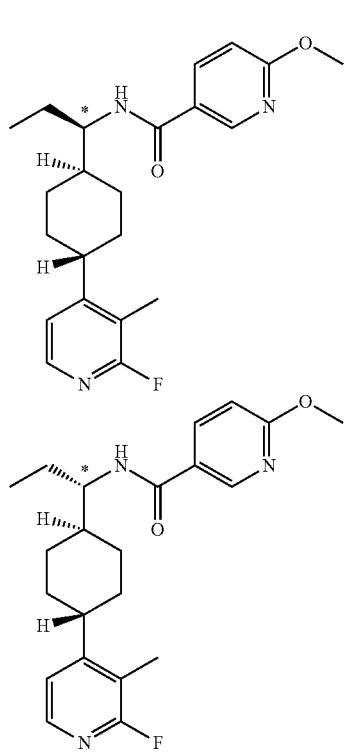

Racemic (±)-N-(1-((1r,4r)-4-(2-fluoro-3-methylpyridin-4-yl)cyclohexyl)propyl)-6-methoxynicotinamide (3.7 mg) was purified by chiral SFC (80/20 CO$_2$/IPA with 0.1% DEA mobile phase, Chiralpak AS 30×250 mm, 5 μm column, 100 ml/min, detector wavelength=220 nm, 40° C.). Concentration of the appropriate (earlier eluting) fractions afforded Example 68-1 (1.1 mg) assigned as N-(1-((1r,4r)-4-(2-fluoro-3-methylpyridin-4-yl)cyclohexyl)propyl)-6-methoxynicotinamide (Enantiomer 1). MS (ES): m/z=386 [M+H]$^+$. T$_r$=1.91 min (Method B). $^1$H NMR (500 MHz, DMSO-d$_6$) δ 8.68 (d, J=1.8 Hz, 1H), 8.14 (dd, J=8.5, 2.1 Hz, 1H), 8.03 (br d, J=8.8 Hz, 1H), 7.95 (br d, J=4.9 Hz, 1H), 7.18 (br d, J=4.9 Hz, 1H), 6.88 (d, J=8.5 Hz, 1H), 3.90 (s, 3H), 3.84-3.71 (m, 1H), 2.74 (br t, J=11.9 Hz, 1H), 2.18 (s, 3H), 1.85 (br t, J=12.2 Hz, 2H), 1.76 (br d, J=11.9 Hz, 2H), 1.68-1.60 (m, 1H), 1.58-1.31 (m, 4H), 1.27-1.14 (m, 2H), 0.85 (br t, J=7.3 Hz, 3H).

Concentration of the later eluting fractions afforded Example 68-2 (0.9 mg) assigned as N-(1-((1r,4r)-4-(2-fluoro-3-methylpyridin-4-yl)cyclohexyl)propyl)-6-methoxynicotinamide (Enantiomer 2). MS (ES): m/z=386 [M+H]$^+$. T$_r$=1.91 min (Method B). $^1$H NMR (500 MHz, DMSO-d$_6$) δ 8.67 (s, 1H), 8.14 (dd, J=8.5, 1.5 Hz, 1H), 8.03 (br d, J=8.8 Hz, 1H), 7.95 (d, J=4.9 Hz, 1H), 7.18 (br d, J=5.2 Hz, 1H), 6.88 (d, J=8.5 Hz, 1H), 3.90 (s, 3H), 3.77 (br d, J=8.5 Hz, 1H), 2.74 (br t, J=11.6 Hz, 1H), 2.18 (s, 3H), 1.85 (br t, J=12.7 Hz, 2H), 1.76 (br d, J=12.5 Hz, 2H), 1.69-1.60 (m, 1H), 1.58-1.32 (m, 4H), 1.28-1.14 (m, 2H), 0.85 (br t, J=7.2 Hz, 3H)

Examples 69-1 and 69-2 N-(1-((1s,4s)-4-(3-(difluoromethyl)-2-(methoxy-d$_3$)pyridin-4-yl)cyclohexyl)propyl)-6-methoxynicotinamide Absolute Stereochemistry not Assigned

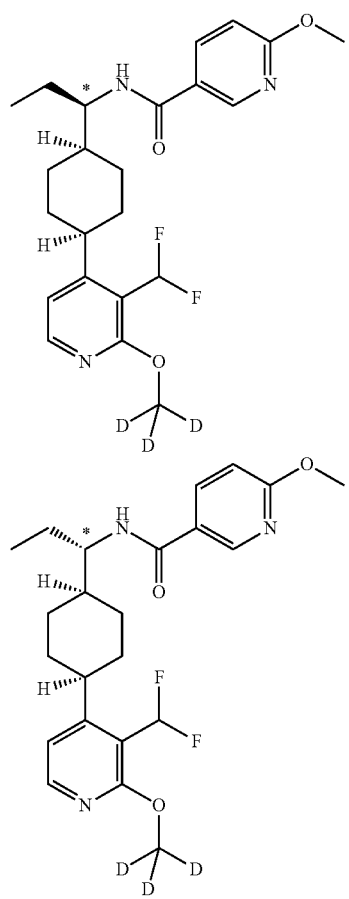

69A. 4-Chloro-2-(methoxy-d$_3$)pyridine

To a flask containing Methanol-d$_4$ (13 mL, 11.5 mmol), at room temperature under nitrogen atmosphere, was added sodium (784.0 mg, 34.1 mmol) portionwise. The mixture was stirred until a homogeneous solution was observed, at which time 4-chloro-2-fluoropyridine (1.5 g, 11.4 mmol) was added in one portion. After stirring at ambient temperature for 6 hours, the reaction mixture was concentrated to approximately one-fourth of its original volume before being quenched with saturated aqueous NH$_4$Cl solution, then partitioned between EtOAc and 1N HCl (aq). The layers were separated and the aqueous layer was extracted once more with EtOAc. The organic extracts were combined, washed with brine, dried (anhydrous Na$_2$SO$_4$), filtered and concentrated in vacuo to afford a residue. Purification by Isco chromatography afforded 4-chloro-2-

(methoxy-d$_3$)pyridine as a white solid (704.0 mg; 42% yield). MS (ES): m/z=147 [M+H]$^+$. t$_R$=0.84 min (Method A). $^1$H NMR (400 MHz, DMSO-d$_6$) δ 8.16 (d, J=5.6 Hz, 1H), 7.10 (d, J=5.5 Hz, 1H), 6.98 (s, 1H).

69B. 4-Chloro-2-(methoxy-d$_3$)nicotinaldehyde

To a solution of lithium diisopropylamide (1M in THF/hexane, 5.8 mL, 5.8 mmol) in anhydrous THF (9 mL), at −78° C. under nitrogen, was slowly added a solution of 4-chloro-2-(methoxy-d$_3$)pyridine (704.0 mg, 4.8 mmol) in THF (2 mL). After stirring for one hour, DMF (0.74 mL, 9.6 mmol) was added dropwise and stirring at −78° C. was continued. After one hour, the mixture was quenched saturated aqueous NH$_4$Cl and the mixture was allowed to warm to room temperature, before being transferred to a separatory funnel. The mixture was partitioned between saturated aqueous NaHCO$_3$ solution and EtOAc, before the layers were separated and the organic layer was washed with saturated aqueous NaHCO$_3$ solution, dried (MgSO$_4$), filtered and concentrated in vacuo to afford a yellow solution. Purification by Isco chromatography afforded 4-chloro-2-(methoxy-d$_3$)nicotinaldehyde) as a white solid (483.1 mg; 58% yield). MS (ES): m/z=175 [M+H]$^+$. t$_R$=0.72 min (Method A). $^1$H NMR (400 MHz, CDCl$_3$) δ 10.46 (s, 1H), 8.19 (d, J=5.5 Hz, 1H), 7.00 (d, J=5.4 Hz, 1H).

69C. 4-Chloro-3-(difluoromethyl)-2-(methoxy-d$_3$) pyridine

To a clear solution of 4-chloro-2-(methoxy-d$_3$)nicotinaldehyde (483.1 mg, 2.8 mmol) in DCM (6 mL), at 0° C. under nitrogen, was added Diethylaminosulfur trifluoride (DAST) (1.35 mL, 9.7 mmol) dropwise. The resultant mixture was stirred at 0° C. for one hour then allowed to slowly warm to room temperature overnight. After 15 hours, the mixture was cooled back down to 0° C. before saturated aqueous NaHCO$_3$ solution was added very slowly. The resulting mixture was stirred at 0° C. for 15 minutes, then allowed to warm to room temperature before being thoroughly extracted with EtOAc. The combined organic layers were dried (anhydrous MgSO$_4$), filtered and concentrated in vacuo to afford a pale gold oil (595.3 mg) which was used, in the next step, without further purification. MS (ES): m/z=197 [M+H]$^+$. t$_R$=0.89 min (Method A). $^1$H NMR (400 MHz, CDCl$_3$) δ 8.13 (d, J=5.5 Hz, 1H), 7.25-6.96 (m, 2H).

69D. Ethyl 2-(4-(3-(difluoromethyl)-2-(methoxy-d$_3$) pyridin-4-yl)cyclohex-3-en-1-yl)butanoate To a mixture of 4-chloro-3-(difluoromethyl)-2-(methoxy-d$_3$)pyridine (0.55 g, 2.8 mmol) and ethyl 2-(4-(4,4,5,5-tetramethyl-1,3,2-dioxaborolan-2-yl)cyclohex-3-en-1-yl)butanoate (1.07 g, 3.3 mmol) in anhydrous dioxane (12 mL), at room temperature in a sealable flask, was added a solution of K$_2$CO$_3$ (1.15 mg, 8.3 mmol) in water (3 mL). The resultant mixture was sparged with nitrogen for 15 minutes before Pd(Ph$_3$P)$_4$ (160 mg, 0.14 mmol) was added. The mixture was sparged with nitrogen for an additional ten minutes before the flask was sealed and the reaction was heated at 100° C. After 22 hours, the mixture was cooled to room temperature then partitioned between EtOAc and water. The layers were separated and the aqueous layer was extracted once more with EtOAc. The organic layers were combined, washed with brine, dried (anhydrous Na$_2$SO$_4$), filtered and concentrated in vacuo to afford a dark brown residue. Purification by Isco chromatography afforded ethyl 2-(4-(3-(difluoromethyl)-2-(methoxy-d$_3$)pyridin-4-yl)cyclohex-3-en-1-yl)butanoate as a pale gold oil (859.5 mg, 85% yield). MS (ES): m/z=357 [M+H]$^+$. t$_R$=1.14 min (Method A). $^1$H NMR (400 MHz, CDCl$_3$) δ 8.13 (d, J=5.3 Hz, 1H), 7.04-6.72 (m, 1H), 6.69 (d, J=5.3 Hz, 1H), 5.68-5.58 (m, 1H), 4.24-4.15 (m, 2H), 2.39-2.18 (m, 4H), 2.03-1.77 (m, 3H), 1.70-1.63 (m, 2H), 1.51-1.37 (m, 1H), 1.30 (t, J=7.1 Hz, 3H), 0.93 (td, J=7.4, 2.0 Hz, 3H).

69E. (cis)-Ethyl 2-((1s,4s)-4-(3-(difluoromethyl)-2-(methoxy-d$_3$)pyridin-4-yl)cyclohexyl)butanoate and (trans)-Ethyl 2-((1r,4r)-4-(3-(difluoromethyl)-2-(methoxy-d$_3$)pyridin-4-yl)cyclohexyl)butanoate To a flask charged with ethyl 2-(4-(3-(difluoromethyl)-2-(methoxy-d$_3$)pyridin-4-yl)cyclohex-3-en-1-yl)butanoate (859.5 mg, 2.4 mmol) and 10% Pd—C (103 mg, 0.096 mmol), at room temperature under nitrogen, was carefully added MeOH (12 mL). The resulting flask was evacuated then filled with hydrogen, bubbled through the reaction mixture. The flask was evacuated a second time then filled again with hydrogen, before being stirred at ambient temperature under balloon of hydrogen. After five hours, the reaction was purged with nitrogen before being filtered through at pad of Celite which was thoroughly rinsed with EtOAc. The pad was then rinsed with a small amount of MeOH followed by EtOAc. The combined filtrates were concentrated in vacuo to afford ethyl 2-(4-(3-(difluoromethyl)-2-(methoxy-d$_3$)pyridin-4-yl)cyclohexyl)butanoate as a clear gold oil (790.0 mg, 91% yield). MS (ES): m/z=359 [M+H]$^+$. t$_R$=1.18 min (Method A).

Ethyl 2-(4-(3-(difluoromethyl)-2-(methoxy-d$_3$)pyridin-4-yl)cyclohexyl)butanoate (790.0 mg) was separated by chiral SFC (10% MeOH in CO$_2$ mobile phase, ADH 5×25 cm, repacked, AD321, column, 250 ml/min, 35° C., detector wavelength=220 nm). Concentration of the appropriate (earlier eluting) fractions afforded (cis)-ethyl 2-((1s,4s)-4-(3-(difluoromethyl)-2-(methoxy-d$_3$)pyridin-4-yl)cyclohexyl) butanoate (250.0 mg). MS (ES): m/z=359 [M+H]$^+$. T$_r$=1.18 min (Method A). $^1$H NMR (400 MHz, CDCl$_3$) δ 8.17 (d, J=5.4 Hz, 1H), 7.32-7.01 (m, 1H), 6.98 (d, J=5.4 Hz, 1H), 4.19 (qd, J=7.1, 0.7 Hz, 2H), 3.30-3.15 (m, 1H), 2.68 (td, J=11.0, 3.9 Hz, 1H), 2.04-1.87 (m, 2H), 1.76-1.59 (m, 7H), 1.54-1.42 (m, 2H), 1.28 (t, J=7.2 Hz, 3H), 0.94 (t, J=7.4 Hz, 3H)

Concentration of the later eluting fractions afforded (trans)-ethyl 2-((1r,4r)-4-(3-(difluoromethyl)-2-(methoxy-d$_3$)pyridin-4-yl)cyclohexyl)butanoate (147.7 mg). MS (ES): m/z=359 [M+H]$^+$. T$_r$=1.19 min (Method A). $^1$H NMR (400 MHz, CDCl$_3$) δ 8.14 (d, J=5.4 Hz, 1H), 7.31-7.00 (m, 1H), 6.89 (d, J=5.5 Hz, 1H), 4.17 (q, J=7.2 Hz, 2H), 3.14 (tt, J=11.9, 3.0 Hz, 1H), 2.11 (td, J=8.4, 5.7 Hz, 1H), 1.98-1.73 (m, 4H), 1.67-1.58 (m, 3H), 1.45 (qd, J=12.5, 3.2 Hz, 2H), 1.29 (t, J=7.1 Hz, 3H), 1.26-1.10 (m, 2H), 0.90 (t, J=7.4 Hz, 3H).

69F. 2-((1s,4s)-4-(3-(difluoromethyl)-2-(methoxy-d$_3$)pyridin-4-yl)cyclohexyl) butanoic Acid To a homogeneous mixture of ethyl 2-((1s,4s)-4-(3-(difluoromethyl)-2-(methoxy-d$_3$)pyridin-4-yl)cyclohexyl)butanoate (250 mg, 0.70 mmol) in THF (3 mL) and MeOH (4 mL), at room temperature in a sealable vial, was added LiOH (3M aqueous, 5.8 mL, 17.4 mmol). The flask was sealed and the resulting mixture was heated and stirred at 80° C. for 24 hours before being allowed to cool to room temperature. After 19 hours, the mixture was diluted with water before being treated with 1N HCl (aq) until pH 6-7 (to pH test strips). AcOH was then added via pipette until the solution was pH 5 and the resulting mixture was twice extracted with EtOAc. The organic layers were combined, dried (MgSO$_4$), filtered and concentrated in vacuo to afford a pale gold oil. Purification by Isco chromatography afforded 2-((1 s,4s)-4-(3-(difluoromethyl)-2-(methoxy-d$_3$)pyridin-4-yl)cyclohexyl) butanoic acid as a white solid (162.9 mg; 71% yield). MS (ES): m/z=331 [M+H]$^+$. t$_R$=1.02 min (Method A). $^1$H NMR (400 MHz, DMSO-d$_6$) δ 12.15 (br s, 1H), 8.24 (d, J=5.4 Hz, 1H), 7.19 (d, J=5.5 Hz, 1H), 7.45-7.09 (m, 1H), 3.16-3.04 (m, 1H), 2.72-2.58 (m, 1H), 1.84 (br t, J=12.5 Hz, 2H), 1.73-1.44 (m, 8H), 1.43-1.30 (m, 1H), 0.90 (t, J=7.3 Hz, 3H)

69G. (±)-1-((1s,4s)-4-(3-(Difluoromethyl)-2-(methoxy-d$_3$)pyridin-4-yl)cyclohexyl)-propan-1-amine To a homogeneous mixture of 2-((1s,4s)-4-(3-(difluoromethyl)-2-(methoxy-d$_3$)pyridin-4-yl)cyclohexyl) butanoic acid (162.9 mg, 0.49 mmol) in dioxane (4 mL), at room temperature under nitrogen, was added Et$_3$N (0.21 mL, 1.48 mmol) followed by diphenylphosphoryl azide (0.14 mL, 0.64 mmol). The resulting solution was heated at 70° C. for 4 hours. After cooling to room temperature, the mixture was treated with a solution of LiOH (83 mg, 3.45 mmol) in water (2.0 mL), slowly dropwise. After stirring at ambient temperature for 1.5 hours, the mixture was diluted with water then extracted with EtOAc. The combined extracts were washed sequentially with 1N NaOH (aq) solution, water then brine before being dried (anhydrous Na2SO4), filtered and concentrated in vacuo to afford (±)-1-((1 s,4s)-4-(3-(difluoromethyl)-2-(methoxy-d$_3$)pyridin-4-yl)cyclohexyl) propan-1-amine as an off-white solid (150.6 mg) which was used without further purification. MS (ES): m/z=302 [M+H]$^+$. t$_R$=0.82 min (Method A). $^1$H NMR (400 MHz, DMSO-d$_6$) δ 8.21 (d, J=5.4 Hz, 1H), 7.41-7.12 (m, 2H), 3.31 (br s, 2H), 3.18-3.05 (m, 1H), 2.94-2.84 (m, 1H), 2.20-2.09 (m, 1H), 1.84-1.75 (m, 1H), 1.67-1.55 (m, 2H), 1.55-1.43 (m, 4H), 1.42-1.34 (m, 2H), 1.20-1.07 (m, 1H), 0.91 (t, J=7.3 Hz, 3H).

69H. (±)-N-(1-((1s,4s)-4-(3-(Difluoromethyl)-2-(methoxy-d$_3$)pyridin-4-yl)cyclohexyl)propyl)-6-methoxynicotinamide To a homogeneous mixture of 6-methoxynicotinic acid (99 mg, 0.63 mmol) in anhydrous DMF (2.5 mL), at 0° C. in a sealable reaction vial, was added HATU (240 mg, 0.63 mmol). The resulting mixture was stirred at 0° C. for 20 minutes before a solution of (+)-1-((1 s,4s)-4-(3-(difluoromethyl)-2-(methoxy-d$_3$)pyridin-4-yl)cyclohexyl)propan-1-amine (146.3 mg, 0.49 mmol) and DIPEA (0.25 mL, 1.46 mmol) in DMF (2.5 mL) was added slowly dropwise. The resulting mixture was then stirred at 0° C. in an ice bath and allowed to slowly warm to rt overnight. After 16 hours, the reaction mixture was partitioned between EtOAc and water. The layers were separated and the aqueous layer was extracted once more with EtOAc. The organic layers were combined, washed sequentially with saturated aqueous NaHCO$_3$ solution then brine, before being dried (anhydrous Na$_2$SO$_4$), filtered and concentrated in vacuo to afford the crude product as a pale orange solid (219.6 mg). MS (ES): m/z=437 [M+H]$^+$. t$_R$=1.12 min (Method A).

Example 69-1. N-(1-((1s,4s)-4-(3-(difluoromethyl)-2-(methoxy-d$_3$)pyridin-4-yl)cyclohexyl)propyl)-6-methoxynicotinamide (Enantiomer 1, Absolute Stereochemistry not Assigned)

and

Example 69-2. N-(1-((1s,4s)-4-(3-(difluoromethyl)-2-(methoxy-d$_3$)pyridin-4-yl)cyclohexyl)propyl)-6-methoxynicotinamide (Enantiomer 2, Absolute Stereochemistry not Assigned)

Racemic preparation 69H (220 mg) was purified by chiral SFC (85/15 CO$_2$/MeOH mobile phase, Chiralpak IC 25×3 cm, 5 μm column, 85 ml/min, detector wavelength=220 nm). Concentration of the appropriate (earlier eluting) fractions afforded Example 69-1 (75.1 mg) assigned as N-(1-((1s,4s)-4-(3-(difluoromethyl)-2-(methoxy-d$_3$)pyridin-4-yl)cyclohexyl)propyl)-6-methoxynicotinamide (Enantiomer 1). MS (ES): m/z=437 [M+H]+. T$_r$=1.12 min (Method A). $^1$H NMR (400 MHz, chloroform-d) δ 8.59 (d, J=2.3 Hz, 1H), 8.17 (d, J=5.4 Hz, 1H), 8.02 (dd, J=8.7, 2.4 Hz, 1H), 7.31-7.01 (m, 2H), 6.80 (d, J=8.6 Hz, 1H), 5.64 (br d, J=9.7 Hz, 1H), 4.77-4.40 (m, 1H), 3.99 (s, 3H), 3.34-3.11 (m, 1H), 2.01-1.81 (m, 4H), 1.80-1.67 (m, 3H), 1.60-1.57 (m, 4H), 1.00 (t, J=7.3 Hz, 3H).

Concentration of the later eluting fractions afforded Example 69-2 (68.0 mg) assigned as N-(1-((1 s,4s)-4-(3-(difluoromethyl)-2-(methoxy-d$_3$)pyridin-4-yl)cyclohexyl) propyl)-6-methoxynicotinamide (Enantiomer 2). MS (ES): m/z=437 [M+H]$^+$. T$_r$=1.11 min (Method A). $^1$H NMR (400 MHz, chloroform-d) δ 8.59 (d, J=2.3 Hz, 1H), 8.17 (d, J=5.4 Hz, 1H), 8.02 (dd, J=8.6, 2.5 Hz, 1H), 7.32-7.01 (m, 2H), 6.80 (d, J=8.7 Hz, 1H), 5.64 (br d, J=9.7 Hz, 1H), 4.64-4.50 (m, 1H), 3.99 (s, 3H), 3.33-3.16 (m, 1H), 2.01-1.81 (m, 4H), 1.80-1.67 (m, 3H), 1.60-1.57 (m, 4H), 1.00 (t, J=7.3 Hz, 3H).

Exemplary compounds were tested for inhibition of IDO activity. Experimental procedures and results are provided below.

Assessment of inhibitor activity in HeLa cell-based indoleamine 2,3-dioxygenase (IDO) assay.

HeLa (ATCC® CCL-2) cells were obtained from the ATCC® and cultured in Dulbecco's Modified Eagle Medium supplemented with 4.5 g/L glucose, 4.5 g/L L-glutamine and 4.5 g/L sodium pyruvate (#10-013-CV, Corning), 2 mM L-alanyl-L-glutamine dipeptide (#35050-061, Gibco), 100U/mL penicillin, 100 μg/mL streptomycin (#SV30010, HyClone) and 10% fetal bovine serum (#SH30071.03 HyClone). Cells were maintained in a humidified incubator at 37° C. in 5% CO$_2$.

IDO activity was assessed as a function of kynurenine production as follows: HeLa cells were seeded in a 96-well culture plate at a density of 5,000 cells/well and allowed to equilibrate overnight. After 24 hours, the media was aspirated and replaced with media containing IFNγ (#285-IF/CF, R&D Systems) at a final concentration of 25 ng/mL. A serial dilution of each test compound was added to the cells in a total volume of 200 μL of culture medium. After a further 48 hour incubation, 170 μL of supernatant was transferred from each well to a fresh 96-well plate. 12.1 μL of 6.1N trichloroacetic acid (#T0699, Sigma-Aldrich) was added to each well and mixed, followed by incubation at 65° C. for 20 minutes to hydrolyze N-formylkynurenine, the product of indoleamine 2,3-dioxygenase, to kynurenine. The reaction mixture was then centrifuged for 10 mins at 500×g to sediment the precipitate. 100 μL of the supernatant was transferred from each well to a fresh 96-well plate. 100 μl of 2% (w/v) p-dimethylaminobenzaldehyde (#15647-7, Sigma-Aldrich) in acetic acid (#A6283, Sigma-Aldrich) was added to each well mixed and incubated at room temperature for 20 mins. Kynurenine concentrations were determined by measuring absorbance at 480 nm and calibrating against an L-kynurenine (#K8625, Sigma-Aldrich) standard curve using a SPECTRAMAX® M2e microplate reader (Molecular Devices). The percentage activity at each inhibitor concentration was determined and $IC_{50}$ values assessed using nonlinear regression.

Activity for compounds described herein is provided in Table 1, wherein potency levels are provided as follows: (Potency: IDO $IC_{50}$: A<0.01 μM; B<0.1 μM; C<10 μM)

Assessment of inhibitor activity in HEK293 cell-based indoleamine 2,3-dioxygenase (IDO) assay.

HEK293 cells were transfected with a pCDNA-based mammalian expression vector harboring human IDO1 cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 μL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% $CO_2$.

The compound treatments were stopped by adding trichloroacetic acid (Sigma-Aldrich) to a final concentration at 0.2%. The cell plate was further incubated at 50° C. for 30 minute. The equal volume supernatant (20 μL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Activity for compounds described herein is provided in Table 1, wherein potency levels are provided as follows: (Potency: IDO $IC_{50}$: A<0.01 μM; B<0.1 μM; C<10 μM)

TABLE 1

| Example # | IDO1 HEK Human IC50 (uM) | Patent Potency HEK IC50 A < 10 nM, B > 10 nM, C > 100 nM | IDO Hela IC50 (uM) | Patent Potency Hela IC50 A < 10 nM, B > 10 nM, C > 100 nM |
|---|---|---|---|---|
| 1 | 0.056 | B | 0.03 | |
| 2 | 0.001 | A | 0.00 | A |
| 3 | 0.252 | C | | |
| 4 | 0.011 | B | 0.01 | B |
| 5 | 0.010 | B | 0.00 | A |
| 6 | 0.488 | C | | |
| 7 | 0.005 | A | 0.01 | B |
| 8 | 0.005 | A | 0.01 | B |
| 9 | 0.028 | B | | |
| 10a | 0.224 | C | | |
| 10b | 0.000 | A | 0.00 | A |
| 10c | 0.055 | B | | |
| 10d | 0.037 | B | | |
| 11a | | | 0.10 | B |
| 11b | | | 0.00 | A |
| 12a | | | 0.08 | B |
| 12b | | | 0.00 | A |
| 13a | | | 0.08 | B |
| 13b | | | 0.00 | A |
| 13d | | | 0.94 | C |
| 14a | | | 0.00 | A |
| 14b | | | 0.01 | B |
| 15a | | | 0.00 | A |
| 15b | | | 0.01 | B |
| 16a | | | 0.04 | B |
| 16b | | | 0.00 | A |
| 17a | | | 0.03 | B |
| 17b | | | 0.35 | C |
| 17c | | | 1.00 | C |
| 17d | | | 1.00 | C |
| 18a | | | 0.83 | C |
| 18b | | | 0.00 | A |
| 19a | | | 1.00 | C |
| 19b | | | 0.01 | B |
| 20a | | | 0.25 | C |
| 20b | | | 1.00 | C |
| 20c | | | 0.24 | C |
| 20d | | | 0.06 | B |
| 21c | | | 1.00 | C |
| 21d | | | 0.38 | C |
| 22 | | | 1.00 | C |
| 23 | | | 0.11 | C |
| 24a | | | 0.00 | A |
| 24b | | | 0.90 | C |
| 25b | | | 0.01 | B |
| 26a | | | 1.00 | C |
| 26b | | | 0.01 | B |
| 27a | | | 0.49 | C |
| 27b | | | 0.00 | A |
| 28a | | | 0.54 | C |
| 28b | | | 0.00 | A |
| 29b | | | 0.01 | B |
| 30b | | | 0.02 | B |
| 30d | | | 0.25 | C |
| 31a | | | 1.00 | C |
| 31b | | | 0.97 | C |
| 31c | | | 0.19 | C |
| 32a | | | 1.00 | C |
| 32b | | | 0.08 | B |
| 32c | | | 0.74 | C |
| 32d | | | 1.00 | C |
| 31d | | | 1.00 | C |
| 33 | 0.010 | B | 0.01 | B |
| 34 | 0.013 | B | 0.01 | B |
| 35 | 0.022 | B | 0.01 | B |
| 36 | 0.039 | B | 0.03 | B |
| 44 | | | 0.01 | B |
| 45a | | | 0.22 | C |
| 45b | | | 0.62 | C |
| 46a | | | 0.33 | C |
| 46b | | | 1.00 | C |
| 46c | | | 1.00 | C |
| 46d | | | | |
| 47a | | | 0.18 | C |
| 47b | | | 1.00 | C |
| 47c | | | 1.00 | C |
| 47d | | | 0.29 | C |
| 48a | | | 0.36 | C |
| 48b | | | 1.00 | C |
| 48c | | | 0.27 | C |
| 48d | | | 1.00 | C |
| 49a | | | 0.07 | B |
| 49b | | | 0.03 | B |

TABLE 1-continued

| Example # | IDO1 HEK Human IC50 (uM) | Patent Potency HEK IC50 A < 10 nM, B > 10 nM, C > 100 nM | IDO Hela IC50 (uM) | Patent Potency Hela IC50 A < 10 nM, B > 10 nM, C > 100 nM |
|---|---|---|---|---|
| 50a |  |  | 0.99 | C |
| 50b |  |  | 0.25 | C |
| 50c |  |  |  |  |
| 50d |  |  | 0.22 | C |
| 51a |  |  | 0.00 | A |
| 51b |  |  | 0.39 | C |
| 51c |  |  | 0.22 | C |
| 51d |  |  | 0.10 | B |
| 52 |  |  | 0.03 | B |
| 53a |  |  | 0.01 | B |
| 53b |  |  | 0.68 | C |
| 53c |  |  | 1.00 | C |
| 54 |  |  | 0.01 | B |
| 55 |  |  | 0.00 | A |
| 56a |  |  |  |  |
| 56b |  |  | 0.12 | C |
| 56c |  |  | 0.60 | C |
| 57a |  |  | 0.83 | C |
| 57b |  |  | 0.00 | A |
| 57c |  |  | 0.13 | C |
| 57d |  |  | 0.04 | B |
| 58a |  |  | 0.31 | C |
| 58b |  |  | 0.50 | C |
| 58c |  |  | 0.36 | C |
| 58d |  |  | 0.00 | A |
| 59a |  |  | 0.10 | B |
| 59b |  |  | 0.00 | A |
| 59c |  |  | 0.33 | C |
| 59d |  |  | 0.11 | C |
| 60a |  |  | 0.82 | C |
| 60b |  |  | 0.25 | C |
| 60c |  |  | 0.01 | B |
| 60d |  |  | 0.17 | C |
| 61b |  |  | 0.67 | C |
| 61c |  |  | 1.00 | C |
| 61c |  |  | 1.00 | C |
| 61d |  |  | 0.02 | B |
| 62a |  |  | 0.07 | B |
| 62b |  |  | 0.02 | B |
| 63-1 |  |  |  | C |
| 63-2 |  |  |  | B |
| 64-1 |  |  |  | C |
| 64-2 |  |  |  | C |
| 65 |  |  |  | A |
| 66-1 |  |  |  | C |
| 66-2 |  |  |  | A |
| 67 |  |  |  | C |
| 68-1 |  |  |  | B |
| 68-2 |  |  |  | C |
| 69-1 |  |  |  |  |
| 69-2 |  |  |  |  |

What is claimed:

1. A compound of formula I or formula II or formula III

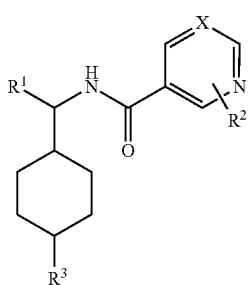

(I)

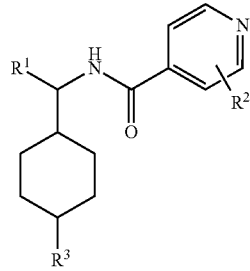

(II)

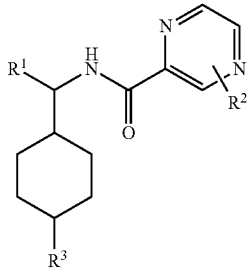

(III)

wherein

X is CH, CR⁴, or N;

R¹ is $C_{1-6}$alkyl, $C_{0-6}$alk-O—$C_{1-6}$alkyl, $C_{0-6}$alk-O—$C_{1-6}$alk-O—$C_{1-6}$alkyl, $C_{0-6}$alk-CN, or $C_{0-6}$alk-heterocycloalkyl;

R² is H, —NH₂; —NH($C_{1-6}$alkyl); —N($C_{1-6}$alkyl)($C_{1-6}$alkyl), $C_{1-6}$alkyl, $d_1$-$d_{13}$-$C_{1-6}$alkyl, $C_{1-6}$alkoxy, $d_1$-$d_{13}$-$C_{1-6}$alkoxy, OH, halo, heterocycloalkyl, or heteroaryl;

R³ is pyridyl; pyrimidinyl; quinolinyl; or naphthyridinyl, wherein the pyridyl, pyrimidinyl, quinolinyl, or naphthyridinyl is optionally substituted on any atom with 1, 2 or 3 R substituents that are independently $C_{1-6}$alkyl, $d_1$-$d_{13}$-$C_{1-6}$alkyl, halo$C_{1-6}$alkyl, halo$C_{1-6}$alkoxy, $C_{1-6}$alkoxy, $d_1$-$d_{13}$-$C_{1-6}$alkoxy, OH, or halo;

R⁴ is NH₂; —NH($C_{1-6}$alkyl); —N($C_{1-6}$alkyl)($C_{1-6}$alkyl), $C_{1-6}$alkyl; $C_{1-6}$alkoxy, OH, halo, heterocycloalkyl, or heteroaryl;

or a stereoisomer thereof or a tautomer thereof;

or a pharmaceutically acceptable salt thereof.

2. The compound of claim 1 that is a compound of formula I, or a stereoisomer thereof or a tautomer thereof; or a pharmaceutically acceptable salt thereof.

3. The compound of claim 2, wherein X is CH or CR⁴.

4. The compound of claim 2, wherein X is N.

5. The compound of claim 1 that is a compound of formula II, or a stereoisomer thereof or a tautomer thereof; or a pharmaceutically acceptable salt thereof.

6. The compound of claim 1, wherein R¹ is $C_{1-6}$alkyl.

7. The compound of claim 1, wherein R¹ is $C_{0-6}$alk-O—$C_{1-6}$alkyl.

8. The compound of claim 1, wherein R¹ is $C_{0-6}$alk-O—$C_{1-6}$alk-O—$C_{1-6}$alkyl.

9. The compound of claim 1, wherein R¹ is $C_{0-6}$alk-CN.

10. The compound of claim 1, wherein R¹ is $C_{0-6}$alk-heterocycloalkyl.

11. The compound of claim 1, wherein R² is H.

12. The compound of claim 1, wherein R² is —NH₂; —NH($C_{1-6}$alkyl); or —N($C_{1-6}$alkyl)($C_{1-6}$alkyl).

13. The compound of claim 1, wherein R² is $C_{1-6}$alkyl or $C_{1-6}$alkoxy.

14. The compound of claim 1, wherein $R^2$ is $d_1$-$d_{13}$-$C_{1-6}$alkyl or $d_1$-$d_{13}$-$C_{1-6}$alkoxy.

15. The compound of claim 1, wherein $R^2$ is OH.

16. The compound of claim 1, wherein $R^2$ is halo.

17. The compound of claim 1, wherein $R^2$ is heterocycloalkyl.

18. The compound of claim 1, wherein $R^2$ is heteroaryl.

19. The compound of claim 1, wherein $R^3$ is pyridyl optionally substituted on any atom with 1, 2 or 3 R substituents that are independently $C_{1-6}$alkyl, $d_1$-$d_{13}$-$C_{1-6}$alkyl, halo$C_{1-6}$alkyl, halo$C_{1-6}$alkoxy, $C_{1-6}$alkoxy, $d_1$-$d_{13}$-$C_{1-6}$alkoxy, OH, or halo.

20. The compound of claim 1, wherein $R^3$ is pyrimidinyl optionally substituted on any atom with 1, 2 or 3 R substituents that are independently $C_{1-6}$alkyl, $d_1$-$d_{13}$-$C_{1-6}$alkyl, halo$C_{1-6}$alkyl, halo$C_{1-6}$alkoxy, $C_{1-6}$alkoxy, $d_1$-$d_{13}$-$C_{1-6}$alkoxy, OH, or halo.

21. The compound of claim 1, wherein $R^3$ is quinolinyl optionally substituted on any atom with 1, 2 or 3 R substituents that are independently $C_{1-6}$alkyl, $d_1$-$d_{13}$-$C_{1-6}$alkyl, halo$C_{1-6}$alkyl, halo$C_{1-6}$alkoxy, $C_{1-6}$alkoxy, $d_1$-$d_{13}$-$C_{1-6}$alkoxy, OH, or halo.

22. The compound of claim 1, wherein $R^3$ is naphthyridinyl optionally substituted on any atom with 1, 2 or 3 R substituents that are independently $C_{1-6}$alkyl, $d_1$-$d_{13}$-$C_{1-6}$alkyl, halo$C_{1-6}$alkyl, halo$C_{1-6}$alkoxy, $C_{1-6}$alkoxy, $d_1$-$d_{13}$-$C_{1-6}$alkoxy, OH, or halo.

23. A pharmaceutical composition comprising a compound according to claim 1 and a pharmaceutically acceptable excipient.

24. A method of treating cancer in a patient in need of such treatment comprising administering to the patient a therapeutically effective amount of a compound according to claim 1; wherein the cancer is brain cancer, skin cancer, bladder cancer, ovarian cancer, breast cancer, gastric cancer, pancreatic cancer, prostate cancer, colon cancer, blood cancer, lung cancer or bone cancer.

* * * * *